(12) United States Patent
Gray et al.

(10) Patent No.: US 7,105,310 B1
(45) Date of Patent: Sep. 12, 2006

(54) DETECTION OF BIOMOLECULES BY SENSITIZER-LINKED SUBSTRATES

(75) Inventors: Harry B. Gray, Pasadena, CA (US); Brian R. Crane, Ithaca, NY (US); Jay R. Winkler, Pasadena, CA (US); Ivan Julian Dmochowski, Philadelphia, PA (US); Jonathan J. Wilker, LaFayette, IN (US); Alexander Robert Dunn, Colorado Springs, CO (US)

(73) Assignee: California Institute of Technology, Pasadena, CA (US)

( * ) Notice: Subject to any disclaimer, the term of this patent is extended or adjusted under 35 U.S.C. 154(b) by 372 days.

(21) Appl. No.: 10/031,532
(22) PCT Filed: Jul. 19, 2000
(86) PCT No.: PCT/US00/19821
§ 371 (c)(1),
(2), (4) Date: May 2, 2002
(87) PCT Pub. No.: WO01/06260
PCT Pub. Date: Jan. 25, 2001

(51) Int. Cl.
G01N 33/573 (2006.01)
(52) U.S. Cl. ............... 435/7.4; 435/4; 435/7.1; 435/7.2; 435/7.7; 435/7.92; 435/7.93; 435/183; 435/968; 436/139; 436/164; 436/172; 436/815
(58) Field of Classification Search ............... 435/4, 435/7.1, 7.9, 7.92–7.93, 25, 175, 7.7, 183, 435/188, 968, 7.2, 7.4; 436/164, 172, 518, 436/524, 532, 537, 544, 501, 56, 136, 815, 436/139; 422/68.1
See application file for complete search history.

(56) References Cited

U.S. PATENT DOCUMENTS 5,157,032 A * 10/1992 Barton .................. 514/185

(Continued)

OTHER PUBLICATIONS

Wilker et al. Sensitizer-linked substrates: Complexes for the rapid generation of reduced and oxidized enzyme states. Book of Abstracts, 217th ACS National Meeting, Mar. 21-25, 1999.*

(Continued)

*Primary Examiner*—Long V. Le
*Assistant Examiner*—Leon Y. Lum
(74) *Attorney, Agent, or Firm*—DLA Piper

(57) ABSTRACT

Methods and compositions for detecting and characterizing target biomolecules using sensitizer-linked substrate molecules are disclosed. High throughput screening assays and therapeutic applications of the inventions are also included

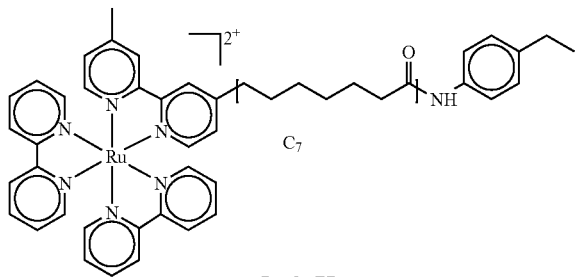

Ru-$C_n$-EB
n=7,9-13

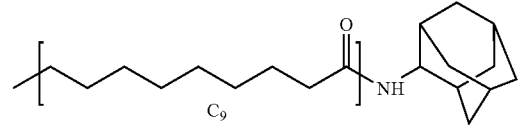

Ru-$C_n$-Ad
n=9,11

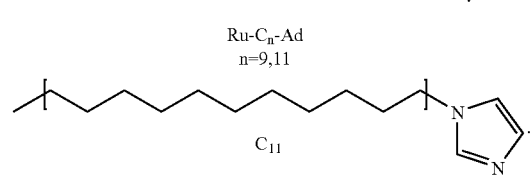

Ru-$C_n$-Im
n=11,13

6 Claims, 54 Drawing Sheets

U.S. PATENT DOCUMENTS

| | | | | |
|---|---|---|---|---|
| 5,478,729 | A | * | 12/1995 | Van Atta et al. ............ 435/7.93 |
| 5,506,251 | A | * | 4/1996 | Thirugnanam ............... 514/383 |
| 5,569,745 | A | * | 10/1996 | Goodbody et al. .......... 530/328 |
| 5,696,157 | A | * | 12/1997 | Wang et al. ................. 514/457 |
| 5,698,401 | A | * | 12/1997 | Fesik et al. ................... 435/7.1 |
| 5,726,041 | A | * | 3/1998 | Chrespi et al. ............. 435/69.1 |
| 6,060,253 | A | * | 5/2000 | Gelboin et al. ............... 435/7.1 |
| 6,251,581 | B1 | * | 6/2001 | Ullman et al. .................. 435/4 |
| 6,372,215 | B1 | * | 4/2002 | Starling et al. ........... 424/141.1 |
| 6,406,913 | B1 | * | 6/2002 | Ullman et al. ............... 252/700 |

OTHER PUBLICATIONS

Dmochowski et al. Sensitizer-linked substrates: Delivery of electrons and holes to the active site of cytochrome P450CAM. Boo of Abstracts, 216th ACS National Meeting, Aug. 23-27, 1998.*

Wilker et al. Sensitizer-linked substrates: Rapid delivery of electrons and holes to protein active sites. Book of Abstracts, 216th ACS National Meeting, Aug. 23-27, 1998.*

Wilker et al. Substrates for rapid delivery of electrons and holes to buried active sites in proteins. Angew. Chem. Int. Ed., vol. 38, No. 1/2, 1999.*

Leung et al. 7-amino-4-methyl-6-sulfocoumarin-3-acetic acid: a novel blue fluorescent dye for protein labeling. Bioorganic & Medicinal Chemistry Letters (1999), vol. 9, pp. 2229-2232.*

* cited by examiner

| compound | $K_D(\mu M)$ | $k_{en}^{-1}$(ns) | Ru-Fe(Å) |
|---|---|---|---|
| $[Ru-C_{13}-EB]^{2+*}$ | 1.7 ± 0.4 | 107 ± 8 | 20.6 ± 0.2 |
| $[Ru-C_{12}-EB]^{2+*}$ | 1.5 ± 0.3 | 103 ± 7 | 20.5 ± 0.2 |
| $[Ru-C_{11}-EB]^{2+*}$ | 0.9 ± 0.4 | 94 ± 7 | 20.1 ± 0.3 |
| $[Ru-C_{10}-EB]^{2+*}$ | 0.9 ± 0.4 | 88 ± 2 | 19.9 ± 0.1 |
| $[Ru-C_9-EB]^{2+*}$ | 0.7 ± 0.1 | 75 ± 2 | 19.4 ± 0.1 |
| $[Ru-C_7-EB]^{2+*}$ | 6.5 ± 1.3 | 77 ± 2 | 19.5 ± 0.1 |
| $[Ru-C_{11}-Ad]^{2+*}$ | 0.8 ± 0.3 | 203 ± 16 | 21.0 ± 0.3 |
| $[Ru-C_9-Ad]^{2+*}$ | 0.7 ± 0.2 | 231 ± 11 | 21.4 ± 0.2 |
| $[Ru-C_{13}-Im]^{2+*}$ | 4.1 ± 1.1 | 190 ± 8 | 21.2 ± 0.1 |
| $[Ru-C_{11}-Im]^{2+*}$ | ---------- | 488 ± 35 | N/A |

Uncertainties represent one standard deviation of the data averaged from three to six experiments.

FIG. 4

(1) [Ru-C$_9$-Ad]$^{2+}$
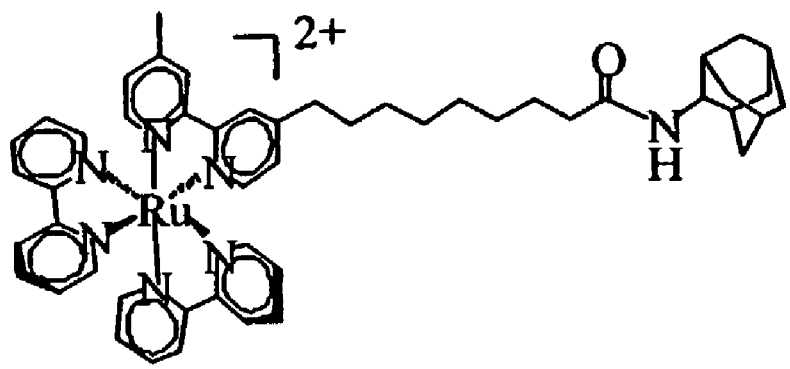
(2) 2-Adamantylacetamid
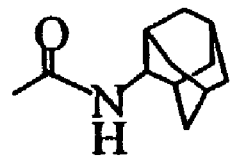
(3) [Ru-C$_{10}$]$^{2+}$
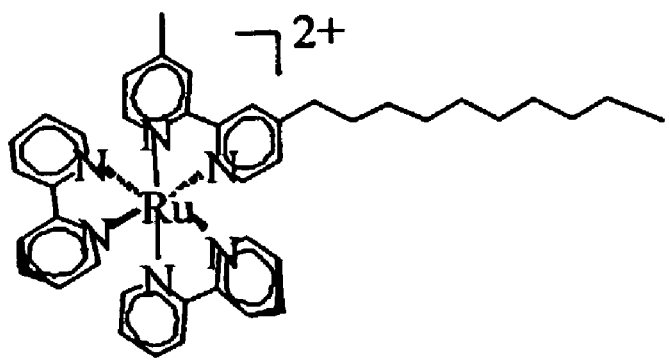
FIG. 14

| Substrate | ν Fe-(CO)[a] |
|---|---|
| None | 463[b] |
| Ru-C$_{11}$-Ad | 472 |
| Ru-C$_9$-Ad | 474 |
| Adamantane | 476 |
| Camphor | 482[b] |

[a] All units are in cm$^{-1}$.
[b] These values are in good agreement with published values for substrate-free (465 cm$^{-1}$) and camphor-bound P450 (484 cm$^{-1}$) (19).

FIG. 18

*Compound I*  *Compound II*

| Ru | $K_D(\mu M)$ | $k_d(s^{-1})$[a] | $k_{en}(s^{-1})$[b] | $k_{ET}(s^{-1})$[c] | $R_0(\text{Å})$ | Ru-Fe(Å)[d] |
|---|---|---|---|---|---|---|
| (a) | 0.9 | 4.6 E6 | 8.0 E6 | N/A | 18.8 | 19.7 |
| (b) | 3.7 (0.4) | 2.0 (0.1) E6 | 8.5 E6 | 1 E6 | 22.1 | 17.7 |
| (c) | 0.5 (0.1) | 4.6 (0.1) E6 | 9.5 E6 | 8 E6 | 18.0 | 17.7 |

*Uncertainties are given in parentheses, and constitute the standard deviation of four different measurements.

[a] Intrinsic rate of excited-state decay of the Ru complex (in the absence of P450).

[b] Rate of energy transfer in the presence of P450, calculated from the emission profile. For (b) and (c) assumptions were made based on (a), $k_{obs}$, and reasonable Ru-Fe distances.

[c] Calculated rate of electron transfer in the presence of P450, based on the observed yield of ET products. Actual yields (and rates), however, are probably much higher. Yields were calculated using extinction coefficients at 420 and 445 nm for $Fe^{2+}$ while subtracting contributions from $Ru^{3+}$ and $Ru^{2+*}$.

[d] The metal-metal (Ru-Fe) distance serves as a useful representation of the D-A pair.

FIG. 33

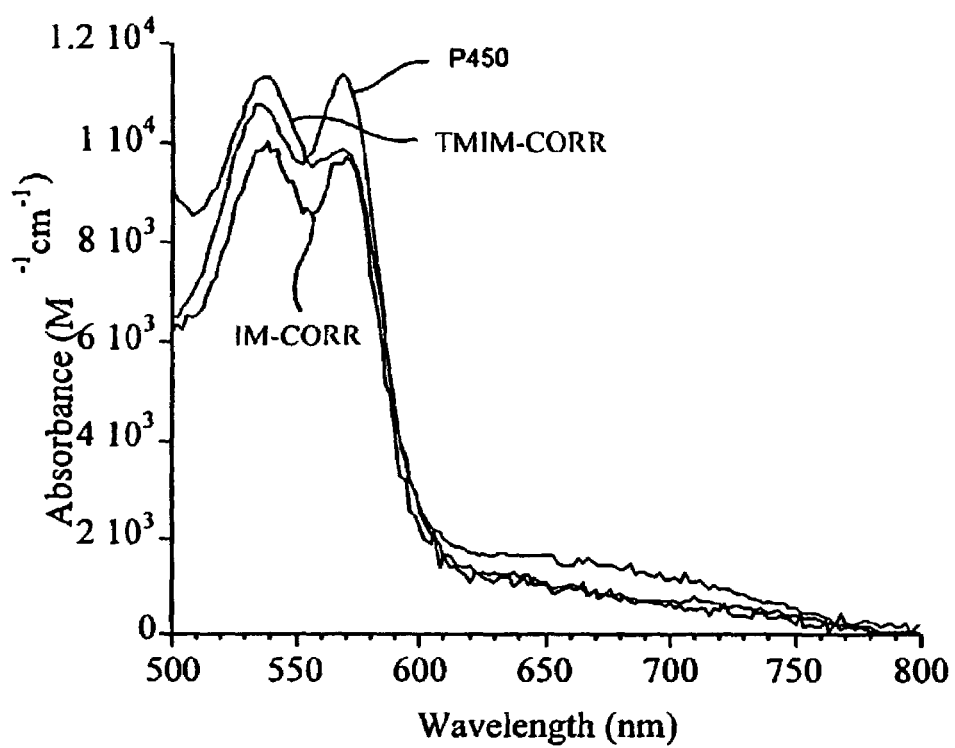
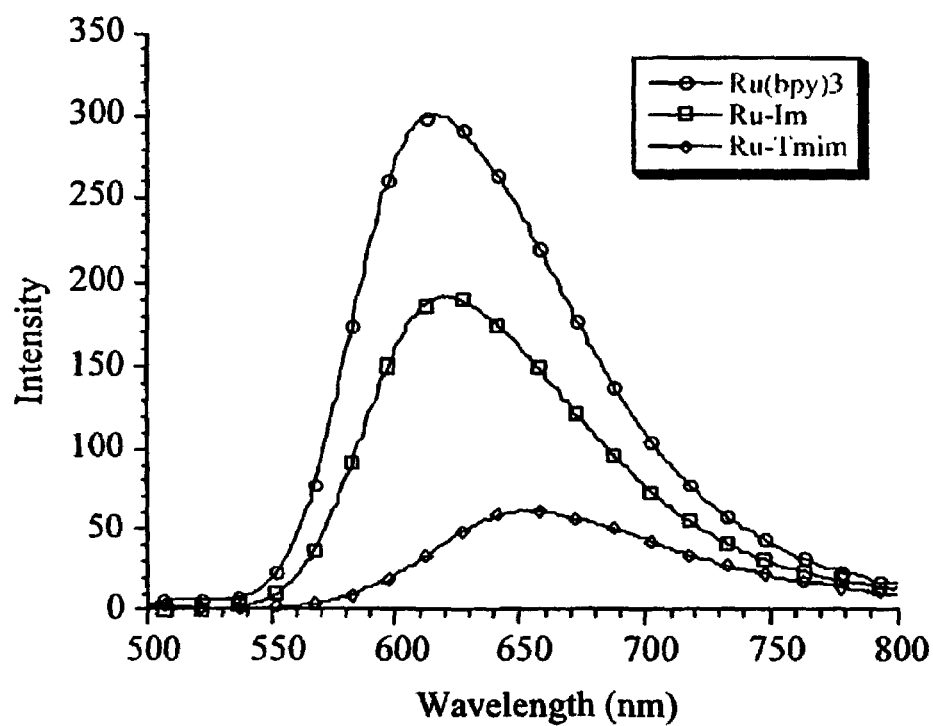
FIG. 34

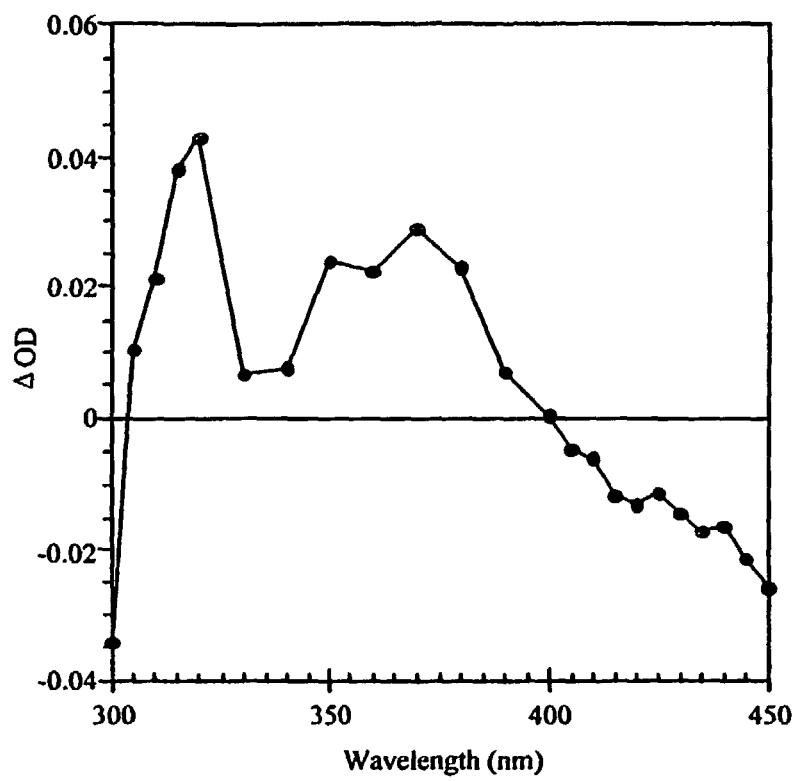
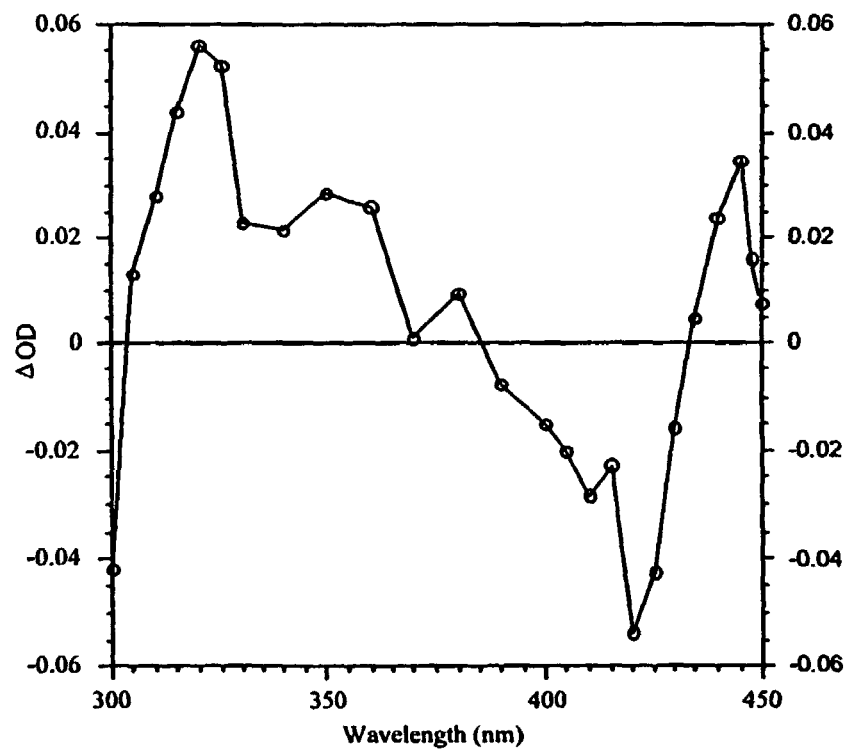
FIG. 39

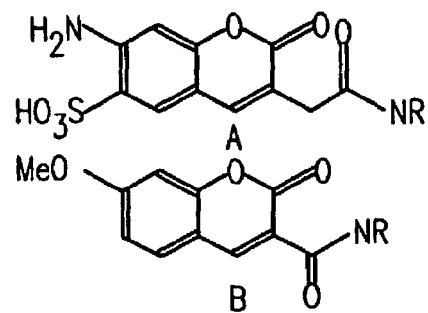
FIG. 51
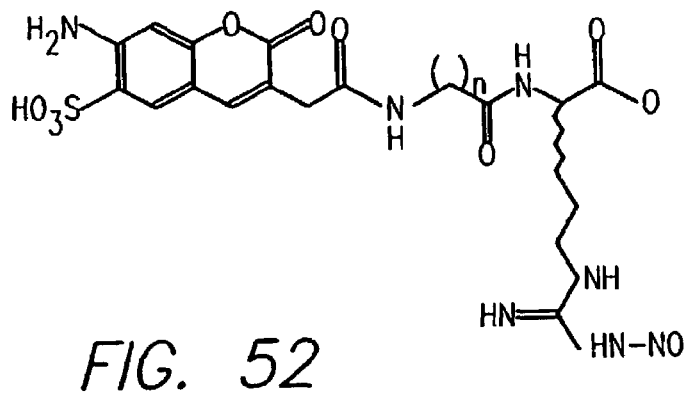
FIG. 52
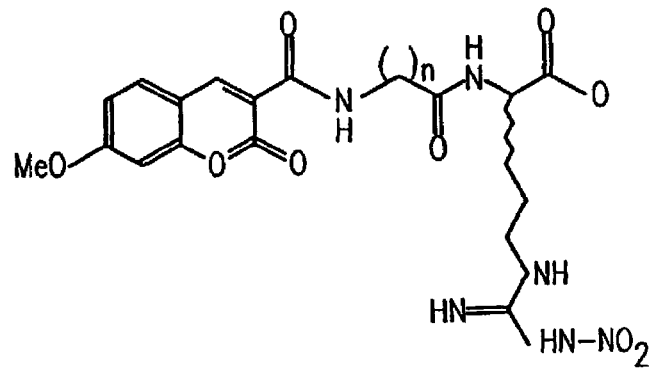
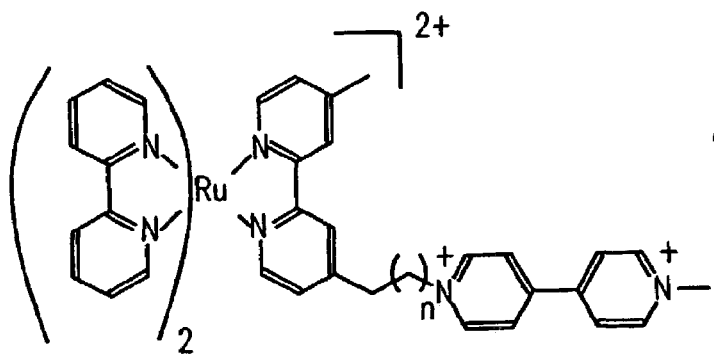
FIG. 55

FIG. 54
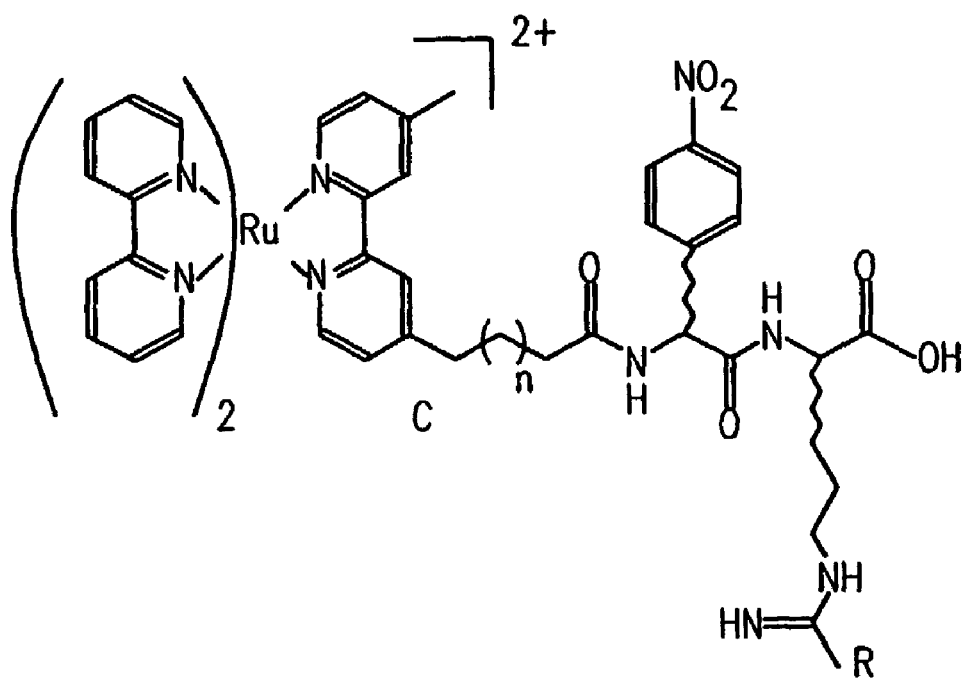
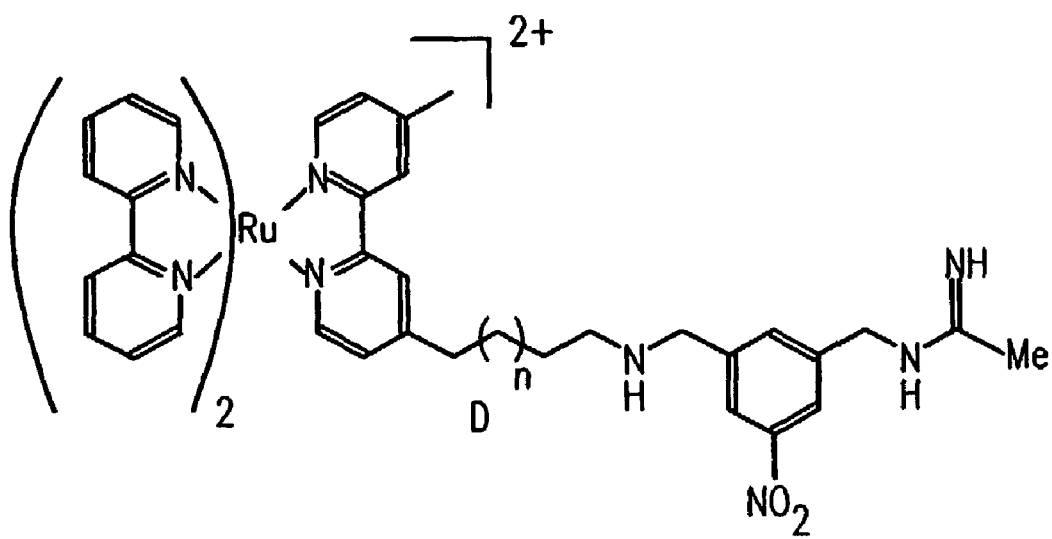

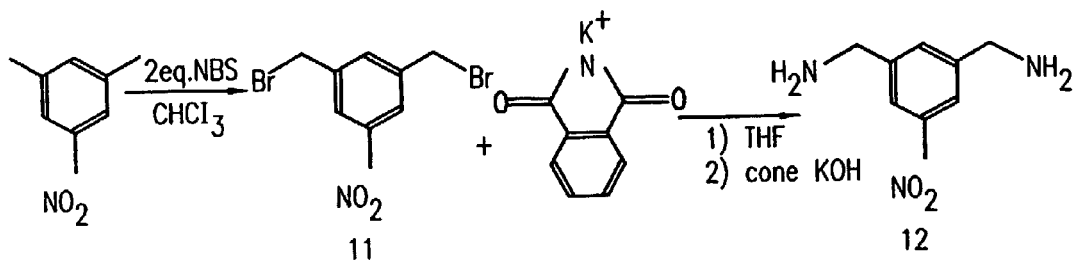
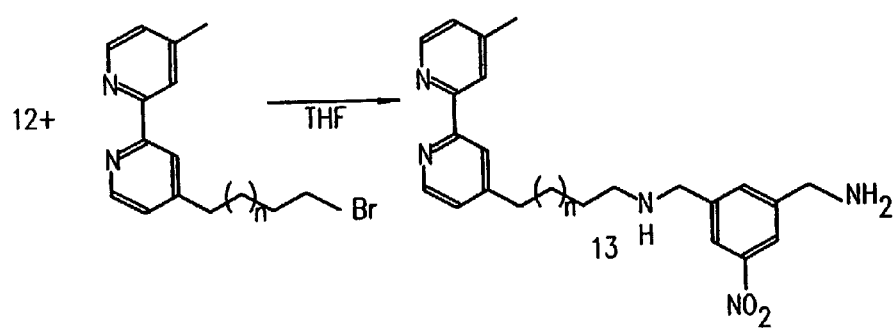
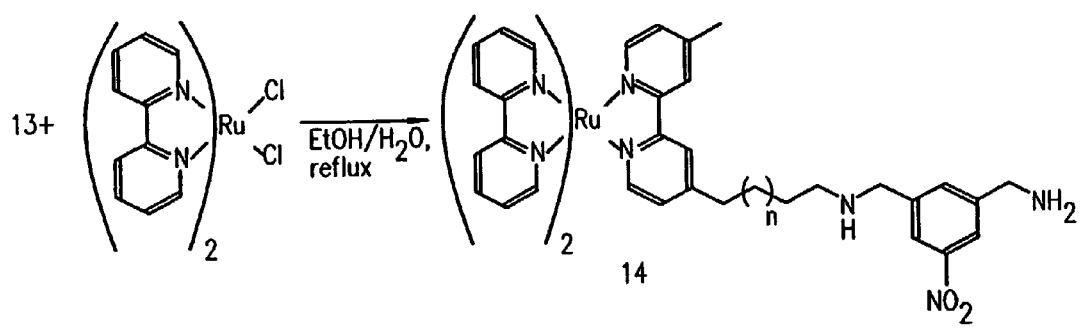
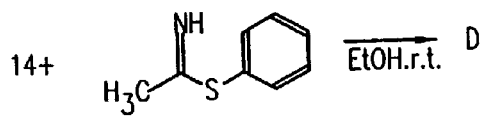
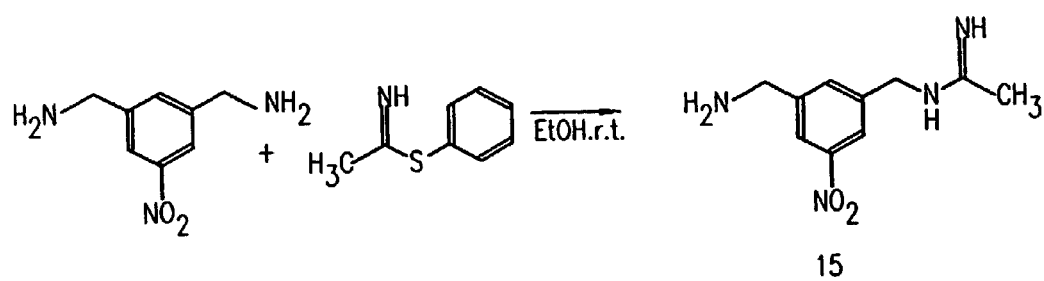
FIG. 56

DETECTION OF BIOMOLECULES BY SENSITIZER-LINKED SUBSTRATES

This invention was made with Government support from the NSF-CHE 9807150 and NIH-GM48495. The Government has certain rights in this application.

FIELD OF INVENTION

The present invention relates to novel methods and compositions for detecting and characterizing biomolecules using sensitizer-linked substrate molecules.

BACKGROUND OF THE INVENTION

The ability to detect, characterize, and manipulate biomolecules in complex media is critical for understanding biochemical and metabolic processes. Methods and systems which are capable of detecting trace amounts of microorganisms, pharmaceuticals, hormones, viruses, antibodies, nucleic acids and other proteins have been based on well known binding reactions, e.g. antigen-antibody reactions, nucleic acid hybridization techniques, and protein-ligand systems. Much attention is being given to the design, synthesis, and employment of molecular probes of enzyme structure and function [Wilker, J. J. et al. *Angew. Chem. Int. Ed.* (1999), 38, 90–92; Hamachi, I. et al., *J. Am. Chem. Soc.* (1999), 121, 5500–5506; Dmochowski, I. J., et al. *Proc. Natl. Acad. Sci. USA* (1999), 96, 12987–12990; Atkinson, R. N. et al. *J. Org Chem.* (1999), 64, 3467–3475; Tschirret-Guth, R. A. et al. *J. Am. Chem. Soc.* (1999), 121, 4731–4737; DiGleria, K. et al. *J. Am. Chem. Soc.* (1998), 120, 46–52; Murthy, Y.; Massey, V. *Meth. Enzymol.* (1997), 280, 436–460; Newcomb, M. et al. *J. Am. Chem. Soc.* (1995), 117, 3312–3313; Atkinson, J. K.; Ingold, K. U. *Biochemistry* (1993), 32, 9209–9214; Liu, K. E. et al., *J. Am. Chem. Soc.* (1993), 115, 939–947; Tschirret-Guth, R. A. et al. *J. Am. Chem. Soc.* (1998), 120, 7404–7410], owing in part to the abundance of naturally occurring cavity proteins [Tainer, J. A. et al. *J. Mol. Biol.* (1982), 160, 181–217; Bigler, T. L. et al., *Prot. Sci.* (1993), 2, 786–799; Badger, J. et al., *Proc. Natl. Acad. Sci. USA* (1988), 85, 3304–3308; Poulos, T. L. et al., *Biochemistry* (1986), 25, 5314–5322] and in part to the power of site-directed mutagenesis, to modify existing cavities and create new substrate binding sites [Wilcox, S. K. et al., *Biochemistry* (1998), 37, 16853–16862; Goldsmith, J. O. et al., *Biochemistry* (1996), 35, 2421–2428; DePillis, G. D. et al., *J. Am. Chem. Soc.* (1994), 116 6981–6982; Fitzgerald, M. M. et al., *Biochemistry* (1994), 33, 3807–3818; Eriksson, A. E. et al., *Nature* (1992), 355, 371–373].

Typically, detection of biomolecules of interest is performed by an observable tag or label attached to one or more of the binding elements (i.e. substrates) of the biomolecule and indicated by the presence or absence of the observable tag. Of particular interest are labels that can emit energy as luminescence through photochemical, chemical, and electrochemical processes.

The detection of specific proteins through luminescence spectroscopy should be useful in a wide variety of fields. The rise of combinatorial chemistry has necessitated the development of sensitive and rapid screens for drug-target interactions. Luminescence is ideal for rapid screening because of its speed and sensitivity. Similarly, a luminescent probe for the in vivo detection of enzyme expression and localization is generally useful. Examples of widely used probes include small molecule detectors for mono- and divalent cations and Green Fluorescent Protein hybrid proteins. (d. Silva, A. P. et al., *Coord. Chem. Rev.* (1999) 185–186, 297–306; Tsien, R. Y. *Annu. Rev. Biochem.* (1998) 67, 509–544; Takahashi, A. et al., *Physiol. Rev.* (1999) 79, 1089–1125). The wide usage of these techniques suggests that a method of detecting the localization and concentration of a given enzyme is highly desirable. However, few techniques currently exist that take advantage of the inherent specificity of an enzyme for its substrate.

In addition, molecules with photosensitizers attached to cofactors [Hamachi, I. et al., *J. Am. Chem. Soc.* (1999), 121, 5500–5506] can rapidly deliver redox equivalents to buried active sites for potential therapeutic applications.

Particularly important target biomolecules are oxygenases (e.g. cytochrome P450) involved in drug metabolism and many disease states, including liver and kidney dysfunction, neurological disorders, and cancer. 54 human cytochrome P450 genes have been identified. The cytochrome P450 genes are broken down into many families and subfamilies. The first isolated human P450s were 1A1, 1A2, 2A6, 2C8, 2C9, 2D6, 2E1, 3A4, 3A5, and 4A11. The 1A family, for example, is actively studied due to its role in carcinogen activation (F. P. Guengrich, "Human Cytochrome P450 Enzymes" in Cytochrome P450: Structure, Mechanism, and Biochemistry, 2nd ed. Ed. Paul R. Ortiz de Montellano, Plenum Press, New York, 1995, pp. 473–536.) and would be an optimal target for characterization.

Although more than 100 mammalian microsomal P450 isozymes have been identified, direct information about their structures and physiological function is lacking. The best characterized of these is, cytochrome $P450_{cam}$(P450). Crystal structures are available for only six P450 oxygenases (Poulos, T. L., et al. (1995) in *Cytochrome P450: Structure, Mechanism, and Biochemistry*, 2nd edn, ed. Ortiz de Montellano, P. R. (Plenum Press, New York), pp. 125–150), all but one of which are water-soluble bacterial enzymes.

New methods for detecting mammalian P450s and characterizing their structures (Tschirret-Guth, R. A., et al. (1999) *J. Am. Chem. Soc.* 121, 4731–4737) would facilitate rational drug design (Ortiz de Montellano, P. R. & Correia, M. A. (1995) in *Cytochrome P450: Structure, Mechanism, and Biochemistry*, 2nd edn, ed. Ortiz de Montellano, P. R. (Plenum Press, New York), pp. 305–364) and the engineering of new catalysts (Joo, H., Zhanglin, L. & Arnold, F. H. (1999) *Nature* 399, 670–673; Stevenson, J.-A., et al. (1996) *J. Am. Chem. Soc.* 118, 12846–12847) for use in diagnosis and/or therapy of diseases.

Another luminescent ruthenium complex $[Ru(phen)_2 dppz]^{2+}$ is nearly undetectable in water but moderate in non-aqueous solvents. (Chambon, J.-C. et al., *New J. Chem.* (1985) 9, 527–529) The discovery that this and similar compounds also emit light when intercalated into doubled stranded DNA resulted in publications, both on the original dppz complexes and on related compounds. (Friedman, A. E. et al., *J. Am. Chem. Soc.* (1990) 112, 4960–4962; Erkkila, K. E. et al., *Chem. Rev.* (1999) 99, 2777–2795) The mechanism of this surprising effect has been elucidated to large degree. Luminescence quenching in aqueous solution seems to occur through water hydrogen bonding to dppz in the excited state, although solvent polarity may also play a role. (Olsen, E. J. C. et al., *J. Am. Chem. Soc.* (1997) 119, 11458–11467).

Another biomolecule of interest is nitric oxide (NO), a recognized ubiquitous biological second messenger molecule, that acts in a myriad of biological processes including neuronal development, regulation of blood pressure, apoptosis, neurotransmission, and immunological responses. (Kendrick, K. M. et al., *Nature* (1997) 388, 670–674;

Huang, P. L. et al., *Nature* (1995) 377, 239–242; Ko, G. Y.; Kelly, P. T. *J. Neurosci.* (1999) 19, 6784–6794; Luth, H. J. et al., *Brain Research* (2000) 852, 45–55;Mize, R. R. et al., *Nitric Oxide in Brain Development, Plasticity and Disease,* Progress in Brain Research (Elesevier, 1998), vol. 118) (D. Nathan, *J. Clin. Invest.* (1997) 100, 2417–2423; J. Lancaster, *Nitric Oxide: Principles and Actions* (Academic Press, San Diego, Calif., 1996)). These diverse functions depend on the production of NO by nitric oxide synthase (NOS), a multi-domain enzyme that catalyzes the overall transformation L-Arg+2$O_2$+3/2(NADPH+$H^+$)→L-citrulline+NO+2$H_2$O+ 3/2 $NADP^+$ where L-Arg is L-arginine and NADPH is nicotinamide adenine dinucleotide phosphate(Stuehr, D. J. *Biochim. Biophys. Acta* (1999) 1411, 217–230).

NO and NOS enzymes appear to play a role in many of the diseases that afflict humanity. This practical importance arises from the deep involvement of NOS in many of the channels of intercellular communication. During the 1990's considerable effort was expended in defining the characteristics of the various isoforms of NOS and their immediate effect on a wide array of cellular phenomena. Currently, the focus is shifting toward understanding how NOS functions within the context of the complex signaling pathways in and between cells. An example of this trend is the recent publication of a structural study of neuronal NOS that focused on the enzyme's interactions with PSD-95 and the NMDA receptor. (Hillier, B. J. et al., *Science* (1999) 284, 812–815)

The NOS monomer contains independently folded reductase and oygenase domains. The reductase domain binds NADPH and contains the cofactors FAD and FMN. The oxygenase domain contains a cysteine-ligated heme and a tetrahydrobiopterin ($H_4$B) cofactor, and catalyses the oxidation of arginine to NO and citrulline. (Crane, B. R. et al., *Science* (1997) 278, 425–431; Crane, B. R. et al., *Science* (1998) 279, 2121–2126; Raman, C. S. et al., *Cell* (1998) 95, 939–950; Fischmann, T. O. et al., *Nature Str. Biol.* (1999) 6, 223–242) The oxygenase and reductase domains are joined by a calmodulin binding peptide that regulates the activity of the NOS isozymes. Interestingly, NOS functions as a dimer. Reduction occurs in trans—the reductase domain from one monomer reduces the oxidase domain of the complementary monomer. (Crane, B. R. et al., *The EMBO Journal* (1999) 18, 6271–6281)

The currently known mammalian NOS enzymes are organized into three classes: nNOS (neuronal), iNOS (immune), and eNOS (endothelial). These classifications reflect the origins of the NOS isoforms. (Bredt, D. S. et al., *Nature* (1991) 351, 714–718; Janssens, S. P. et al., *J. Biol. Chem.* (1992) 267, 22694; Lamas, S. et al., *Proc. Natl. Acad. Sci. USA* (1992) 89, 6348–6352; Lowenstein, C. J. et al., *Proc. Natl. Acad. Sci. USA* (1992) 89, 6711–6715; Xie, Q. W. et al., *Science* (1992) 256, 225–228) However, subsequent research has shown that the various forms of NOS occur in a wide variety of tissues, with a complex distribution.

Although nNOS is constitutively expressed, its level of expression is dynamically regulated. (Dawson, T. M. et al., *Progress in Brain Research* (1998) 118, 3–11) For example, nNOS activity is high in the developing olfactory and visual systems, but low in their mature counterparts. Abnormal nNOS activity has been implicated in a variety of diseases, including both Parkinson's and Alzheimer's disease. (Luth, H. J. et al., *Brain Research* (2000) 852, 45–55; Dawson, V. L.; Dawson, T. M. *Progress in Brain Research* (1998) 118, 215–229) The isozyme eNOS (endothelial NOS) is expressed in smooth muscles, including those lining blood vessels. (Huang, P. L. et al., *Nature* (1995) 377, 239–242) Local production of NO triggers the relaxation of the vascular tissue, leading to reduction in blood pressure. In addition to vasodilation, eNOS also modulates angiogenesis. (Dimmeler, S.; Zeiher, A. M *Cell Death and Differentiation* (1999) 6, 964–968) iNOS has both beneficial and destructive influences in the immune system. (D. Nathan, *J. Clin. Invest.* (1997) 100, 2417–2423) For instance, iNOS is thought to be essential in fighting *Mycobacterium tuberculosis.* (Mac-Micking, J. D. et al., *Proc. Natl. Acad. Sci. USA* (1997) 94, 5243–5248) However, iNOS is also involved in the often destructive inflammation response to infection or injury. (D. Nathan, *J. Clin. Invest.* (1997) 100, 2417-2423)

Despite the intense interest in nitric oxide synthases in the biological and medical community, aspects of the catalytic mechanism of these enzymes remain poorly understood. In particular, the function of the $H_4$B cofactor has not been adequately explained.

Currently, two general methods are used for imaging NOS distribution. (Feelisch, M.; Stamler, J. S. Eds., *Methods in Nitric Oxide Research* (John Wiley and Sons, Inc., New York, 1996)) First, NADPH, arginine, NO, citrulline, nitrates, nitrates and other reactants and products of NOS can be detected chemically, usually through chemiluminescence or a stain (Kikuchi, K. et al., *Analytical Chemistry* (1993) 65, 1794–1799; Kojima, H. et al., *Anal. Chem.* (1998) 70, 2446–2453; Kishimoto, J. et al., *Eur. J. Neuroscience* (1993) 5, 1684–1694). Because these small molecules diffuse rapidly, this limits the spatial resolution of this technique. In addition, the staining techniques kill the sample. The chemiluminescence resulting from the reaction of NO with ozone can also be used to quantify NO production, but again gives limited spatial information. The second technique used is immunohistochemistry (Maines, M. D Ed., *Nitric Oxide Synthase: Characterization and Functional Analysis* (Academic Press, San Diego, Calif., 1996); Kobzik, L., Schmidt, H. H. H. W. in *Methods in nitric oxide synthase* M. Feelish, J. S. Stamler, Eds. (John Wiley and Sons, New York, 1996) pp. 229–236). Briefly, an antibody is raised against NOS. The antibody binds to NOS, and the antibody is then detected through staining or fluorescence. This gives better spatial resolution, but again the staining process destroys the sample.

The disadvantages of many of the prior known probes utilized to study biomolecules are their requirements for chemical or biological modification of the biomolecules for characterization. Furthermore, because Ru-substrates interact with their targets reversibly, they differ from current probes of heme proteins that rely on covalent modification and chemical analysis (Tschirret-Guth, R. A., et al. (1999) *J. Am. Chem. Soc.* 121, 4731–4737; Tschirret-Guth, R. A., et al. (1998) *J. Am. Chem. Soc.* 120, 7404–7410). The shortcomings of many presently available molecular probes for detecting biomolecules demonstrate the need for new agents that can detect and characterize biomolecules without the need for covalent or mutational modification of the protein of interest. The present invention satisfies this and other needs.

SUMMARY OF INVENTION

Accordingly, the present invention provides novel sensitizer-linked substrate molecules having a sensitizer attached via a linker to a substrate molecule for use in detecting and characterizing target biomolecules. The present invention also provides novel methods for detecting and characterizing target biomolecules using the sensitizer-linked substrate molecules. The sensitizer-linked substrate molecules are highly specific and have high affinity for their target biomolecules. Moreover, the detection limits are highly sensitive.

The sensitizer-linked substrate molecules of the invention are the first examples of a substrate attached by a linker to a sensitizer element. The linker is designed to have sufficient length to allow the substrate to bind to the target biomolecule so that upon binding, the sensitizer is located within the biomolecule or near the biomolecule surface. Because of the linker group present in sensitizer-linked substrate molecules, properties such as hydrophobicity and cellular uptake, may be readily modified to form improved sensitizer-linked substrate molecules for use as diagnostic and therapeutic agents.

The invention also provides high-throughput assays for identification of modulators of target biomolecule activity. These assays involve incubating a test mixture that contains a target biomolecule, a sensitizer-linked substrate molecule, and a candidate activity modulator, under conditions suitable for biomolecule activity. The presence or absence of a detectable signal, e.g., a signal by the free sensitizer-linked substrate molecule and/or a signal resulting from a combination of the biomolecule and sensitizer-linked substrate is detected. The presence or absence of the detectable signal indicates whether the sensitizer-linked substrate and the biomolecule remain in close proximity to each other, indicating the modulation of activity by the candidate activity modulator.

Kits, compositions and integrated systems for performing the assays are also provided.

BRIEF DESCRIPTION OF THE FIGURES

FIG. 4 shows a table of dissociation constants, $Ru^{2+*}$ excited-state lifetimes, and Ru—Fe distances, as described in Example I, infra.

FIG. 14. Ru-compounds (1) and (3) for the study of P450 catalysis in an open conformation. While (1) competes with camphor for the P450 active site, (2) is able to share the pocket with camphor. 2-adamantylacetamide (2) is analagous to compound (1), without the Ru-tether; (2) induces a full low to high spin conversion at the heme.

FIG. 18. A table of substrate Analog Induced Changes of the CO-Stretching Mode in P450

Reversible electron-transfer processes return Ru and P450 to their resting states within 100 ms of the initial laser pulse.

Figure 32:
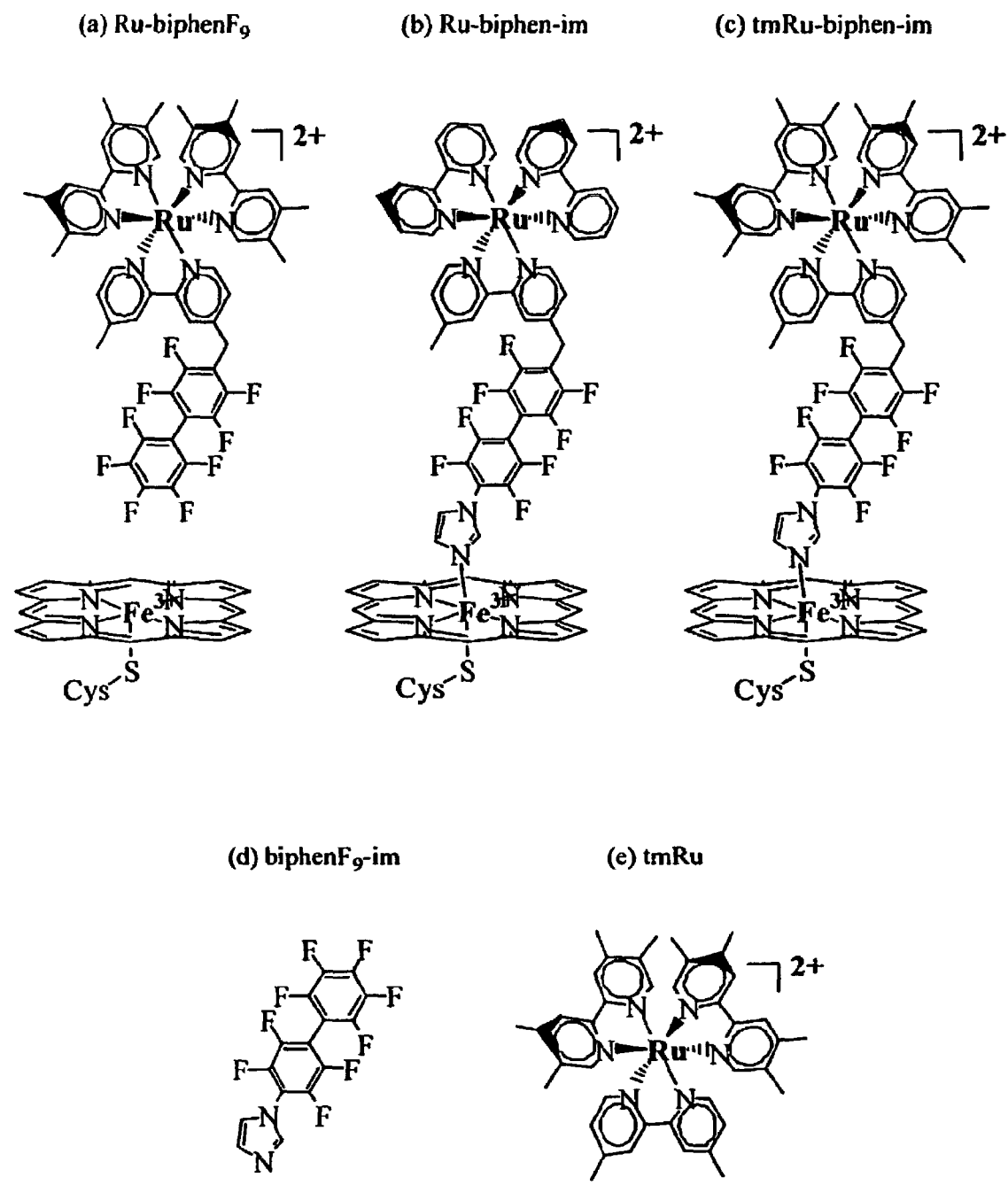

FIG. 32 displays the structures for the compounds, as described in Example V, infra. Top: Three conjugated sensitizer-linked probes in their presumed orientation relative to cytochrome P450$_{cam}$ (thiolate-ligated heme). Bottom: Model compounds (d) and (e) for electrochemical studies and control experiments involving transient absorption spectroscopy.

FIG. 33 depicts the table of $K_D$, $k_{ET}$, $k_{en}$, $R_0$, and Ru—Fe distances of Ru-probes (a–c)*, as described in Example V, infra.

FIG. 34 depict the spectra, as described in Example V, infra. Top: Q-bands of P450 bound to (a) (substrate-free spectrum), (b), and (c). The spectral overlap of the $Ru^{2+*}$ emission with the Q-band absorption gives the Förster distance. Below: Emission spectra of [Ru(bpy)$_3$]$^{2+*}$, Ru-Im (b), and tmRu-Im (a, c). Integration of the area under each spectrum and comparison to a standard [Ru(bpy)$_3$]$^{2+}$ solution gave the quantum yields as described in Appendix D. Q.Y. (Ru(bpy)$_3^{2+}$)=0.042, Q.Y. (Ru-Im, (b))=0.025, Q.Y. (tmRu-Im, (a, c))=0.0094.

Figure 35:
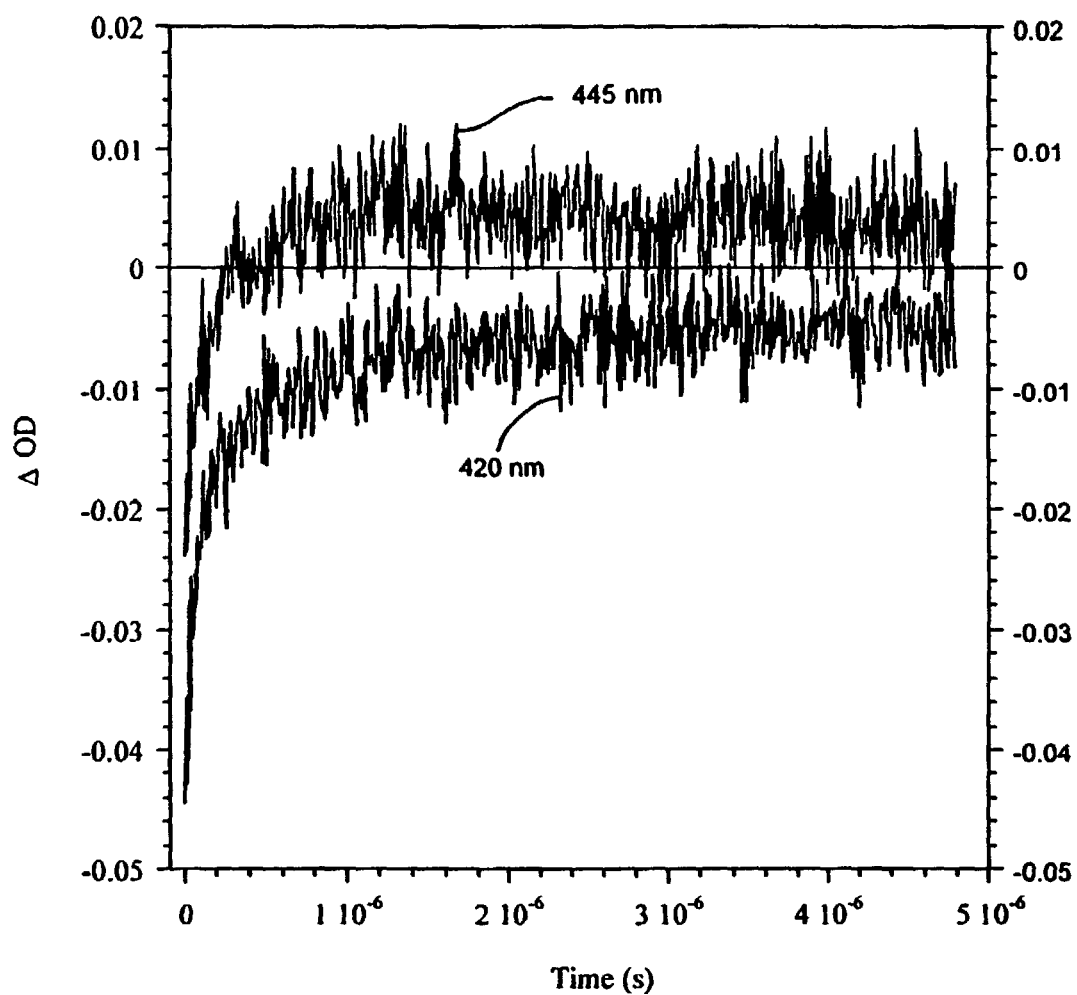

FIG. 35 illustrates single-wavelength transient absorption, as described in Example V, infra: Δ-absorbance versus time plots for the reaction of [Ru-biphenF$_8$-Im]$^+$ with P450. Changes in the Soret region (bleach of $Fe^{3+}$-Im at 420 nm and increase of $Fe^{2+}$-Im at 445 nm) were observed after laser excitation of a 5.3 µM P450, 5.3 µM Ru sample.

Figure 36:
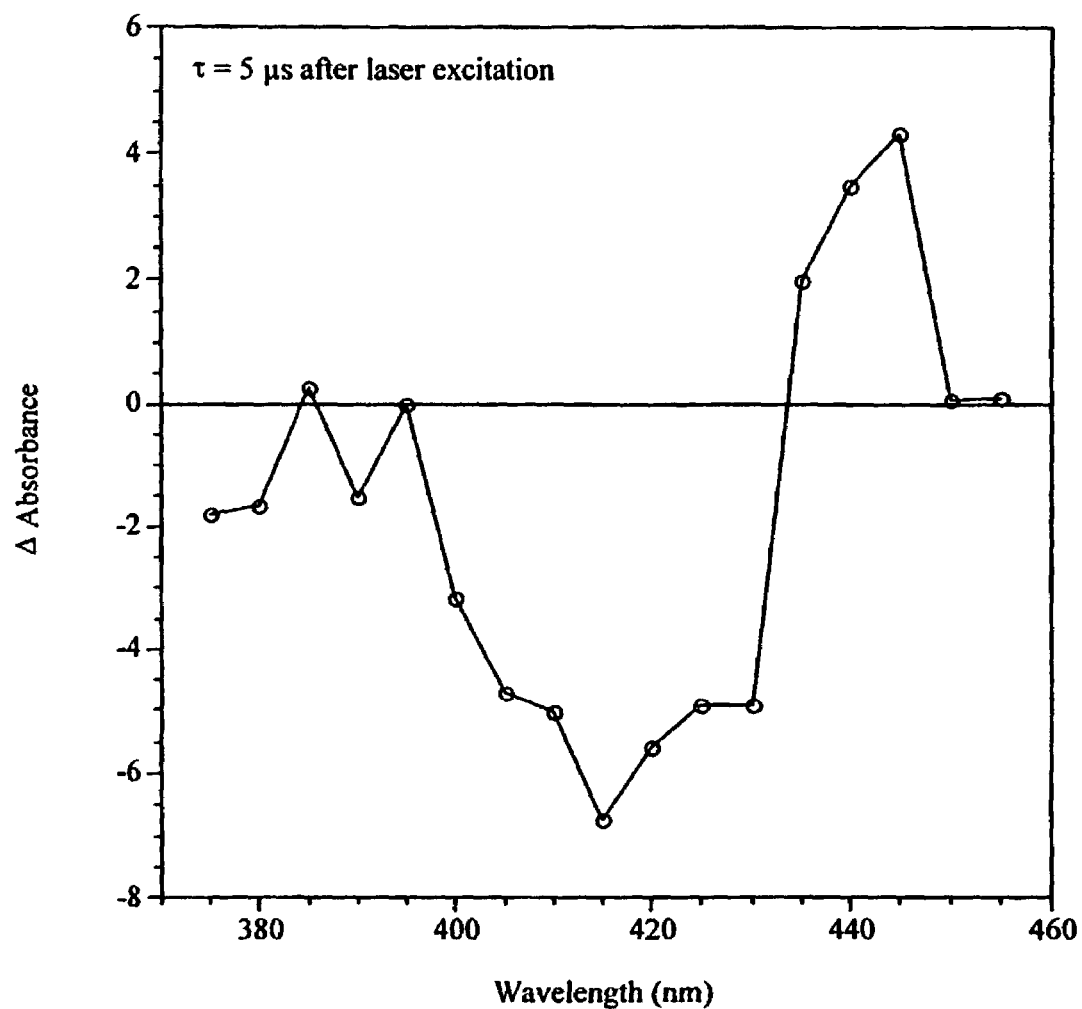

FIG. 36 depicts transient absorption of the P450:Ru-biphenF$_8$-im complex, collected 5 µs after laser excitation, as described in Example V, infra. A Absorption intensities were obtained by fitting transient absorption kinetics for several different wavelengths in the Soret region. At 5 µs, all of the $Ru^{2+*}$ has been consumed, and the observed difference spectrum is a sum of the absorption changes caused by (P450) $Fe^{2+}$-Im and Ru$^{3+}$.

Figure 37:
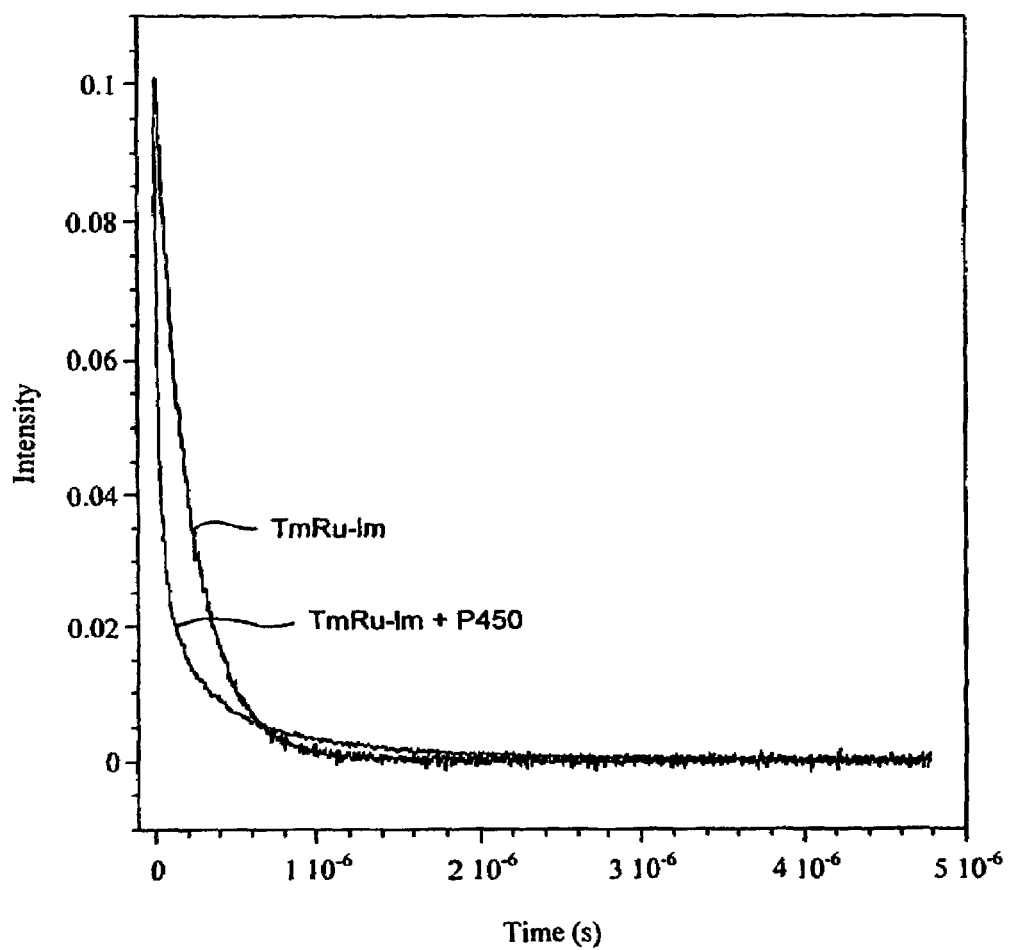

FIG. 37 depcits luminescence decay profile (620 nm) for tmRu-biphenF$_8$-im$^{2+*}$ both free in solution (monophasic) and bound to P450 (biphasic), as described in Example V, infra.

Figure 38:
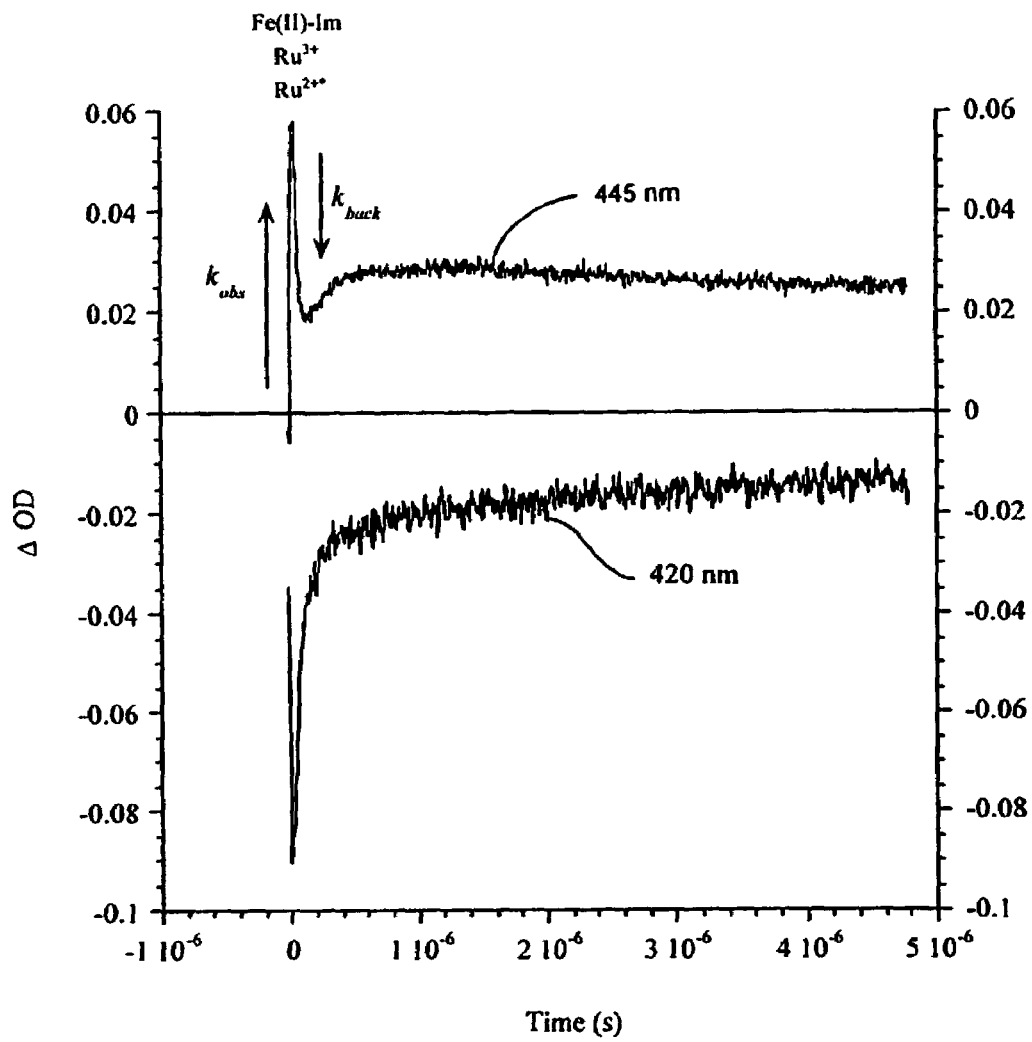

FIG. 38 illustrates transient absorption kinetics profile of P450 bound to (c), collected at 445 nm (top) and 420 nm (bottom). P450]=[Ru]=11 µM, laser power=3.3 mJ/pulse, as described in Example V, infra.

FIG. 39 depicts the absorption spectra, as described in Example V, infra. Top: Transient absorption of the excited state of Ru-biphenF$_8$-im, collected 10 ns after laser excitation ([Ru]=8.9 µM, laser power=3.3 mJ/pulse). Bottom: Transient absorption of the P450:Ru-biphenF$_8$-im complex, collected 30 ns after laser excitation ([P450]=[Ru]=8.9 µM, laser power=3.3 mJ/pulse). A Absorption intensities were obtained by fitting transient absorption kinetics for several different wavelengths in the Soret region. At 30 ns, the observed difference spectrum is a sum of the absorption changes caused by $Ru^{2+*}$ (shown above, $\Delta\epsilon Ru^{2+*}$–$Ru^{2+}$=–2400 M$^{-1}$cm$^{-1}$ at 445 nm, –1500 M$^{-1}$cm$^{-1}$ at 420 nm), Ru$^{3+}$ ($\Delta\epsilon$ Ru$^{3+}$–Ru$^{2+}$=–9000 M$^{-1}$cm$^{-1}$ at 445 nm, –6000 M$^{-1}$cm$^{-1}$ at 420 nm), and P450 $Fe^{2+}$-Im ($\Delta\epsilon$ $Fe^{2+}$–$Fe^{3+}$=81,000 M$^{-1}$cm$^{-1}$ at 445 nm, –82,000 M$^{-1}$cm$^{-1}$ at 420 nm, calculated from the spectra shown in FIG. 37).

Figure 40:
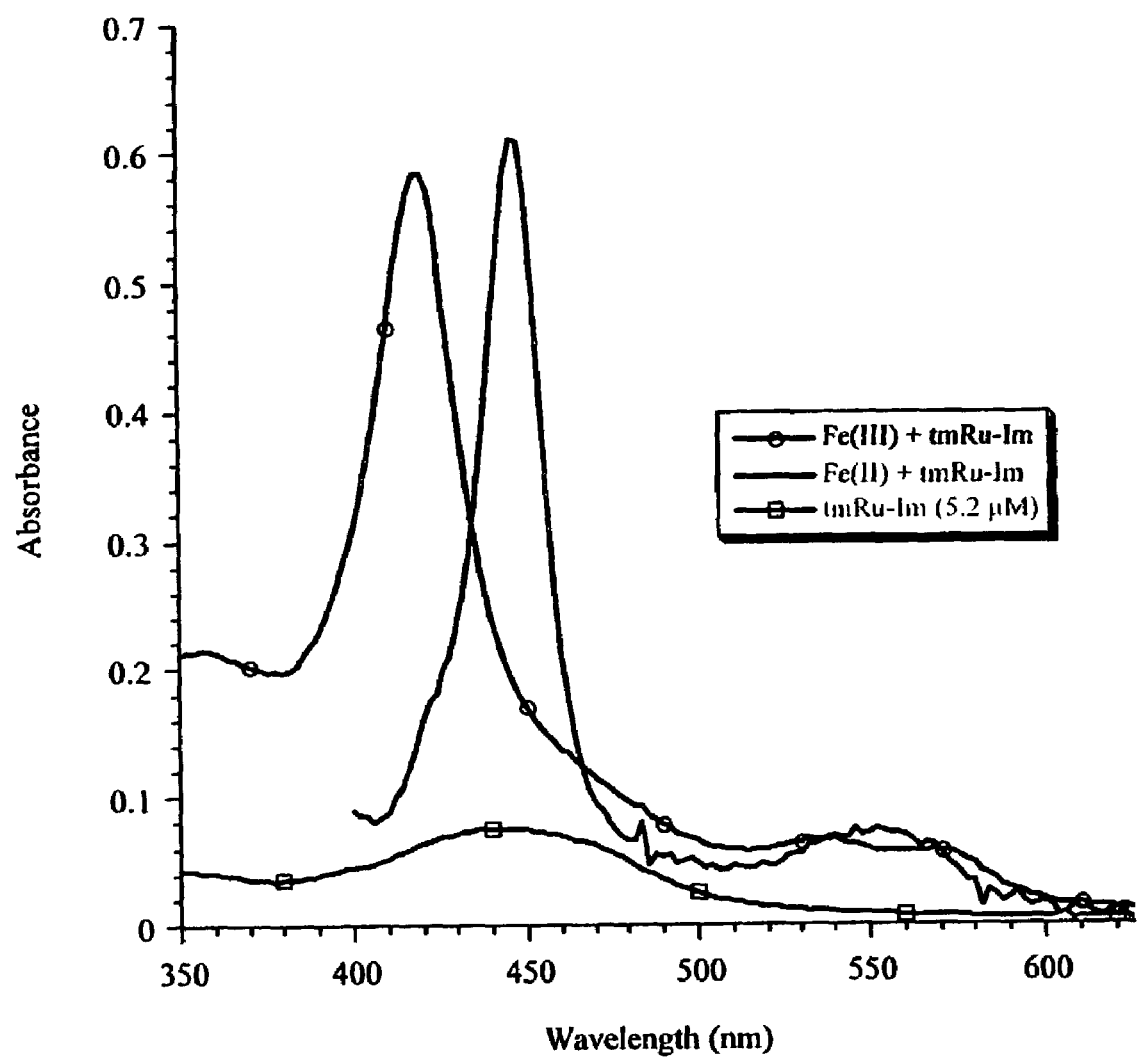

FIG. 40 shows the UV-vis absorption spectra of tmRu-biphenF$_8$-Im (c) alone and complexed with both ferric and ferrous P450; all species are 5.2 µM, as described in Example V, infra. The $Fe^{2+}$-Im spectrum is not shown below 400 nm, because dithionite dominates the absorbance in this region. Extinction coefficients at the absorbance maxima of ferric ($\epsilon_{420}$=100,000 M$^{-1}$cm$^{-1}$) and ferrous ($\epsilon_{445}$=103,000

$M^{-1}cm^{-1}$) are quite similar. tmRu-biphenF$_8$-Im has an absorbance maximum at 444 nm ($\epsilon_{444}$=14,500 $M^{-1}cm^{-1}$). In the ferrous state, the P450 Q-bands coalesce and gain intensity (ferric, $\epsilon_{540}$=11,000 $M^{-1}cm^{-1}$, $\epsilon_{568}$=10,000 $M^{-1}cm^{-1}$; ferrous, $\epsilon_{546}$=12,700 $M^{-1}cm^{-1}$), as is typical for P450:imidazole complexes.

Figure 41:
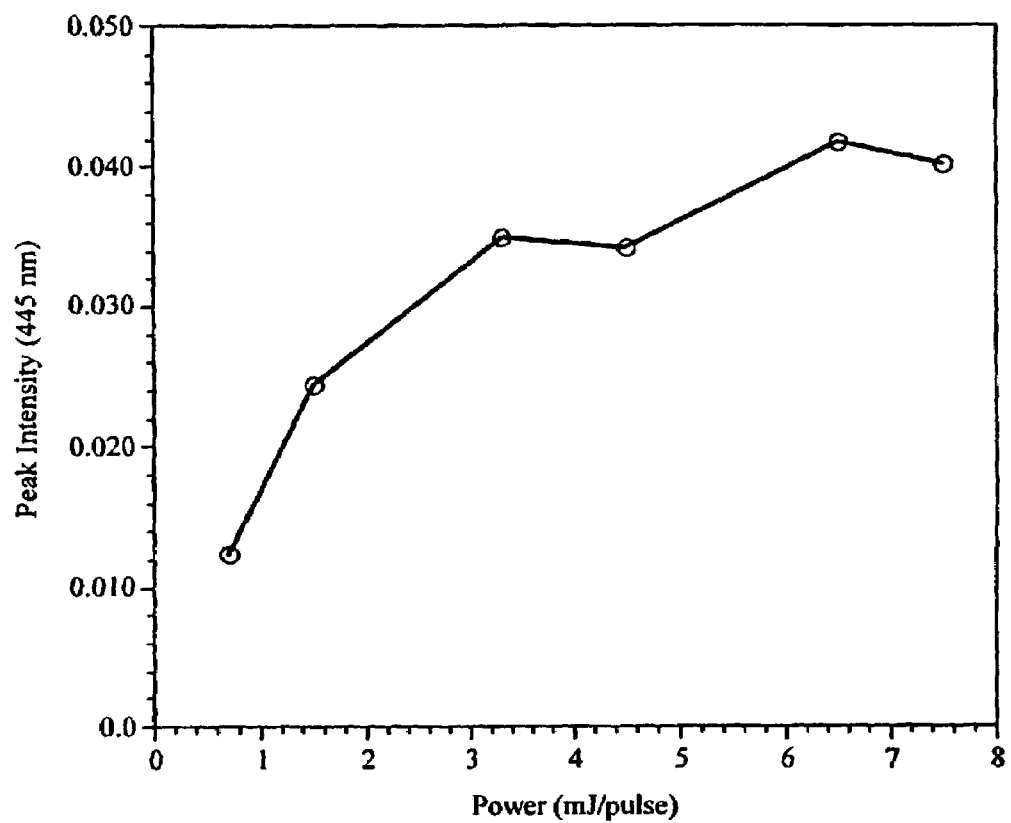

FIG. 41 depicts the power dependence of the ΔOD at 445 nm ([P450]=[tmRu-biphenF$_8$-Im]=10 µM). Saturation occurs ~3.3 mJ/pulse, showing that nearly 100% of the Ru has been excited.

Figure 42:
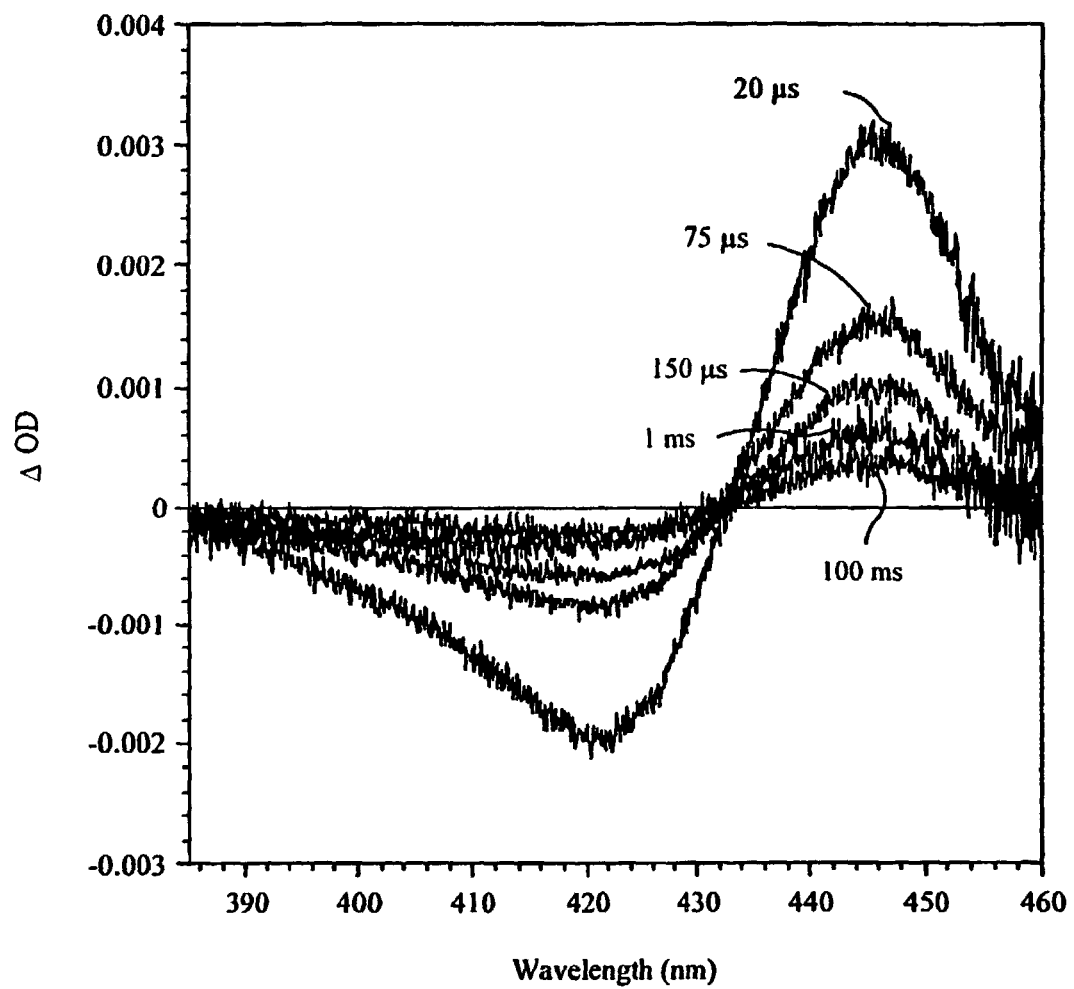

FIG. 42 displays the diode array spectra of direct photo-induced reduction of the (P450) Fe$^{3+}$-im-biphenF$_8$-Rutm complex at various time intervals after laser excitation, as described in Example V, infra. The reduced enzyme returns to the ferric resting state by three different channels, with some of the ET products persisting for up to a second.

Figure 43:
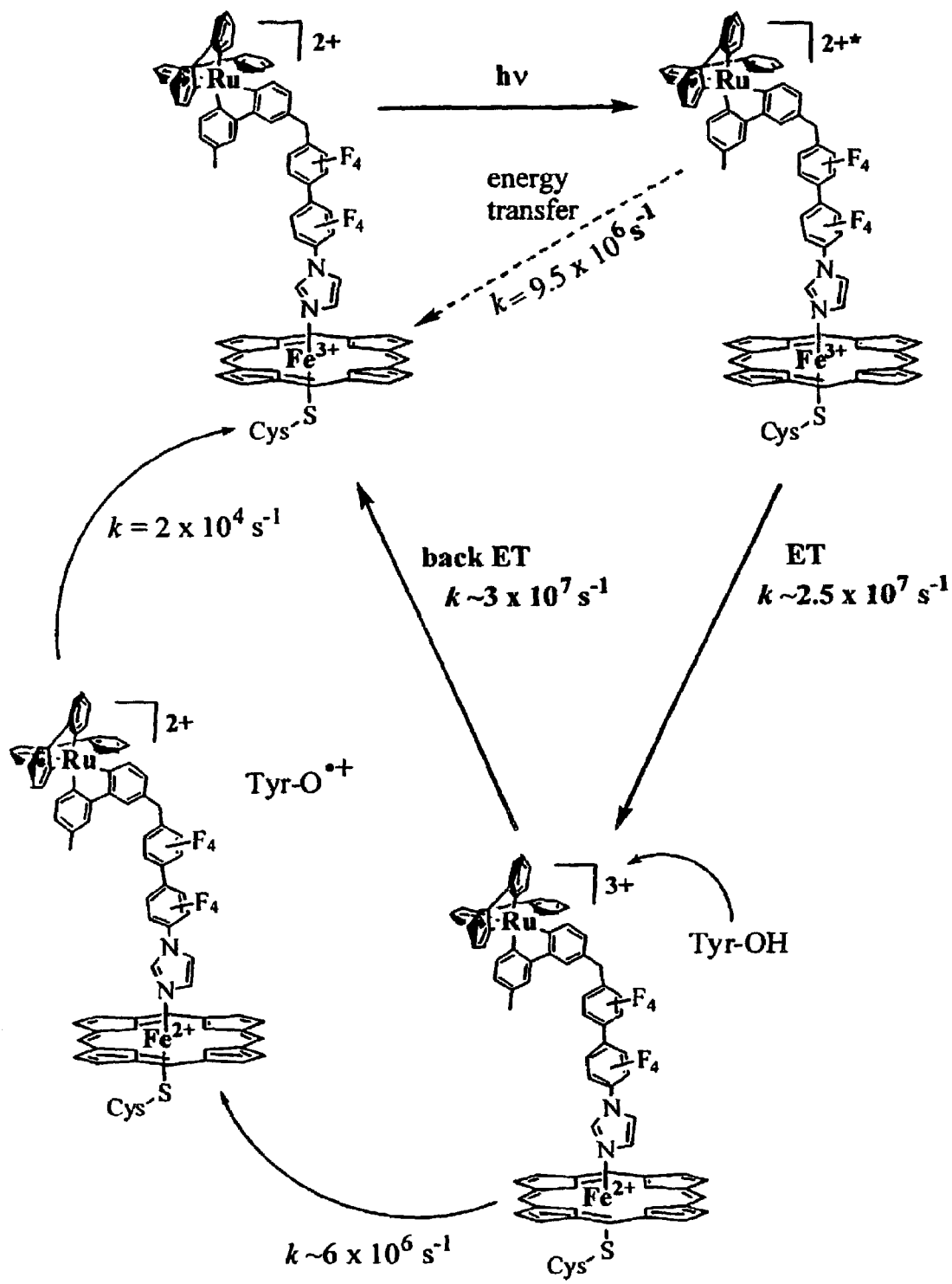

FIG. 43 illustrates the overall electron-transfer scheme for photoreduction of the P450:[Ru(tmbpy)$_2$(bpy-biphenF$_9$-im)] Cl$_2$ complex, as described in Example V, infra. Rates of energy transfer and electron transfer are based on the calculated yields of the reduced (Fe$^{2+}$-im) enzyme (see text for details). For this complex, the dominant decay channel for Ru$^{2+*}$ is ET, presumably due to the fully conjugated path to the heme, and the extra driving force for reduction provided by the tetramethylated bipyridyl ligands. Highly exergonic back electron transfer occurs rapidly from Fe$^{2+}$-im to Ru$^{3+}$. Competing with this process is believed to be oxidation of Tyr 29 which sits in close proximity (~3 Å) to the Ru moiety, and allows the reduced protein to persist for tens of microseconds. A third back ET pathway (not shown) must involve scavenging of the tyrosyl radical, either by oxidation of exogenous Ru$^{2+}$ or other reductants in solution. This bimolecular process allows a small fraction (~5%) of the reduced, imidazole-bound protein to persist for 1 second in solution.

Figure 44:
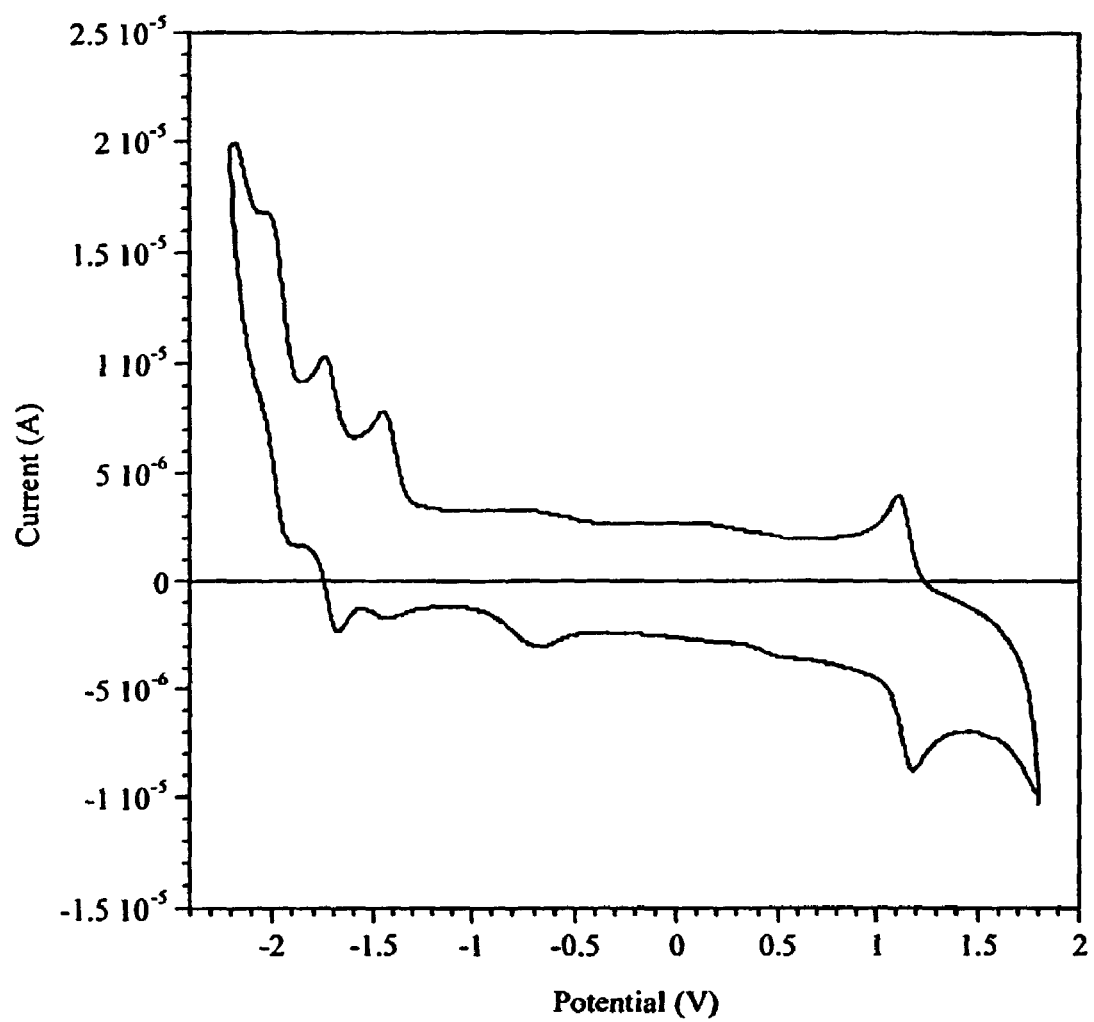

FIG. 44 shows the cyclic voltammogram on an edge-plane graphite electrode of tmRu (e) in acetonitrile at a scan rate of 100 mV s$^{-1}$ at 298 K, as described in Example V, infra.

Figure 45:
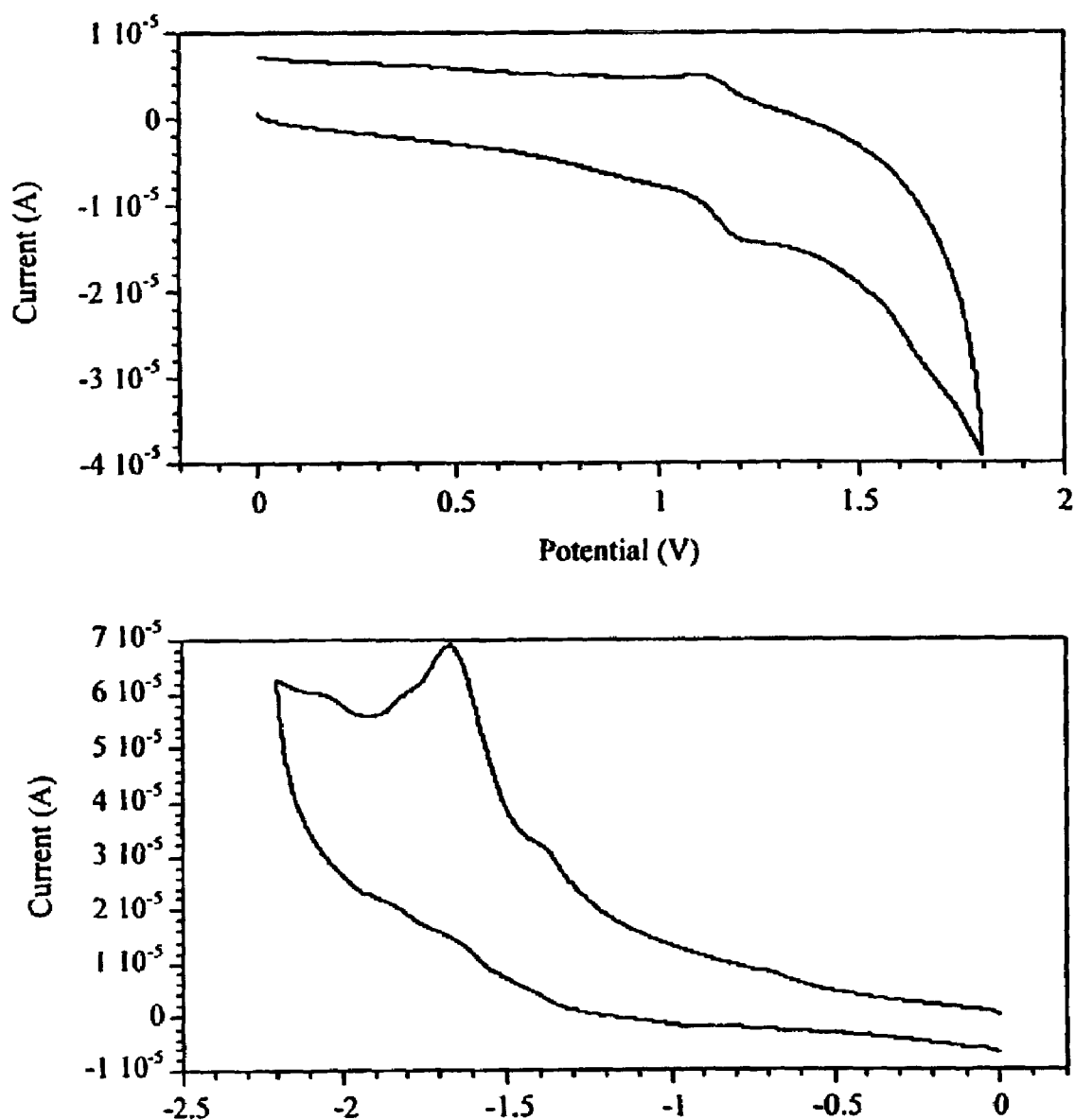

FIG. 45 illustrates the cyclic voltammogram on an edge-plane graphite electrode of tmRu-biphenF$_8$-im in acetonitrile at a scan rate of 100 mV s$^{-1}$ at 298 K, as described in Example V, infra.

Figure 46:
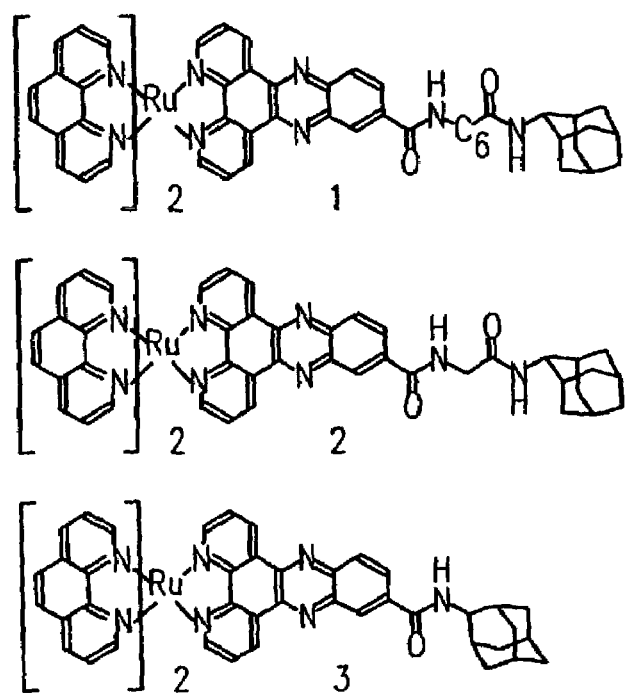

FIG. 46 depicts the compounds as described in Example VI, infra.

Figure 47:
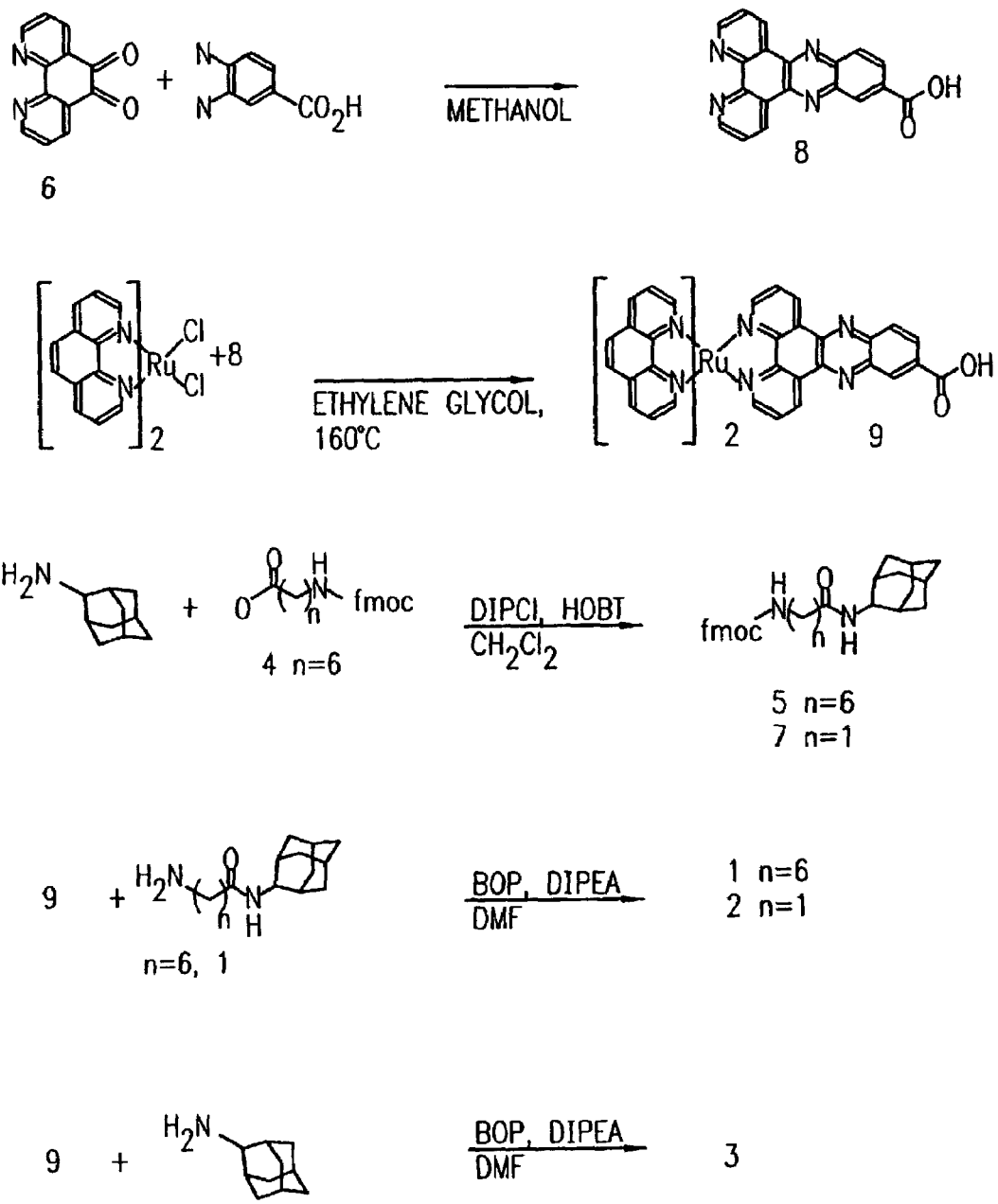

FIG. 47 shows the synthetic scheme of compound 3, as described in Example VI, infra.

Figure 48:
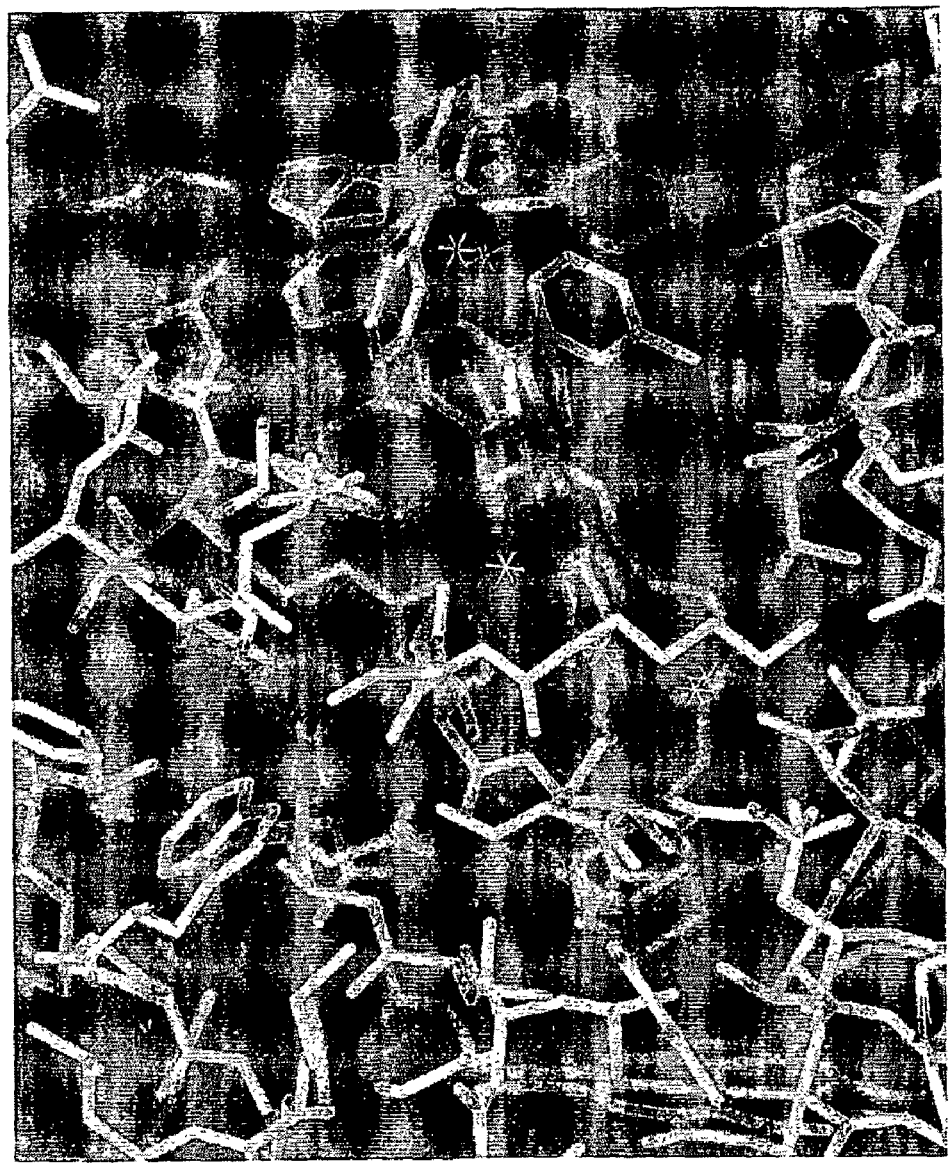

FIG. 48 illustrates compound 3 docked in the open conformation of P450, as described in Example VI, infra. The original Ru$^{II}$(bpy)$_3$ complex is shown for reference.

Figure 49:
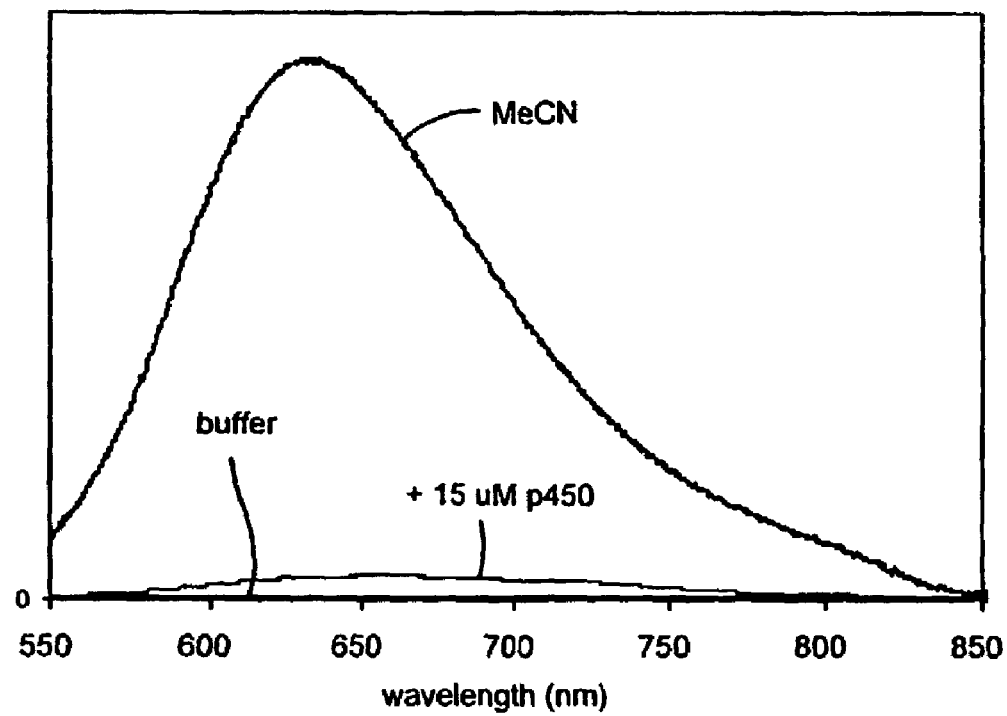

FIG. 49 shows the luminescence of 3 in 10 µM 3 in buffer, in buffer with P450 and in acetonitrile, as described in Example VI, infra.

Figure 50:
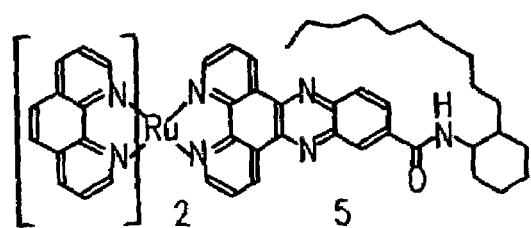

FIG. 50 depicts how the alkyl chain will fold back ideally, filling the channel and protecting the dppz from water, as described in Example VI, infra.

FIG. 51 illustrates the fluorophore classes A (7-amino-40methyl-6-sulfocoumarin-3-acetamide) and B (7-methoxy-coumarin-3acetamide), as described in Example VII, infra.

FIG. 52 depicts luminescent probes, as described in Example VII, infra.

Figure 53:
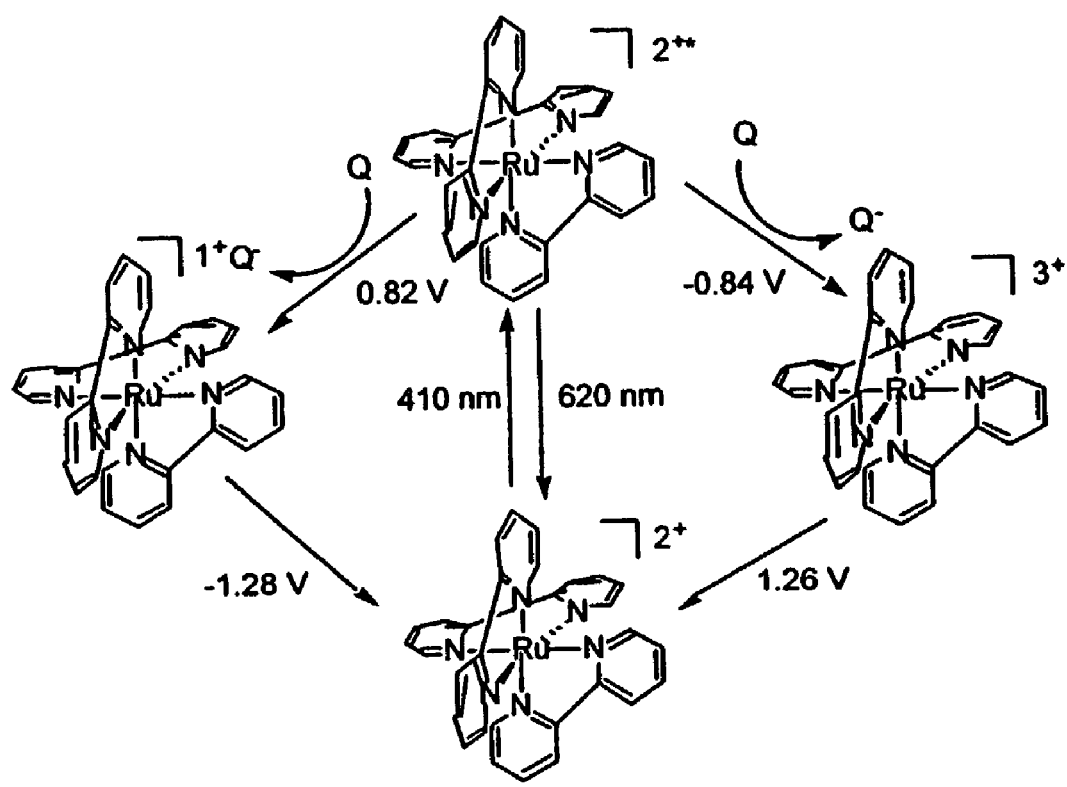

FIG. 53 shows the excited state processes of Ru$^{II}$(bpy)$_3$, as described in Example VII, infra.

FIG. 54 illustrates the luminescent probe classes C and D, as described in Example VIII, infra.

FIG. 55 depicts the series of molecules synthesized by Yonemoto et al. (Yonemoto, E. H. et al., *J. Am. Chem. Soc.* (1994) 116, 4786–4795), as described in Example VIII, infra.

FIG. 56 depicts the synthesis of the class D probes, as described in Example VIII, infra.

DETAILED DESCRIPTION OF THE INVENTION

The subject invention is a modular approach to generating the sensitizer-linked substrate molecules. These molecules are useful, e.g., in methods for detection of target biomolecules. These detection methods in which sensitizer-linked substrates assess ligand specificity and enzyme structure are (1) superior to existing enzyme- and antibody-based assays; and (2) are amenable to combinatorial chemistry. In addition, enantiospecific interactions may be exploited in the design of enzyme-metallosubstrate conjugates using the invention.

Definitions

As used in this application, the following words or phrases have the meanings specified.

As used herein a "target biomolecule" is any protein that can be targeted with a high affinity molecule (i.e. binding element or substrate) specific for that protein. Such biomolecules include, but are not limited to, enzymes such as oxidases, reductases, synthases, synthetases, kinases, phosphatases, G proteins, membrane proteins, receptor proteins, and ion channels. The biomolecule may or may not contain a chromophore.

As used herein a "sensitizer-linked substrate" molecule is a compound having a substrate (i.e. binding element) attached by a linker (i.e. tether) to a sensitizer element.

As used herein a "sensitizer" is an element (i.e. moiety, group, label, or tag) that can emit energy, e.g., as luminescence through photochemical, chemical, and/or electrochemical processes. Photoluminescence can be defined as a process whereby a material is induced to luminesce when it absorbs electromagnetic radiation. Fluorescence and phosphorescence are forms of photoluminescence.

As used herein a "substrate" is a binding element, compound, or molecule that has a high affinity and/or high specificity of binding for the target biomolecule.

As used herein a "linker" is a molecule of a length sufficient to allow the substrate to bind to the active site of the biomolecule so that upon binding the sensitizer is located within the protein or near the protein surface.

As used herein a "modulator" is any agent that can alter the activity of a target biomolecule, the agent can be a small organic molecule, protein or protein fragment, nucleic acid.

In order that the invention herein described may be more fully understood, the following descriptions are set forth.

Compositions of the Invention

The present invention is directed to the detection and characterization of target biomolecules by novel sensitizer-linked substrate molecules. The invention provides for novel sensitizer-linked substrate molecules having a sensitizer, a linker, and a substrate for use in detecting and characterizing target biomolecules. The sensitizer-linked substrate molecules are highly specific, selective, and have high affinity for its target biomolecule and the signal emitted by these molecules allows detection at low concentrations.

A preferred embodiment of a target biomolecule is a protein that possesses natural or unnatural cofactors that would quench sensitizers or modifies the signal of the molecule of the invention which binds to its target.

Such target biomolecules having a metal chromophore are termed metalloproteins. Such metalloproteins include, but are not limited to, Cytochrome P450, Superoxide Dismutase (SOD), Nitric Oxide Synthase (NOS), heme oxygenase, prostaglandin H synthase, soluble guanydylate cyclase, prostacyclin synthase, and amine oxidases.

Examples of Cytochrome P450 include, but are not limited to, 1A1, 1A2, 2A6, 2C8, 2C9, 2D6, 2E1, 3A4, 3A5, and 4A11.

Examples of NOS include, but are not limited to, NOS isozymes are iNOS (inducible), nNOS (neuronal), and eNOS (endothelial), but the method of the invention could also be extended to the discovery of new NOS isozymes (Feelisch, M.; Stamler, J. S. Eds., *Methods in Nitric Oxide Research* (John Wiley and Sons, Inc., New York, 1996)).

Target biomolecules include those having a flavin chromophore such as FMN or FADH. Examples of flavoproteins include, but are not limited to P450 reductase, D-amino-acid oxidase and flavocytochrome b2.

Types of substrates that have a high affinity for target biomolecules include, but are not limited to, molecules that bind to the active site, recognition, allosteric, or cofactor site of the biomolecule, such that the substrate molecule can bind in the selected site and occupy the cavity or space, or that bind to the active site and undergo transformation of the substrate, the biomolecule, and/or both the substrate and biomolecule.

Substrates are any agents that can bind to the target biomolecule. Substrates can include activators or inhibitors of the target biomolecule. Substrates of the invention include, but are not limited to, small organic molecules, protein fragments, nucleic acid molecules, and/or CDR of antibodies.

Substrates of Cytochrome P450 include, but are not limited to, caffeine, testosterone, progesterone, ethylmorphine, aminopyrine, benzphetamine, 7-ethoxycoumarin, warfarin, ethylbenzene, adamantane, carbon monoxide, metyrapone, allylisopropylacetamide, and imidazole and its derivatives.

Substrates of NOS include, but are not limited to, $N^G$-monomethyl, dimethyl, nitro, and amino arginines, $N^G$-nitro-L-arginine methyl ester, $N^\delta$-(iminoethyl-L-ornithine, L-thiocitrulline, S-alkyl-L-thiocitrulines, bisthioureas, 7-nitroindazoles, aminogaunidine, 2-amino-5,6-dihydro-6-methyl-4H-1,3-thiazine, 2-iminoazahetercylces, N-phenylisothioureas, N-phenylamidines, nitroaromatic amino acids and modifications of these compounds. (Collins, J. L. et al., *J. Med. Chem.* (1998) 41, 2858–2871; Hibbs, J. B. et al. *J. Immunol.* (1987) 138, 550–565; Lamber, L. E. et al., *Life Sci.* (1991) 48, 69–75; Rees, D. D. et al. *Br. J. Pharmacol.* (1990) 101, 746–752; Gross, S. S. et al., *Biochem. Biophys. Res. Commun.* (1990) 270, 96–203; Furfine, E. S. et al., *Biochemistry* (1993) 32, 8512–8517; Narayanan, K. et al., *J. Med. Chem.* (1994) 37, 885–887; Narayanan, K. et al., *J. Biol. Chem.* (1995) 270, 11103–11110; Furfine, E. S. et al., *J. Biol. Chem.* (1994) 269, 26677–26683; Garvey, E. P. et al., *J. Biol. Chem.*, (1994) 269, 26669–26676; Wolff, D. J. et al., *Arch. Biochem. Biophys.* (1994) 311, 300–306; Hasan, K. J. et al., *Pharmacol.* (1993) 249, 101–106; Moore, W. M. et al., *J. Med. Chem.* (1996) 39, 669–672; Moore, W. M. et al., *Bioorg. Med. Chem.* (1996) 4, 1559–1564; Shearer, B. G. et al., *J. Med. Chem.*, (1997) 40, 1901–1905; Garvey, E. P. et al., *J. Biol. Chem.* (1997) 272, 4959–4963. Cowart, M. et al., *J. Med. Chem.* (1998) 41,2636–2642).

Types of linkers that can be used to connect the sensitizer to the substrate include substituted or unsubstituted, cyclic or acyclic alkyl, alkene, alkynyl, alkoxy chains, or aryl groups, extended fused aromatic ring systems (e.g. naphthalene, anthracene), peptides, ethers, thioethers, esters, amines, amides and oligomers thereof.

The length of the linker is designed to be sufficient to allow the substrate to interact favorably with the target biomolecule and that upon binding, the sensitizer is located within the biomolecule or near the biomolecule surface. The distance between the sensitizer and the biomolecule can be varied depending on the site to which the sensitizer-linked substrate molecule binds, e.g. active site, recognition, allosteric, or cofactor site of the biomolecule. For example, the distance can be less than or equal to 100 Å.

A linker can be tailor made to enhance properties of the sensitizer-linked substrate molecules such as hydrophobicity and cellular uptake, and may be readily modified to form improved sensitizer-linked substrate molecules for use as diagnostic and therapeutic agents. Where electron transfer is not a factor, any linkage of sufficient length, hydrophobicity, and charge will be useful in the methods of the invention. In an embodiment of the invention, where the linker is a methylene chain, the length of the linker between the sensitizer and the substrate can be varied for $(CH_2)_n$ where n is 1 to 13.

Types of sensitizers that can emit energy as luminescence include both organic and inorganic photosensitizers (Erkkila, K. E. et al., *Chem Rev.* 1999, 99, 2777–2795) and fluorophores.

Photosensitizers for use in the invention include, but are not limited to, $[Ru(bpy)_3]^{2+}$, $[Ru(phen)_2dppz]^2$, $[Ru(bpy)CN_4]^{2-}$, $[Os(tpy)_2]^{2+}$, where tpy is 2,2':6',2"-terpyridine, $[Os(ttpy)_2]^{2+}$, where ttpy is 4'-(p-tolyl)-2,2':6',2"-terpyridine, $[Os(tptpy)_2]^{2+}$, where tptpy is 4,4',4"-triphenyl-2,2':6', 2"-terpyridine(M. Beley, J.-P. Collin, J.-P. Sauvage, H. Sugihara, F. Heisel, A. Miehe, J. Chem. Soc. Dalt. 1991, 3157–3159.), as well as $[Os(phen)_3]^{2+}$ and $[Os(phen)_2(Me_2PhP)_2]^{2-}$ (E. M. Kober, et al., J. Am. Chem. Soc., 1980, 102, 7383–7385; E. M. Kober et al., Inorg. Chem. 1985, 24, 2755.), or where applicable, a geometric or optical isomer or racemic mixture thereof.

Sensitizers can include luminescent metal complexes. Luminescent metal complexes include, but are not limited to, homo- and heteroleptic ruthenium terpyridine, bipyridine, pyridine, imidazole, cyano and carbonyl complexes, as well as complexes of other transition metals, including but are not limited to osmium, platinum, iridium, rhenium, rhodium, molybdenum, tungsten and copper[Roundhill, D. M. *Photochemistry and Photophysics of Metal Complexes* (Plenum Press, New York, 1994; Horvath, O. and Stevenson, K. L. *Charge Transfer Photochemistry of Coordination Compounds* (VCH Publishers, Inc., New York, 1992).

Luminescence compounds include, but are not limited to, methyl viologens, quinones, N,N-dialkylanilines, N,N-dialkyl-p-methoxyanilines and triarylamines. [Horvath, O. and Stevenson, K. L. *Charge Transfer Photochemistry of Coordination Compounds* (VCH Publishers, Inc., New York, 1992].

Types of organic fluorophores include, but are not limited to, coumarins, Texas red, 1- and 2-aminonaphthalenes, p,p'-diaminostilbenes, pyrenes, anthracenes, fluoresceins, and rhodamnues.

Types of sensitizer-linked substrate molecules of the invention include, but are not limited to, $[Ru—C_{13}-EB]^{2+}$, $[Ru—C_{12}-EB]^{2+}$, $[Ru—C_{11}-EB]^{2+}$, $[Ru—C_{10}-EB]^{2+}$, $[Ru—C_9-EB]^{2+}$, $[Ru—C_7-EB]^{2+}$, $[Ru—C_{11}-Ad]^{2+}$, $[Ru—C_9-$ Ad]$^{2+}$, [Ru—C$_{13}$-Im]$^{2+}$, [Ru—C$_{13}$-Im]$^{2+}$, [Ru-dppa-C$_6$-Ad],. [Ru-dppa-gly-Ad], and [Ru-dppa-Ad]. Where, Ru is [Ru(bpy)$_3$]$^{2+}$ complex, Ru-dppa is [Ru(phen)$_2$dppa]$^{2+}$ complex, the C$_n$ is a methylene chain of n carbon atoms long, EB is ethylbenzene, Ad is adamantane, and Im is imidazole.

Methods of the Invention

In addition, the invention provides novel methods for detecting and characterizing target biomolecules using the sensitizer-linked substrate molecules of the invention.

Characterization of biomolecules includes, but is not limited to, measurement of structural properties of the biomolecule such as the active site size, shape, and volume, aspects of substrate specificity, elucidation of the mechanism of action of the biomolecule, and interactions between biomolecules, i.e. regulation or modulation of the biomolecule, especially by other biomolecules.

The methods of detection and characterization of a biomolecule by a sensitizer-linked substrate molecules are performed by contacting a biomolecule with a sensitizer-linked substrate molecule designed to interact with said biomolecule, under suitable conditions, and measuring a detectable signal for the interaction, e.g., a signal by the free sensitizer-WO linked substrate molecule and/or a signal resulting from a combination of the biomolecule and sensitizer-linked substrate. The presence or absence of the detectable signal indicates whether the sensitizer-linked substrate and the biomolecule remain in close proximity to each other.

In one embodiment of the method of the invention, the target biomolecule is Cytochrome P450, and the sensitizer-linked substrate molecules of the invention are selected from the group comprising [Ru—C$_{13}$-EB]$^{2+}$, [Ru—C$_{12}$-EB]$^{2+}$, [Ru—C$_{11}$-EB]$^{2+}$, [Ru—C$_{10}$-EB]$^{2+}$, [Ru—C$_9$-EB]$^{2+}$, [Ru—C$_7$-EB]$^{2+}$, [Ru—C$_{11}$-Ad]$^{2+}$, [Ru—C$_9$-Ad]$^{2+}$, [Ru—C$_{13}$-Im]$^{2+}$, [Ru-dppa-C$_6$-Ad], [Ru-dppa-gly-Ad], and [Ru-dppa-Ad]. Where, Ru is [Ru(bpy)$_3$]$^{2+}$ complex, Ru-dppa is [Ru(phen)$_2$dppa]$^{2+}$ complex, the C$_n$ is a methylene chain of n carbon atoms long, EB is ethylbenzene, Ad is adamantane, and Im is imidazole.

Isolation and purification of human Cytochrome P450s is very difficult as these enzymes are generally membrane-bound. The method of the invention for detecting P450s in solution offers several advantages over traditional isolation protocols. First, where Ru sensitizers are used, due to the tight binding of Ru-linker-substrates, it is possible to work with cytochrome P450s at low concentrations where most isozymes should be soluble. Additionally, due to the sensitivity of the fluorescence technique, lower concentrations of P450 can be used to perform inhibitor binding studies or in assays to detect specific P450 isozymes. The potential for isozyme-specific binding may minimize the need for extended purification protocols in studies involving, a system such as the liver, where numerous P450 isozymes are present.

Fluorescence quenching may be used to determine biomolecule dimerization or protein-protein interactions. Alternatively, as has been shown extensively in work with blue and green fluorescent protein (GFP), fluorescence resonance energy transfer (FRET) may be employed to quantify distances between biomolecules. (A. Miyawaki, J. Llopis, R. Heim, J. M. McCaffery, J. A. Adams, M. Ikura, R. Y. Tsien, Nature 1997, 388, 882–887.) Upon excitation, the blue fluorophore transfers its energy to the green fluorophore. (R. Heim and R. Y. Tsien, Curr. Biol. 1996, 6, 178–182.) Quantifying the intensity, decay kinetics, or polarisation of the emission by the green fluorophore provides a "molecular yardstick" by which to measure the separation between fluorophores. For example, a sensitizer-linked substrate attached to biomolecule X could identify interactions with biomolecule Y, provided that Y possesses a fluorophore that is sufficiently in resonance (overlap of absorption and emission profiles) with the sensitizer-linked substrate.

In cases where the target biomolecule does not contain a suitable chromophore (e.g., heme, flavin) to interact with the sensitizer, structural characterization may be achieved by labeling the biomolecule with a commercially available fluorescent probe (i.e. dansyl probes synthesized by Molecular Probes, Eugene, Oreg.). Binding of a sensitizer-linked substrate to the labeled biomolecule is assessed by fluorescence quenching experiments as described for P450.

Methods of Screening

Also included within the scope of methods of detection of the invention are screening assays for detecting and identifying potential modulators of target biomolecules. These assays involve incubating a test mixture that contains a target biomolecule, a sensitizer-linked substrate molecule, and a candidate activity modulator, under conditions suitable for biomolecule activity. The presence or absence of a detectable signal, e.g., a signal by the free sensitizer-linked substrate molecule and/or a signal resulting from a combination of the biomolecule and sensitizer-linked substrate are detected. The presence or absence of the detectable signal indicates whether the sensitizer-linked substrate and the biomolecule remain in close proximity to each other.

In an embodiment of the methods of the invention, the target biomolecule and sensitizer-linked substrate can be complexed and placed together in a series of isolated compartments, such as those found on microtiter plates or pico-nano- or micro-liter arrays. Concentrations of the biomolecules and sensitizer linked substrate can be as low as their dissociation constant for each other (<10$^{-5}$ M). Each well can be individually assessed for changes in luminescence intensity by automated laser confocal fluorescence scanning (Fodor S., et al. Nature (1993) 364 555–556, Duggan D. J., et al (2000) Nature Genetics 21 suppl, 10–14) or by screening an entire set of wells by digital imaging (Joo H. et al., Nature (1999) 399, 670–673). Upon introduction of different candidate inhibitors for the target biomolecule to each compartment or well, changes in luminescence of the sensitizer indicates successful competition between the biomolecule and the modulator.

The methods of the invention also include high throughput screening of large chemical libraries, e.g. by automating the assay steps and providing compounds from any convenient source to assay. The assays are typically run in parallel (e.g., in microtiter formats on microtiter plates in robotic assays).

The high throughput screening methods of the invention involve providing a combinatorial library containing a large number of potential therapeutic compounds (potential modulator compounds) (Borman, S, C. & E. News, 1999, 70(10), 33–48). Such "combinatorial chemical libraries" are then screened in one or more assays, as described herein, to identify library members (particular chemical species or subclasses) that display the ability to modulate the target biomolecule activity (Borman, S., supra; Dagani, R. C. & E. News, 1999, 70(10), 51–60). The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks," such as reagents. For example, a linear combinatorial chemical library, such as a polypeptide library, is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.*, 1991, 37:487–493 and Houghton, et al., *Nature*, 1991, 354, 84–88). Other chemistries for generating chemical diversity libraries can also be used. Such chemistries include, but are not limited to, peptoids (PCT Publication No. WO 91/19735); encoded peptides (PCT Publication WO 93/20242); random bio-oligomers (PCT Publication No. WO 92/00091); benzodiazepines (U.S. Pat. No. 5,288,514); diversomers, such as hydantoins, benzodiazepines and dipeptides (Hobbs, et al., *Proc. Nat. Acad. Sci. USA*, 1993, 90, 6909–6913); vinylogous polypeptides (Hagihara, et al., *J. Amer. Chem. Soc.* 1992, 114, 6568); nonpeptidal peptidomimetics with .beta.-D-glucose scaffolding (Hirschmann, et al., *J. Amer. Chem. Soc.*, 1992, 114, 9217–9218); analogous organic syntheses of small compound libraries (Chen, et al., *J. Amer. Chem. Soc.*, 1994, 116, 2661; Armstrong, et al. *Acc. Chem. Res.*, 1996, 29, 123–131); or small organic molecule libraries (see, e.g., benzodiazepines, Baum *C&E News*, 1993, Jan. 18, page 33,); oligocarbamates (Cho, et al., *Science*, 1993, 261, 1303); and/or peptidyl phosphonates (Campbell, et al., *J. Org. Chem.* 1994, 59, 658); nucleic acid libraries (see, Seliger, H et al., *Nucleosides & Nucleotides*, 1997, 16, 703–710); peptide nucleic acid libraries (see, e.g., U.S. Pat. No. 5,539,083); antibody libraries (see, e.g., Vaughn, et al., *Nature Biotechnology*, 1996, 14(3), 309–314 and PCT/US96/10287); carbohydrate libraries (see, e.g., Liang, et al., *Science*, 1996, 274, 1520–1522 and U.S. Pat. No. 5,593,853, Nilsson, U J, et al., *Combinatorial Chemistry & High Throughput Screening*, 1999 2, 335–352; Schweizer, F; Hindsgaul, O. *Current Opinion In Chemical Biology*, 1999 3, 291–298); isoprenoids (U.S. Pat. No. 5,569,588); thiazolidinones and metathiazanones (U.S. Pat. No. 5,549,974); pyrrolidines (U.S. Pat. Nos. 5,525,735 and 5,519,134); morpholino compounds (U.S. Pat. No. 5,506,337); benzodiazepines (U.S. Pat. No. 5,288,514); and other similar art.

For high-throughput screening, the number of potential inhibitors tested are further increased by combining an expanded multiple array format with light-directed combinatorial chemical synthesis and laser confocal fluorescence scanning (Fodor S. et al, Science (1991) 251, 767–773; Fodor S., et al. Nature (1993) 364 555–556; Cho C. et al, Science (1993) 261, 1202–1305; Fodor S., et al. Nature (1993) 364 555–556; Rozsnyai L., Angew. Chem. (1992) 31, 759–761; McGall G. et al, Proc. Natl. Acad. Sci. USA (1996), 93, 13555–13560; McGall G. et al., J. Am. Chem. Soc. (1997) 119, 5081–5090). For example, light-directed combinatorial chemistry is used to generate a library of potential inhibitors adhered in a 2-dimensional microarray format on a solid glass surface.

Alternatively, robotic spotting of an inhibitor library on a surface may be used to generate the array (Cheung V. G. et al, (2000) Nature Genetics 21 suppl, 15–19). In this application, every inhibitor can contain within it a chemical moiety for bonding to the surface and an appropriately linked sensitizer element capable of responding to a chromophore(s) contained in the biomolecule to be assayed. The substrate (i.e. recognition element) directed at the biomolecule and linkage to the sensitizer can be varied combinatorially. Thus, each position on the grid can include a sensitizer-linked substrate each containing a different substrate moiety for recognizing the biomolecule A solution of the biomolecule can then be passed over the surface of the glass slide in a suitable aqueous solution. The biomolecule can selectively bind to the highest affinity inhibitors presented on the surface and signals this event by changing the luminescent properties of the sensitizer. Automated scanning laser confocal fluorescence (Fodor S. et al, Science (1991) 251, 767–773; Fodor S., et al. Nature (1993) 364 555–556; Cho C. et al, Science (1993) 261, 1202–1305; Fodor S., et al. Nature (1993) 364 555–556; Rozsnyai L., Angew. Chem. (1992) 31, 759–761; McGall G. et al, Proc. Natl. Acad. Sci. USA (1996), 93, 13555–13560; McGall G. et al., J. Am. Chem. Soc. (1997) 119, 5081–5090) can systematically test each position on the grid for changes in luminescence when the target biomolecule is present.

Other solid supports suitable for use in the methods of the invention are known to those of skill in the art. A solid support is a matrix in a substantially fixed arrangement. Types of solid supports include, but are not limited to, glass, plastics, polymers, metals, metalloids, ceramics, and/or organic compounds. Solid supports can be planar, flat, or can have substantially different conformations. For example, the sensitizer-linked substrate can be attached to particles, beads, strands, precipitates, gels, sheets, tubing, spheres, containers, capillaries, pads, slices, films, plates, and/or slides. Magnetic beads or particles (e.g. magnetic latex beads and iron oxide particles) are representative of the solid support to which the sensitizer-linked substrate molecules can be displayed. Magnetic particles are described, (e.g. U.S. Pat. No. 4,672,040) and are commercially available (for example from, PerSeptive Biosystems, Inc. (Framingham, Mass.), Ciba Coming (Medfield, Mass.), Bangs Laboratories (Carmel, Ind.), and BioQuest, Inc. (Atkinson, N. H.)).

In addition to screening for potential inhibitors of a P-450 or another enzyme, this approach may also be used to test the binding profile of an uncharacterized P-450 mammalian isozyme, and thereby lend important insight into the structure and functional characteristics of its binding site.

Therapeutic Applications

The methods of the invention further include therapeutic methods of inhibiting or killing a cell having a target biomolecule on the cell surface. The method of the invention uses sensitizer-linked substrate molecules to specifically target a biomolecule on a selected cell surface and use of the sensitizer to generate an active species, such as the free radical superoxides, to inhibit growth of the cell or to kill the cell. The method applies photodynamic therapies (PDTs) to target biomolecules on selected cells.

As used herein, PDT is largely a method for the treatment of neoplastic and selected nonneoplastic pathogenic diseases. The illumination of a photosensitizer with light of selected wavelength and intensity can induce energy transfer to triplet oxygen which can result in the formation of cytotoxic singlet oxygen. PDT offers the potential for selective ablation of tumor cells and other pathogens. The three PDT requirements are the drug (photosensitizer), light, and oxygen. Thus, PDT is most amenable to the treatment of skin conditions. Sensitizers can be topically applied and have been approved for a variety of dermatological cancers, but drugs with particular affinity for an affected organ may also be ingested. The Food and Drug Administration has approved PDT for the treatment of advanced esophageal and lung cancers, as well as retinal macular degeneration.

Two of the greatest challenges in the development of PDT are the need for greater cell discrimination (ideally, exclusive targeting of damaged cells) and the need for modalities that allow greater tissue penetration. The sensitizer-linked substrate molecules of the invention can offer solutions to both problems. The attachment of a photosensitizer to a substrate that specifically recognizes target biomolecules on the surfaces of cancerous cells, for example, can offer distinct advantages in selectivity and targeting over current drugs, which rely on nonspecific hydrophobic interactions. The development of sensitizers that absorb at red wavelengths (>600 nm) and possess high singlet oxygen quantum yields opens possibilities for treatments involving 2-photon excitation. Such modalities allow greater tissue penetration. A. M. Rouhi, "Let There Be Light and Let It Heal," C. & EN. News, Nov. 2, 1998 pp. 22–27; R. A. Hsi, D. I. Rosenthal, E. Glatstein, "Photodynamic Therapy in the Treatment of Cancer," Drugs, 57 (5) 725–734; W. Spiller, H. Kliesch, D. Wohrle, S. Hackbarth, B. Roder, G. Schnurpfeil, "Singlet oxygen quantum yields of different photosensitizers in polar solvents and micellar solutions," Journal of Porphyrins and Phthalocyanines, 2 (2) 145–158; K. O. Zahir and A. Haim, "Yields of Singlet Oxygen Produced by the Reaction between the Excited-State of Tris(bipyridine)ruthenium(II) and Triplet Dioxygen in Various Solvents," Journal of Photochemistry and Photobiology A-Chemistry, 63 (2) 167–172.

Advantages of the Invention

The invention represents an improvement over present technology, for detecting and characterizing biomolecules, in various ways. For example, (a) there are no requirements for radioactive reagents; (b) the methods take advantage of a known recognition element and binding interaction; (c) there is no requirement for chemical or biochemical modification of the target biomolecule; (d) there is no covalent modification of the target biomolecule; (e) there is no requirement for mutant forms of the target biomolecules; (f) the signal or emission generated by the assay is significantly larger and more robust than those typically obtained using previously known biomolecule probe methodologies; (g) a positive luminescence signal is generated by the presence of a candidate modulator, thus facilitating the identification of specific modulatory agents; (h) there are a large variety of luminescent agents that are available (if the modulator decreases affinity, coumarin dyes can be used, if the modulator increases affinity [Ru(bpy)$_3$]$^{2+}$ lumophores can be used); (i) through use of different binding elements and linkers, one can adapt the assays of the invention to screen for modulators of numerous biomolecules; (j) one can assay for a target biomolecule in the presence of others; (k) one can assay multiple isoforms of biomolecules in a single reaction; (l) the assay format does not require that the enzyme be immobilized on a solid support during the course of the assay; and (m) each of the formats described is readily amenable for automation and high-throughput screening.

EXAMPLE I

This Example Describes the Optical Detection of Cytochrome P450 by Sensitizer-Linked Substrates.

Materials and Methods

Synthesis of Sensitizer-Linked Substrates

All manipulations were conducted under an argon atmosphere using standard Schlenk techniques. Solvents used for synthesis were dried, degassed and distilled according to standard procedures (A. J. Gordon, R. A. Ford, *The Chemist's Companion. A Handbook of Practical Data, Techniques, and References* (John Wiley and Sons, New York, 1972). D. D. Perrin, W. L. F. Armarego, *Purification of Laboratory Chemicals* (Butterworth-Heinemann Ltd., Boston, 3rd Ed., 1988).). Reactions were performed at room temperature unless otherwise stated. All reagents were used as received. NMR spectra were recorded on a General Electric QE300, and later a Varian Mercury 300, generally using dry CDCl$_3$ or CDCl$_2$ as solvent. $^1$H NMR spectral assignments refer to the schematic provided in depicting a typical bpy' ligand used in this study.

General

All manipulations were conducted under an argon atmosphere using standard Schlenk techniques. Solvents used for synthesis were dried, degassed and distilled according to standard procedures (A. J. Gordon, R. A. Ford, *The Chemist's Companion. A Handbook of Practical Data, Techniques, and References* (John Wiley and Sons, New York, 1972). D. D. Perrin, W. L. F. Armarego, *Purification of Laboratory Chemicals* (Butterworth-Heinemann Ltd., Boston, 3rd Ed., 1988).). Reactions were performed at room temperature unless otherwise stated. All reagents were used as received. NMR spectra were recorded on a General Electric QE300, and later a Varian Mercury 300, generally using dry CDCl$_3$ or CDCl$_2$ as solvent. $^1$H NMR spectral assignments refer to the schematic provided in depicting a typical bpy ligand used in this study.

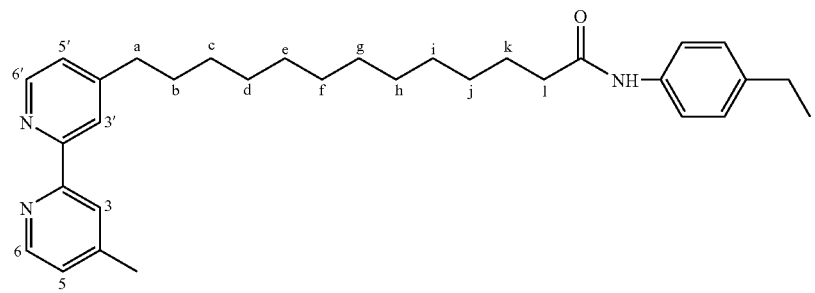

Synthesis of Ru-Substrates and Ru-Ligands

Synthesis of bpy-C$_9$-Ad.

The synthesis of bpy-C$_9$-Ad is typical of all bpy-C$_x$-Ad complexes presented. Thionyl chloride (24.50 g, 206 mmol) and 8-bromooctanoic acid (5.46 g, 24.5 mmol) were combined and refluxed for 1.5 h. Excess SOCl$_2$ was removed by vacuum to yield a brown liquid that was dissolved in ether (20 ML) and transferred to an addition funnel. The acid chloride was added over 20 min to an ether (20 mL) solution of 2-adamantanamine hydrochloride (11.97 g, 63.8 mmol) and triethylamine (22.50 g, 222 mmol) chilled in an ice bath. The resulting slurry was stirred at 0° C. for 3 h and then overnight at room temperature. The reaction solution was added to water (75 mL) and extracted with ether (75 mL) in a separatory funnel. After washing the organic layer with 0.1 M HCl (3×75 mL), water (2×75 mL), and saturated brine (2×75 mL), the solution was dried over MgSO$_4$ and solvent removed by rotary evaporation. The off-white solid was used directly without purification for attachment to Me$_2$bpy.

Diisopropylamine (8.09 g, 79.9 mmol), n-butyl lithium (80 mmol in hexanes), and cold THF (25 mL) were combined in a 500 mL Schlenk flask at 0° C. A cold solution of 4,4'-dimethyl-2,2'-bipyridine (6.41 g, 34.8 mmol) in THF (180 mL) was added by cannula over 15 min, and was stirred for an additional 15 min. The amide was dissolved in THF (120 mL) and cannulated dropwise into the bipyridine, turning the solution from burgundy to black. After 3 h on an ice bath, the reaction was allowed to proceed overnight at room temperature. The reaction solution was transferred to a separatory funnel with water (250 mL) and extracted with ether (150 mL). The organic layer was washed with saturated NaHCO$_3$ (2×125 mL), water (3×300 mL), and saturated brine (2×200 mL). After drying with MgSO$_4$ and vacuum, a beige solid was obtained. The product was eluted as the second band by silica gel column chromatography (3:2 ethyl acetate/hexanes). Yield was 3.40 g (30.2% based on 8-bromooctanoic acid) of a pale yellow oil. $^1$H NMR (CDCl$_3$): δ 1–2 (m's), 2.20 (t, CH$_2$-amide), 2.42 (s, bpy-CH$_3$), 2.59 (t, bpy-CH$_2$), 4.09 (m), 5.79 (m), 7.21 (d, bpy 5 and 5'), 8.23 (s, bpy 3 and 3'), 8.58 (d, bpy 6 and 6').

Synthesis of bpy-C$_{11}$-Ad.

The synthesis of this compound is similar to that described for bpy-C$_9$-Ad. The starting material 2-adamantanamine hydrochloride necessitated the addition of 3.5 equivalents of triethylamine. $^1$H NMR (CDCl$_3$): δ 1–2 (m's), 2.21 (t, CH$_2$-amide), 2.42 (s, bpy-CH$_3$), 2.60 (t, bpy-CH$_2$), 4.02 (m), 5.78 (m), 7.19 (d, bpy 5 and 5'), 8.23 (s, bpy 3 and 3'), 8.59 (d, bpy 6 and 6').

Synthesis of bpy-C$_{10}$.

This compound was prepared in a manner analogous to that of bpy-C$_{16}$. $^1$H NMR (CDCl$_3$): δ 0.82 (t, chain —CH$_3$), ~1.3 (m, CH$_2$c-i), 1.78 (p, CH$_2$b), 2.55 (s, bpy-CH$_3$), 2.79 (t, bpy-CH$_2$), 7.31 (t, bpy 5 and 5'), 8.51 (s, bpy 3 or 3'), 8.59 (s, bpy 3 or 3'), 8.70 (t, bpy 6 and 6').

Synthesis of bpy-C$_{16}$.

Diisopropylamine (5.79 g, 57.2 mmol), n-butyl lithium (57.3 mmol in hexanes) and cold THF (30 mL) were combined in a 500 mL Schlenk flask over an ice bath. A cold solution of 4,4'-dimethyl-2,2'-bipyridine (4.56 g, 24.7 mmol) in 180 mL of THF was added by cannula over 5 min. To this solution was added 1-bromohexadecane (6.29 g, 21.6 mmol) in THF (50 mL). The reaction was stirred on ice for ~3 h, then allowed to warm to room temperature for further stirring overnight. The reaction solution was transferred to a 1 L separatory funnel with water (250 mL) and ether (150 mL). The organic layer was washed with saturated NaHCO$_3$ (2×125 mL), water (2×300 mL) and saturated brine (3×200 mL). After drying with MgSO$_4$, solvent was removed by vacuum and the product purified by silica gel column chromatography using 4:1 hexanes:ethyl acetate as eluent. Yield was 2.40 g (34.4%) of a white solid. $^1$H NMR (CDCl$_3$): δ 0.89 (t, chain —CH$_3$), ~1.3 (m, CH$_2$c-o), 1.75 (p, CH$_2$b), 2.57 (s, bpy-CH$_3$), 2.80 (t, bpy-CH$_2$), 7.33 (t, bpy 5 and 5'), 8.52 (s, bpy 3 or 3'), 8.55 (s, bpy 3 or 3'), 8.67 (t, bpy 6 and 6').

Synthesis of bpy-C$_{11}$—Br.

This compound was prepared in a manner analogous to that of bpy-C$_{13}$—Br. $^1$H NMR (CDCl$_3$): δ~1.7 (m, CH$_2$c-i), 1.71 (p, CH$_2$b), 1.79 (p, CH$_2$j), 2.43 (s, bpy-CH$_3$), 2.70 (t, bpy-CH$_2$), 3.40 (t, CH$_2$—Br), 7.18 (d, bpy 5 and 5'), 8.25 (s, bpy 3 and 3'), 8.59 (t, bpy 6 and 6').

Synthesis of bpy-C$_{13}$—Br.

Diisopropylamine (0.770 g, 7.61 mmol), n-butyl lithium (7.60 mmol in hexanes) and THF (10 mL) were combined in a Schlenk flask at –70° C. The solution was warmed to 0° C. over 15 min. The solution was again chilled to –70° C. and 1,12-dibromododecane (25.0 g, 7.62 mmol) added as a solid. After warming to 0° C., stirring continued for ~4 h. The solution was transferred to a separatory funnel to which water (15 mL) and ether (15 mL) were added. The organic layer was washed with saturated NaHCO$_3$, dried with MgSO$_4$ and evaporated to a solid under vacuum. Silica gel column chromatography with CHCl$_3$ as the eluent yielded 1.31 g (40.0%) of a white solid. $^1$H NMR (CDCl$_3$): δ~1.7 (m, CH$_2$c-k), 1.75 (p, CH$_2$b), 1.85 (p, CH$_2$l), 2.55 (s, bpy-CH$_3$), 2.76 (t, bpy-CH$_2$), 3.48 (t, CH$_2$—Br), 7.26 (d, bpy 5 and 5'), 8.40 (d, bpy 3 and 3'), 8.65 (t, bpy 6 and 6').

Synthesis of bpy-C$_{11}$-Im.

This compound was prepared by a procedure identical to that of bpy-C$_{13}$-Im. $^1$H NMR (CDCl$_3$): δ~1.3 (m, CH$_2$c-i), 1.72 (m, CH$_2$b and j), 2.45 (s, bpy-CH$_3$), 2.72 (t, bpy-CH$_2$), 3.91 (t, CH$_2$-imid), 6.82 (s, imid H-5), 7.09 (s, imid H-4), 7.20 (d, bpy 5 and 5'), 7.45 (s, imid H-2), 8.21 (s, bpy 3 and 3'), 8.55 (t, bpy 6 and 6').

Synthesis of bpy-C$_{13}$-Im.

Imidazole (1.0 g, 15 mmol) and bpy-C$_{13}$—Br (0.30 g, 0.70 mmol) were combined in a flask with THF (50 mL) and refluxed for 4 days. Solvent was removed under vacuum and the resulting solid was dissolved in CHCl$_3$ for washing by saturated NaHCO$_3$, water and saturated brine. The product was purified by silica gel column chromatography using ethyl acetate as eluent to yield 0.26 g (90%) of a white solid. $^1$H NMR (CDCl$_3$): δ~1.3 (m, CH$_2$c-k), 1.71 (p, CH$_2$b), 1.76 (p, CH$_2$l), 2.42 (s, bpy-CH$_3$), 2.73 (t, bpy-CH$_2$), 3.95 (t, CH$_2$-imid), 6.90 (s, imid H-5), 7.10 (s, imid H-4), 7.19 (d, bpy 5 and 5'), 7.68 (s, imid H-2), 8.24 (s, bpy 3 and 3'), 8.60 (t, bpy 6 and 6').

Synthesis of bpy-C$_7$-EB.

This compound was prepared by a procedure analogous to that provided for bpy-C$_{11}$-EB. $^1$H NMR (CDCl$_3$): δ 1.24 (t, ethyl-CH$_3$), 1.42 (m, CH$_2$c and d), 1.77 (m, CH$_2$b and e), 2.39 (t, CH$_2$-amide), 2.59 (q, ethyl-CH$_2$), 2.60 (s, bpy-CH$_3$), 2.77 (t, bpy-CH$_2$), 7.11 (d, benzene), 7.29 (d, bpy 5 or 5'), 7.42 (d, bpy 5 or 5'), 7.51 (d, benzene), 8.08 (s, br, amide-H), 8.58 (s, bpy 3 and 3'), 8.69 (t, bpy' 6 and 6').

Synthesis of bpy-C$_9$-EB. This compound was prepared by a procedure analogous to that provided for bpy-C$_9$-EB. $^1$H NMR (CDCl$_3$): δ 1.19 (t, ethyl-CH$_3$), 1.40 (m, CH$_2$c-f), 1.77 (p, CH$_2$g), 1.80 (p, CH$_2$b), 2.42 (t, CH$_2$-amide), 2.60 (q, ethyl-CH$_2$), 2.75 (s, bpy-CH$_3$), 2.81 (t, bpy-CH$_2$), 7.11 (d, benzene), 7.50 (d, benzene), 7.59 (m, bpy 5 and 5'), 8.10 (s, br, amide-H), 8.75 (m, bpy 3 and 3'), 9.00 (m, bpy 6 and 6').

Synthesis of bpy-C$_{10}$-EB.

This compound was prepared by a procedure analogous to that provided for bpy-C$_{11}$-EB. $^1$H NMR (CDCl$_3$): δ 1.26 (t, ethyl-CH$_3$), 1.36 (m, CH$_2$c-g), 1.74 (m, CH$_2$b and h), 2.34 (t, CH$_2$-amide), 2.52 (s, bpy-CH$_3$), 2.61 (q, ethyl-CH$_2$), 2.75 (t, bpy-CH$_2$), 7.15 (d, benzene), 7.26 (m, bpy 5.5'), 7.47 (d, benzene), 8.41 (s, amide-H), 8.45 (m, bpy 3 and 3'), 8.60 (t, bpy 6 and 6').

Synthesis of bpy-C$_{11}$-EB.

The synthesis of bpy-C$_{11}$-EB is typical for all bpy-C$_x$-EB compounds presented. Thionyl chloride (19.6 g, 165 mmol) and 9-bromononanoic acid (5.16 g, 20.5 mmol) were combined and refluxed for 2.5 h. Excess SOCl$_2$ was removed by vacuum to yield a brown solution that was transferred to an addition funnel. The acid chloride was added over 5 min to an ether (20 mL) solution of 4-ethylaniline (6.63 g, 54.7 mmol) chilled on an ice bath. The resulting slurry was stirred on the ice bath for ~3 h and then overnight at room temperature. Water (75 mL) and ether (75 mL) were added to the reaction solution in a separatory funnel. After washing of the organic layer with 0.1 M HCl (3×75 mL), water (2×75 mL) and saturated brine (2×75 mL), the solution was dried over MgSO$_4$ and solvent removed under vacuum. This grey/brown solid amide is used for attachment to 4,4'-dimethyl-2,2'-bipyridine without purification. Yields of the final ligand are highest when the amide is used immediately after preparation.

Diisopropylamine (2.92 g, 28.9 mmol), n-butyl lithium (28.8 mmol in hexanes) and cold THF (25 mL) were combined in a 500 mL Schlenk flask chilled over an ice bath. A cold solution of 4,4'-dimethyl-2,2-bipridine (2.30 g, 12.5 mmol) in 120 ML of THF was added by cannula over 15 min. To this solution was added the amide in THF (90 mL) by cannula over 15 min. After ~3 h on the ice bath, the reaction was allowed to proceed overnight at room temperature. The reaction solution was transferred to a separatory funnel with water (250 mL) and ether (150 mL). The organic layer was washed with saturated NaHCO$_3$ (2×125 mL), water (3×300 mL) and saturated brine (2×200 mL). After drying with MgSO$_4$ and vacuum, a beige solid resulted. The product was purified by silica gel column chromatography using 3:1 hexanes:ethyl acetate for an eluent. Yield was 1.52 g (16.2% based on 9-bromononanoic acid) of a white solid. $^1$H NMR (CDCl$_3$): δ 1.19 (t, ethyl-CH$_3$), 1.25 (m, CH$_2$c-h), 1.73 (m, CH$_2$b and i), 2.28 (t, CH$_2$-amide), 2.41 (s, bpy-CH$_3$), 2.60 (q, ethyl-CH$_2$), 2.71 (t, bpy-CH$_2$), 7.17 (d, benzene), 7.18 (m, bpy 5.5'), 7.22 (s, amide-H), 7.38 (d, benzene), 8.22 (s, bpy 3 and 3'), 8.56 (t, bpy 6 and 6').

Synthesis of bpy-C$_{12}$-EB.

This compound was prepared by a procedure analogous to that provided for bpy-C$_{11}$-EB. $^1$H NMR (CDCl$_3$): δ 1.23 (t, ethyl-CH$_3$), 1.24 (m, CH$_2$c-i), 1.73 (m, CH$_2$b and j), 2.28 (t, CH$_2$-amide), 2.49 (s, bpy-CH$_3$), 2.68 (q, ethyl-CH$_2$), 2.75 (t, bpy-CH$_2$), 7.22 (d, benzene), 7.30 (m, bpy 5.5'), 7.43 (d, benzene), 7.41 (s, amide-H), 8.29 (s, bpy 3 and 3'), 8.60 (t, bpy 6 and 6').

Synthesis of bpy-C$_{13}$-EB.

This compound was prepared by a procedure analogous to that provided for bpy-C$_{11}$-EB. $^1$H NMR (CDCl$_3$): δ 1.20 (t, ethyl-CH$_3$), 1.26 (m, CH$_2$c-j), 1.74 (m, CH$_2$b and k), 2.29 (t, CH$_2$-amide), 2.43 (s, bpy-CH$_3$), 2.70 (q, ethyl-CH$_2$), 2.79 (t, bpy-CH$_2$), 7.18 (d, benzene), 7.21 (m, bpy 5.5'), 7.40 (s, amide-H), 7.45 (d, benzene), 8.29 (s, bpy 3 and 3'), 8.61 (t, bpy 6 and 6').

Synthesis of [Ru(bpy)$_2$(bpy-C$_9$-Ad)]Cl$_2$.

The synthesis of [Ru(bpy)$_2$(bpy-C$_9$-Ad)]Cl$_2$ is typical of all [Ru(bpy)$_2$(bpy')]Cl$_2$ complexes presented here. The ligand bpy-C$_9$-Ad (505 mg, 1.10 mmol) and cis-[Ru(bpy)$_2$Cl$_2$] (538.6 mg, 1.04 mmol) were combined with 5:1 water/ethanol (18 mL) and refluxed for 12 h. Solvent was removed under vacuum and the dark red solid was dissolved in water (60 mL). This aqueous solution was combined with a solution of NH$_4$PF$_6$ (1.20 g, 7.36 mmol) in water (20 mL) to yield an orange precipitate. The aqueous slurry was extracted with CH$_2$Cl$_2$ (75 mL); the organic layer was washed with 1 M HCl (2×50 mL), 1 M NaOH (2×50 mL), and water (2×75 mL) prior to rotary evaporation. The PF$_6^-$ salt of this ruthenium complex was purified by silica gel flash chromatography (column dimensions 30×4.5 cm) employing an eluent of 3% methanol in CH$_2$Cl$_2$. Pure product PF$_6^-$ salt was found in elution volumes 550–1300 mL. Further product could be obtained by running a second column on the initial 200–550 mL. Volumes 550–1300 mL were combined and dried by rotary evaporation.

In order to metathesize the ruthenium complex to the Cl$^-$ salt, the purified PF$_6^-$ salt was dissolved in MeOH (10 mL) and loaded onto a CM Sepharose cation exchange column (2×13 cm). The column was washed with water (600 mL) and 25 mM NaCl (600 mL). The ruthenium complex was then eluted with 500 mM NaCl (300 mL) and dried by vacuum. The desired [Ru(bpy)$_2$(bpy-C$_9$-Ad)]Cl$_2$ was isolated from the NaCl-containing solid by repeated washings with CH$_2$Cl$_2$, followed by filtering and drying under vacuum. Yield of the dark red solid was 195 mg (20.0%). Yields of this procedure are generally 20–30%, and approach 60% with repeated column chromatography on the crude reaction mixture. $^1$H NMR (CD$_2$Cl$_2$): δ 0.8–2 (m's), 2.21 (t, CH$_2$-amide), 2.65 (s, bpy'-CH$_3$), 2.78 (t, bpy'-CH$_2$), 3.62 (m), 3.95 (m), 6.32 (m), 7.23 (m), 7.45 (m), 7.70 (m), 8.18 (m), 8.77 (s), 8.80 (s), 9.20 (m). LRMS (electrospray, positive ion) calcd for C$_{50}$H$_{57}$N$_7$ORu (M+H$^+$) m/z 874, found 874. UV-vis [λ (Δε), H$_2$O]: 206 nm (74,200), 244 (26,000), 286 (80,100), 454 (14,500).

Synthesis of [Ru(bpy)$_2$(bpy-C$_{11}$-Ad)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 0.8–2 (m's), 2.18 (t, CH$_2$-amide), 2.64 (s, bpy'-CH$_3$), 2.81 (t, bpy'-CH$_2$), 3.96 (m), 5.90 (m), 7.25 (m), 7.49 (m), 7.72 (m), 8.19 (m), 8.59 (s), 8.69 (s), 9.95 (m). LRMS (electrospray, positive ion) calcd for C$_{52}$H$_{61}$N$_7$ORu (M–H$^+$) m/z 900, found 900.

Synthesis of [Ru(bpy)$_2$(bpy-C$_{10}$)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 0.91 (t, chain-CH$_3$), ~1.3 (m, CH$_2$c-i), 1.76 (p, CH$_2$b), 2.72 (s, bpy'-CH$_3$), 2.81 (t, CH$_2$a), 7.27 (m), 7.51 (m), 7.72 (m), 8.15 (m), 8.74 (s), 8.79 (s), 9.22 (m). LRMS (electrospray, positive ion) calcd for C$_{41}$H$_{46}$N$_6$Ru (M–H$^+$) m/z 723, found 723.

Synthesis of [Ru(bpy)$_2$(bpy-C$_{16}$)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 0.90 (t, chain-CH$_3$), ~1.3 (m, CH$_2$c-o), 1.77 (p, CH$_2$b), 2.69 (s, bpy'-CH$_3$), 2.80 (t, CH$_2$a), 7.29 (m), 7.55 (m), 7.76 (m), 8.20 (m), 8.75 (s), 8.80 (s), 9.21 (m). LRMS (electrospray, positive ion) calcd for C$_{47}$H$_{58}$N$_6$Ru (M–H$^+$) m/z 807, found 807.

Synthesis of [Ru(bpy)$_2$(bpy-C$_{11}$-Im)]Cl$_2$.

This complex was prepared by a procedure similar to that described for [Ru(bpy)2(bpy-C$_9$-Ad)]C12. 1H NMR (CD3OD): δ~1.3 (m, CH2c-i), 1.78 (CH2b and j), 2.65 (s, bpy'-CH3), 2.76 (t, bpy'-CH2), 4.01 (t, CH2-imid), 6.92 (s, imid H-5), 7.12 (s, imid H-4), 7.33 (m), 7.49 (m), 7.68 (m), 7.75 (m), 8.19 (t), 8.62 (s), 8.68 (s), 8.74 (d).

Synthesis of [Ru(bpy)$_2$(bpy-C$_{13}$-Im)Cl$_2$.

This complex was prepared by a procedure similar to that described for [Ru(bpy)2(bpy-C$_9$-Ad)]C12. 1H NMR (CD2C12): δ~1.3 (m, CH2c-k), 1.72 (CH2b and l), 2.60 (s, bpy'-CH3), 2.85 (t, bpy'-CH2), 3.99 (t, CH2-imid), 7.04 (m), 7.26 (m), 7.48 (m), 7.71 (m), 8.13 (m), 8.63 (s), 8.70 (s), 9.07 (m). LRMS (electrospray, positive ion) calcd for C$_{47}$H$_{54}$N$_8$Ru (M+H$^+$) m/z 833, found 833.

Synthesis of [Ru(bpy)$_2$(bpy-C$_7$-EB)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.05 (t, ethyl-CH$_3$), 1.25 (m, CH$_2$c and d), 1.51 (p, CH$_2$e), 1.70 (p, CH$_2$b), 2.35 (t, CH$_2$-amide), 2.40 (q, ethyl-CH$_2$), 2.52 (s, bpy'-CH$_3$), 2.80 (t, bpy'-CH$_2$), 6.82 (d, benzene), 7.20 (m), 7.40 (m), 7.60 (m), 7.73 (d, benzene), 8.00 (m), 9.05 (m), 9.18 (s). LRMS (electrospray, positive ion) calcd for C$_{46}$H$_{47}$N$_7$ORu (M–H$^+$)m/z 814, found 814.

Synthesis of [Ru(bpy)$_2$(bpy-C$_9$-EB)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.21 (t, ethyl-CH$_3$), 1.30 (m, CH$_2$c-f), 1.60 (p, CH$_2$g), 1.77 (p, CH$_2$b), 2.45 (t, CH$_2$-amide), 2.52 (q, ethyl-CH$_2$), 2.58 (s, bpy'-CH$_3$), 2.65 (t, bpy'-CH$_2$), 7.05 (d, benzene), 7.26 (t), 7.50 (m), 7.70 (m), 7.78 (d, benzene), 8.15 (m), 8.85 (s), 9.00 (t). LRMS (electrospray, positive ion) calcd for C$_{48}$H$_{51}$N$_7$ORu (M–H$^+$) m/z 842, found 842.

Synthesis of [Ru(bpy)$_2$(bpy-C$_{10}$-EB)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.13 (t, ethyl-CH$_3$), 1.21 (m, CH$_2$c-g), 1.52 (p, CH$_2$h), 1.68 (p, CH$_2$b), 2.41 (t, CH$_2$-amide), 2.52 (q, ethyl-CH$_2$), 2.58 (s, bpy'-CH$_3$), 2.83 (t, bpy'-CH$_2$), 7.00 (d, benzene), 7.24 (t), ~7.4 (m), 7.67 (m), 7.73 (d, benzene), ~8.1 (m), 8.83 (s), 8.92 (m), 9.05 (m). LRMS (electrospray, positive ion) calcd for C$_{49}$H$_{53}$N$_7$ORu (M–H$^+$) m/z 856, found 856.

Synthesis of [Ru(bpy)$_2$(bpy-C$_{11}$-EB)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.17 (t, ethyl-CH$_3$), 1.25 (m, CH$_2$c-h), 1.61 (p, CH$_2$i), 1.77 (p, CH$_2$b), 2.48 (t, CH$_2$-amide), 2.59 (q, ethyl-CH$_2$), 2.63 (s, bpy'-CH$_3$), 2.90 (t, bpy-CH$_2$), 7.06 (d, benzene), 7.29 (m), ~7.5 (m), 7.78 (d, benzene), ~8.1 (m), 8.83 (s), 8.93 (s), ~9.1 (m). LRMS (electrospray, positive ion) calcd for C$_{50}$H$_{55}$N$_7$ORu (M–H$^+$) m/z 870, found 870.

Synthesis of [Ru(bpy)$_2$(bpy-C$_{12}$-ED)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.22 (t, ethyl-CH$_3$), 1.32 (m, CH$_2$c-i), 1.60 (p, CH$_2$j), 1.72 (p, CH$_2$b), 2.40 (t, CH$_2$-amide), 2.56 (q, ethyl-CH$_2$), 2.60 (s, bpy'-CH$_3$), 2.74 (t, bpy'-CH$_2$), 7.08 (d), 7.25 (d), ~7.5 (m), 7.70 (m), 8.10 (m), 8.65 (s), 8.72 (s), 8.95 (m), 9.65 (s). LRMS (electrospray, positive ion) calcd for C$_{51}$H$_{57}$N$_7$ORu (M–H$^+$) m/z 884, found 884.

Synthesis of [Ru(bpy)$_2$(bpy-C$_{13}$-EB)]Cl$_2$.

This complex was prepared by a procedure similar to that described for [Ru(bpy)$_2$(bpy-C$_9$-Ad)]Cl$_2$. $^1$H NMR (CD$_2$Cl$_2$): δ 1.25 (CH$_2$-j), 1.28 (t, ethyl-CH$_3$), 1.61 (p, CH$_2$k), 1.74 (p, CH$_2$b), 2.46 (t, CH$_2$-amide), 2.59 (q, ethyl-CH$_2$), 2.62 (s, bpy'-CH$_3$), 2.81 (t, bpy'-CH$_2$), 7.10 (d), 7.26 (t), ~7.5 (m), 7.73 (m), ~8.1 (m), 8.59 (s), 8.62 (s), ~8.9 (m). LRMS (electrospray, positive ion) calcd for C$_{52}$H$_{59}$N$_7$ORu (M–H$^+$) m/z 898, found 898.

Synthesis of para-methoxy-N,N-dimethylaniline.

This quencher was prepared according to published procedures (M. Sekiya, M. Tomie, N. J. Leonard, *J. Org. Chem.* 33, 318–322 (1968)). para-methoxyaniline (p-anisidine, Aldrich, 5.0 g) was placed in a flask with neat methyl iodide (15 mL), fit with a condenser and refluxed for 12 hours under argon. The precipitated iodide salt of the quaternary amine was filtered and dried under high vacuum. Crude yield=11.62 grams, 98% by weight. The aniline salt was put in a flask with 1.5 equivalents of NaOH (2.4 g) and amyl alcohol as solvent (50 mL). Refluxing for 6 hours (~152° C.) gave a yellow solution which was filtered on a coarse frit to remove the brown precipitate. The filtrate was washed in a separatory funnel with saturated NaCl solution (100 mL). The top (dark brown) organic layer was dried with MgSO$_4$, and a short path distillation removed the amyl alcohol (59–79° C.) under high vacuum (~1 mm Hg).

Column chromatography was performed in the dark, using 50% EtOAc/50% hexanes as eluent. Three bands emerged; the first band was a fluorescent impurity, the second and third bands were the di-(r$_f$~0.7) and monomethyl aniline (r$_f$~0.65), respectively. Rotary evaporation of the middle fractions gave the product in modest yield (~1 gram, 16% based on starting p-anisidine). The off-white solid was further purified by sublimation (high vacuum, heated at 30° C., collected on a small cold finger). Product isolated at this stage was sufficiently pure for reductive quenching purposes. Due to its short shelf-life (stored at 4° C., under argon, protected from light), the compound was frequently recrystallized from warm water before use. $^1$H NMR (CDCl$_3$): δ 3.30 (s, N—CH$_3$, 6H), 3.88 (s, O—CH$_3$, 3H), 7.58 (d, 21), 7.15 (d, 21). GC-MS calcd for C$_9$H$_{13}$NO (M–H$^+$) m/z 150, found 150.

Synthesis of 4'-(dimethylamino)-benzo-15-crown-5.

4-aminobenzo-15-crown-5 (Aldrich, 610 mg) and MeI (5 mL) were refluxed for 3 hours under argon while stirring. The solution was filtered to remove most MeI, and the gray powder was dried on a high vacuum line. The solid was put in a 25 mL round bottom flask with Na$_2$CO$_3$ (0.00132 mol, 0.140 g) and amyl alcohol (3 mL) and refluxed under argon for five hours. The amyl alcohol was washed twice with water, and dried on a high vacuum line overnight. Column chromatography proved unable to separate the monomethyl and dimethyl products, which appeared to be stoichiometric by NMR.

Thus, the mixture was reacted with 1 equivalent of decanoyl chloride (to generate the amide from the monomethyl impurity and render it separable by column chromatography). Dropwise addition of the acid chloride was performed in chloroform at 0° C. The reaction ran 6 hours, and was extracted with water. Most of the desired product was in the aqueous phase, and was isolated by rotary evaporation. Purification was achieved by silica gel chromatography (FtOAc, 6% MeOH, 1% NEt$_3$), and the first few fractions contained the pure dimethyl aniline derivative (colorless oil). Yield=125 mg, 19% based on starting crown ether. $^1$H NMR (CDCl$_3$): δ 2.85 (s, N—CH$_3$, 6H), 3.67 (m, —CH$_2$CH$_2$—, 8H), 3.81 (m, —CH$_2$, 2H), 3.84 (m, —CH$_2$, 2H), 4.01 (m, —CH$_2$, 2H), 4.08 (m, —CH$_2$, 2H), 6.24 (pair of doublets, 1H), 6.80 (d, 1H), 6.36 (d, 1H), 6.80 (d, 1H). ESI (electrospray, positive ion) calcd for C$_{16}$H$_{25}$NO$_5$ (M–H$^+$) m/z 312, found 312. Also found, 334 (+Na$^+$) and 350 (+K$^+$). The 15-crown-5 ether derivative prefers sodium, but binds both cations in the gas phase.

Synthesis of 2-adamantylacetamide.

The hygroscopic white solid 2-adamantylamine was prepared by dissolving 2-adamantylamine•HCl (Aldrich) in H$_2$O/NaOH, extracting with methylene chloride, drying with MgSO$_4$, filtering, and rotary evaporating. This reagent (500 mg) was dissolved in methylene chloride (20 mL), put on ice, and acetic anhydride (~5 equiv.) added dropwise. The reaction was left to run overnight, and worked up by addition of sodium bicarbonate solution, and extraction with MeCl$_2$. The solution was washed twice with H$_2$O and dried with MgSO$_4$. The white crystalline product looked clean by TLC (50% CH$_2$Cl$_2$/EtOAc, imaged with paraanisaldehyde, r$_f$~0.25) and NMR without further purification. $^1$H NMR (CDCl$_3$): δ 1.62–1.90 (m's, 15H), 4.05 (br's, —CH$_3$), 5.82 (br's, N—H, amide).

Synthesis of 4-(N-imidazole)-2,2',3,3',4',5,5',6,6'-fluorobiphenyl.

Perfluorobiphenyl (133.6 mg, 0.4 mmol), imidazole (27.2 mg, 0.4 mmol), and K$_2$CO$_3$ (55.3 mg, 0.4 mmol) were put in a round bottom flask with freshly distilled DMSO, and the reaction was run under argon for 24 hours at 30° C. Work up involved adding 25 mL H$_2$O and extracting three times with 25 mL MeCl$_2$. The organic layer was dried over MgSO4, filtered, and rotovapped. TLC (EtOAc) showed two spots (monoimidazole, r$_f$=0.75; diimidazole, r$_f$=0.5; consumed starting perfluorobiphenyl, r$_f$=1). The mixture was purified on silica gel using 50% EtOAc/hexanes as the eluent. Yield=75 mg (49%) of the desired monoimidazole product with nearly an equal amount of the bisimidazole compound. $^1$H NMR (CD$_2$Cl$_2$): δ 7.20 (br, 1H), 7.23 (m, 1H), 7.78 (br, 1H). $^{19}$F NMR (CD$_2$Cl$_2$): δ 129 (m, 2F), –130 (m, 2F), –139 (m, 2F), –141.5 (m, 2F), –151.7 (m, 1F). ESI (electrospray, positive ion) calcd for C$_{15}$H$_3$N$_2$F$_9$(M–H$^+$) m/z 383, found 383.

Synthesis of 4,4'-bis(N,N'-imidazole)-2,2',3,3',5,5',6,6'-fluorobiphenyl.

Isolated in the procedure above, this compound was synthesized in nearly quantitative yields by using three equivalents of imidazole and K$_2$CO$_3$. The product was purified on silica gel using 70% EtOAc/hexanes as eluent. $^1$H NMR (CD$_2$Cl$_2$): δ 7.32 (br, 1H), 7.37 (m, 1H), 7.87 (br, 1H). F NMR (CD$_2$Cl$_2$): δ –136.9 (m, 4F), –148 (d, 4F). ESI (electrospray, positive ion) calcd for C$_{18}$H$_6$N$_4$F$_9$8g(M–H$^+$) m/z 431, found 431.

Synthesis of 4,4',5,5'-tetramethyl-2,2'-bipyridine.

This bipyridyl ligand (Me$_4$bpy) was synthesized following published procedures (G. A. Mines, et al., *J. Am. Chem. Soc.* 118, 1961–1965 (1996)). The brown liquid lutidine (3,4-dimethylpyridine, Aldrich, 477 g, 4.45 mol) and Pd/C (10% Pd on carbon, Aldrich, ~40 g) were combined in a 2-liter flask with a reflux condenser, refluxed and stirred for 8 days. While still hot, the black solution was filtered on celite and cooled on ice. The beige crystals were collected with a Bückner funnel, washed with ether, and recrystallized with 1:1 CHCl$_3$/toluene. The off-white crystals crashed out of solution in the freezer, and were collected by filtration. Yield=18.9 g, 4.0%. $^1$H NMR (CDCl$_3$): δ 2.31 (s, —CH$_3$, 6H), 2.37 (s, —CH$_3$, 6H), 8.20 (s, 2H), 8.40 (s, 2H).

Synthesis of [Ru(Me$_4$bpy)$_2$Cl$_2$]·2H$_2$O.

This was synthesized by a modification of published procedures (S. Gould, T. R. O'Toole, T. J. Meyer, *J. Am. Chem. Soc.* 112, 9490–9496 (1990)). RuCl$_3$·3H$_2$O (Aldrich, 927 mg, 3.56 mmol), Me$_4$bpy (1.50 g, 7.08 mmol), LiCl (2.23 g, 52.6 mmol), and hydroquinone (EM, 1.96 g, 17.8 mmol) were dissolved in anhydrous dimethoxyethane (100 mL) and distilled methanol (50 mL). The solution was purged with argon for 20 minutes and refluxed under argon for 24 hours. Water (225 mL) was added to the cooled solution, and the brownish purple solid was collected on a medium frit and washed thoroughly with H$_2$O. The product was dissolved in MeCl$_2$ (450 mL) and washed with water (3×450 mL) until the aqueous layer was colorless. The organic layer was dried with MgSO$_4$ and rotary evaporated. The dark purple powder was reprecipitated from minimal MeCl$_2$ with ether, collected by filtration, and dried under high vacuum; yield=600 mg, 28%.

Synthesis of [Ru(tmbpy)$_2$(4-hydroxymethyl-4'-methylbipyridine)](PF$_6$)$_2$.

Ru(tmbpy)$_2$Cl$_2$ (100 mg, 0.168 mmol) and 4-hydroxymethyl-4'-methylbipyridine (73.9 mg, 0.369 mmol, synthesized exactly according to published procedures (14)) were put in a round bottom flask with H$_2$O (5 mL) and EtOH (2 mL) and refluxed under argon for 3 hours. The ethanol was removed by rotary evaporation, and orange crystals were obtained by adding a concentrated solution of (NH$_4$)PF$_6$, filtering on a frit and drying on an aspirator. Purification was performed on an 8" alumina column eluting with 2:1 toluene/acetonitrile. A dark nonfluorescent band eluted first, followed by the major orange band (product); brown and red junk stuck to the column. Yield=40 mg, 25%.

A general methodology was developed to synthesize Ru-probes in good yields and with minimal effort. The first chromatography step generally gave 30% yields of the pure bpy' ligand, based on the starting bromoamide. Non-fluorescing silica TLC plates were used for all bpy ligand syntheses, since bpy coordinates the metal in the fluorescing plates, causing the spot to streak. The TLC plates were stained with a ferric salt solution, which turned the bpy spots red and made imaging easy, quick, and non-toxic. The second chromatography step was tried on ion exchange as well as alumina media before settling on silica gel as the best support.

The ruthenation step generally yielded 60% pure Ru-substrate, while for Ru-ligands this final step yielded only ~30%. Elute the Ru-compounds with nitrate in the solvent—this minimizes streaking and isolates the product as the water soluble nitrate salt (obviating the need for metathesis). Metathesis was not always time consuming, however; it was possible to dissolve the more hydrophobic [Ru-substrate] (PF$_6$)$_2$ salts in dry acetone, and metathesize directly with tetrabutylammonium chloride, avoiding ion exchange chromatography completely. Unfortunately, due to the high solubility of many Ru-substrate chloride salts in both organic and aqueous solutions, this was not always possible. Cation exchange chromatography often served as a final purification, as well as metathesis step.

The synthesis of p-MDMA was quite straightforward; the purification, however, was not. Unfortunately, separation of the mono and di-methyl products proved difficult. One tip worth following would be to react the mixture with decanoyl chloride, as was done to synthesize 4'-(dimethylamino)-benzo-15-crown-5. The conversion of the monomethyl side product to the decyl amide should make purification much easier.

Finally, Ru(Me$_4$bpy)$_2$(Cl)$_2$.2H$_2$O is a useful precursor for many high driving force excited-state ET reactions. The redox potential generally decreases 20 mV/methyl group, making [Ru(Me$_4$bpy)$_2$(dmbpy)]$^{2+}$~200 mV more negative than Ru(bpy)$_3$. Several different variants were synthesized to tune the driving force (i.e., Ru(dmbpy)$_2$Cl$_2$) or to make the complex reactive with surface cysteines (i.e., Ru(tmbpy)$_2$(4-bromomethyl-4'-methylbipyridine](PF$_6$)$_2$) (L. Geren, S. Hahm, B. Durham, F. Millet, *Biochemistry* 30, 9450-9457 (1991)), but it is left to the reader to explore these other avenues.

Protein Isolation

P450$_{cam}$ Expression/Crystallization Conditions. *P. putida* cytochrome P450$_{cam}$ (residues 1–414) containing the mutation Cys334Ala (Quickchange mutagenesis, Stratagene) was overexpressed in *E. coli* TBY cells from plasmid pUS200 (Unger, B. P., et al. (1986) *J. Biol. Chem.* 261, 1158–1163) and purified in the presence of camphor as previously described (Nickerson, D., et al. (1998) *Acta Crystallogr.* D54, 470–472). P450:Ru—C$_9$-Ad seed crystals of space group P2$_1$2$_1$2$_1$ (cell dimensions 65.4×74.5×91.7 Å$^3$, one molecule/asymmetric unit, Matthews coefficient (V$_M$)=2.4, solvent content=49%) nucleated overnight (4° C., vapor diffusion) from protein separated from camphor and complexed with stoichiometric Ru—C$_9$-Ad. Hanging drops contained an equal volume mixture of reservoir and 430 μM P450:Ru—C$_9$-Ad in 20 mM HEPES pH 7.5, 100 mM KCl, and 1 mM dithiothreitol. The reservoir contained 100 mM NaOAc pH 4.9, 200 mM NH$_4$OAc pH 7.0, and 9–11% polyethylene glycol (PEG) MW 8000 (W/V) (final pH ~6.0). Diffraction quality crystals (0.15×0.15×0.5 mm$^3$) were grown over 24–48 hours by moving seed crystals into sitting drops of reduced PEG concentrations (5–7%).

Structure Determination.

An initial molecular replacement solution (correlation coefficient=0.53 and R$_{cryst}$=Σ||F$_{obs}$|−|F$_{calc}$||/Σ|F$_{obs}$|=43.4%, for 15.0 to 3.5 Å resolution data) was found by AMoRe (Navaza, J. (1994) *Acta Crystallogr.* A50, 157–163) with a probe derived from the structure of camphor-bound P450$_{cam}$, PDB code: 2 cpp (Poulos, T. L., et al. (1987) *J. Mol. Biol.* 195, 687–700), using diffraction data collected from P450:Ru—C$_9$-Ad crystals (1.55 Å resolution, overall R$_{sym}$=ΣΣ$_j$|I$_j$−<I>|/ΣΣ$_j$I$_j$=4.8%, overall signal-to-noise ratio=I/σI=37.4, redundancy=6.5, 99.2% complete). Diffraction data were collected at 100 K on Beam-line 7-1 (1.08 Å) of the Stanford Synchrotron Research Laboratory (SSRL) and processed with DENZO (Otwinowski, Z. & Minor, W. (1997) *Meth. Enzymol.* 276, 307–326). Substantial changes in the regions of P450 distal to the heme were modeled to omit electron density maps with XFIT (McRee, D. E. (1992) *J. Mol. Graphics* 10, 44). Ru—C$_9$-Ad was positioned into the remaining difference density. The structure was refined by torsion-angle molecular dynamics and positional refinement with CNS (Brünger, A. T., et al. (1998) *Acta Crystallogr.* D54, 905–921) amidst model rebuilding, water molecule placement, and resolution extension to 1.55 Å. Following an overall anisotropic thermal factor correction, bulk-solvent correction, and individual thermal factor refinement, grouped occupancy refinement of Ru—C$_9$-Ad and those residues in multiple conformations produced the final model (4019 scatterers, 1 Ru—C$_9$-Ad as a superposition of the two (Δ and Λ) {Ru(bpy)$_3$}$^{2+}$ enantiomers, 23 residues in multiple conformations, 427 water molecules, and 5 acetate molecules; R$_{cryst}$=21.6%, R$_{free}$=22.6% for 8% of the reflections removed at random, no σ cutoff). The adamantyl moiety of Ru—C$_9$-Ad is well ordered, but static and/or dynamic disorder increases up the methylene chain toward the sensitizer, where only one of the three bpy ligands is well resolved. The ruthenium atom position was confirmed by the largest peak in the initial F$_{obs}$−F$_{calc}$ electron density map (4σ) and also by a peak in the Bijvoet difference Fourier map (calculated with coefficients |F$^+$|−|F$^-$| and phases φ$_{model}$−π/2), which identified all sulfur and metal atoms in the model. The final model has excellent stereochemistry (root mean square deviation from ideal bond lengths <0.009 Å and ideal bond angles <1.3°) with 90.3% of all residues in the most favored regions of φ/φ space, as defined by PROCHECK(Laskowski, R. A., et al. (1993) *J. Appl. Crystallogr.* 26, 283–291). No residues fall in disallowed regions. Larger refined thermal factors for Ru—C$_9$-Ad (<B>=48.2 Å$^2$) compared to the overall model (<B>=28.0 Å$^2$, <B>$_{mainchain}$=19.4 Å$^2$, <B>$_{sidechain}$=20.4 Å$^2$) reflect the mobility and conformational heterogeneity of the bound {Ru(bpy)$_3$}$^{2+}$. The ribbon representation (FIG. 1) was generated using Molscript (Kraulis, P. J. (1991) *J. Appl. Cryst.* 24, 946–950) and Raster3D (Merritt, E. A. & Bacon, D. J. (1997) *Methods Enzymol.* 277, 505–524). The methylene linker occupies a large channel from the enzyme surface to the heme. A hydrogen bond connects the Ru-substrate amide carbonyl (red atom) to Tyr 96 (orange). The adamantyl moiety (center) resides at the P450 active site above the heme (orange) in the same position as the natural adamantane substrate (magenta), shown in superposition from the 4 cpp crystal structure (Raag, R. & Poulos, T. L. (1991) *Biochemistry* 30, 2674–2684). Although both Δ and Λ {Ru(bpy)$_3$}$^{2+}$ enantiomers are present in the complex, only Λ is shown.

Energy Transfer Measurements

Solution experiments were performed under an argon atmosphere with P450 and Ru-substrate in 100 mM KCl and 20 mM KPhos buffer, pH 7.4. Single crystal experiments were conducted aerobically. Samples were excited with XeCl excimer-pumped dye laser pulses (25 ns, 480 nm, 1–2 mJ/pulse). The emission decay traces were fit to the biexponential function, $y=c_0+c_1 e^{-(k_{en}+k0)t}+c_2 e^{-k0t}$. The ratio $c_1:(c_1+c_2)$ was used to calculate dissociation constants. Donor-acceptor spectral overlap gives a Förster distance (Ru—Fe distance at which half the emission is quenched by energy transfer) (Förster, T. (1965) in *Modern Quantum Chemistry*, ed. Sinanoglu, O. (Academic Press, New York), Vol. 3, pp. 93–137) of R$_0$=26.2 Å for the ferriheme enzyme and R$_0$=27.6 Å for the carbonmonoxy species. Ru—Fe distances, r, were calculated using the equation, $k_{en=k0}(R_0/r)^6$.

Results and Discussion

Figure 2:
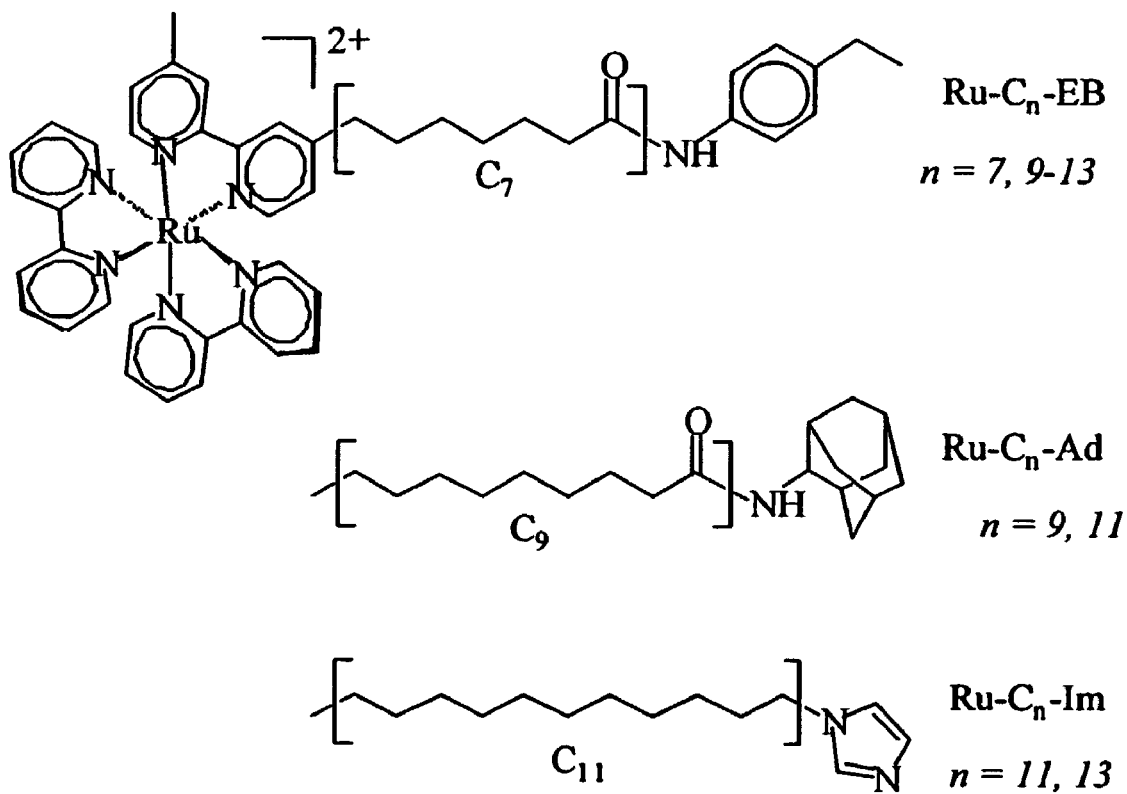
FIG. 2 shows the Ruthenium sensitizer-linked substrates, as described in Example I, infra.

Ru-substrates (FIG. 2) were modeled into the substrate-free P450 crystal structure (Poulos, T. L., et al. (1986) *Biochemistry* 25, 5314–5322) to position ethyl benzene (EB) and adamantane (Ad) at the active site and {Ru(bpy)$_3$}$^{2+}$ at the protein surface. Ru—C$_n$-EB and Ru—C$_n$-Ad were constructed by the covalent attachment of EB and Ad to variable length methylene chains [(CH$_2$)$_{7-13}$] terminating in the photosensitizer (Wilker, J. J., et al. (1999) *Angew. Chem. Int. Ed.* 38, 90–92). An amide functionality was incorporated into the Ru-substrates to permit hydrogen bonding, as occurs between Tyr 96 and camphor (Poulos, T. L., et al. (1987) *J. Mol. Biol.* 195, 687–700). To generate Ru-ligands that could bind the heme iron (Dawson, J. H., et al. (1982) *J. Biol. Chem.* 257, 3606–3617), imidazole was linked to alkyl-tethered {Ru(bpy)$_3$}$^{2+}$ (Ru—C$_n$-Im). Ru-EB/Ad compounds, as well as Ru-Im, have been shown to bind P450 with high affinity (Wilker, J. J., et al. (1999) *Angew.*

Figure 1:
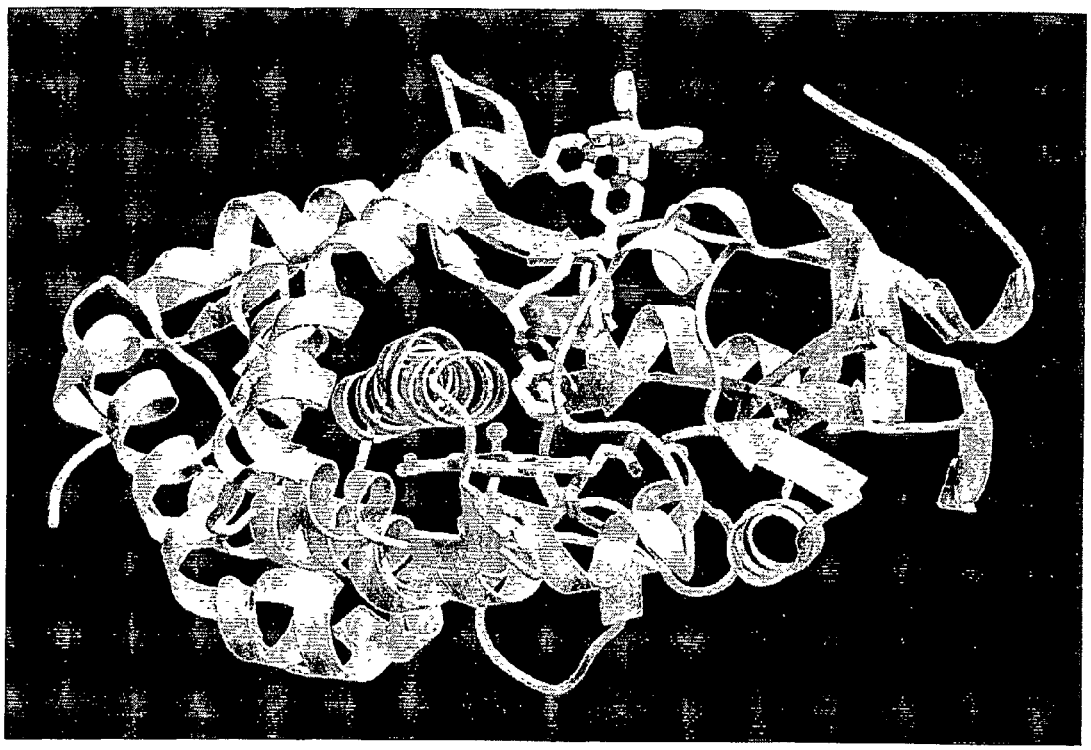
FIG. 1 depicts the crystal structure of the $P450_{cam}$:Ru—$C_9$-Ad complex, as described in Example I, infra. The Ru-substrate is shown in yellow to highlight docking of $\{Ru(bpy)_3\}^{2+}$ at the surface of the protein, as predicted by computer modeling and energy-transfer experiments.

*Chem. Int. Ed.* 38, 90–92). One of these complexes, P450:Ru—$C_9$-Ad, was crystallized and structurally characterized to 1.55 Å (FIG. 1). The Ru-substrate binds as predicted, with the Ad moiety mimicking substrate (Raag, R. & Poulos, T. L. (1991) *Biochemistry* 30, 2674–2684), a hydrogen bond between Tyr 96 and the amide functionality, and {Ru(bpy)$_3$}$^{2+}$ at the mouth of a large channel that has opened to accommodate the sensitizer.

Figure 3:
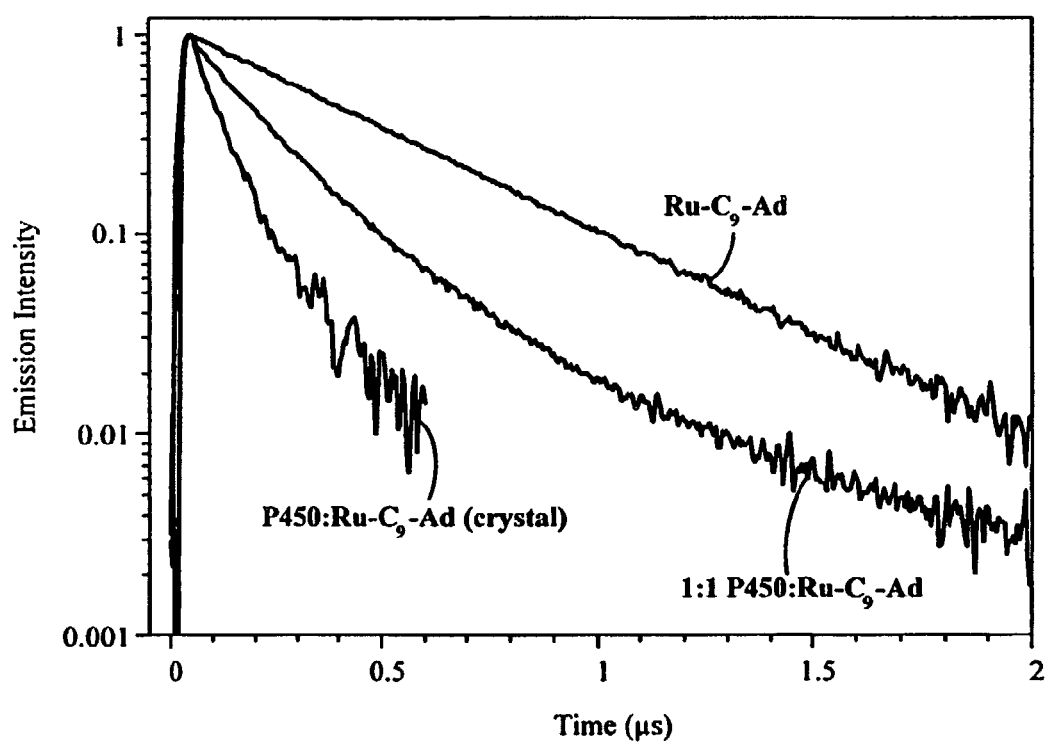
FIG. 3 illustrates the kinetics traces of $[Ru—C_9-Ad]^{2+*}$ emission decay at room temperature in solution and in a single crystal of $P450_{cam}$:Ru—$C_9$-Ad. $[Ru—C_9-Ad]^{2+*}$ (10 µM) exhibits monophasic decay (black), as described in Example I, infra. Emission decay of $[Ru—C_9-Ad]^{2+*}$ equimolar with P450 (10 µM) is biphasic (red). In a P450:Ru—$C_9$-Ad crystal, $\{Ru(bpy)_3\}^{2+*}$ quenching is predominantly monophasic (blue).

Binding of the Ru—$C_n$-EB/Ad/Im compounds to the P450 target was detected by decreases in Ru$^{2+}$ excited-state (Ru$^{2+*}$) lifetimes (Wilker, J. J., et al. (1999) *Angew. Chem. Int. Ed.* 38, 90–92). [Ru-substrate]$^{2+*}$ emission decay is normally monophasic ($k_0$=2.1×10$^6$s$^{-1}$), but becomes biphasic with a dominant fast component ($k_{en}$=0.5–1.4×10$^7$s$^{-1}$; $k_0$=2.1×10$^6$s$^{-1}$) in the presence of P450 (FIG. 3). A secondary (<10%) slower phase ($k_0$=4.8×10$^6$s$^{-1}$) also was observed, suggesting that a small percentage of the Ru-substrate may remain unbound in the crystal. Faster {Ru(bpy)$_3$}$^{2+*}$ emission decay, $k_{en}$, in the crystal relative to solution most likely reflects small conformational differences in P450 between the two phases. Faster decay of the intrinsic {Ru(bpy)$_3$}$^{2+*}$ emission, $k_0$, in the crystal is attributable to quenching by oxygen. Thus, upon addition of enzyme, the Ru-substrate or Ru-ligand partitions between a "bound" state, in which Ru$^{2+*}$ is quenched, and a "free" state, in which it is not. Photoexcitation of a P450:Ru—$C_9$-Ad single crystal yields a predominantly monophasic luminescence decay (FIG. 3) that is strongly quenched by the protein ($k_{en}$=1.1×10$^7$s$^{-1}$), thereby confirming that the fast decay component, $k_{en}$ is attributable to P450:Ru-substrate complex formation.

Figure 5:
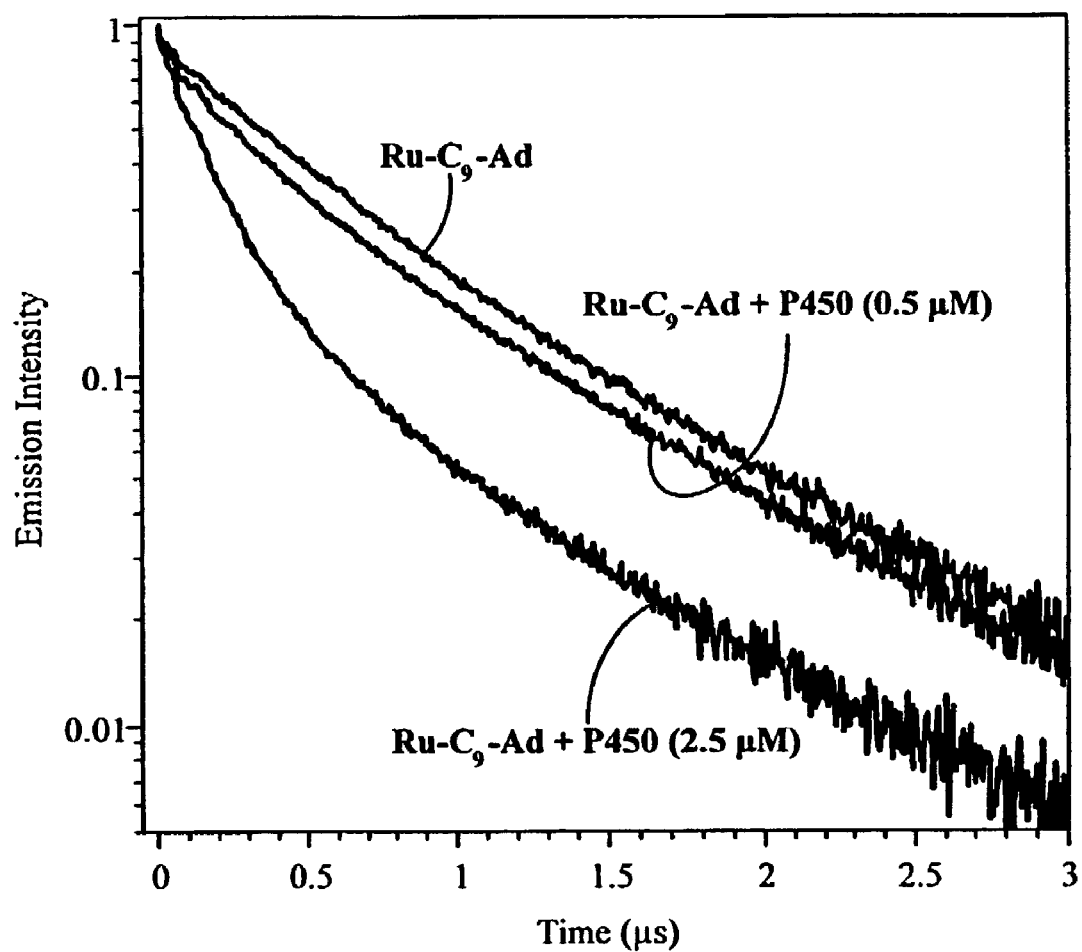
FIG. 5 depicts the specific detection of Cytochrome P450 by Ru—C9-Ad, as described in Example I, infra.

Competitive binding between Ru-substrates and camphor at the active site is indicated by the ability of the natural substrate ($K_D$~1 μM) to diminish the fraction of bound [Ru-substrate]$^{2+*}$ decaying at the faster rate, $k_{en}$. At the titration end-point, camphor completely displaces the Ru-substrate from P450, as shown by monophasic Ru$^{2+*}$ emission decay kinetics ($k_0$=2.1×10$^6$s$^{-1}$). Analysis of Ru—$C_{11}$-Ad emission quenching by P450 yields a dissociation constant ($K_D$=0.8 μM) in excellent agreement with Ru—$C_{11}$-Ad/camphor competitive binding assays monitored by UV/Vis spectroscopy ($K_D$=0.7 μM). Association of Ru-substrates and Ru-ligands with P450 is sufficiently strong to allow detection of the enzyme at submicromolar concentrations (FIG. 4). The emission decay profile of Ru—$C_9$-Ad (2.5 μM) in 50 mM sodium phosphate buffer, pH 7, was monophasic ($k_0$=2.1×10$^6$s$^{-1}$) in the presence of six heme proteins (yeast cytochrome c, horse skeletal muscle myoglobin, bovine lipase cytochrome $b_5$, bovine liver catalase, recombinant yeast cytochrome c peroxidase, and horseradish peroxidase), each at 5 [M. The finding that the addition of 500 nM P450$_{cam}$ to this mixture yielded biphasic Ru$^{2+*}$ kinetics (~10% $k_{en}$, ~90% $k_0$) demonstrates the feasibility of detecting specific target biomolecules in complex media (FIG. 5).

Specificity of Ru-substrates for P450 is controlled largely by interactions of the substrate moiety with the active site. Particularly noteworthy is the fact that {Ru(bpy)$_3$}$^{2+}$ is a sensitive reporter of binding even for substrates that do not shift the heme absorption spectrum by displacing ligated water (Wilker, J. J., et al. (1999) *Angew. Chem. Int. Ed.* 38, 90–92). Dissociation constants for Ru—$C_n$-EB compounds are the first presented for derivatives of ethyl benzene. The chain-length dependence of binding in the Ru—$C_n$-EB series ($K_D$=0.7–6.5 μM for n=7–13) demonstrates that detection of P450 by Ru-substrates may be fine-tuned by modification of the linker component. In the case of Im-terminated terminated tethers, however, Ru—$C_{11}$-Im has low affinity for P450, whereas Ru—$C_{13}$-Im binds the enzyme tightly (FIG. 4). Apparently, the shorter linker does not allow the Im to extend far enough into the protein to ligate the heme iron.

Förster (dipole—dipole) energy transfer (FET) dominates the quenching in P450:Ru-substrate complexes. Evidence that electron transfer does not contribute significantly to this quenching is the finding that ferriheme reduction by {Ru(bpy)$_3$}$^+$ is ~10$^3$ times slower than $k_{en}$ (Wilker, J. J., et al. (1999) *Angew. Chem. Int. Ed.* 38, 90–92). Spectral overlap of {Ru(bpy)$_3$}$^{2+*}$ emission with the absorption of Fe(CO)$^{2+}$ P450 is greater than with the ferriheme enzyme, suggesting that FET should be more efficient in the carbonyl complex (where both oxidation and reduction of the heme-CO complex are energetically disfavored). Not only is the decay of Ru$^{2+*}$ in P450 Fe(CO)$^{2+}$:Ru—$C_{11}$-EB 1.5 times faster ($k_{en}$=1.6×10$^7$ s$^{-1}$), the calculated Ru—Fe distances differ by only 0.4 Å for the two heme oxidation states (Förster, T. (1959) *Discussions Faraday Soc.* 27, 7–17; Galley, W. C. & Stryer, L. (1969) *Biochemistry* 8, 1831–1833).

The Ru—Fe distance found in the P450:Ru—$C_9$-Ad crystal (21 Å) is in excellent agreement with the Förster analysis of energy-transfer kinetics for this complex in solution. Similar Ru—Fe distances were calculated for the various Ru-substrates, suggesting a common mode of Ru-substrate binding at the P450 active site. The shallow Ru—Fe distance dependence on chain length in the Ru—$C_n$-EB series confirms that {Ru(bpy)$_3$}$^{2+}$ always binds at the protein surface. The shortest ethyl benzene derivatives, Ru—$C_7$-EB and Ru—$C_9$-EB, report the minimum length of the substrate access channel to be 19.5 Å. These data also indicate that the region occupied by the methylene linker represents the most likely path followed by natural substrates to access the P450 active center. The swath cut by Ru-substrates in P450 is a channel of considerable breadth (3–8 Å) and depth (~20 Å).

This example demonstrates the novel method of the invention for sensing specific biomolecules that involves tethering a photosensitizer to a substrate molecule with high affinity for an active site of a target biomolecule. Analysis of Ru/heme FET kinetics revealed the dimensions and conformational flexibility of the access channel, and probed the mechanism of substrate binding. This approach can be broadly expanded through a combinatorial approach to designing substrate moieties that target P450s as well as other enzymes, modifying sensitizers to produce desired signals, and optimizing linkages to fine-tune specificity or probe target conformations. Replacement of {Ru(bpy)$_3$}$^{2+}$ with osmium polypyridyl complexes (Kober, E. M., et al. (1985) *Inorg Chem.* 24 2755–2763) would tune the emission further towards the near infrared, thereby improving tissue penetration and optical detection over the background of scattered light from cellular components. The ability of sensitizer-linked substrates to detect proteins and perform photochemical oxidation and reduction reactions at specific enzyme active sites (Wilker, J. J., et al. (1999) *Angew. Chem. Int. Ed.* 38, 90–92) opens new avenues for intervention in metabolic processes.

EXAMPLE II

Figure 6:
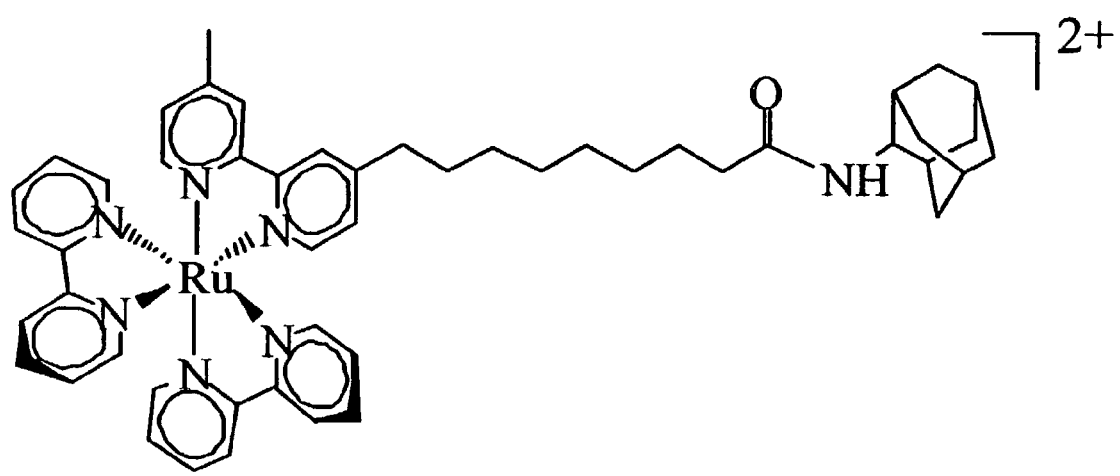
FIG. 6 depicts sensitizer-linked substrate, Ru—$C_9$-Ad, as described in Example II, infra.
Figure 7:
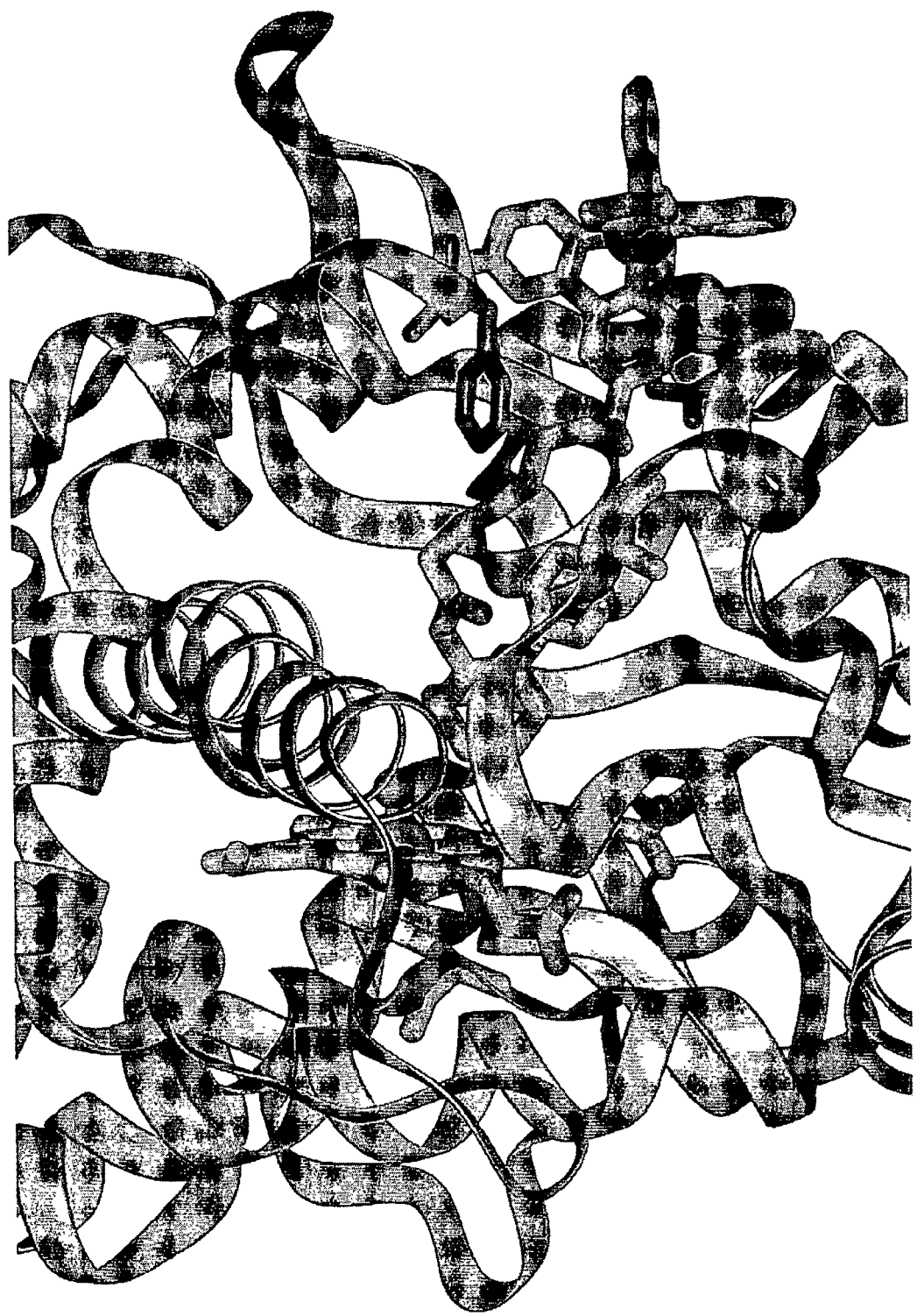
FIG. 7 shows the crystal structure of the $P450_{cam}$:Ru—$C_9$-Ad conjugate, as described in Example II, infra. Although both Λ and Δ isomers are present, only Λ (magenta) is shown. The substituted bipyridyl ligand sits at the mouth of the cavity in close proximity to several hydrophobic residues, including Phe 193 and Tyr 29 (blue). The Ru-substrate amide carbonyl (red) hydrogen bonds to Tyr 96 (green).
Figure 8:
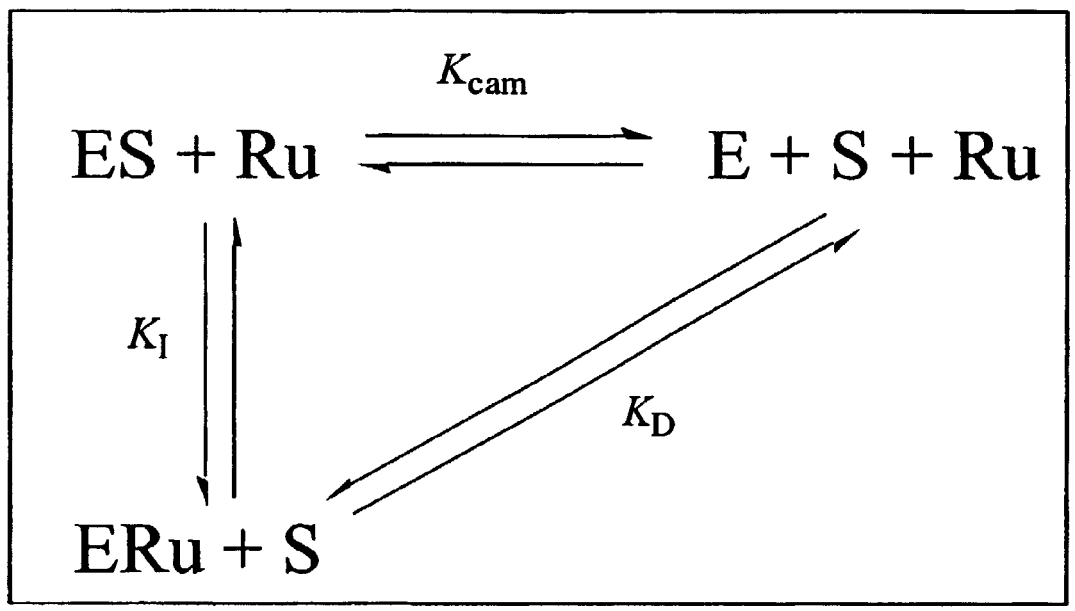
FIG. 8 illustrates the binding of a single substrate to P450, as described in Example II, infra.

This Example Describes Enantiomeric Discrimination of Ru-Substrates by Cytochrome P450$_{cam}$ It was found that substrates and ligands attached via an alkyl chain to the inorganic photosensitizer [Ru(bpy)$_3$]$^{2+}$ (where bpy is 2,2'-bipyridine) bind P450 reversibly [Wilker, J. J. et al. *Angew. Chem. Int. Ed.* (1999), 38, 90–92] with high affinity ($K_D$~1 µM) and specificity [as described in Example I infra, Dmochowski, I. J., et al. *Proc. Natl. Acad. Sci. USA* (1999), 96, 12987–12990]. The substrate [Ru—$C_9$-Ad]$Cl_2$ (FIG. 6) was recently crystallized with P450 and the X-ray structure determined to 1.55 Å (PDB code, 1 qmq; FIG. 7) [as described in Example I infra, Dmochowski, I. J., et al. *Proc. Natl. Acad. Sci USA* (1999), 96, 12987–12990]. The adamantyl moiety resides in the heme pocket, much like the substrate adamantane. Electron density from the ruthenium and bipyridyl ligands appears in multiple positions near the substrate channel, thereby indicating either considerable mobility of the $\{Ru(bpy)_3\}^{2+}$ moiety or the existence of stable enzyme-Ru conjugates that could correspond to specific interactions of Λ and Δ enantiomers with the protein surface. High thermal factors for the $\{Ru(bpy)_3\}^{2+}$ moiety in the crystal structure prevented unambiguous assignment of either isomer. The inherent chirality of both P450 and $\{Ru(bpy)_3\}^{2+}$ raises the possibility that hydrophobic interactions with aromatic residues at the channel entrance favor the binding of one isomer relative to the other. This potential enantioselectivity was probed by resolving the Λ and Δ [Ru—$C_9$-Ad]$Cl_2$ isomers and comparing their affinities for P450.

Chromatographic techniques using SP Sephadex C-25 with chiral eluents have been developed for the separation of many enantiomeric ruthenium polypyridyl complexes [Fletcher, N. C.; Keene, F. R.; *J. Chem. Soc., Dalton Trans.* (1999), 5 683–689; Fletcher, N. C. et al., *J. Chem. Soc. Dalton* (1998), 1 133–138; Rutherford, T. J. et al., *Eur. J. Inorg. Chem.* (1998), 11 1677–1688; Rutherford, T. J. et al., *Inorg. Chem.* (1995), 34 3857–3858]. The Sephadex ion exchange matrix itself is chiral, since it is made of dextran, a 3-dimensional network of cross-linked D-glucose units. Interestingly, the ability of dextran to achieve chiral resolutions of $d^6$($Re^I$, $Ru^{II}$, $Os^{II}$, $Co^{III}$, $Rh^{III}$) polypyridyl compounds is greatly enhanced by the addition of tartrate salts [Yoshikawa, Y.; Yamasaki, K. Coord. *Chem. Rev.* (1979), 28 205–229]. X-ray structures of these metal complexes crystallized with aromatic tartrate counterions (i.e., (+)—O,O'-di-4-toluoyl-D-tartrate) show well-ordered stacking interactions between the ditoluoyl and phenanthroline groups [Yoshikawa, Y.; Yamasaki, K. Coord. *Chem. Rev.* (1979), 28 205–229]. Well-defined structures incorporating a variety of organic salts also have been observed in solution by $^1$H NMR [Fletcher, N. C.; Keene, F. R.; *J. Chem. Soc., Dalton Trans.* (1999), 5 683–689]. Aromatic stacking has been implicated as a major factor in the mechanism of stereoisomer separation with these eluents [Rutherford, T. J. et al., *Eur. J. Inorg. Chem.* (1998), 11 1677–1688], and provides a mechanism for chiral discrimination by the enzyme. In this example, sodium (−)—O,O'-dibenzoyl-L-tartrate was chosen for the isolation of the (±)—[Ru—$C_9$-Ad]$Cl_2$ isomers because it most efficiently resolves the parent compound, [Ru(bpy)$_2$ (Me$_2$bpy)]$Cl_2$(Me$_2$bpy is 4,4'-dimethyl-2,2'-bipyridine).

Time-resolved luminescence measurements precisely quantify the binding of Ru-substrates to P450 [Wilker, J. J. et al. *Angew. Chem. Int. Ed.* (1999), 38, 90–92; as described in Example I infra, Dmochowski, I. J., et al. *Proc. Natl. Acad. Sci. USA* (1999), 96, 12987–12990]. Laser excitation of the Ru-protein solutions yields biphasic luminescence kinetics. The faster quenching process (k=4–×$10^6$ $s^{-1}$, depending on substrate and chain length) has been identified as Förster energy transfer from $Ru^{2+*}$ to the heme [as described in Example I infra, Dmochowski, I. J., et al. *Proc. Natl. Acad. Sci. USA* (1999), 96, 12987–12990]. The slower luminescence decay process (τ~500 ns) is the same as that of $Ru^{2+*}$ in deoxygenated solution. Thus, dissociation constants can be calculated from the quenched fraction of [Ru-substrate]$^{2+*}$ luminescence. Traditional P450 substrate-binding assays rely on monitoring the low-to-high-spin shift (417 392 nm) associated with water loss from a ferric-aquo heme. Time-resolved emission profiles much more reliably assess the affinity of substrates (e.g., (±)—[Ru—$C_9$-Ad]$Cl_2$) that displace little water from the channel and only slightly perturb the spin state of the heme.

Materials and Methods

Protein Preparation

Cytochrome P450$_{cam}$ was overexpressed in *E. coli* TBY cells from plasmid pUS200 [Unger, B. P. et al., *J. Biol. Chem.* (1986), 261 1158–1163] and purified in the presence of camphor according to standard procedures [Nickerson, D. et al., *Acta Crystallogr.* (1998), D54 470–472].

Synthesis of [Ru—$C_9$-Ad]$Cl_2$

General Procedures

All manipulations were conducted under an argon atmosphere using standard Schlenk techniques. Solvents used for synthesis were dried, degassed and distilled according to standard procedures [Perrin, D. D.; Armarego W. L. F. *Purification of Laboratory Chemicals,* 3rd ed.; Butterworth-Heinemann Ltd., Boston, 1988; A. J. Gordon, R. A. Ford *The Chemist's Companion. A Handbook of Practical Data, Techniques, and References*; John Wiley and Sons, New York, 1972]. Reactions were performed at room temperature unless otherwise stated. NMR spectra were recorded on a General Electric QE300.

Synthesis of bpy-$C_9$-Ad

Thionyl chloride (24.50 g, 206 mmol) and 8-bromooctanoic acid (5.46 g, 24.5 mmol) were combined and refluxed for 1.5 h. Excess SOCl$_2$ was removed by vacuum to yield a brown liquid that was dissolved in ether (20 mL) and transferred to an addition funnel. The acid chloride was added over 20 min to an ether (20 mL) solution of 2-adamantanamine hydrochloride (11.97 g, 63.8 mmol) and triethylamine (22.50 g, 222 mmol) chilled in an ice bath. The resulting slurry was stirred at 0° C. for 3 h and then overnight at room temperature. The reaction solution was added to water (75 mL) and extracted with ether (75 mL) in a separatory funnel. After washing the organic layer with 0.1 M HCl (3×75 mL), water (2×75 mL), and saturated brine (2×75 mL), the solution was dried over MgSO$_4$ and solvent removed by rotary evaporation. The off-white solid was used directly without purification for attachment to Me$_2$bpy.

Diisopropylamine (8.09 g, 79.9 mmol), n-butyl lithium (80 mmol in hexanes), and cold THF (25 mL) were combined in a 500 mL Schlenk flask at 0° C. A cold solution of 4,4'-dimethyl-2,2'-bipyridine (6.41 g, 34.8 mmol) in THF (180 mL) was added by cannula over 15 min, and was stirred for an additional 15 min. The amide was dissolved in THF (120 mL) and cannulated dropwise into the bipyridine, turning the solution from burgundy to black. After 3 h on an ice bath, the reaction was allowed to proceed overnight at room temperature. The reaction solution was transferred to a separatory funnel with water (250 mL) and extracted with ether (150 mL). The organic layer was washed with saturated NaHCO$_3$ (2×125 mL), water (3×300 mL), and saturated brine (2×200 mL). After drying with MgSO$_4$ and vacuum, a beige solid was obtained. The product was eluted as the second band by silica gel column chromatography (3:2 ethyl acetate/hexanes). Yield was 3.40 g (30.2% based on 8-bromooctanoic acid) of a pale yellow oil. $^1$H NMR (CDCl$_3$): δ 1–2 (m's), 2.20 (t, CH$_2$-amide), 2.42 (s, bpy-CH$_3$), 2.59 (t, bpy-CH$_2$), 4.09 (m), 5.79 (m), 7.21 (d, bpy 5 and 5'), 8.23 (s, bpy 3 and 3'), 8.58 (d, bpy 6 and 6').

[Ru(bpy)$_2$(bpy-C$_9$-Ad)]Cl$_2$. The ligand bpy-C$_9$-Ad (505 mg, 1.10 mmol) and cis-[Ru(bpy)$_2$Cl$_2$] (538.6 mg, 1.04 mmol) were combined with 5:1 water/ethanol (18 mL) and refluxed for 12 h. Solvent was removed under vacuum and the dark red solid was dissolved in water (60 mL). This aqueous solution was combined with a solution of NH$_4$PF$_6$ (1.20 g, 7.36 mmol) in water (20 mL) to yield an orange precipitate. The aqueous slurry was extracted with CH$_2$Cl$_2$ (75 mL); the organic layer was washed with 1 M HCl (2×50 mL), 1 M NaOH (2×50 mL), and water (2×75 mL) prior to rotary evaporation. The PF$_6^-$ salt of this ruthenium complex was purified by silica gel flash chromatography (column dimensions 30×4.5 cm) employing an eluent of 3% methanol in CH$_2$C$_2$. Pure product PF$_6^-$ salt was found in elution volumes 550–1300 mL. Further product could be obtained by running a second column on the initial 200–550 mL. Volumes 550–1300 mL were combined and dried by rotary evaporation. In order to metathesize the ruthenium complex to the Cl$^-$ salt, the purified PF$_6^-$ salt was dissolved in MeOH (10 mL) and loaded onto a CM Sepharose cation exchange column (2×13 cm). The column was washed with water (600 mL) and 25 mM NaCl (600 mL). The ruthenium complex was then eluted with 500 mM NaCl (300 mL) and dried by vacuum. The desired [Ru(bpy)$_2$(bpy-C$_9$-Ad)]Cl$_2$ was isolated from the NaCl-containing solid by repeated washings with CH$_2$Cl$_2$, followed by filtering and drying under vacuum. Yield of the dark red solid was 195 mg (20.0%). Yields of this procedure are generally 20–30%, and approached 60% with repeated column chromatography on the crude reaction mixture. $^1$H NMR (CD$_2$Cl$_2$): δ 0.8–2 (m's), 2.21 (t, CH$_2$-amide), 2.65 (s, bpy'-CH$_3$), 2.78 (t, bpy'-CH$_2$), 3.62 (m), 3.95 (m), 6.32 (m), 7.23 (m), 7.45 (m), 7.70 (m), 8.18 (m), 8.77 (s), 8.80 (s), 9.20 (m). LRMS (electrospray, positive ion) calcd for C$_{50}$H$_{57}$N$_7$ORu (M+H$^+$) m/z 874, found 874. UV-vis [λ (Δε), H$_2$O]: 206 nm (74,200), 244 (26,000), 286 (80,100), 454 (14,500).

Chiral Resolution of (±)—[Ru—C$_9$-Ad]Cl$_2$

Circular dichroism (CD) spectra were measured on samples dissolved in acetonitrile (50–100 μM) using an Aviv Model 62A DS spectropolarimeter. Chiral separation was achieved by cation exchange chromatography (SP Sephadex C-25, Fluka) using 50 mM sodium (−)—O,O'-dibenzoyl-L-tartrate as the eluent. The aqueous tartrate solution was prepared by neutralization of the acid with two equivalents of NaOH, followed by filtration to remove insoluble impurities. Racemic [Ru—C$_9$-Ad]Cl$_2$ (4 mg) was loaded onto a column (dimensions 120×3.5 cm) covered with aluminum foil to eliminate the possibility of photoracemization. Eluent flow was regulated (~1 mL/min) with a peristaltic pump. The resolution of two bands occurred after traversing an effective column length (ECL) of 2 meters. Upon separation, the Sephadex was expelled from the column with air, and the first and second bands were collected and soaked in acetonitrile to remove Ru from the dextran. The red solutions were rotary evaporated at room temperature, redissolved in water, and metathesized by ion exchange to their chloride salts. Band 1 (the first eluted fraction) had a negative rotation and was assigned the Δ absolute configuration based on the CD characteristics of similar complexes [Rutherford, T. J. et al., *Eur. J. Inorg Chem.* (1998), 11 1677–1688]. CD [λ (Δε), CH$_3$CN]: Δ-(−): 227 nm (+26), 240 (+23), 260 (−10), 278 (+134), 294 (+307), 325 (+18), 365 (+11), 424 (+19), 476 (−15); Λ-(+): 227 (−27), 240 (−23), 260 (+7), 278 (−126), 294 (+281), 325 (−17), 365 (−11), 424 (−19), 476 (+13).

K$_I$ Determination

A Hewlett Packard 8452A spectrophotometer was used to collect UV-vis data. Buffer conditions were 50 mM potassium phosphate, 100 mM potassium chloride, pH 7.4 for all protein solutions (~5 μM P450). UV-vis titrations were performed at 20° C. with stirring (500 rpm) using a Hewlett Packard 89090A stirrer/temperature controller. Λ and Δ-[Ru—C$_9$-Ad]Cl$_2$ displace little water from the ferric-aquo heme and binding results in only 30% conversion to the high-spin species, due, presumably, to the abundance of water in Ru-bound (open) structure. Thus, affinities were determined by the ability of these complexes to inhibit the low- to high-spin transition produced by camphor. Concentrated ethanolic stock solutions of camphor titrated in small aliquots (0.5–1.0 μL) into the protein solutions gave the desired range of camphor concentrations (250 nM–2 mM). The concentration of ethanol never exceeded 1% of the total volume. Apparent dissociation constants of camphor, K$_S$, were spectroscopically determined at three concentrations (0–20 μM, 99% bound) of both Ru—C$_9$-Ad isomers. K$_S$ was calculated by fitting the data to 1/ΔA vs. 1/[S], the slope of which yields K$_S$/([E]Δε) from the relationship 1/ΔA=((K$_S$/[S])+1)/([E]Δε), where ΔA is the absorbance change from the initial value, [S] is the concentration of camphor, [E] is the concentration of P450, and Δε is the difference in molar absorptivity between [Ru—C$_9$-Ad]- and camphor-bound P450. Absorbance changes were recorded at 392 and 416 nm. Values of K$_I$, the equilibrium constant between Ru-bound and camphor-bound P450, were determined for both isomers by plotting K$_S$ against the Ru—C$_9$-Ad concentration. The dissociation constants, K$_D$, of (±)—[Ru—C$_9$-Ad]Cl$_2$ were calculated based on a single-substrate binding model (FIG. 7). By definition, K$_D$=K$_{cam}$/K$_I$, where K$_{cam}$ is the dissociaton constant of camphor (in the absence of Ru-substrate), and K$_I$ is the equilibrium constant between camphor- and ruthenium-bound P450, spectroscopically determined by measuring the dissociation constant of camphor at multiple Ru concentrations. Luminescence experiments measure K$_D$ directly.

K$_D$ Determination

Emission experiments were conducted under similar conditions (20° C., buffered solutions, 5 μM in both Ru-substrate and protein). Samples were prepared in a 1-cm-pathlength quartz cuvette with a long neck fitted with a 24/40 joint and a threaded compression seal. The samples (1.5 mL) were deoxygenated by repeated cycles of vacuum followed by argon back-filling. Bubbling of the samples was avoided to minimize protein denaturation. UV-vis spectra were measured routinely before and after each luminescence measurement to verify that the protein samples had not degraded. Nanosecond emission kinetics were fit to the sum of two exponentials (I(t)=c$_0$+c$_1$exp(−k$_1$t)+c$_2$exp(−k$_2$t)) using an in-house nonlinear least-squares fitting program. Dissociation constants for both isomers were determined using the ratio of the coefficients for the fast and slow phases, c$_1$/(c$_1$+c$_2$).

Time-Resolved Emission

The excitation source for all experiments was a tunable (220–2000 nm) optical parametric oscillator (Spectra Physics, MOPO) pumped by a frequency-tripled Q-switched Nd:YAG laser (Spectra Physics, 355 nm, 350 mJ/pulse, 8-ns FWHM). The OPO output power was attenuated by passage through a polarizer; laser shots with energies differing by more than 10% from the mean value (laser pulses detected by a photodiode and selected by a discriminator, Phillips Scientific Model 6930) were rejected. Deoxygenated Ru-protein samples were excited at 470 nm, typically 2 mJ/pulse at the sample. Emission was collected 180° to the incident excitation with reflective optics (f/10), sent through a long-pass filter ($\lambda$>600 nm), and focused onto the entrance slit of an ISA double 0.1 meter monochromator. Luminescence was detected by a Hamamatsu photomultiplier tube (R928); the output signal passed through a high-speed (100 MHz) current to voltage amplifier, digitized (Sony/Tektronix digitizer, Model RTD710A), and recorded on a personal computer. Instrument response was 10 ns (FWHM). Emission kinetics data are averages of at least 250 laser shots.

Results

Figure 9:
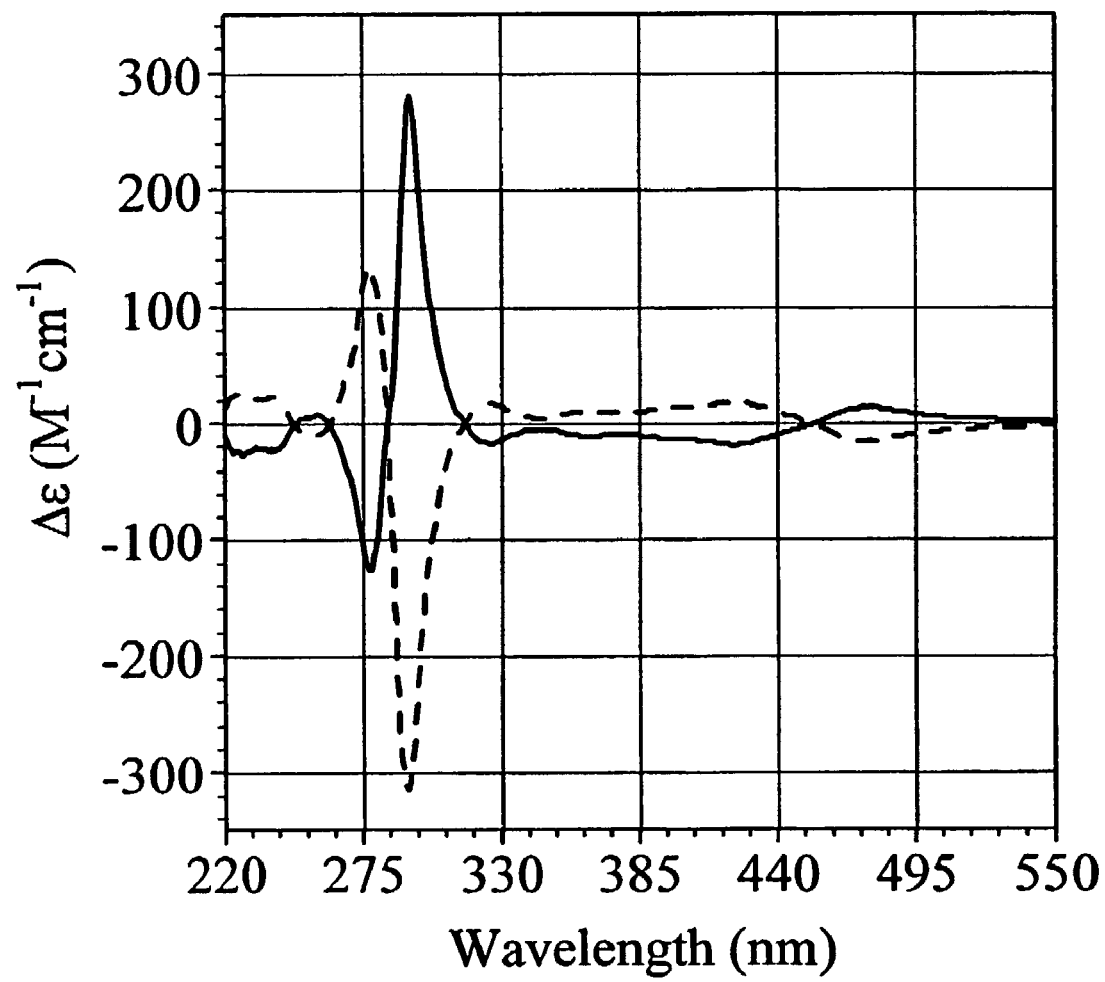
FIG. 9 shows the CD spectra of the enantiomeric forms of $[Ru(bpy)_2(bpy-C_9-Ad]^{2+}$: Δ (dotted line); Λ (solid line), as described in Example II, infra.

Resolution of racemic $[Ru-C_9-Ad]^{2+}$ was accomplished by cation-exchange chromatography using a chiral eluent, sodium (−)—O,O'-dibenzoyl-L-tartrate. The CD spectra of the $\Lambda$-(+) and $\Delta$-(−)—$[Ru-C_9-Ad]Cl_2$ isomers are shown in FIG. 9. In both cases, enantiomeric excess is >90% based on the similarity of their extinction coefficients at every wavelength (<10% deviation), as well as their similarity to published values for (±)—$[Ru(bpy)_3]Cl_2$ [Rutherford, T. J. et al., Eur. J. Inorg. Chem. (1998), 11 1677–1688]. Initial efforts to purify $[Ru-C_9-Ad]Cl_2$ in larger quantities (40 mg) and with more concentrated eluent (150 mM) were unsuccessful.

Figure 10:
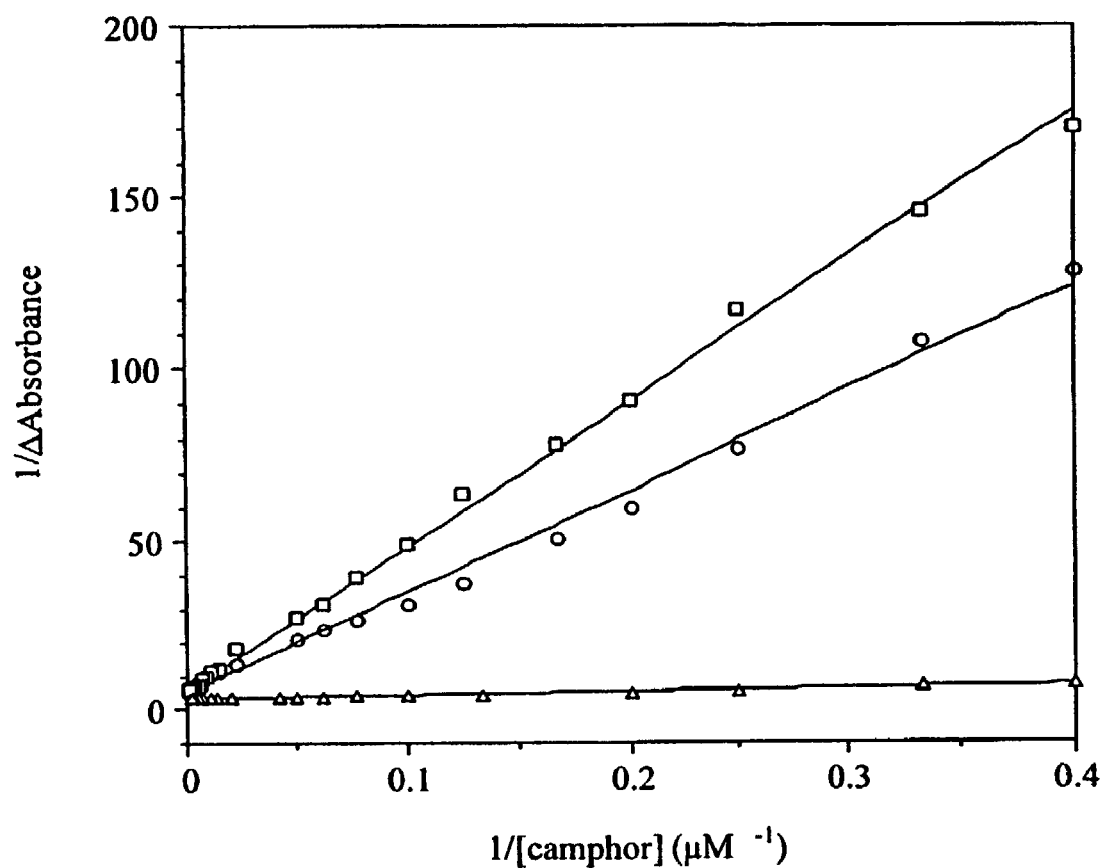
FIG. 10 illustrates the inverse absorbance changes at 392 nm as functions of inverse camphor concentration on titrating camphor into buffered (50 mM potassium phosphate, 100 mM potassium chloride, pH 7.4) solutions of ferric-aquo cytochrome $P450_{cam}$ (~5 µM), as described in Example II, infra. The triangles denote the binding of camphor to P450 in the absence of any Ru-substrate (slope=$K_S$/([P450] Δε; $K_S$=3.0±0.2 µM, [P450]=5.50 µM, $Δε_{392\,nm}$=54,000 $M^{-1}cm^{-1}$). Inhibition of camphor binding by Λ-[Ru—$C_9$-Ad]$Cl_2$ (squares, $K_S$=74±10, [P450]=5.15 µM, $Δε_{392\,nm}$=34,000 $M^{-1}cm^{-1}$ (difference between camphor- and [Ru—$C_9$-Ad]-bound P450), [Ru]=4.83 µM, $K_I$=15±1, $K_D$=200±50 nM) and Δ-[Ru—$C_9$-Ad]$Cl_2$ (circles, $K_S$=53±10, [P450]= 5.29 µM, [Ru]=4.99 µM, $K_I$=10±1, $K_D$=300±50 nM) is reflected by steeper slopes. Reported dissociation constants are averages of three titrations.
Figure 11:
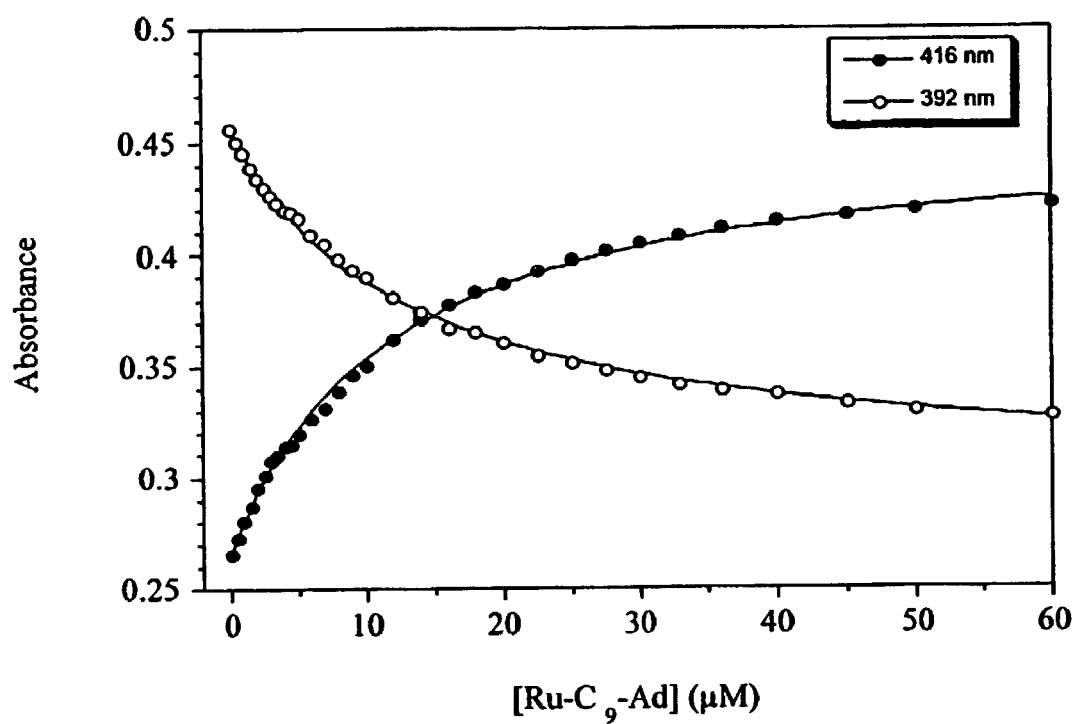
FIG. 11 shows the absorbance (open circles, 392 nm; filled circles, 416 nm) versus Ru—$C_9$-Ad concentration, as described in Example II, infra; Uv-vis data monitored the displacement of camphor from P450, and were corrected for Ru absorbance. Data are fit by the function: $A=A_0+Δε^*$ ([P450]*[Ru])/([Ru]+$K_S$), where $A_0$ is the initial absorbance, $Δε_{392}$=34,000, $Δε_{416}$=41,000 $M^{-1}cm^{-1}$, [P450]=4.67 µM; $K_S$(392 nm)=13.3, $K_S$(416 nm)=11.7. $K_D=K_{cam}K_S$=240±20 nM.

FIG. 10 shows a standard low- to high-spin conversion involving the titration of camphor into the P450 active site in the presence of $\Lambda$ and $\Delta$-$[Ru-C_9-Ad]$ isomers. The dissociation constant for camphor alone ($K_{cam}$) was found to be 3.0±0.2 μM under the experimental conditions, in good agreement with the literature value [Mueller, E. J. et al. Ed.): Twenty-five years of $P450_{cam}$ research, Cytochrome P450: Structure, Mechanism, and Biochemistry, 2nd ed., Plenum Press, New York 1995, pp. 83–124]. The steric bulk of Ru-substrates appears to preclude co-occupation of the active site with camphor, an observation supported by the P450:Ru—$C_9$-Ad crystal structure in which the adamantyl moiety binds above the heme and hydrogen bonds to Tyr 96 much like camphor [Dmochowski, I. J., et al. Proc. Natl. Acad. Sci. USA (1999), 96, 12987–12990]. UV-vis absorption measurements of Ru—$C_9$-Ad displacement show a preference for the $\Lambda$ isomer ($K_D(\Lambda)$=200±50 nM; $K_D(\Delta)$=300±50 nM). It was found empirically that displacement of camphor (100 μM camphor, 4.67 μM P450, 99% bound) by Ru-substrates yields dissociation constants with higher precision. The apparent dissociation constant, $K_D$=240±20 nM, of racemic Ru—$C_9$-Ad determined by this Ru-titration method (FIG. 11) is in excellent agreement with the predicted value ($K_D$=248 nM).

Figure 12:
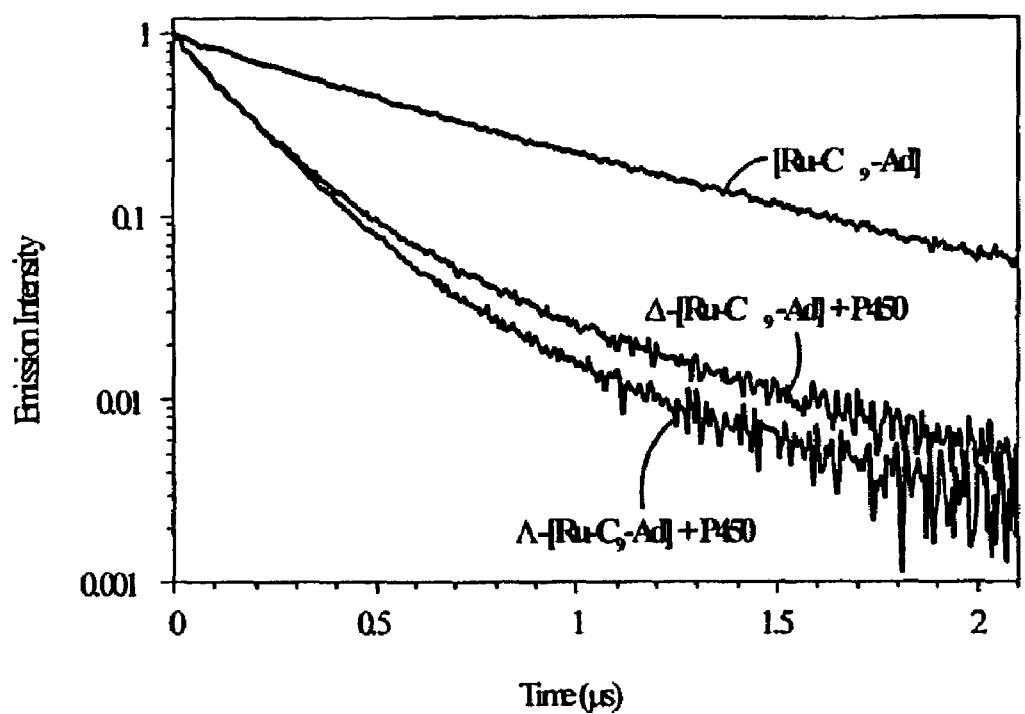
FIG. 12 depicts the kinetics traces of $[Ru—C_9-Ad]^{2+*}$ emission decay, as described in Example II, infra. A larger fraction of Λ-[Ru—$C_9$-Ad]$Cl_2$ emission (monitored at 620 nm) is quenched by P450.

Time-resolved luminescence measurements also distinguish the binding of $\Lambda$ and $\Delta$-$[Ru-C_9-Ad]$ isomers to P450 (FIG. 12). The monophasic emission decay (k=2.0×10$^6$ s$^{-1}$) of Ru—$C_9$-Ad alone in solution is nearly identical with that of the slower phases of the two solutions containing P450. This provides strong evidence that binding can be modeled as a two-state equilibrium, and in the "free" state the Ru-substrates are completely dissociated from the protein. Virtually the same quenching rate constants (k=4.5×10$^6$ s$^{-1}$) from the $\Lambda$ and $\Delta$ "bound" states indicate comparable Ru—Fe distances for the two isomers. The proportion of the decay ($\Lambda$, 87.5±0.5%; $\Delta$, 82.5±0.5%; 5 μM P450, 5 μM Ru) that is attributable to this faster (quenched) phase is clearly greater for $\Lambda$-$[Ru-C_9-Ad]$. The $K_D$ values for the enantiomers determined by time-resolved emission ($\Lambda$, 90±20; $\Delta$, 190±20 nM) are in good agreement with the $K_D$ for racemic Ru—$C_9$-Ad (150±30 nM).

Figure 13:
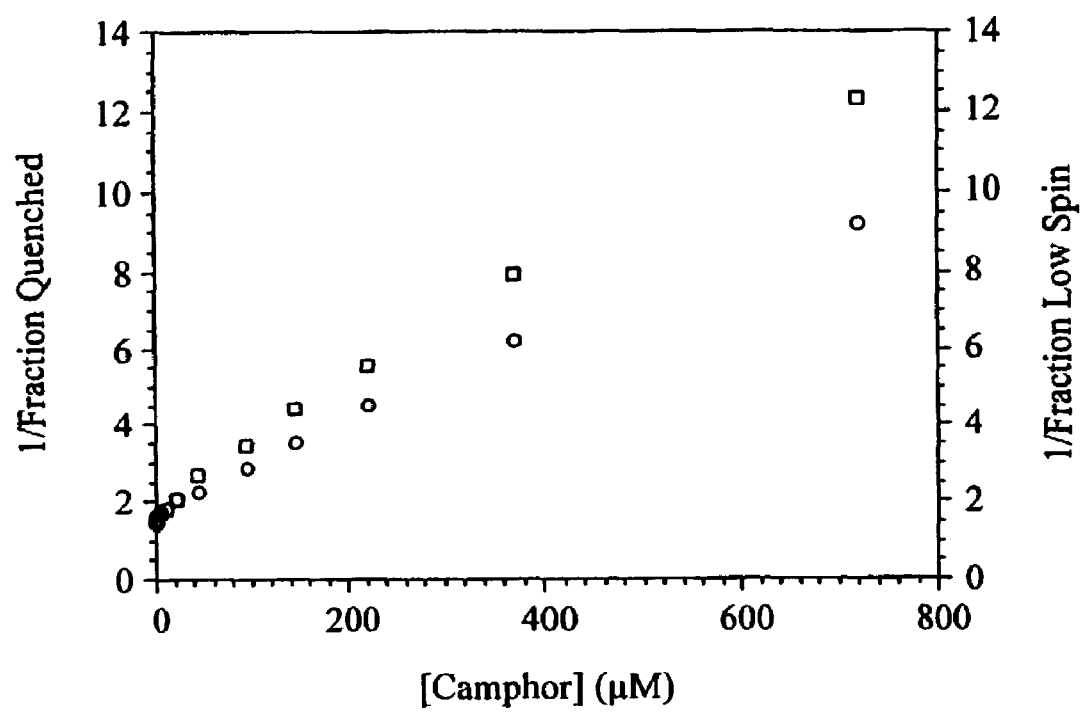
FIG. 13 shows the 1/fraction of quenched $Ru^{2+*}$ luminescence and 1/fraction of low-spin P450 as functions of camphor concentration, as described in Example II, infra.

In order to test whether the single-substrate binding model (FIG. 7) accurately describes camphor displacement of Ru—$C_9$-Ad from P450, a series of UV-vis absorption and emission experiments were performed in parallel. FIG. 13 reveals that the amounts of unbound Ru$^{2+*}$ (by luminescence) and low-spin P450 (by UV-vis) track closely during camphor titration into the 1:1 P450:Ru—$C_9$-Ad complex. Luminescence data (samples at ambient conditions, monitored at 620 μm; kinetics fit to biphasic decay give fraction Ru$^{2+*}$ quenched by P450) were collected subsequent to each UV-vis measurement. The spin state of the heme was calculated from changes in absorbance at 416 nm. Luminescence measurements report persistent Ru$^{2+*}$ binding at high camphor concentrations. However, persistent quenching of Ru$^{2+*}$ at high camphor concentrations suggests that a small fraction (% quenched−% low spin~5%) of Ru—$C_9$-Ad binds cooperatively in the P450 channel, presumably above the camphor binding site. Energy-transfer kinetics do not change during the titration, indicating that $\{Ru(bpy)_3\}^{2+}$ remains at the surface (~20 Å from the heme) in this ternary complex.

Confirmation that $\Lambda$-$[Ru-C_9-Ad]$ binds P450 with roughly twice the affinity of the $\Delta$ isomer comes from an experiment in which buffered P450 (20 μM) and (±)—$[Ru-C_9-Ad]Cl_2$ (40 μM) were centrifuged together through a size-selective membrane (Centricon, YM-10). CD measurement showed that the Ru-substrate effluent (23 μM, in good agreement with the dissociation constant) was enantiomerically enriched by 15% with the $\Delta$ (more weakly bound) isomer. In the absence of P450, no enantiomeric enhancement was found to occur during filtration. Thus, of the 17 μM Ru—$C_9$-Ad remaining bound to the enzyme, 10.2 μM corresponded to $\Lambda$ and 6.8 μM to the $\Delta$ isomer. The ratio of the concentrations of bound isomers ($\Lambda/\Delta$~1.5) is in reasonable agreement with the corresponding $K_D$ ratio ($\Delta/\Lambda$~2).

Discussion

Sodium (−)—O,O'-dibenzoyl-L-tartrate proved much less efficient at resolving (±)—$[Ru-C_9-Ad]Cl_2$ (ECL=200 cm) than reported for the model compound $(Ru(bpy)_2(Me_2bpy)]Cl_2$ (ECL=70 cm) [Rutherford, T. J. et al., Eur. J. Inorg. Chem. (1998), 11 1677–1688], presumably due to interference from the long alkyl substituent. Chiral ruthenium polypyridyl compounds have been synthesized directly by starting with one of the enantiomers of $[Ru(bpy)_2(CO)_2]^{2+}$ [Rutherford, T. J. et al., Eur. J. Inorg. Chem. (1998), 11 1677–1688]. Addition of the third bipyridyl ligand occurs with stereoretention if the temperature, solvent, and ligand concentration are carefully controlled [Fletcher, N. C. et al., J. Chem. Soc. Dalton (1998), 1 133–138]. This method would seem preferable to chiral separations of functionalized $[Ru(bpy)_2(bpy')]Cl_2$ compounds, which required 2–3 weeks for purification of milligram quantities of material.

That $K_D$(energy transfer)<$K_D$(UV-vis) reflects subtle, method-dependent differences in the quantification of Ru-substrate binding. Nonspecific binding of Ru—$C_9$-Ad to the enzyme will affect the Ru$^{2+*}$ emission decay profile, owing to energy transfer to the heme, but will not perturb the UV-vis spectrum if camphor is in place at the active site. Interestingly, when the Ru—$C_9$-Ad concentration exceeds that of P450, the luminescence results begin to deviate from predictions based on a single-substrate binding model. Energy-transfer experiments reveal that when [Ru]>>

[P450], at least four equivalents of Ru—C$_9$-Ad associate with the enzyme (5 μM P450, 50 μM Ru; 20 μM Ru quenched at ~20 Å from the heme). In fact, the P450 interior is greatly expanded in this open form (FIG. 7) and should permit orientations of Ru—C$_9$-Ad different from that found in the crystallized complex.

An electrostatic map of the protein surface indicates that the entrance to the substrate channel is neutral, favoring hydrophobic rather than electrostatic interactions in recruiting {Ru(bpy)$_3$}$^{2+}$ to this region, especially at high ionic strengths. Evidence of the dominance of hydrophobic interactions is the finding that bipyridyl-substituted adamantane itself, before ruthenation, strongly binds P450. It also is of interest that hydrophobic interactions appear to play a role in certain stereoselective bimolecular electron-transfer reactions between metalloproteins and inorganic complexes [Sakaki, S. et al, *Inorg. Chem.* (1989) 28, 4061–4063; Sakaki, S. et al., *J. Chem. Soc. Dalton Trans.* (1991) 4, 1143–1148;Pladziewicz, J. R. et al., *Inorg. Chem.* (1993) 32, 2525–2533].

Experiments with other Ru-linked moieties [Wilker, J. J. et al. *Angew. Chem. Int. Ed.* (1999), 38, 90–92; Dmochowski, I. J., et al. *Proc. Natl. Acad. Sci. USA* (1999), 96, 12987–12990] indicate that the terminal group moderately influences the overall affinity of the Ru-substrate for P450. (Ru-adamantane compounds bind with 3-fold higher affinity than Ru-(ethyl benzene) analogs, and 9-fold higher affinity than unsubstituted Ru-alkyl chains). A comparable effect ($K_D$ increases 9-fold) is observed when short linkers connecting the ethyl benzene to the photosensitizer prohibit optimal positioning of the substrate within the active-site pocket [Dmochowski, I. J., et al. *Proc. Natl. Acad. Sci. USA* (1999), 96, 12987–12990]. Sufficient chain length is especially critical for imidazole-terminated compounds, where the ability to bind the iron is requisite for association. The modest 2-fold discrimination of Λ and Δ-[Ru—C$_9$-Ad] provides strong evidence that interactions near the protein surface are of lesser importance than the shape complementarity and hydrophobicity of the Ru-substrate in binding to the enzyme.

Enantiospecific binding indicates that noncovalent interactions over 10 Å from the active site impact substrate selection even when the channel is open, as must occur during entrance and egress of natural substrates. Similar long-range secondary interactions also influence the binding of benzenesulfonamide ligands to carbonic anhydrase [Boriak, P. A. et al., *J. Med. Chem.* (1995) 38, 2286–2291]. Based on the P450:Ru—C$_9$-Ad crystal structure [Dmochowski, I. J., et al. *Proc. Natl. Acad. Sci. USA* (1999), 96, 12987–12990], which confirms the ability of P450 to accommodate large substrates, and identifies hydrophobic interactions of the bipyridyl groups with Phe 193 and Tyr 29 (FIG. 7), it can be inferred that aromatic stacking plays an important role in chiral discrimination. Aromatic residues at the mouth of the P450 channel have been implicated previously in the recognition of hydrophobic substrates [Raag, R. et al., *Biochemistry* (1993) 32, 4571–4578].

Sub micromolar affinities, protein specificity, reversible binding, and synthetic versatility make sensitizer-linked substrates ideal for probing P450 active sites. Employing UV-vis and time resolved luminescence measurements, it was found that P450 has a 2-fold preference for Λ-[Ru—C$_9$-Ad]Cl$_2$. Emission experiments, especially with highly luminescent {Ru(bpy)$_3$}$^{2+}$ complexes, are particularly sensitive and convenient for measuring substrate binding. It is well known that the chirality and shape of substrate pocket promote enantio-and regioselective P450 catalysis. It was demonstrated in this example that long-range interactions with a pendant metal complex also affect substrate binding at the active site of the enzyme.

EXAMPLE III

This Example Provides Data for Sensitizer-Linked Substrate Molecules as Viable Substrates for Cytochrome P450$_{cam}$

[Ru—C$_9$-Ad]Cl$_2$, despite opening the P450 cavity, is a viable substrate, as shown by this example using electrospray mass spectroscopy assay. The rate and efficiency of [Ru—C$_9$-Ad]Cl$_2$ hydroxylation is compared to the untethered analog, 2-adamantantyl acetamide (FIG. 14). Resonance Raman spectroscopy of Fe$^{2+}$—CO substrate complexes has been shown previously to be a sensitive reporter of the heme environment (O. Bangcharoenpaurpong, et al., *J. Chem. Phys.* 87, 4273–4284 (1987); C. Jung, et al., *Biochemistry* 31, 12855–12862 (1992); T. Uno, et al., *J. Biol. Chem.* 260, 2023–2026 (1985); A. V. Wells, et al., *Biochemistry* 31, 4384–4393 (1992)), and solution measurements comparing the binding of Ru—C$_9$-Ad to adamantane agree with the crystal structure and substrate turnover results. Experiments attempting P450-mediated Ru—C$_9$-Ad hydroxylation with steady-state photolysis suggested that turnover may be occurring in very low yields. In addition, a ternary complex involving P450, camphor, and Ru—C$_{10}$ (FIG. 14) has been characterized by time-resolved emission measurements (while (1) competes with camphor for the P450 active site, (2) is able to share the pocket with camphor. 2-adamantylacetamide (2) is analagous to compound (1), without the Ru-tether; (2) induces a full low to high spin conversion at the heme). By comparing camphor hydroxylation rates in the ternary complex to natural camphor catalysis, the enzymatic activity of this previously uncharacterized, but potentially biologically relevant open conformation of the enzyme, was probed.

Materials and Methods

General

[Ru—C$_9$-Ad]Cl$_2$ (1), 2-adamantylacetamide (2), and [Ru—C$_{10}$]Cl$_2$ (3) were synthesized as described in Example I. P450, PdR, and Pd were expressed and purified according to literature procedures (J. A. Peterson, et al., *J. Biol. Chem.* 265, 6066–6073 (1989); P. W. Roome, et al., *J. Biol. Chem.* 258, 2593–2598 (1983); C. A. Tyson, et al., *J. Biol. Chem.* 247, 5777–5784 (1972); M. J. Hintz, et al., *J. Biol. Chem.* 257, 14324–14332 (1982)). NADH and adamantane were purchased from Sigma Chemical Co. (St. Louis, Mo.) and used without further purification. A miniature oxygen electrode was purchased from Microelectrodes, Inc. (Microelectrodes, Inc., Bedford, N.H.) and the voltage output calibrated with solutions containing 0%, 21% (ambient), and 100% dioxygen.

UV-vis titrations were performed using a Hewlett Packard 8452A spectrophotometer and a Hewlett Packard 89090A (Hewlett Packard, Palo Alto, Calif.) stirrer/temperature controller, at 20° C. with stirring (500 rpm). Time-resolved emission experiments and data analysis with Kinfit, Decon, and MATLAB were performed as described previously (Example II), with the exception that the P450:Ru—C$_{10}$: camphor ternary complexes were not degassed during the titration or subsequent laser experiments.

Resonance Raman Spectroscopy on P450 Fe$^{2+}$—CO Substrate Complexes.

Samples (200 μL, 100 μM P450 in standard KPi/KCl buffer, substrate concentration=1 mM) were prepared in glass NMR tubes fitted with a rubber septum. The solutions were gently bubbled with CO for several minutes before adding a spatula tip of dithionite. Formation of the $Fe^{2+}$—CO complex was verified by UV-vis ($\lambda_{max}$=446 nm). Samples were excited at 441 nm with a HeCd laser (Liconix, Sunnyvale, Calif., model 424ONB, 40 mW), and the Raman scatter was focused using longitudinal and transverse collection optics onto a double spectrometer (SPEX 1403, 0.85 m) interfaced to a PC via the SPEX MSD2 module. The signal was collected using a PMT (Photomultiplier tube) (Hamamatsu R955, Hamamatsu City, Japan) powered by Pacific Precision Instruments (1100 V). The sample control unit, photon counter, amplifier/discriminator, and buffered interface were all from EG&G Instruments (Oak Ridge, Tenn.).

Hydroxylation of [Ru—$C_9$-Ad]$Cl_2$ with NADH/PdR/Pd/P450.

Figure 15:
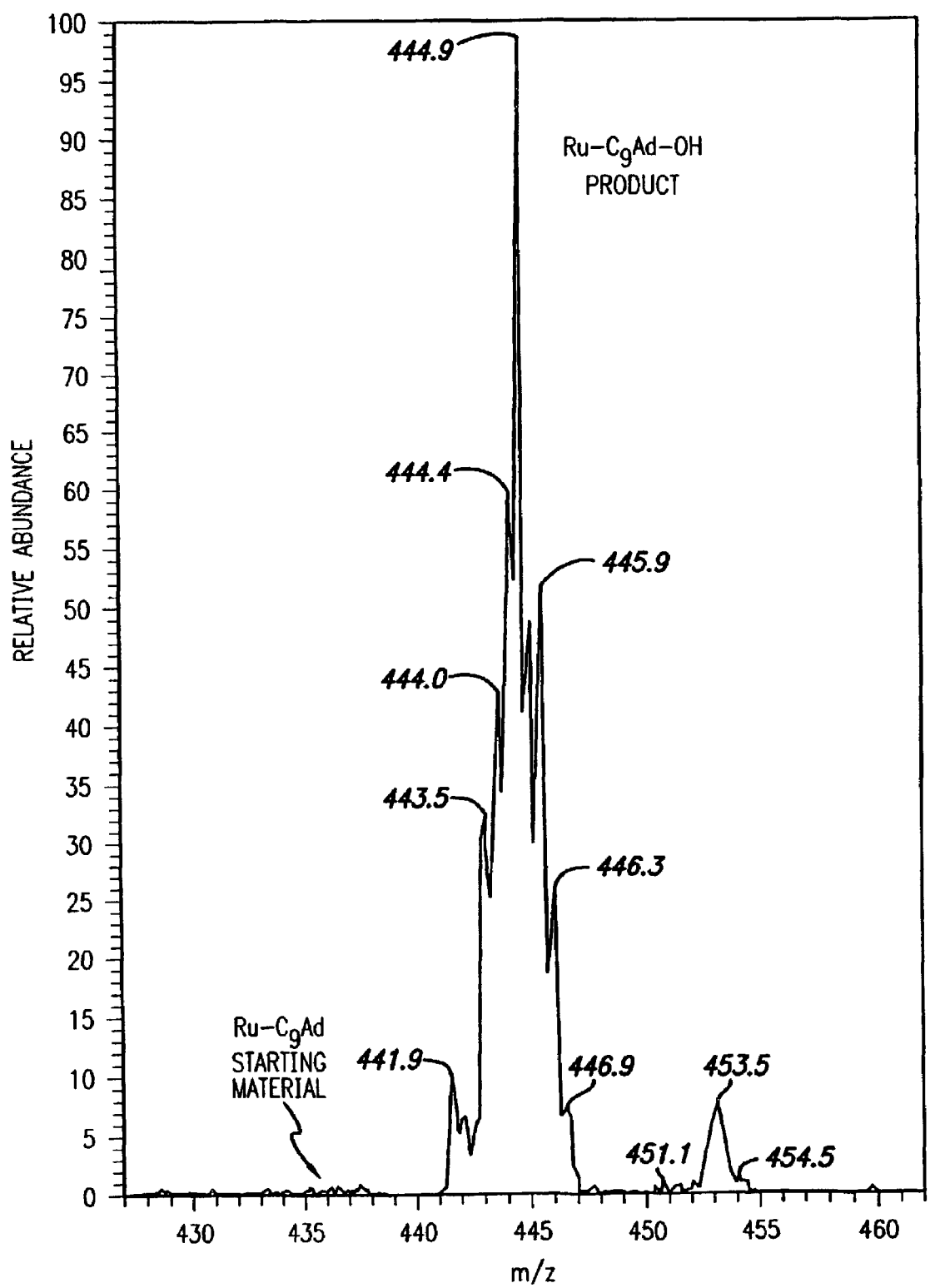
FIG. 15. ESI mass spectra showing the doubly charged starting material, $[Ru—C_9-Ad]^{2+}$ barely visible on the left, and the conversion to products, $[Ru—C_9-Ad-OH]^{2+}$, on the right.

A 4 mL solution (20 mM potassium phosphate buffer, 100 mM KCl, pH=7.4) was prepared containing 1 μM P450, 1 μM PdR, 10 μM Pd, 20 μM (Ru—$C_9$-Ad]$Cl_2$, and 200 μM NADH ($\epsilon$=6.22 $M^{-1}$ $cm^{-1}$ @340 nm). The consumption of NADH was monitored at 340 nm by UV-vis spectroscopy. Once >95% of the NADH was consumed, the reaction was quenched by the addition of 40 μL of a 1 M ethanolic camphor solution (ratio camphor/[Ru—$C_9$-Ad]$Cl_2$~500) to displace [Ru—$C_9$-Ad]$Cl_2$ from P450 and rapidly consume any remaining NADH. This solution was concentrated by centrifugation (Centricon, YM-10) to a minimum volume, and an additional milliliter of camphor-saturated phosphate buffer was added to the protein and centrifuged to remove any remaining Ru. The flow-through, containing hydroxylated [Ru—$C_9$-Ad]$Cl_2$, camphor, and buffer was rotary evaporated to dryness. Two cycles of acetonitrile (5 mL) addition, decanting, and rotary evaporation were performed to separate the buffer salts from the ruthenated species. The ruthenium concentration was quantified by UV-vis ($\epsilon_{456}$=14,500 $M^{-1}$ $cm^{-1}$). [Ru—$C_9$-Ad-OH]$Cl_2$ was diluted to 10 μM in acetonitrile, and its purity confirmed by electrospray mass spectroscopy (FIG. 15).

Attempted Light-Activated Hydroxylation of [Ru—$C_9$-Ad].

Steady-state visible irradiation of a 4 mL solution (20 mM potassium phosphate buffer, 100 mM KCl, pH=7.4) containing 10 μM P450, 10 μM [Ru—$C_9$-Ad]$Cl_2$, and 100 μM catalase was performed for two hours. The Ru-complex was extracted as described above and analyzed by ESI.

Electrospray Mass Spectroscopy.

Samples (~10 μM) contained in a 500 μL Hamilton syringe were injected at a rate of 5 μL/min into the LcQ (Finnigan Mat); typical runs required less than 100 μL per sample, and data sets were averages of 50 scans.

Calibration of ESI (Electrospray Ionization).

Figure 16:
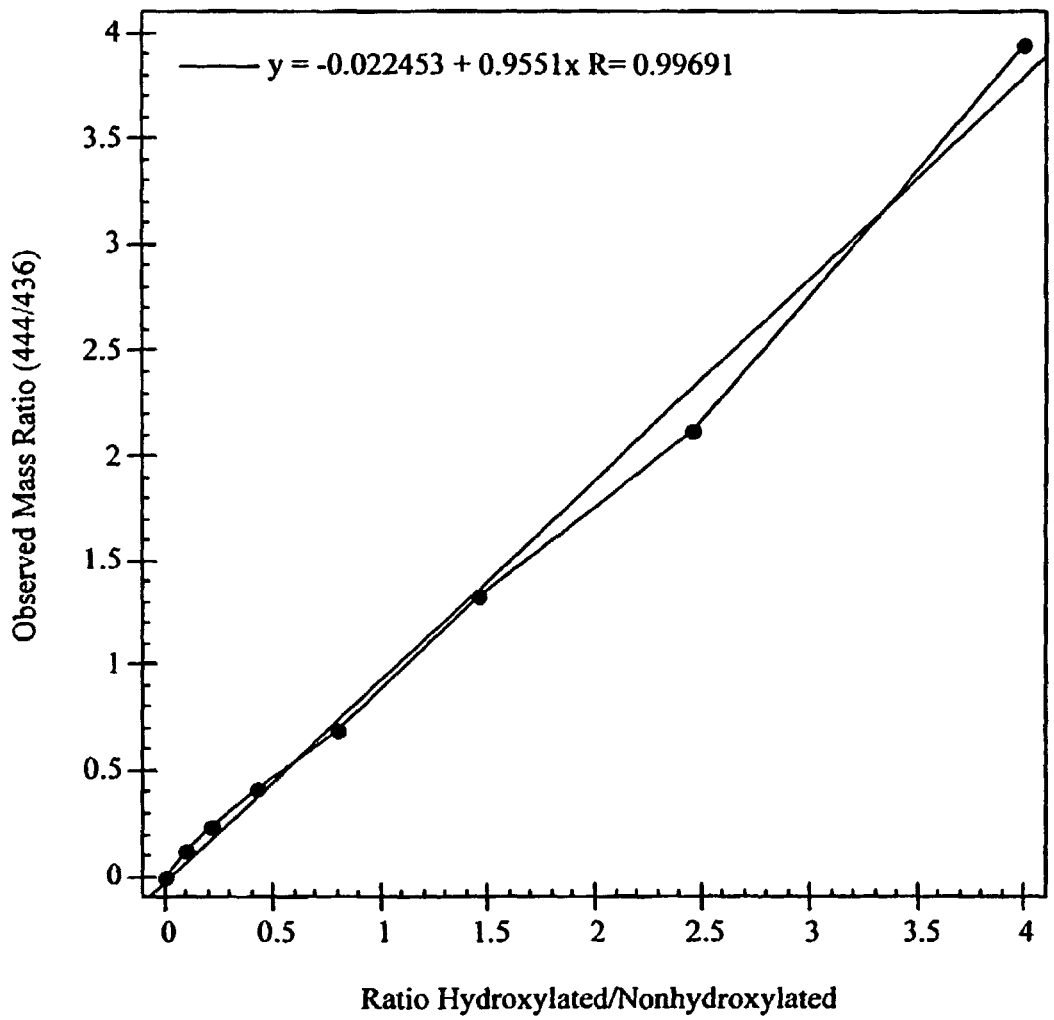
FIG. 16. Calibration line showing the relationship between the ratio of $[Ru—C_9-Ad]^{2+}/[Ru—C_9-Ad-OH]^{2+}$ in solution to the relative ionization intensity of both cations in the ESI.

A 10 μM stock solution of [Ru—$C_9$-Ad]$Cl_2$ in acetonitrile was combined with 10 μM [Ru—$C_9$-Ad-OH]$Cl_2$ in varying proportions (4:1 to 1:4). Each solution was injected three different times, with intermediary blank runs of pure acetonitrile. Relative peak intensities were determined using analysis software, which deconvolved the spectra to assign one singly charged peak to each compound. A calibration graph (FIG. 16) was generated from this data which showed that the ionization efficiency of Ru—$C_9$-Ad and Ru—$C_9$-Ad-OH were identical (slope =0.96) within experimental error. This information was crucial in quantifying hydroxylated product yields relative to starting material in the analysis of subsequent turnover experiments.

Monitoring $O_2$/NADH Consumption.

The oxygen electrode was calibrated at 20° C. (linear response with [$O_2$], 0–100% $O_2$), and connected to a LeCroy oscilloscope interfaced to a PC using freely available LeCroy software (LeCroy, Chestnut Ridge, N.Y.). The $O_2$ electrode (3 mm diameter with Teflon casing) was pushed through a septum, which formed an airtight seal with the mouth of a standard 1 cm pathlength cuvette. The quality of the seal was tested by filling the cuvette with deoxygenated buffer and monitoring oxygen concentration; insignificant leakage was observed during 1 hour. All UV-vis experiments were conducted with stirred samples at 20° C. Kinetics experiments were run in kinetics mode (Biosym) with 1 mL samples containing 1 μM PdR, 10 μM Pd, 1 μM P450, and either 50 μM [Ru—$C_9$-Ad]$Cl_2$ or 1 mM adamantane. Experiments were initiated upon addition of 200 μM NADH, and absorbance at 340 nm was measured simultaneously with $O_2$ consumption.

Enzyme Turnover of Camphor.

A 4 mL solution (20 mM potassium phosphate buffer, 100 mM KCl, pH=7.4) was prepared containing 1 μM P450, 1 μM PdR, 10 μM Pd, 400 μM camphor, and 200 μM NADH ($\epsilon$=6.22 $M^{-1}$ $cm^{-1}$ at 340 nm). The consumption of NADH was monitored at 340 nm by UV-vis spectroscopy and $O_2$ consumption monitored with the microelectrode. Once all of the NADH was consumed, a known amount of 3-endo-bromo-camphor was added, and the mixture was extract three times with an equal volume of methylene chloride. The organic extract was concentrated by evaporation and analyzed by GC.

GC-MS.

Samples were analyzed by a VG 7070E mass spectrometer in line with an HP 5700 gas chromatograph equipped with a 30-m HP-1 capillary column (0.25 mm inner diameter, film thickness 0.25 μm) and interfaced with a PC. The organic extract was loaded onto the column at 40° C., and eluted with a standard program (40° C.–150° C., 40° C./min; 150° C.–250° C., 15° C./min).

Results

Resonance Raman Studies of P450 $Fe^{2+}$—CO:Substrate Complexes

Figure 17:
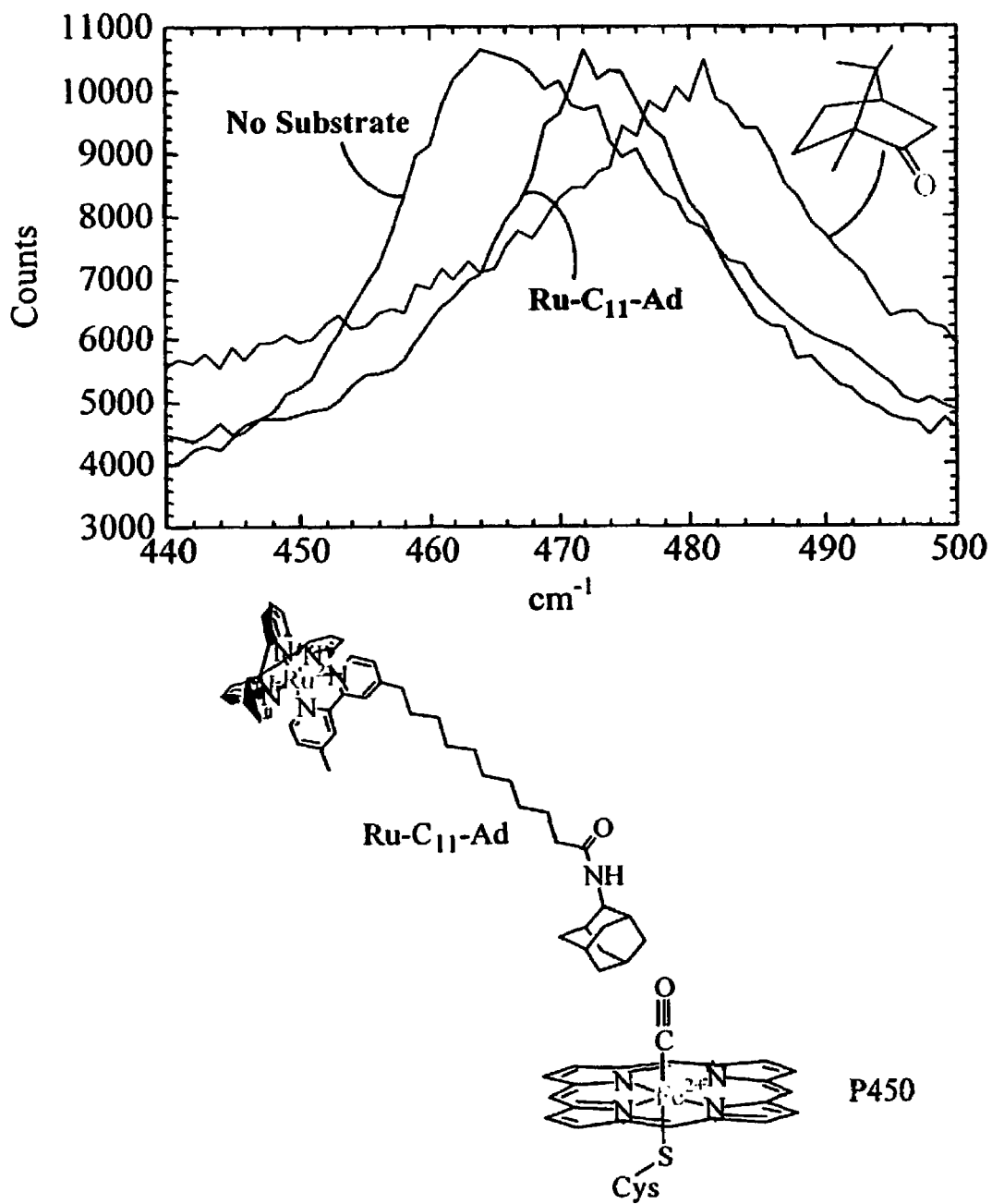
FIG. 17. Variation of the resonance Raman $Fe^{2+}$—(CO) stretching mode with substrate. Spectra for Ru—$C_{11}$-Ad, Ru—$C_9$-Ad, and adamantane differ little, varying by only a few $cm^{-1}$ in their peak maximum.

As shown in FIG. 17 and as was reported previously (C. Jung, et al., *Biochemistry* 31, 12855–12862 (1992)), the CO-stretching mode in the P450-carbon monoxide complex is quite sensitive to the nature of the substrate. This indicates a direct interaction between the bound CO and the substrate molecule which agrees with IR absorption work of O'Keefe et al. (D. H. O'Keefe, et al., *Biochemistry* 17, 5845–5852 (1978)). Camphor-bound $Fe^{2+}$—CO P450 has $v_{CO}$~1940 $cm^{-1}$ and camphor-free has two bands at ~1942 $cm^{-1}$ and 1963 $cm^{-1}$ which have been assigned to a bent and upright geometry, respectively. The Fe—(CO) stretching frequency differs by 4 $cm^{-1}$ between Ru—$C_{11}$-Ad, Ru—$C_9$-Ad, and adamantane, suggesting that these substrates bind with slightly increasing proximity to the heme (FIG. 18). The fact that these stretching frequencies (472–476 $cm^{-1}$) are approximately midway between those found for substrate-free and camphor-bound suggests that CO is bound mostly upright in solution. The similarity between the binding modes of Ru-Ad compounds and adamantane in solution agrees with the X-ray structure determination.

Kinetics and Efficiency of Ru—$C_9$-Ad and 2-Adamantylacetamide Hydroxylation

Figure 19:
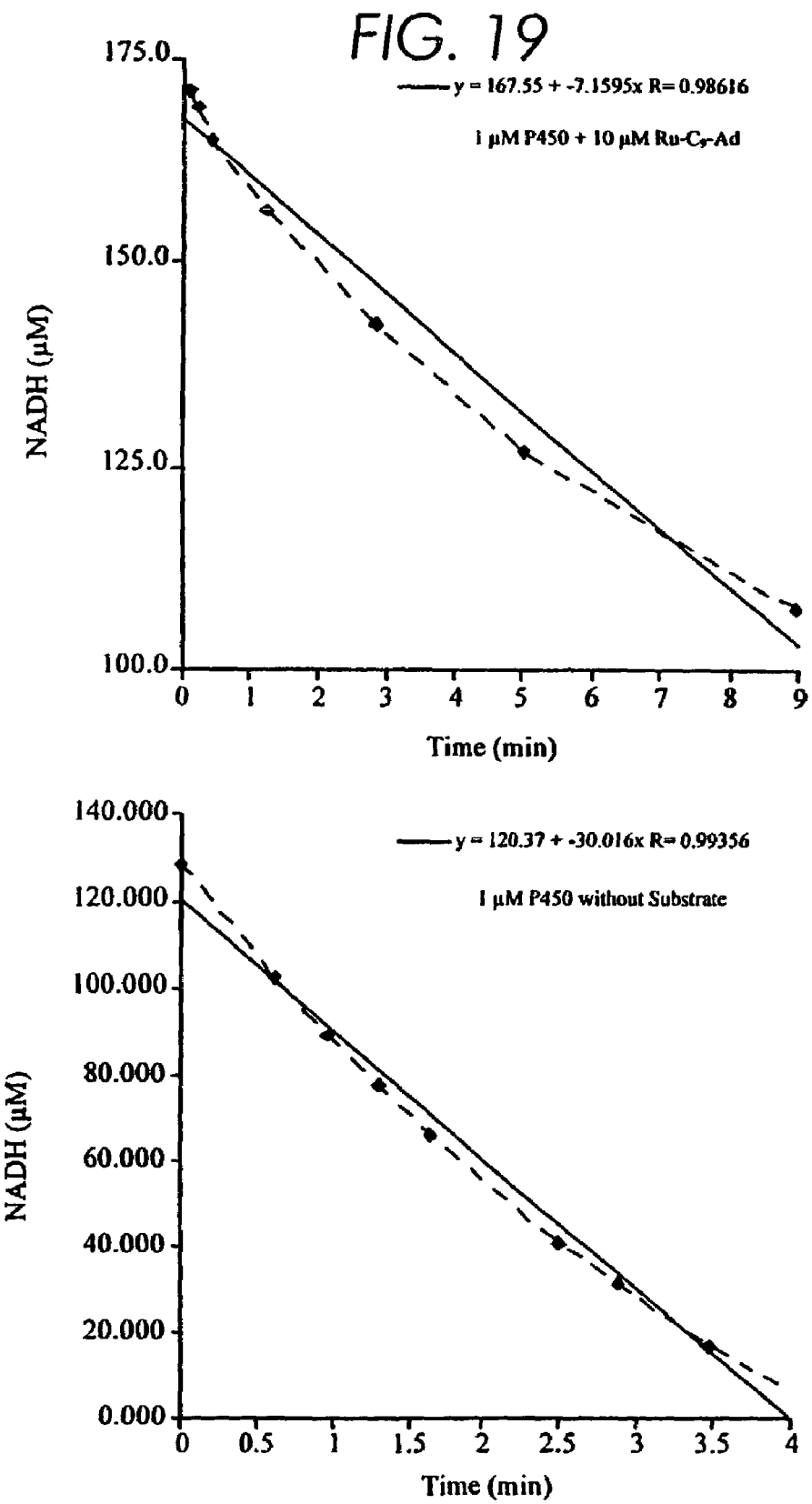
FIG. 19. Top: Rate of NADH consumption in turnover studies of Ru—$C_9$-Ad. The slope indicates a rate of 8 µmol NADH/min/µmol P450. Bottom: Control experiment showing the rate of NADH consumption (~30 µmol NADH/min/µmol P450) in the absence of any substrate.

By supplying electrons to P450 via the natural route (NADH—>PdR—>Rd—>P450), the rate of Ru—$C_9$-Ad hydroxylation was found to be 10±2 µmol NADH/min/µmol P450 (FIG. 19). The error in the rate measurement stemmed mostly from the choice of data points—the rate appeared fastest at the earliest time points, as is generally observed for enzyme-mediated catalysis. This rate is remarkably slower than the consumption of NADH in the absence of any substrate (30 µmol NADH/min/µmol P450, FIG. 19). These data suggest that P450 oxidase chemistry (conversion of $O_2$ into water) outcompetes hydroxylation of Ru—$C_9$-Ad threefold. In a control experiment with NADH/PdR/Pd and no P450, the rate was found to be roughly 1 µmol NADH/min, thus most of the observed NADH decay may be attributed to P450-mediated catalysis. Product assays indeed show that the yield of hydroxylated product, Ru—$C_9$-Ad-OH, is only 10% based on the starting NADH concentration. Based on the competing oxidase activity, the maximum predicted yield of hydroxylated product would be ~25%. Thus, a 10% product yield is effectively a 40% yield based on the background oxidase activity.

The rate of 2-adamantylacetamide (2) hydroxylation was found to be 90±20 µmol NADH/min/µmol P450, in good agreement with the literature value for 1-adamantylacetamide (~110 µmol NADH/min/µmol P450) (J. J. D. Voss, and P. R. Ortiz de Montellano, J. Am. Chem. Soc. 117, 4185–4186 (1995)). This hydroxylation rate is roughly ten times faster than that of Ru—$C_9$-Ad, which is not surprising in light of the fact (2) produces a 95% spin conversion of the heme, compared to only 25% for Ru—$C_9$-Ad. The hydroxylation of Ru—$C_9$-Ad may also be slowed by the conformational changes observed in Asp 251 and Thr 252, which could affect the delivery of protons leading to dioxygen scission. The ratio of product formation/NADH consumption with 2-adamantylacetamide is only 47±3%, however, which is half that reported for 1-adamantylacetamide (J. J. D. Voss, and P. R. Ortiz de Montellano, J. Am. Chem. Soc. 117, 4185–4186 (1995)). Thus, these results show that hydroxylation of the model compound, 2-adamantylacetamide, while much faster than Ru—$C_9$-Ad, occurs with roughly the same efficiency when the background oxidase activity has been subtracted.

Light-Activated Ru—$C_9$-Ad Hydroxylation

Figure 20:
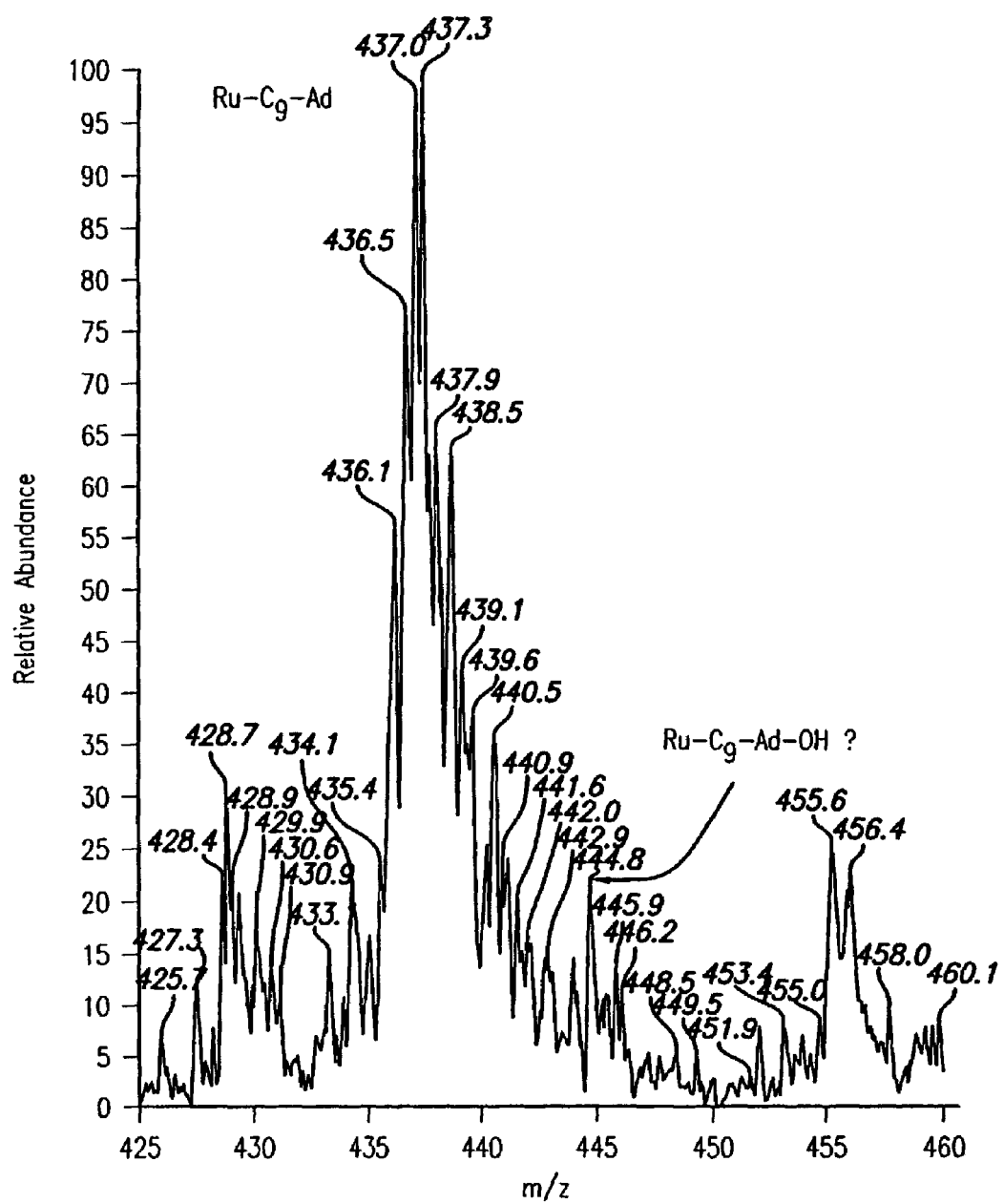
FIG. 20. Electrospray mass spectrum showing a possible oxidized Ru—$C_9$-Ad product isolated after photolysis of the P450:Ru—$C_9$-Ad complex. Zooming in on this species shows it is doubly charged and has a similar profile to the spectrum of hydroxylated Ru—$C_9$-Ad, shown in FIG. 4.4.

Having established that Ru—$C_9$-Ad turnover is possible via the biological electron transfer route, numerous attempts were made to effect enzyme turnover through steady-state visible irradiation of P450:Ru—$C_9$-Ad in the presence of para-methoxydimethylaniline and dioxygen. Precautions were taken to minimize photodegradation: a 450 nm cutoff filter was used to shield the sample from UV light, and most experiments were conducted at 4° C. to minimize sample heating and to decelerate P420 formation. In addition, experiments were conducted in the presence of catalase to eliminate $H_2O_2$ which would both damage the enzyme and hydroxylate adamantane, giving a false positive result. Preliminary results suggested that oxidized products are formed in this reaction (FIG. 20).

Figure 21:
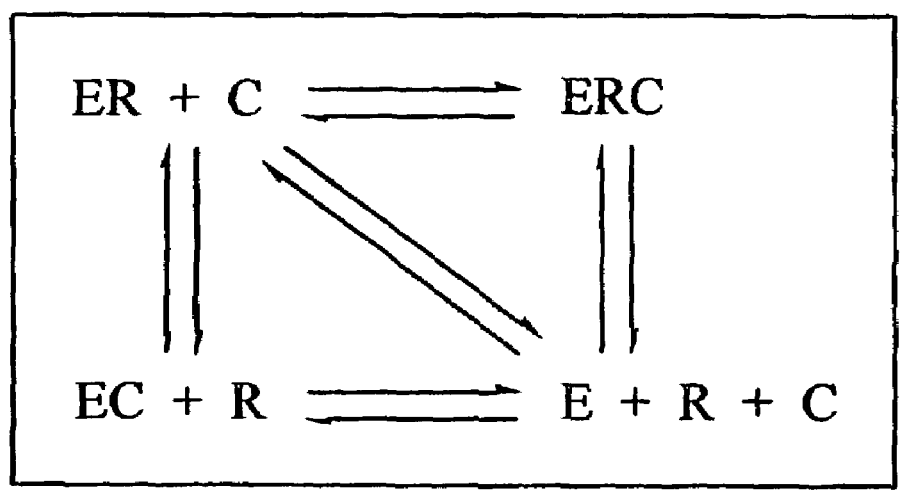
FIG. 21. A two substrate, ternary binding model for the P450 (E):camphor (C): Ru—$C_{10}$ (R) system.

Energy-Transfer Measurements Identifying a P450:Camphor:Ru—$C_{10}$ Ternary Complex Titration of camphor into a stoichiometric (5 µM) solution of P450 and Ru—$C_{10}$ was monitored by UV-vis and energy-transfer measurements, as described in Examples I and II. The binding of camphor to this P450:Ru complex ($K_D$=3.6±0.2 µM) is virtually the same as that observed for P450 alone ($K_D$=3.1±0.2 µM, Chapter 3) (E. J. Mueller, et al., in Cytochrome P450: Structure, Mechanism, and Biochemistry, 2nd edn P. R. Ortiz de Montellano, Ed. (Plenum Press, New York, 1995) pp. 83–124). Additionally, a full low-to-high spin conversion of the heme group is observed upon camphor titration. These results indicate that Ru—Clo does not perturb camphor binding at the active site. Confirmation of ternary complex formation came from $Ru^{2+*}$ decay profiles at varying camphor concentrations which showed only modest changes in the fraction of quenched $Ru^{2+*}$ emission. The "two-substrate ternary binding model" is shown in FIG. 21.

Figure 22:
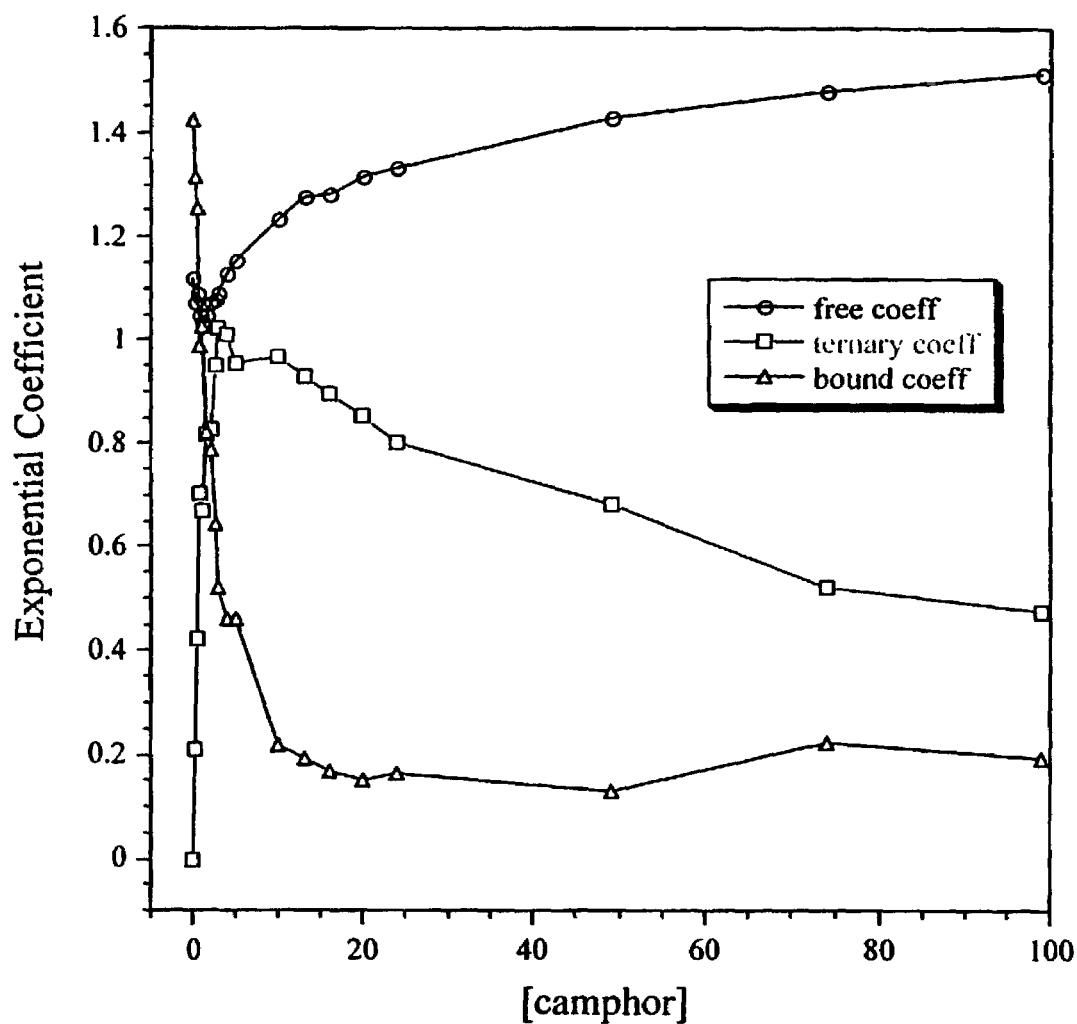
FIG. 22. The coefficients corresponding to the three different states of Ru (free, bound to P450 alone, or bound in the ternary complex) as a function of camphor concentration. The rate of decay, $k_d$, of unbound $Ru^{2+*}$ in aerated solution was determined: $k_d=2.5\times10^6$ s$^{-1}$. The rate of $Ru^{2+*}$ decay when bound to P450 was found to be $k_{P450}=9.8\times10^6$ s$^{-1}$. Finally, the $Ru^{2+*}$ emission is considerably longer-lived in the ternary complex, decaying with the rate constant $k_{tern}=7.8\times10^6$ s$^{-1}$. The relative percentage of each component can be calculated by dividing one coefficient by the sum of all of the coefficients.
Figure 22A:
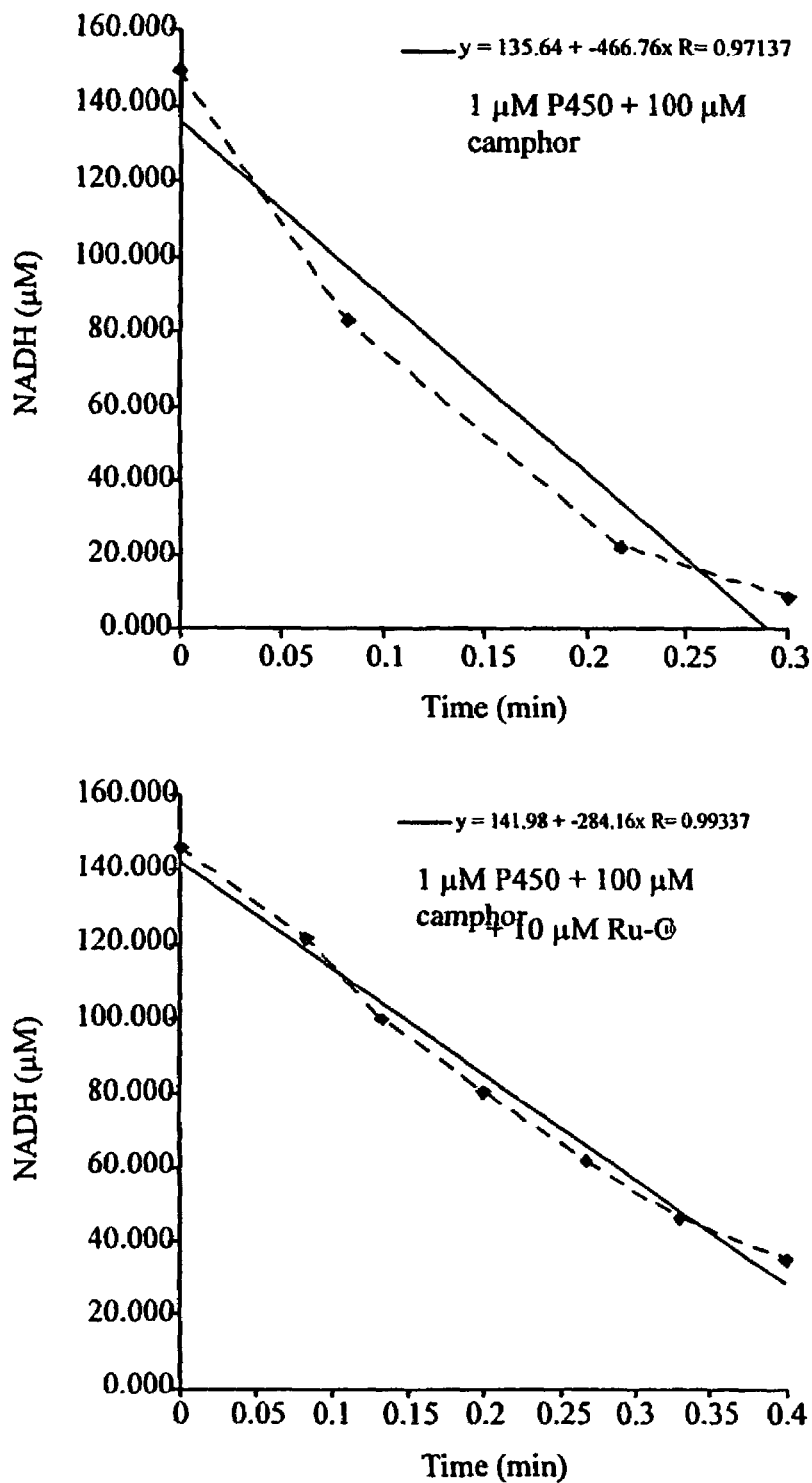
FIG. 22A. Top: Rate of NADH consumption in the complex between P450 (1 µM) and camphor (1 mM). The initial decay rates were typically ~600 µmol NADH/min/µmol P450. Bottom: Rate of NADH consumption in the complex between P450 (1 µM), camphor (100 µM) and Ru—C$_{10}$ (10 µM). The initial decay rates were typically ~300 µmol NADH/min/µmol P450.

The persistence of roughly 25% bound (quenched) [Ru—$C_{10}$]$^{2+*}$ at high camphor concentrations represents half of the originally bound Ru (~50%, $K_D$~2 µM), and indicates that the affinity of Ru—$C_{10}$ for the P450:camphor complex ($K_D$~10 µM) is not greatly different than for P450 alone. The presence of three distinct quenching processes became evident upon fitting the emission profile to a tri-exponential decay; constraining the fit to three distinct rate constants improved the fitting considerably and gave the consistently best chi$^2$ values. Weighting the relative coefficients gave the percentage of Ru—$C_{10}$ in each phase (FIG. 22).

Kinetics and Efficiency of Camphor Hydroxylation in the Ternary Complex

The rate of NADH consumption was found to be ~600 µmol NADH/min/µmol P450, in good agreement with literature values (W. A. Atkins, and S. G. Sligar, J. Am. Chem. Soc. 109, 3754–3760 (1987); P. J. Loida, and S. G. Sligar, Biochemistry 32, 11530–11538 (1993)). The addition of Ru—$C_{10}$ (10 equivalents relative to enzyme) was found to decrease the rate of hydroxylation to approximately 300 µmol NADH/min/µmol P450. Further experiments with varying concentrations of Ru—$C_{10}$ will determine the extent to which the Ru-substrate inhibits camphor turnover.

Discussion

The result that the yield of hydroxylated 2-adamantylacetamide is only half that observed with 1-adamantylacetamide may shed insight on the positioning of critical residues at the active site. While only a small perturbation of the substrate, moving the amide may greatly affect its ability to hydrogen bond with Asp 251 and Thr 252. The movement of these amino acids has been shown to stabilize water molecules at the active site (Dmochowski, I. J. et al., Proc. Natl. Acad. Sci. USA (1999) 96, 12987–12990; I. Schlichting, et al., Science 287, 1615–1622 (2000)) and may affect the delivery of protons necessary for efficient coupling. Repositioning the amide of Ru—$C_9$-Ad would be predicted to double the yield of hydroxylation. The design of bulkier Ru-substrates which displace water from the pocket in the open conformation should also promote hydroxylation chemistry. For example, methylation of the sensitizer (i.e., employing 4,4',5,5'-tetramethyl-2,2'-bipyridyl ligands), methylation of the linker (i.e, para-xylyl spacers), or increasing the volume of the substrate (i.e., by alkylation) should serve to fill the open hydrophobic pocket and exclude water.

P450 hydroxylates most substrates, including adamantane, much more slowly than camphor, most likely because solvation of the heme lowers the reduction potential for the first electron transfer. In most cases, ET is rate limiting in the substrate hydroxylation reaction. The fact that camphor displaces water and converts the heme to high spin in the presence of Ru—$C_{10}$ indicates that the reduction potential should be unchanged in the ternary complex. The factors controlling the overall efficiency of the hydroxylation reaction are not completely understood. Almost 100% coupling and high stereoselectivity in the reaction with camphor has been attributed to the substrate's tight binding ($K_D$~1 µM), a hydrogen bond with Tyr 96 and hydrophobic contacts with the protein that orient the molecule correctly.

While not wishing to be bound by any theory, the finding that the rate of NADH consumption during camphor hydroxylation was roughly halved in the ternary complex may be due to 1) changes in the reduction potential of the heme; 2) greater solvent access leading to uncoupling; or 3) inactivation of the enzyme in the ternary complex. Monitoring NADH consumption as a function of the concentration of ternary complex (which is a function of Ru—$C_{10}$ concentration), as well as quantification of the uncoupling yields will elucidate this rate discrepancy.

It is interesting to note that the conditions for achieving crystallization of the open enzyme—high ionic strength (100 mM NaOAc, 200 mM $NH_4OAc$), and low solvent dielectric (~10% PEG 8000)—have been shown in other work to destabilize the salt bridges holding the F-G loop (Deprez, E. et al., *Biochemistry* (1994) 33, 14464–14468; V. Lounnas, and R. C. Wade, *Biochemistry* 36, 5402–5417 (1997)). "Loosening" the channel in this way has been shown to be similar to changing Asp 251 to asparagine (C. DiPrimo, et al. Hoa, *Biochemistry* 36, 112–118 (1997)). Normally, P450 is crystallized in the presence of 0.25 M KCl, with potassium stabilizing the substrate bound in the closed conformation (C. DiPrimo, et al. Hoa, *Biochemistry* 36, 112–118 (1997)). Therefore, replacement of $K^+$ with $Na^+$, should disfavor the closed conformation. Furthermore, the finding that the crystals nucleated best at 4° C. mirrors the thermodynamics of camphor binding to the Asp251Asn; the association constant for camphor (In $K_{eq}$~14.2) decreases above 15° C. for this mutant. This behavior is in marked contrast to WT P450, in which the association constant for camphor (In $K_{eq}$~14.2) decreases below 15° C. (B. W. Griffin, and J. A. Peterson, *Biochemistry* 11, 4740–4746 (1972)). The perturbation of the bifurcated salt bridge upon Ru—$C_9$-Ad binding changes the thermodynamics of substrate binding and appears to dictate the conditions under which the complex crystallizes.

The results show that open P450 structures hydroxylate both natural and unnatural substrates with appreciable rates and yields. This example represents the first study of P450 in this solvent-exposed conformation, and may shed light on important mechanistic questions regarding amino acid conformational changes and the delivery of protons associated with dioxygen activation. Although the enzyme is optimized for the substrate camphor, P450 exhibits considerable flexibility in the range of molecules it binds and oxidizes.

In addition, these energy-transfer studies have identified one of the first examples of a ternary complex in cytochrome P450. Energy transfer provides a sensitive tool for studying complex P450:substrate interactions in solution. This technique can yield significant structural information about P450 active sites in the absence of a crystal structure. The large size and hydrophobic nature of P450 substrate channels makes multiple substrate binding a likely event during catalysis.

EXAMPLE IV

This Example Describes the Submillisecond Photooxidation and Reduction of Cytochrome P450 Via Sensitizer-Linked Substrates.

Presented in this example is a new photochemical method for the delivery of both electrons and holes to buried redox sites. By tethering a Ru-photosensitizer to a protein substrate, reducing the P450 heme has occurred much more rapidly than has been possible previously, and a hitherto unobserved oxidized state of the enzyme has also been generated. The strategy of linking sensitizers to substrates opens the door to exploration of reactive redox states in enzyme interiors.

Rigorous characterization of metalloenzyme oxidation states is essential to understanding metabolic processes at a molecular level. Reactive intermediates in enzymatic catalysis are of special interest, but they are frequently too short-lived to be examined directly. A case in point is the high-valent heme that is believed to be a catalytic intermediate in the oxygenation reactions of cytochrome P450cam (P450) (M. Sono, et al., *Chem. Rev.* 96, 2841–2887 (1996); E. J. Mueller, et al., in *Cytochrome P450. Structure, Mechanism, and Biochemistry* P. R. Ortiz de Montellano, Ed. (Plenum Press, New York, 1995), pp. 83–124). This oxidant has eluded detection thus far, raising questions concerning its role in the catalytic cycle (M. Sono, et al., *Chem. Rev.* 96, 2841–2887 (1996); L.-L. Wong, *Curr. Op. Chem. Biol.* 2, 263–268 (1998)).

It has previously been shown that reactive high-valent hemes of peroxidases can be prepared in solutions containing photogenerated ruthenium-diimine oxidizing agents (J. Berglund, et al., *J. Am. Chem. Soc.* 119, 2464–2469 (1997); D. W. Low, et al., *J. Am. Chem. Soc.* 118, 117–120 (1996)). Formation of $[Ru(bpy)_3]^{3+}$ via the flash-quench approach oxidizes the heme of both horseradish peroxidase (HRP) and microperoxidase-8

Equation 1:

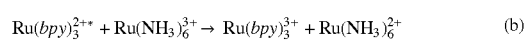
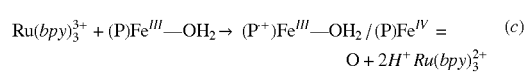

Figure 23:
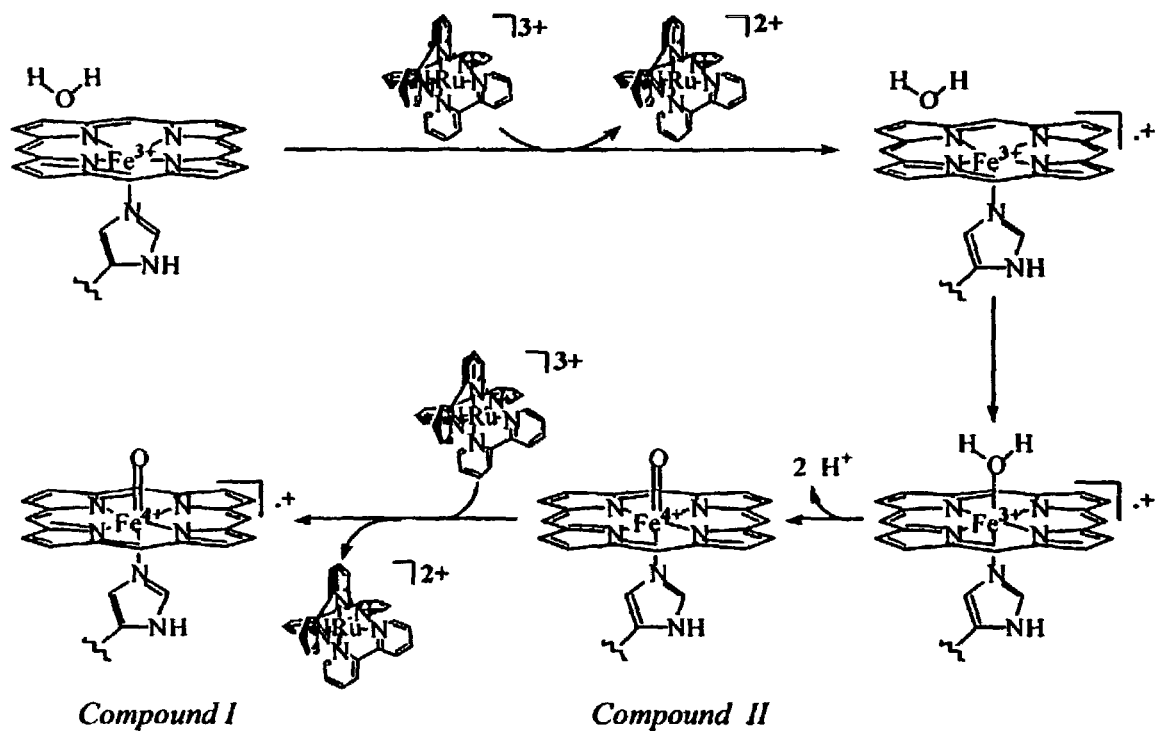
FIG. 23 depicts the oxidative flash-quench scheme by which HRP is oxidized to the compound I state, as described in Example IV, infra. These chemistries, and the oxidation states shown, serve as a model for possible high-valent intermediates in oxygenases, such as P450.

(MP-8) in less than a microsecond (Eq. 1abc). In both heme systems, electron transfer is observed to occur from the iron to the oxidized porphyrin (Eq. 1c). HRP, however, achieves a twice oxidized state after reaction with a second equivalent of $Ru(bpy)_3^{3+}$. This compound I, $(P.^+)Fe^{IV}=O$, species can be observed either under steady-state conditions, or be generated in a time resolved fashion by starting with the ferryl, compound II species (FIG. 23).

Figure 24:
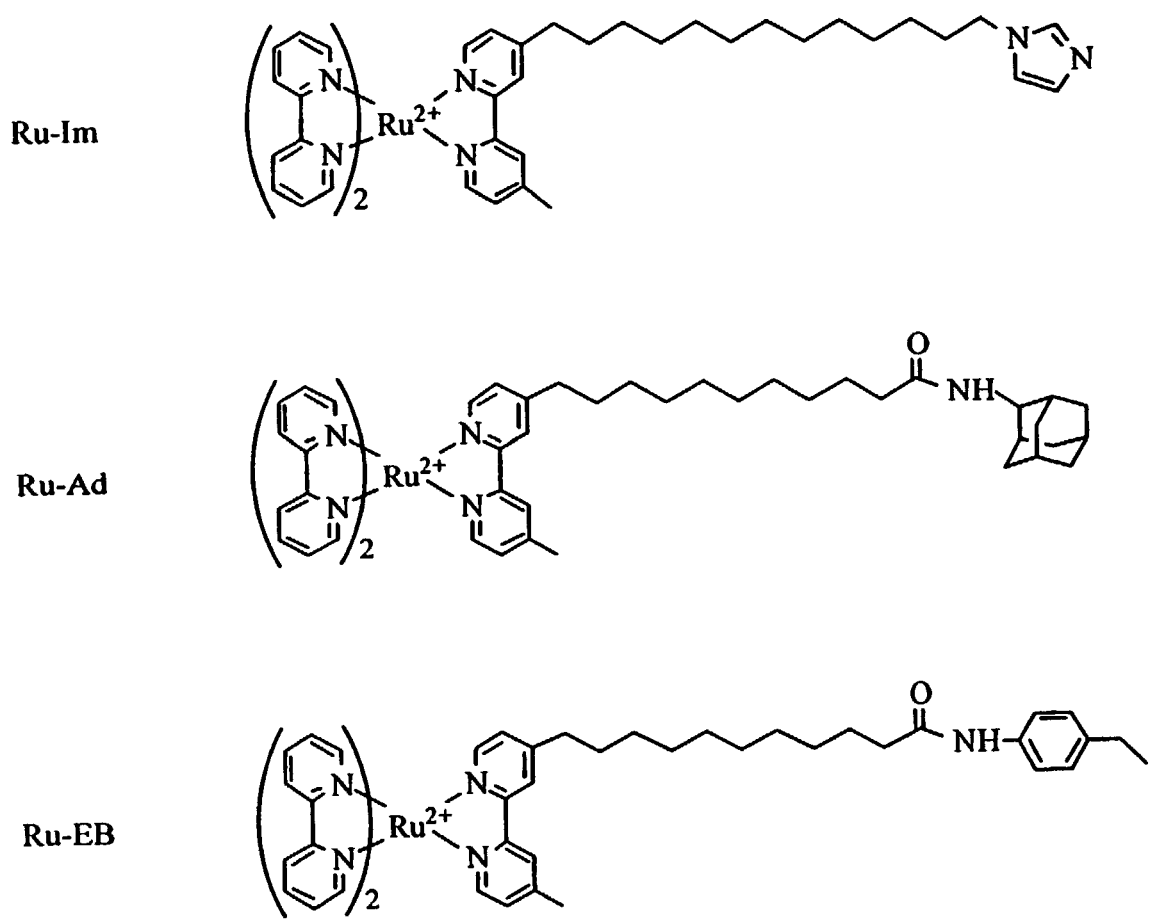
FIG. 24 shows the sensitizer-linked substrates (Ru-Ad, Ru-EB) and ligands (Ru-Im) for photooxidation and reduction of P450, as described in Example TV, infra.

It was described previously (Example I–III) that the photosensitizer $[Ru(bpy)_3]^{2+}$ is linked by a hydrocarbon chain to a species with high affinity for the P450 heme pocket: imidazole (Im), adamantane (Ad) or ethyl benzene (EB) (FIG. 24). The synthesis of Ru-EB is typical: reaction of thionyl chloride with 10-bromodecanoic acid, followed by addition of 4-ethylaniline, gives the corresponding amide. Addition of the amide to a solution of 4,4'-dimethyl-2,2'-bipyridine and lithium diisopropylamide yielded the derivatized bpy, which was reacted with $[Ru(bpy)_2Cl_2]$ to give Ru-EB. Imidazole may ligate the heme iron directly (J. H. Dawson, et al., *J. Biol. Chem.* 257, 3606–3617 (1982)), whereas the substrates adamantane (R. E. White, et al., *Arch. Bioch. Biophys.* 228, 493–502 (1984)) and ethyl benzene (D. Filipovic, et al., *Biochem. Biophys. Res. Comm.* 189, 488–495 (1992)) bound strongly to the hydrophobic active site cavity. Adamantanone displaced ligated water from the enzyme active site, $[P_{cys}Fe^{3+}—OH_2]$ ($P_{cys}$ is the cysteine thiolate-ligated protoporphyrin IX of P450), to yield five-coordinate [$P_{cys}Fe^{3+}$] (R. Raag, T. L. Poulos, *Biochemistry* 30, 2674–2684 (1991)). Ethyl benzene binding, in contrast, leaves the six-coordinate resting state relatively unperturbed.

Addition of stoichiometric Ru-Ad to ferric P450 shifted the Soret absorption maximum from 417 to 415 nm and created a shoulder at 391 nm, indicating binding of the adamantyl moiety in the heme region (all studies were performed under an argon atmosphere with 10 µM ruthenium complex, 10 µM enzyme in 100 mM potassium chloride, 20 mM potassium phosphate buffer at pH 7.4 and room temperature.). This peak shift is attributed to lengthening of the $Fe^{III}$—$H_2$ bond or partial water displacement from the [$P_{cys}Fe^{3+}$—$OH_2$] resting state, both of which accompany the binding of adamantyl compounds in the heme cavity (T. L. Poulos, et al., in *Cytochrome P450.Structure, Mechanism, and Biochemistry* P. R. Ortiz de Montellano, Ed. (Plenum Press, New York, 1995), pp. 125–150). In addition to this absorbance change, there was a decrease in the excited state ($Ru^{2+*}$-Ad) lifetime (Excitation at 480 nm (20-ns pulse width); the experimental setup has been described, D. W. Low, et al., *J. Am. Chem. Soc.* 118, 117–120 (1996)) that has been attributed to quenching by a Förster energy-transfer process. The normally monophasic luminescence decay profile of $Ru^{2+*}$-Ad ($k_{1decay}$=2.2×10$^6$ s$^{-1}$) becomes biphasic ($k_{1decay}$=2.2×10$^6$ s$^{-1}$, $k_{2decay}$=7.7×10$^6$ s$^{-1}$) in the presence of P450, with the faster phase accounting for 77% of $Ru^{2+*}$ quenching. The rapid luminescence decay ($k_{2decay}$) has been attributed to Ru-Ad-P450 interaction; the dissociation constant ($K_D$) is 0.69 µM for the complex between Ru-Ad and P450. Soret shifts from addition of the ruthenium complexes to P450 were small. Competitive binding assays of camphor and Ru-Ad with P450 by Soret absorption shifts yielded a $K_D$ value of 0.68 µM.

The Soret absorption maximum of ferric P450 in the presence of equimolar Ru-Im shifted from 417 to 420 nm, indicating ligation of the imidazole by the heme iron (J. H. Dawson, et al., *J. Biol. Chem.* 257, 3606–3617 (1982)). Luminescence decay of the $Ru^{2+*}$-Im:P450 complex was also biphasic ($k_{1decay}$=2.2×10$^6$ s$^{-1}$, $k_{2decay}$=7.0×10$^6$ s$^{-1}$). Approximately 68% of $Ru^{2+*}$ quenching occured via the faster, energy-transfer, phase ($k_{2decay}$); $K_D$=1.5 µM for Ru-Im:P450. A 1:1 mixture of Ru-EB and P450 did not display an altered Soret absorption maximum; however, $Ru^{2+*}$-EB was quenched in the presence of P450. The faster of two decay processes ($k_{1decay}$=2.2×10$^6$ s$^{-1}$, $k_{2decay}$=1.2×10$^7$ s$^{-1}$) accounted for 70% of $Ru^{2+*}$-EB decay, indicating $K_D$=1.0 µM for the Ru-EB:P450 complex. Addition of excess camphor ($K_D$~1 µM) (E. J. Mueller, et al., in *Cytochrome P450.Structure, Mechanism, and Biochemistry* P. R. Ortiz de Montellano, Ed. (Plenum Press, New York, 1995), pp. 83–124) to Ru-EB:P450 displaces the Ru-linked substrate completely, as judged by an increased contribution of the slower luminescence decay process ($k_{1decay}$). It is concluded that all three sensitizer-linked substrates bound tightly to the active site of P450.

Methods And Materials

General

Cytochrome P450$_{cam}$ and the Ru-substrates and reductive quenchers were prepared as described, in Example I supra. Highly purified ($R_z$>1.4), decamphored P450 was stored at −70° C. and thawed just before use. Distilled water was further purified by a Barnstead Nano-Pure system. Tris(2,2'-bipyridine)ruthenium(II) chloride and cobalt (III) pentammine chloride (Strem) were used as received. Hexaammineruthenium(III) chloride (Strem) was recrystallized from a minimum of warm hydrochloric acid. The reductive quencher, para-methoxy-N,N-dimethylaniline (p-MDMA), was sublimed (at 30° C.) and stored sealed under argon in a refrigerator. Precautions were taken to avoid exposing the quencher to light, oxygen, and heat. Periodically, either sublimation or recrystallization of p-MDMA from warm water was performed to restore the purity of the white solid. Static absorption spectra were recorded on an HP-8452A spectrophotometer. Steady-state photolysis experiments were conducted with an Oriel 75 watt halogen lamp.

Transient Absorbance Spectroscopy

Solution experiments were performed in sealed cuvettes with P450 and Ru-substrate in 100 mM KCl and 20 mM KPhos buffer, pH 7.4. Samples were fitted with a magnetic stir bar and deoxygenated by repeated evacuations on a vacuum line followed by backfilling with purified argon (3×10 cycles). The quenchers, cobalt (III) pentammine chloride and p-MDMA are poorly soluble in aqueous buffer at 5 mM and 10 mM, respectively, and required considerable stirring to dissolve.

All samples were excited with either a XeCl excimer (Lambda-Physik LPX 210i, 308 nm)-pumped dye laser (Lambda-Physik FL 3002, 25-ns FW) with coumarin 480 dye (Exciton, 480 nm) or a tunable (220–2000 nm, excitation at 480 nm) optical parametric oscillator (Spectra Physics, MOPO) pumped by a frequency-tripled Q-switched Nd:YAG laser (Spectra Physics, 355 nm, 350 mJ/pulse, 8-ns FWHM). The YAG fired continuously at 10 Hz; thus, for longer time base experiments (>50 ms) software was written to control the opening and closing of a shutter to select desired pulses.

The laser output was attenuated with a polarizer as needed to give 1–2 mJ/pulse at the sample. Laser shots with energies differing by more than 10% from the mean value (laser pulses detected by a photodiode and selected by a discriminator, Phillips Scientific Model 6930) were rejected. The probe light for single-wavelength transient absorption measurements was provided by a 75 watt continuous-wave arc lamp (PTI model A 1010) and focused on the entrance slit of an ISA double 0.1 meter monochromator. For time bases ≦100 µs, increased light intensity and, correspondingly, higher signal to noise was achieved by pulsing the lamp synchronously with the laser excitation (generally 10 Hz). Counter-propagating pump and probe beams were aligned on the sample cuvette. Signal was detected by a Hamamatsu photomultiplier tube (R928); the output signal amplified, digitized (Sony/Tektronix digitizer, Model RTD710A), and recorded on a PC. For time bases 5 µs-1 ms (1024 points/data array), a high-speed (200 MHz) current to voltage amplifier built at Brookhaven National Laboratory was used. For time bases ≧1 ms, a slow amplifier (PSD Corp.) was used. Kinetics data are averages of at least 250 laser shots. Transient absorption traces were typically fit to mono- or biexponential functions $y=c_0+c_1e^{-(ken+k0)t}+c_2e^{-k0t}$) using the least-squares fitting program Kinfit.

Figure 25:
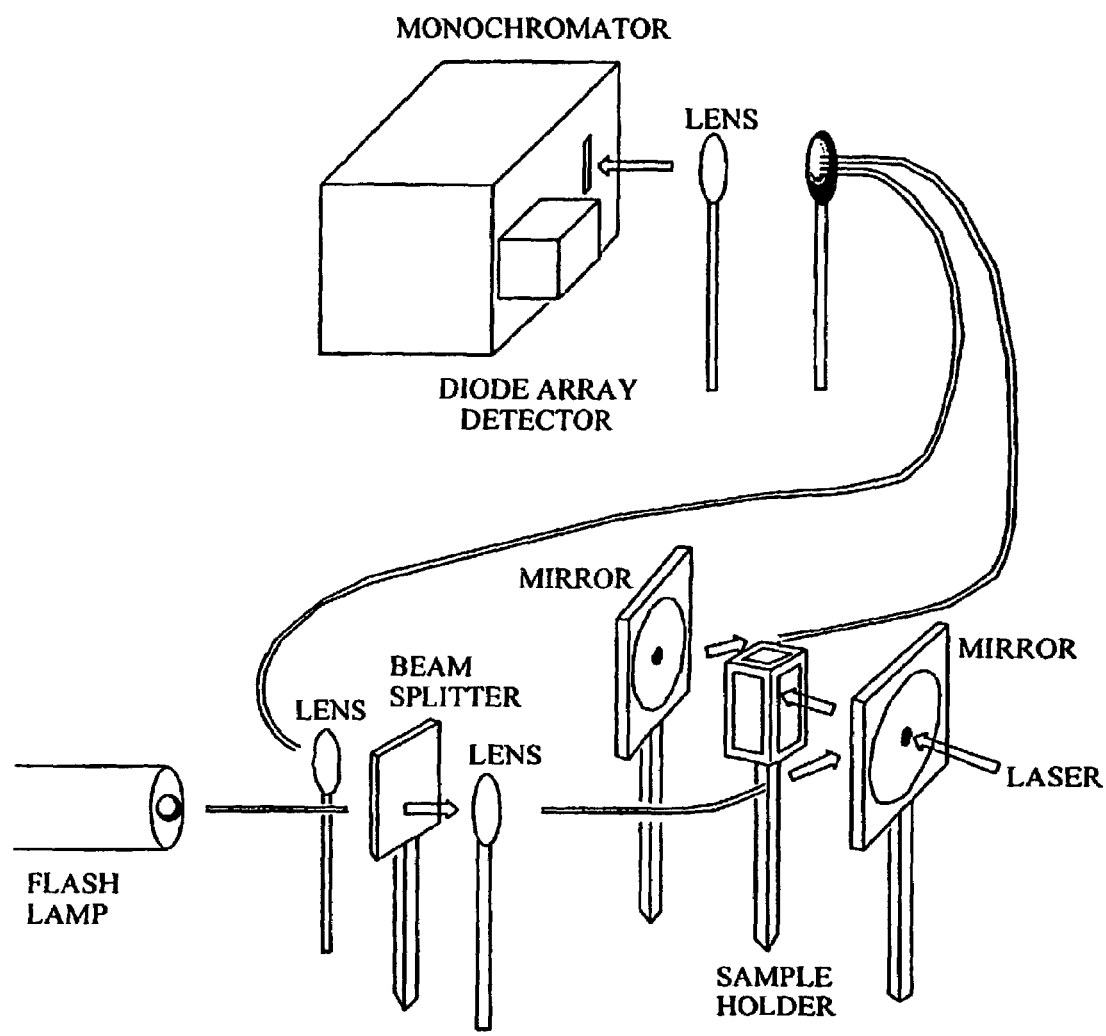
FIG. 25 is a scheme of the BILRC nanosecond experiment table used to collect full spectrum transient absorption data with a diode array detector, as described in Example IV, infra. Probe light from the flash lamp is sent via a fiber optic through a beam splitter and focused onto separate reference and sample fiber optics.

For multiwavelength transient absorption experiments (FIG. 25), probe light was provided by either a microsecond or nanosecond flash lamp powered by the discharge of a variable number of capacitors. The probe beam was delivered by a short fiber optic cable to a beam splitter; roughly 10% of the light was reflected and focused on a fiber optic leading to the reference channel of the diode array detector. The remaining probe light was focused onto a fiber optic directed towards the sample, and made coincident with the pump beam. The probe light was collected by f/2.5 mirrors (bored at the center with small holes for passage of the laser beam) and focused on a fiber optic cable. The fibers containing the reference and probe channels were vertically aligned (3.5 mm apart) and the beams focused onto the entrance slit of the monochromator (SPEX 270M).

Efficient light collection at the sample necessitated minimization of laser scatter by focusing and collimating the pump beam. Particularly in instances where it was important to measure absorbance changes at wavelengths near the laser line, extra probe light was directed at the sample and then filtered (with any scattered laser light) before the monochromator. [Ru(bpy)$_3$]$^{2+}$ (MLCT centered at 456 nm) was generally excited between 480 and 490 nm to minimize spectral overlap (and therefore, collected scatter) during observations in the Soret (380–450 nm). Intensities of probe and reference beams were determined by a diode array detector that was controlled by a Princeton Instruments (model ST-116) instrument and interfaced to a PC using commercial data collection software (Winspec). The time resolution was set by delaying the probe pulse (after the laser fire) using a signal delay generator (EG&G). Without a programmed delay, the microsecond flash lamp fired 14±14 μs after the laser, as determined by an oscilloscope. For all but the longest time bases (>1 s), the 10 Hz laser pulses emitted from the YAG were intercepted from the MOPO at 1 Hz (with the variable-delay shutter described above).

Data were collected and arithmetically manipulated by running a homemade WinSpec macro to control the position of a shutter and the timing sequence of blank, excitation, and intermittent stirring cycles. The position of the monochomator and the grating (either 300 or 1200 grooves/mm) was set with a LabView routine. Due to the changing dispersion of light with wavelength, it was necessary to calibrate the x (wavelength) axis by sticking at least three different interference filters in front of the probe light and measuring their peak intensities as recorded by the diode array detector. A calibration function for the diode array was generated by fitting these peaks to the known interference wavelengths. Likewise, offset problems on the y axis (most problematic for data sets with small OD changes) were normalized from the intensities collected during single-wavelength experiments.

Results

Laser excitation of Ru$^{2+}$-Im followed by reductive quenching with p-MDMA (G. A. Mines et al., *J. Am. Chem. Soc.* 118, 1961–1965 (1996)) yields a powerful reductant, [Ru-Im]$^+$ (E$^0$=–1.24 V vs. NHE). Reductive quenching of [Ru$^{II}$(bpy)$_3$]$^{2+}$ yields a ruthenium complex containing a coordinated bpy anion radical, [Ru$^{II}$(bpy)$_2$(bpy$^-$.)]$^+$ (K. Kalyanasundaram, *Photochemistry of Polypyridyl and Porphyrin Complexes* (Academic Press Ltd., London, 1992), p. 108). Reduction potentials are for [Ru(bpy)$_3$]$^{2+}$ (K. Kalyanasundaram, *Photochemistry of Polypyridyl and Porphyrin Complexes* (Academic Press Ltd., London, 1992), p. 144). The E$^0$ values of derivatives with substrate-terminated hydrocarbon chains should be similar.

Figure 26:
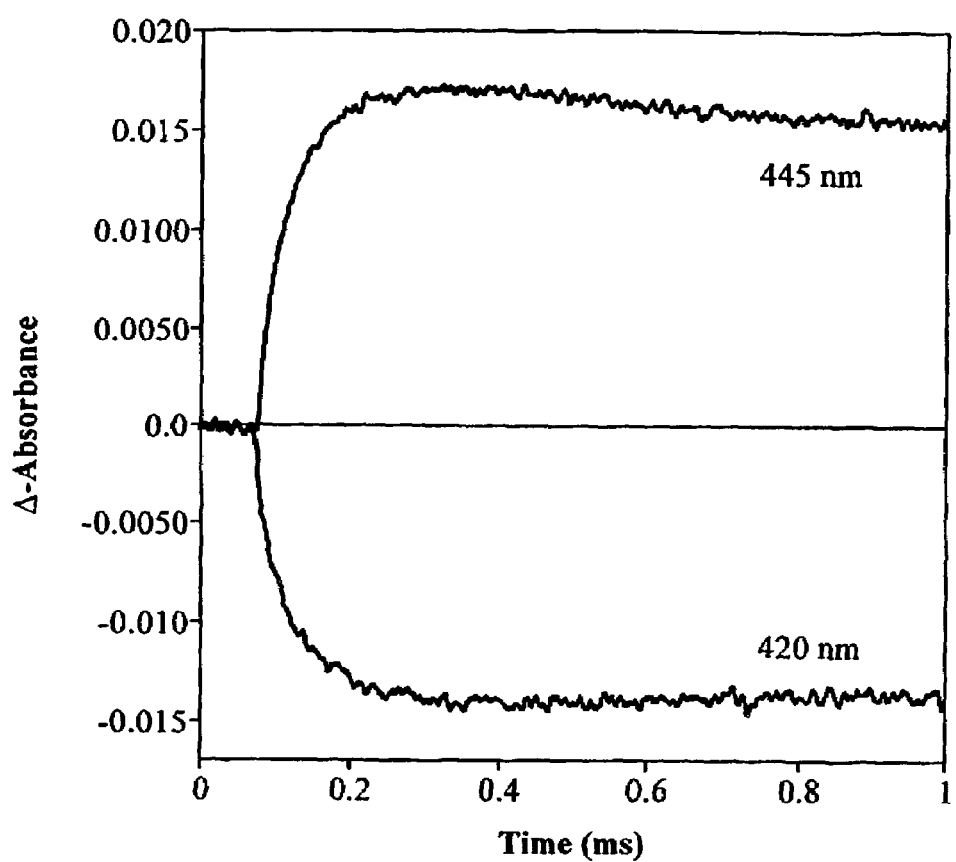
FIG. 26 shows a single-wavelength transient absorption spectra, as described in Example IV, infra: Δ-absorbance versus time plots for the reaction of [Ru-Im]$^+$ with P450. Changes in the Soret region (bleach of $Fe^{3+}$-Im at 420 nm and increase of $Fe^{2+}$-Im at 445 nm) were observed after laser excitation of a 10 µM P450, 10 µM Ru—C$_{13}$-Im, 10 mM p-MDMA sample.
Figure 27:
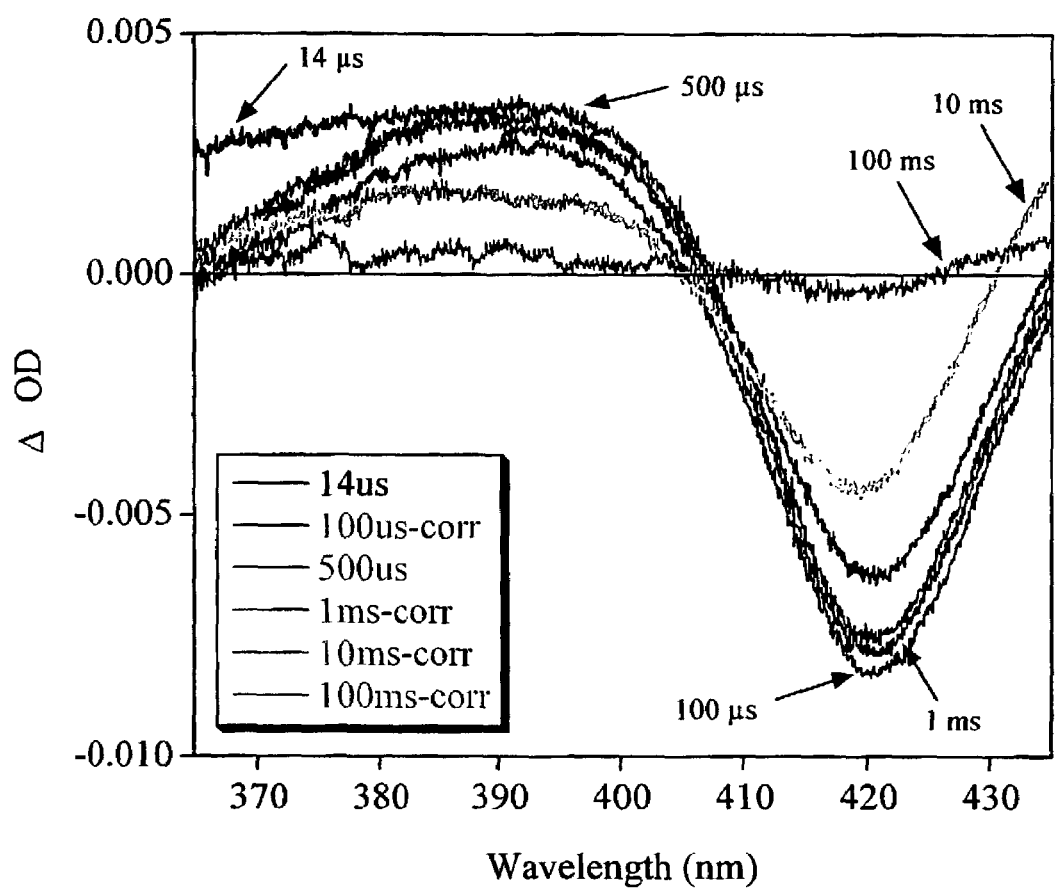
FIG. 27 depicts the diode array spectra of P450 at various time delays during and after photoreduction by [Ru-EB]$^+$, as described in Example IV, infra. The broad, sloping intensity at 350 nm at 14 µs can be assigned to spectral contributions from [Ru-EB]$^+$ and p-MDMA.

In the presence of P450, [Ru-Im]$^+$ is converted rapidly to Ru$^{2+}$-Im. Concomitant with this [Ru-Im]$^+$ oxidation is heme reduction, as evidenced by a Soret shift from 420 to 445 nm (J. H. Dawson, et al., *J. Biol. Chem.* 257, 3606–3617 (1982); J. H. Dawson, et al., *J. Biol. Chem.* 258, 13637–13645 (1983)). The rate constant ($k_{ET}$) for [Ru-Im]$^+$ Fe$^{3+}$ electron transfer is 2×10$^4$ s$^{-1}$ (FIG. 26). Similar kinetics ($k_{ET}$=2×10$^4$ s$^{-1}$) were observed upon reductive quenching of the Ru$^{2+*}$-EB:P450 complex; a 417 to 390 nm Soret shift results from the [Ru-EB]$^+$ Fe$^{3+}$ reaction (FIG. 27). Reductive quenching of the Ru$^{2+*}$-Ad:P450 complex yielded spectroscopic changes comparable to those seen for Ru$^{2+*}$-EB:P450. This blue-shifted Soret indicates that the reduction product is the previously unobserved [P$_{cys}$Fe$^{2+}$—OH$_2$]$^-$ form of P450 (FIG. 27) (the [P$_{his}$Fe$^{2+}$—OH$_2$] form of myoglobin exhibits a Soret band 15-nm blue-shifted from [P$_{his}$Fe$^{2+}$] (D. C. Lamb, V. Prusakov, N. Engler, A. Ostermann, P. Schellenberg, F. G. Parak, G. U. Nienhaus, *J. Am. Chem. Soc.* 120, 2981–2982 (1998)). Typical bulk reduction of P450 results in five-coordinate [P$_{cys}$Fe$^{2+}$]$^-$ with a Soret peak at 408 nm. The product of [P$_{cys}$Fe$^{3+}$—OH$_2$] reduction by [Ru-EB]$^{1+}$ displayed a Soret peak at 390 nm.). Further confirmation of heme reduction was the production of [P$_{cys}$Fe$^{2+}$—CO]$^-$ ($\lambda_{max}$=446 nm) upon steady-state visible irradiation of Ru$^{2+}$-EB:P450 in the presence of p-MDMA and carbon monoxide. The relatively high rate of heme reduction in the photogenerated [Ru-EB]$^+$:P450 complex shows that a direct bond to the iron is not required for efficient Ru-heme electronic coupling. Indeed, electron tunneling to the P450 active site via Ru-linked ethyl benzene is over two orders of magnitude faster than reduction by putidaredoxin (k~50 s$^{-1}$), a natural redox partner (M. J. Hintz, et al., *J. Biol. Chem.* 257, 14324–14332 (1982)). The efficient coupling of the sensitzer-linked substrate to the heme can be exploited to generate a high-valent state of the enzyme.

Figure 28:
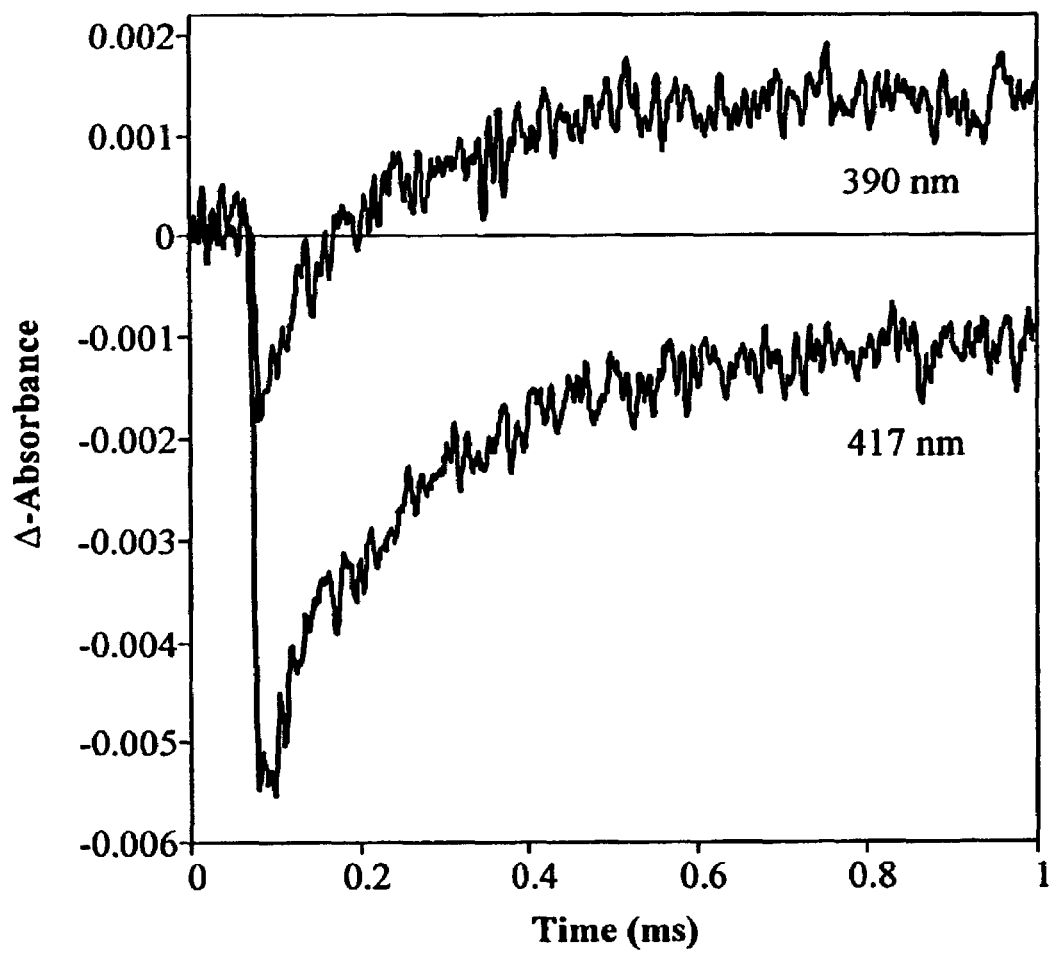
FIG. 28 illustrates the single-wavelength transient absorption spectra, as described in Example IV, infra: Δ-absorbance versus time plots for the reaction between $Fe^{3+}$-aquo P450 ($\lambda_{max}$=417 nm) and [Ru-EB]$^{3+}$. The photooxidation product, centered at 390 nm, was observed with the same kinetics as the disappearance of the starting species at 417 nm. Samples were 10 µM P450, 10 µM Ru-EB, and 5 mM [Co(NH$_3$)Cl]$^{2+}$.
Figure 29:
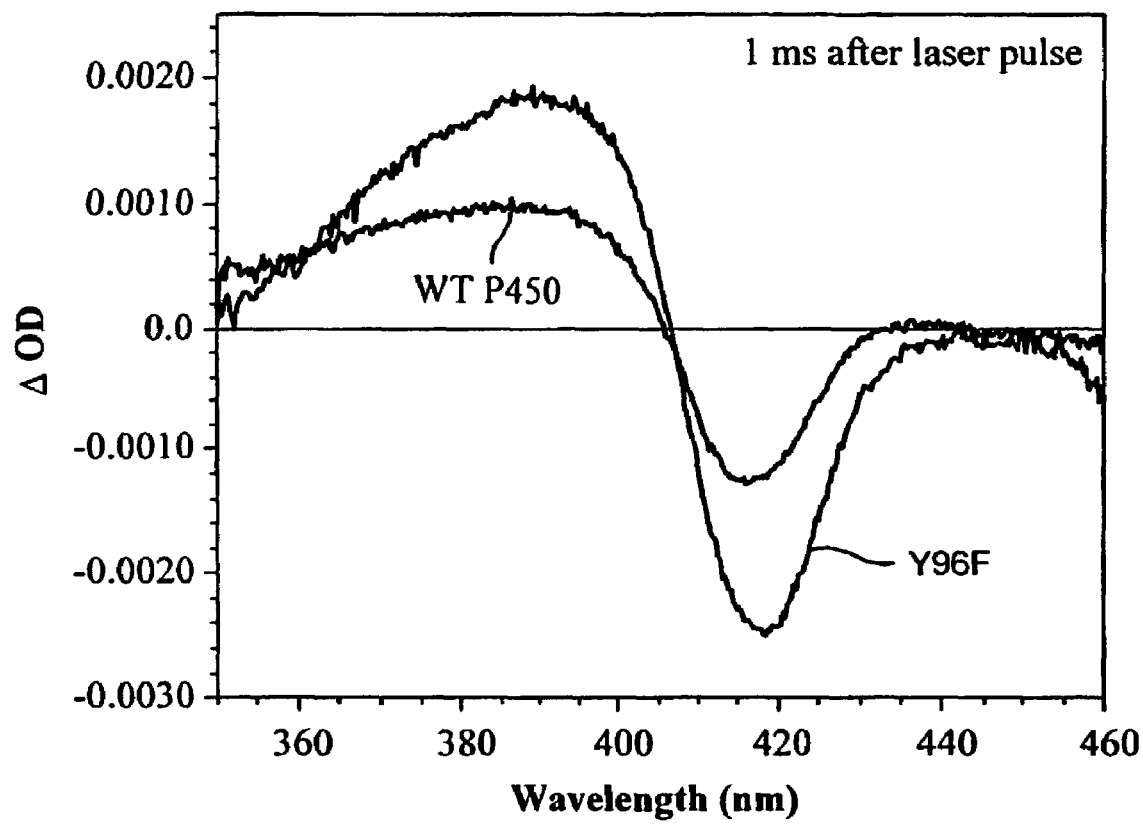
FIG. 29 shows the diode array spectra of P450 showing photooxidation by [Ru-EB]$^{3+}$ 1 ms after laser excitation, as described in Example IV, infra. The absorbance changes are due mostly to oxidation of P450. Oxidized spectra of WT P450 and Y96F are fairly similar in profile, but differ in intensity; higher yields in the mutant enzyme suggest that tyrosine intercepts some of the Ru$^{3+}$ before it oxidizes the heme.

Oxidative quenching of the photoexcited species Ru$^{2+*}$-EB by [Co(NH$_3$)$_5$Cl]$^{2+}$ yielded Ru$^{3+}$-EB, a strong oxidant (E$^0$=1.26 V vs. NHE) (J. Berglund, et al., *J. Am. Chem. Soc.* 119, 2464–2469 (1997); Reduction potentials are for [Ru(bpy)$_3$]$^{2+}$ (K. Kalyanasundaram, *Photochemistry of Polypyridyl and Porphyrin Complexes* (Academic Press Ltd., London, 1992), p. 144). The Ru$^{3+}$-EB:P450 complex undergoes heme to Ru$^{3+}$ electron transfer ($k_{ET}$=6×10$^3$ s$^{-1}$), yielding an oxidized product with a Soret peak at 390 nm (FIG. 28). This absorption change is not observed upon laser photolysis of the Ru$^{2+}$-EB:P450 complex in the absence of [Co(NH$_3$)$_5$Cl]$^{2+}$. A comparison of diode array spectra (FIG. 29) showing WT and Y96F photooxidation (1 ms after laser excitation) suggests that Tyr 96 scavenges [Ru-EB]$^{3+}$, resulting in smaller yields of oxidized WT P450. The oxidized species could be a porphyrin π-cation radical, [P$^+$cysFe$^{3+}$—OH$_2$]$^+$, or an iron$^{IV}$ species, [P$_{cys}$Fe$^{4+}$—OH$_2$]$^+$. The blue-shifted Soret band in the spectrum of the oxidized heme accords with the radical formulation; the cysteine thiolate ligand could stabilize an Fe$^{IV}$ state of P450. Hydrogen bonding to this thiolate (T. L. Poulos, B. C. Finzel, A. J. Howard, *J. Mol. Biol.* 195, 687–700 (1987)), however, decreases the donor strength. Although the reaction product of iodosobenzene and P450 exhibits a 393 nm Soret band (R. C. Blake II, M. J. Coon *J. Biol. Chem.* 264, 3694–3701 (1989)), the Soret of chloroperoxidase red-shifts upon ferryl formation (R. Nakajima, I. Yamazaki, B. W. Griffin *Biochem. Biophys. Res. Comm.* 128, 1–6 (1985)). The blue-shifted Soret band exhibited by the heme in the oxidized Ru-EB:P450 complex is not unlike that of P420, a common P450 decomposition product (S. A. Martinis, S. R. Blank, L. P. Hager, S. G. Sligar, G. H. B. Hoa, J. J. Rux, J. H. Dawson *Biochemistry* 35, 14530–14536 (1996)). Formation of P420, however, is largely irreversible, whereas oxidized Ru-EB:P450 returns to the resting state without appreciable decomposition; indeed, porphyrin π-cation radicals often display Soret bands that are blue-shifted from those of resting hemes (P. Gans, et al., *J. Am. Chem. Soc.* 108, 1223–1234 (1986); R. H. Felton, et al., *J. Am. Chem. Soc.* 93, 6332–6334 (1971); A. Wolberg, and J. Manassen, *J. Am. Chem. Soc.* 92, 2982–2991 (1970)).

The same rate of P450 reduction was observed with Ru-Im, Ru-Ad, and Ru-EB. The ET rate is relatively insensitive to chain length for the Ru—(CH$_2$)$_{9-13}$ series. One possibility that would explain both sets of anomalous data is that ET occurs through the protein rather than through the methylene chain. Computer modeling, however, shows no well-coupled pathway from the top of the channel to the heme. Additionally, it is observed that the yield of electron injection from the shorter [Ru—C$_7$-EB]$^+$ to the heme is markedly smaller (and the rate is an order of magnitude slower), suggesting that electrons, in fact, tunnel through the methylene chain (and through space) to the heme.

While not wishing to be bound by any theory, the observed reduction rate may be dominated by the back electron transfer between [Ru(bpy)$_3$]$^+$ and p-MDMA$^{\cdot+}$ (k$^q$~4×10$^9$ M$^{-1}$s$^{-1}$). The observed rate and yield of the forward reaction (Ru$^+$-EB Fe$^{3+}$—>Ru$^{2+}$-EB Fe$^{2+}$) correlates with the yield of Ru$^+$ generated ($\epsilon$=12,000 M$^{-1}$cm$^{-1}$ for Ru(bpy)$^+$ and $\epsilon$=8000 M$^{-1}$cm$^{-1}$ for p-MDMA$^{\cdot+}$ at 510 nm). Because the yield of Ru$^+$-EB Fe$^{3+}$ varies with laser power, the quencher concentration, and the accessibility of {Ru(bpy)$_3$}$^{2+*}$ to the quencher (each Ru-substrate binds slightly differently), it is extremely difficult to draw comparisons between compounds. However, qualitatively, the yields of ET products appear to be highest with Ru—C$_9$-EB and Ru—C$_{10}$-EB and decrease by roughly a factor of 10 as the chain length is shortened (—(CH$_2$)$_7$) or lengthened (—(CH$_2$)$_{13}$).

Figure 30:
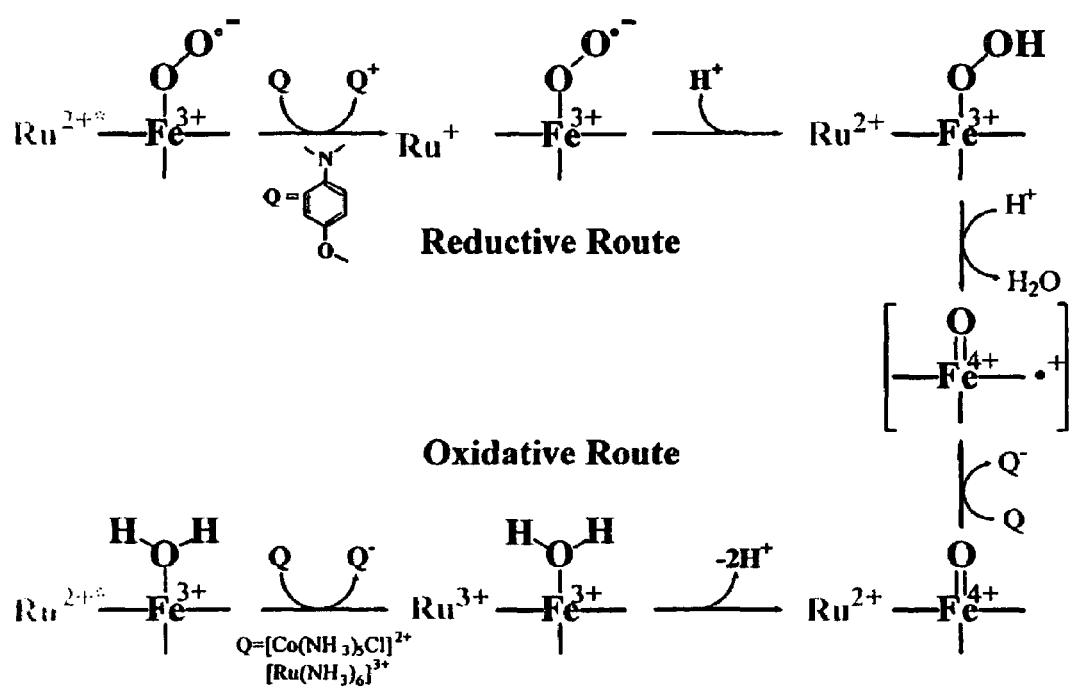
FIG. 30 depicts the proposed flash-quench scheme for generating P450 high-valent intermediates by both oxidative and reductive chemistries, as described in Example IV, infra.

Low yields, and possibilities for P450 photodegradation by the oxidative flash/quench chemistry make it unlikely that high-valent intermediates will be accessible to study by this route (FIG. 30). Additionally, P450 has many tyrosines and tryptophans that compete with the heme for the highly oxidizing Ru$^{3+}$. Prospects for generating reactive intermediates via the reductive route (FIG. 30) appear much more promising. Improvements in the design of Ru-substrates (conjugated linkers, optimized driving forces and chain lengths) will permit electron transfer to P450 in the submicrosecond regime. Such advances are necessary to observe short-lived intermediates, but also to study P450 in the presence of dioxygen, since O$_2$ reacts rapidly with photoinduced reducing agents to form superoxide. Rapid electron injection into oxy P450 should allow the observation of reactive intermediates on the catalytic pathway.

Figure 31:
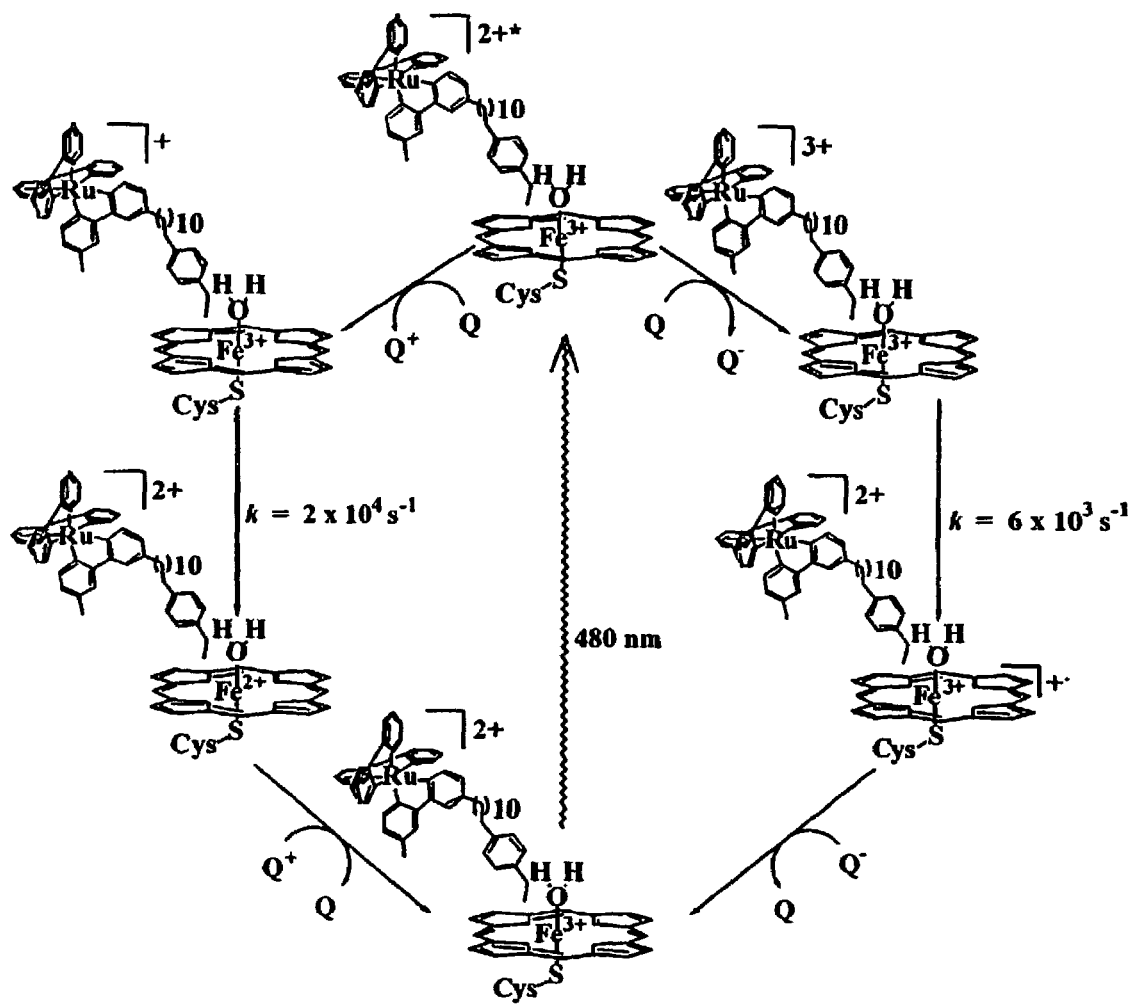
FIG. 31 illustrates the overall flash/quench reaction scheme showing the preparation of new redox states in the P450:Ru-EB complex, as described in Example IV, infra.

By employing sensitizer-linked substrates, new oxidized and reduced states of P450 were been prepared (FIG. 31). These flash/quench methods provide a wide time window to study highly reactive forms of the enzyme. Both [P$^{cys}$Fe$^{II}$—OH$_2$]$^{31}$ and [P$^+$·$_{cys}$Fe$^{III}$—OH$_2$]$^+$ are formed in ~0.1 ms and persist for ~100 ms. Improved design of sensitizers, quenchers, linkers, and substrates will lead to even faster electron and hole injection into P450 and other redox-active enzymes.

EXAMPLE V

This Example Describes Sensitizer-Linked Substrates with Conjugated Linker Sections for Submicrosecond Electron Injection into Cytochrome P450

The development of ruthenium photosensitizers with high affinity for the cytochrome P450$_{cam}$ (P450) active site has established a new method for rapidly modulating enzyme oxidation states. Photoexcitation of P450:Ru-(alkyl linker)-substrate conjugates in the presence of an oxidative or reductive quencher has been shown to effect heme redox chemistry on submillisecond time scales (J. J. Wilker, et al., *Angew. Chem. Int. Ed.* 38, 90–92 (1999)). Recently, efforts have been focused on accelerating the rate-limiting electron-transfer (ET) step in P450 catalysis on route to generating reactive catalytic species (E. J. Mueller, et al., in *Cytochrome P450: Structure, Mechanism, and Biochemistry*, 2nd edn P. R. Ortiz de Montellano, Ed. (Plenum Press, New York, 1995) pp. 83–124). With this goal, three new conjugated sensitizer-linked probes were synthesized (FIG. 32). Compound (a) cannot form a covalent bond to the heme; the perfluorobiphenyl moiety most likely occupies the substrate pocket. Luminescence quenching of the excited state of (a) by P450 has been assigned to a purely Förster energy-transfer process. Compounds (b) and (c) may bind the heme iron directly, as judged from a blue shift (417 420 nm) in the Soret. Luminescence quenching of the excited states of (b) and (c) by P450 has been assigned to both Förster energy-transfer and electron-transfer processes. Laser excitation of (c) allows direct photoreduction of P450 on submicrosecond time scales. These rate enhancements, in the absence of a reductive quencher, greatly extend the utility of this approach for biophysical studies of short-lived enzyme intermediates.

In previous work with saturated, alkyl-tethered, sensitizer-linked substrates (I. J. Dmochowski, et al., *Proc. Natl. Acad. Sci. USA* 96, 12987–12990 (1999)), it was shown that P450 complexation significantly quenches {Ru(bpy)$_3$}$^{2+*}$ by Förster energy transfer, not ET. Due to the shortened Ru excited-state lifetime, even an efficient reductive quencher such as para-methoxy-N,N-dimethylaniline (p-MDMA) (S. Gould, et al., *J. Am. Chem. Soc.* 112, 9490–9496 (1990);K. Miedlar, and P. K. Das, *J. Am. Chem. Soc.* 104, 7462–7469 (1982)), generates little of the long-lived, highly reducing (E$^0$=–1.24 V vs. the normal hydrogen electrode, NHE) (K. Kalyanasundaram, *Photochemistry of Polypyridine and Porphyrin Complexes* (Academic Press, Lmtd., London, 1992)) [Ru-substrate]$^+$ necessary for P450 reduction. Myriad problems with p-MDMA include poor water solubility, dioxygen sensitivity, ability to displace Ru-substrates from the active site, and intense spectral features in the oxidized state, p-MDMA$^{\cdot+}$. Ongoing efforts to photogenerate reactive metalloenzyme intermediates in both solution and protein crystals motivated the design of sensitizer-linked probes capable of injecting electrons more rapidly and without ancillary quenchers.

In this example the emission lifetimes and transient absorption of three similar conjugated compounds (a–c) bound to P450 were examined; these data highlight the importance of two parameters—driving force and pathway—in excited-state electron injection. Substantial differences in binding and rates of reduction accompany subtle steric and electronic changes in the Ru-probes (a–c). The optimized compound, tmRu-biphenF$_8$-im (c), reduces P450$_{cam}$ with a rate constant almost one million times that of the natural Fe$_2$S$_2$ redox partner, putidaredoxin (k=50 s$^{-1}$). Importantly, the hydrophobicity and histidine-mimicking imidazole functionality of Ru-probes such as (b) and (c) should permit studies of many other natural and unnatural enzyme active sites.

General Methods

Absorption spectra were recorded on an HP-8452A spectrophotometer. Steady-state emission measurements were made on an ISS K2 fluorometer exciting at 470 nm and scanning from 500–800 nm. All electrochemical measurements were made using a CH Instruments Electrochemical Workstation interfaced to a PC using CH Instruments software. Time-resolved luminescence, steady-state emission, single-wavelength and diode array transient absorption measurements, and all standard procedures involving sample preparation were performed as described in previous chapters. Unless stated otherwise, all experiments were performed in 50 mM KPi, 100 mM KCl, pH 7.4 buffer.

Syntheses

Compounds (a–c) were synthesized by procedures similar to those described for Ru-substrates and Ru-Im probes (Example I). Addition of excess perfluorobiphenyl to a solution of 4,4'-dimethyl-2,2'-bipyridine (GFS) and lithium diisopropylamide yields the derivatized bpy. Reacting this compound directly with $[Ru(bpy)_2Cl_2]$ yields (a). Otherwise, addition of stoichiometric imidazole and $K_2CO_3$ in freshly distilled DMSO yields bpy-biphenyl($F_8$)-im, which was reacted with either $[Ru(bpy)_2Cl_2]$ or $[Ru(tmbpy)_2Cl_2]$ to yield (b) and (c), respectively. The syntheses of (d) and (e) are described in full detail in Example I, supra.

Electrochemistry

Cyclic voltammetry (CV) was performed at ambient temperature with a normal three-electrode configuration consisting of a highly polished glassy carbon working electrode, a platinum auxiliary electrode, and a standard calomel electrode reference. The working electrode was separated from the reference compartment by a fritted disk. Acetonitrile solutions contained 0.1 M tetrabutylammonium hexafluorophosphate (freshly recrystallized) as the supporting electrolyte. Samples were rigorously bubbled with argon for several minutes prior to data collection. All compounds were studied as their $PF_6^-$ salts. All potentials are reported vs. NHE, using the relationship $E^0(NHE)=E^0(SCE)+242$ mV.

$Ru^{3+/2+}$ and $Ru(bpy_2)(bpy')^{0/*-}]^{2+}$ couples for compounds (a), (b), (c), and (e) were recorded and corrected for the junction potential using ferrocenium/ferrocene as an internal standard. In the cell, CV of 0.05 mM ferrocene solution in 0.1 M tetrabutylammonium hexafluorophosphate gave $E^0(Fc^+/Fc)=498$ mV vs. SCE. Junction potentials in acetonitrile were found to be 191 mV.

Results

Binding of Ru compounds to P450 was determined by UV-vis and luminescence lifetime measurements, as described previously (Example I and in I. J. Wilker, et al., *Angew. Chem. Int. Ed.* 38, 90–92 (1999); I. J. Dmochowski, et al., *Proc. Natl. Acad. Sci. USA* 96, 12987–12990 (1999)). Addition of equimolar tmRu-biphenF$_9$ (a) to substrate-free P450 perturbed the absorption spectrum very little ($\lambda_{max}$ remained at 417 nm). Time-resolved emission experiments, however, showed that P450 binds (a) tightly ($K_D$=0.9 μM). The normally monophasic $Ru^{2+*}$ luminescence profile became biphasic in the presence of P450 ([enzyme]=4.8 μM, [Ru]=4.5 μM, 65% $k_{bound}$=1.0×10$^7$ s$^{-1}$, 35% $k_{free}$=2.0×10$^6$ s$^{-1}$). The observed decay is attributed to quenching of the bound $Ru^{2+*}$ by a Förster energy-transfer process (T. Förster, in *Modern Quantum Chemistry* O. Sinanoglu, Ed. (Academic Press, New York, 1965), vol. III, pp. 93–137), similar to that observed with other Ru-probes (Example I and in I. J. Dmochowski, et al., *Proc. Natl. Acad. Sci. USA* 96, 12987–12990 (1999)). No transient absorption signals other than those associated with the decay of $Ru^{2+*}$ were observed for this complex, indicating the absence of an ET process. Based on Förster analysis of the overlap between $Ru^{2+*}$ emission and P450 absorption spectra (FIG. 34), $R_0$ is calculated to be 18.8 Å (Table 33). The rate of $Ru^{2+*}$ energy transfer ($k_{en}$=$k_{bound}$−$k_{free}$=8.0×10$^6$ s$^{-1}$) predicts a Ru—Fe distance of 19.7 Å, which agrees well with modeling studies of Ru-biphenF$_9$ bound to the open P450 structure.

Addition of equimolar Ru-biphenF$_8$-im (b) to substrate-free P450 red shifted the absorption spectrum ($\lambda_{max}$=417–420 nm), similarly to known $Fe^{3+}$-imidazole P450 complexes (J. H. Dawson, et al., *J. Biol. Chem.* 257, 3606–3617 (1982)). The Q-bands were also red shifted from ferric-aquo P450 (FIG. 34), although less than most ferric-imidazole complexes. The observed biphasic $Ru^{2+*}$ luminescence profile ([P450]=[Ru]=10 μM, 55% $k_{bound}$=1.2×10$^7$ s$^{-1}$, 45% $k_{free}$=2.0×10$^6$ s$^{-1}$) confirmed P450 binding ($K_D$=3.7±0.2 M). At early times (τ~300 ns) transient absorption signals were observed for not only decaying $Ru^{2+*}$ but also increasing $Ru^{3+}$-Im-$Fe^{2+}$ (FIG. 35), permitting assignment of $Ru^{2+*}$ quenching to both Förster energy-transfer and electron-transfer processes. All of the unbound $Ru^{2+*}$ returned to the ground state within 5 μs of laser excitation, and the remaining signal (FIG. 36, absorption increase centered at 445 nm, bleach centered at 420 nm) agreed with numerous $Fe^{2+}$-imidazole P450 species (J. H. Dawson, et al., *J. Biol. Chem.* 258, 13637–13645 (1983)).

Stoichiometric addition of tmRu-biphenF$_8$-im (c) to substrate-free P450 red shifted the absorption spectrum ($\lambda_{max}$=417—>420 nm), similarly to (b). Time-resolved emission experiments showed P450 bound this methylated compound ($K_D$=0.5±0.2 μM) considerably better than Ru-biphenF$_8$-im. The observed biphasic $Ru^{2+*}$ luminescence profile ([P450]=[Ru]=10 μM, 80% $k_{bound}$=4.0×10$^7$ s$^{-1}$, 20% $k_{free}$=4.5×10$^6$ s$^{-1}$) (FIG. 37) was attributed to quenching of the bound $Ru^{2+*}$ by predominantly electron transfer. Transient absorption signals were observed for both $Ru^{2+*}$ and tmRu$^{3+}$-Im-Fe$^{2+}$ at the earliest times (τ~10 ns) accessible to the BILRC nanosecond laser system (FIG. 38), and achieved a maximum Δ absorbance 30 ns after the laser pulse (FIG. 39). The product of this direct photoinduced ET appears virtually the same as that observed upon reduction of the P450:(c) complex with dithionite and laser photolysis (FIG. 40). This $Fe^{2+}$:imidazole-Ru complex persists for several hours at room temperature without degradation.

Direct Photoinduced Reduction

Having established that excited-state ET, $Ru^{2+*}$—>$Fe^{3+}$, occurs with conjugated Ru-Im probes (b) and (c), it remains to determine the rates of both the forward and back, $Fe^{2+}$—>$Ru^{3+}$, ET processes. The observed rate ($k_{obs}$) at which the ruthenium excited state decays is the sum of three competing first-order processes: ET ($k_{ET}$), energy transfer ($k_{en}$), and the intrinsic (radiative+nonradiative) decay to ground state ($k_d$) (Eq. 6.1).

$$k_{obs}=k_{ET}+k_{en}+k_d \quad (6.1)$$

$k_d$ may be determined by time-resolved emission experiments of the Ru-probes themselves, alone in solution. Since all of the $Ru^{2+*}$ emission profiles are biphasic exponential decays in the presence of P450, it is best to subtract the unquenched rate ($k_d$) from the quenched rate ($k_{obs}$) in order to get $k_{obs}$−$k_q$=$k_{ET}$+$k_{en}$. Solving for $k_{ET}$ requires finding the yield of reduction based on the concentration of bound excited state generated each laser pulse. Based on the dissociation constant for calculated for (b) and (c):

$$\% \; Ru^{2+*}(bound)=\% \; Ru(bound)\times[Ru^{2+*}] \quad (Eq. \; 6.2)$$

The dependence of the ET rate on excited-state yield makes such calculations extremely sensitive to the laser power. Power dependence studies gave a good indication of the fraction of the ruthenium excited with each laser shot (FIG. 41). It was found empirically that exciting the sample with more than ~3.3 mJ/pulse (beam diameter~2 mm) was sufficient to achieve nearly quantitative $Ru^{2+*}$. Additionally, the ΔOD amplitudes (from fits of kinetics traces) make it is possible to calculate the concentration of $Ru^{2+*}$ at 370 nm ($Ru^{2+*}$–$Ru^{3+}$, Δε=8050 $M^{-1}$ $cm^{-1}$, work by I. J. Chang). Calculations of the $Fe^{2+}$ yield can be made at 420 nm ($Fe^{2+}$–$Fe^{3+}$, Δε=–82,000 $M^{-1}$ $cm^{-1}$), and at 445 nm ($Fe^{2+}$–$Fe^{3+}$, Δε=81,000 $M^{-1}$ $cm^{-1}$, once the back reaction is taken into account (Eq. 6.3):

$$\frac{\partial (Fe^{II})}{\partial t} = k_{ET}[Ru^{2+*}] - k_{back}[Fe^{2+}] \quad \text{(Eq. 6.3)}$$

From Eq. 6.1 and the definition of a first-order rate expression, gives:

$$\frac{\partial (Ru^{2+*})}{\partial t} = k_{obs}[Ru^{2+*}] \quad \text{(Eq. 6.4)}$$

which integrates to:

$$[Ru^{2+*}] = Ru^{2+*}]_0 e^{(-k_{obs}t)} \quad \text{(Eq. 6.5)}$$

where $[Ru^{2+*}]_0$ is the initial concentration of bound excited-state Ru. Plugging this back into Eq. 6.3, gives:

$$\frac{\partial (Fe^{II})}{\partial t} = k_{ET}[Ru^{2+*}]_0 e^{(-k_{obs}t)} - k_{back}[Fe^{2+*}] \quad \text{(Eq. 6.6)}$$

Solving the differential equation for $Fe^{II}$ as a function of time gives:

Thus, plugging in the concentration of $Fe^{II}$ and the time (t) yields $k_{ET}$, since all of the other variables are experimentally measurable quantities. For the P450:(c) complex ([P450]=[Ru]=8.9 μM; [unbound Ru]=1.85 μM, Δε=–2400 $M^{-1}$ $cm^{-1}$ at 451 nm), the maximum ΔOD at 445 nm (observed at 30 ns) was 40±2 mOD (FIG. 40). Adjusting for the bleach from the unbound $Ru^{2+*}$ at 445, the ΔOD at 445 nm increases to 44.5 mOD. Since $[Ru^{3+}]=[Fe^{2+}]$, and Δε(Ru)/Δε(Fe)=1/9 at 445 nm, the total absorbance change due to the reduction of iron is adjusted upward to 49.5 mOD, which corresponds to 0.61 μM $Fe^{2+}$-Im (8.7% yield based on bound Ru). Plugging this concentration (at t=30 ns) into Eq. 6.7 with a measured back electron transfer rate, $k_{back}$, of $3\times10^7$ $s^{-1}$, and a $k_{obs}$ of $3.9\times10^7$ $s^{-1}$, yields an ET rate, $k_{ET}=8.1\times10^6$ $s^{-1}$. Evaluating Eq. 6.1 gives $k_{en}\sim2.6\times10^7$ $s^{-1}$, which is a factor of 3 faster than predictions for a Förster energy-transfer process. Judging from the energy-transfer rate and distance found in the P450:(a) complex, $k_{en}$ should be roughly $9.5\times10^6$ $s^{-1}$. Using this value, Förster analysis of the overlap between $tmRu^{2+*}$ emission and P450 absorption spectra predicts $R_0$=22.1 Å and a Ru—Fe distance of 17.7 Å, in good agreement with the crystal structure (FIG. 33).

The reason for the discrepancy between calculated and predicted rates stems from one of three reasons: 1) the calculated yield of reduced P450 is only 25% of the true value, 2) the back ET rate is considerably faster (~$1\times10^8$ $s^{-1}$) than measured and is poorly resolved in the response time of the instrument, or 3) the majority of $Ru^{2+*}$ decays by a different and unassigned pathway (i.e., Dexter energy transfer). Without further experiments, particularly picosecond transient absorption, and better spectral deconvolution, it will be difficult to discriminate between these alternate explanations.

Yields of reduction in the P450:Ru-biphenF$_8$-im complex, observed 5 μs after laser excitation, are 1±0.5% (based on the fraction of bound Ru) using the procedure described for tmRu-biphenF$_8$-Lm. This yield predicts that the rate of electron transfer is approximately $1\times10^6$ $s^{-1}$, and by Förster analysis, $R_0$=22.1 Å, and Ru—Fe=17.7 Å. The transient absorption kinetics (FIG. 35) failed to exhibit the submicrosecond reduction phase observed with (c), but otherwise yielded similar spectral features.

Interestingly, in P450 complexes of both (b) and (c), the ground state back electron transfer ($Ru^{3+}$-Im-$Fe^{2+}$—>$Ru^{2+}$-Im-$Fe^{3+}$) does not return all of the enzyme to its resting ferric state. In fact, three observably different back ET processes whose rates span 6–7 orders of magnitude were observed. Since the OD changes are much larger with (c), and the back ET rates are similar for both compounds, our analysis shall focus on the latter.

Any explanation for the three observed back ET rates must be consistent with the observation that the initially formed $Fe^{2+}$-Im P450 species bleaches but does not change its spectral profile (i.e., imidazole remains bound) during the entire back reaction (microseconds to seconds). The diode array spectrum of (c) shows a consistently red-shifted Soret on all time scales (FIG. 42). Having excluded, therefore, the possibility of ligand exchange, and considering that bimolecular ET reactions should not compete with the rapid intramolecular ($Ru^{3+}$-im-$Fe^{2+}$—>$Ru^{2+}$-im-$Fe^{3+}$) ET, it is most likely that the protein scavenges some of the $Ru^{3+}$. Indeed, Tyr 29 has recently been implicated in the chiral discrimination of Ru-substrates binding to the P450 channel. Based on the yield of reduced P450 at 5 μs (~2%) relative to 30 ns (~9%), and the predicted back ET rate ($k_{back}=3\times10^7$ $s^{-1}$), we infer that the Tyr—>$Ru^{3+}$ ET reaction must be occurring with a rate constant of $k\sim6.0\times10^6$ $s^{-1}$. The low yields of this reaction make observations of a tyrosine radical (Tyr.$^+$) difficult by transient absorption spectroscopy ($\lambda_{max}$=420 nm) (Y. Chen-Barrett, et al., *Biochemistry* 34, 7847–7853 (1995)). Consistent with this explanation, however, is the apparent disappearance of most $Ru^{3+}$ absorbance (observed at 320 nm) by 250 ns. The slower back ET rate ($k=2\times10^4$ $s^{-1}$) is proposed to occur from $Fe^{2+}$-Im—>Tyr.$^+$. The forward and back ET processes are summarized in FIG. 43.

Most (~80%) of the remaining $Fe^{2+}$-In appears, in fact, to decay by this second back ET process, but a small fraction of the reduced P450 persists for ~1 second after the laser pulse. Presumably, one of several bimolecular processes is at play—bound and free $Ru^{2+/3+}$ exchange reactions, as well as protein-protein ET reactions. In support of this hypothesis is the finding that the addition of micromolar tmRu (e) to a 1:1 P450:(c) complex changed the back electron transfer step from a primarily first-order process to a second-order process dependent on the concentration of (e).

No changes in the Soret were observed upon laser excitation of P450 complexed with perfluorobiphyenyl imidazole (d). Thus, photodissociation appears to be an unlikely process with any of these compounds. Compound (e) and $[Ru(bpy)_3]^{2+}$ were not quenched upon addition of P450, indicating that a tether is essential for binding as well as energy/electron transfer. In all cases, sample integrity was monitored by UV-vis before and after each experiment, and no photo-mediated degradation was observed. Binding of the Ru-probes was shown to be fully reversible by displacing the compounds with camphor and returning the enzyme to its 5-coordinate ferric resting state.

To determine whether rapid electron injection from the Ru excited state of (c) to the heme operates by hopping (bipyridyl→perfluorobiphenyl→heme) rather than tunneling, electrochemistry was performed on both the model compound (e) (FIG. 44) and on (c) (FIG. 45). The bridging model compound (d) exhibited quasi-reversible waves by CV as observed previously for perfluorobiphenyl (B. H. Campbell, *Anal. Chem.* 44, 1659–1663 (1972)). The reduction potential of the bridge lies several hundred millivolts below that of the excited state of (a–c), and electron hopping may be discounted as a viable mechanism for electron transfer.

The bulkier, conjugated Ru-probes described in this Example bind extremely well; (c) binds, in fact, better than the saturated Ru-Im probes synthesized previously (Example I). It is likely that the enhanced affinity is driven by hydrophobic interactions, particularly involving the perfluorinated bridge and the addition of 8 methyl groups on the terminal Ru moiety. Evidently, the greater steric bulk does not preclude binding, and raises the question of how close to the heme a slightly smaller photosensitizer (i.e., [Ru(CN)$_4$(bpy)]$^{2-}$) might bind the active site. Energy-transfer calculations predict that (b) and (c) bind 2–3 Å closer to the heme than the Ru-probes described in Example I. The rigidity of the conjugated bridge, and also, perhaps, the angle at which the bridge is canted from the bipyridyl ligand (FIG. 32), appears to promote smaller Ru—Fe distances.

It is possible that the heme iron does not covalently bond (perfluorobiphenyl)imidazole in the ferric state. The Soret and Q-bands are only modestly red-shifted, with the relative intensities of the α and β bands changing slightly relative to the Fe$^{3+}$—OH$_2$ resting state (FIG. 33). This behavior contrasts the binding of imidazole and Ru—C$_{13}$-Im which red shift the Q-bands by several nanometers. In principle, the imidazole could act as a Lewis base and deprotonate Fe$^{3+}$-aquo; the modestly red-shifted Soret would then correspond to a Fe$^{3+}$-hydroxy species.

Interestingly, the imidazole-perfluorobiphenyl model compound (d) shows a similar absorption spectrum ($\lambda_{max}$=420 nm) upon binding P450 in the ferric state. This suggests that the lack of significant absorbance changes may be due to the electron-withdrawing nature of the perfluorobiphenyl bridge rather than the size of these conjugated molecules. The predicted π-acidity and weakened σ-donating ability of this interesting new imidazole ligand would greatly stabilize lower oxidation states, and, in fact, the standard Fe$^{2+}$-Im spectrum ($\lambda_{max}$=446 nm) is observed upon reduction (FIG. 40). Further support for this hypothesis comes from emission lifetime binding studies of the 1:1 P450:(b) complex; the Ru$^{2+*}$ profile is highly quenched by ET and predominantly monophasic, suggesting that the Ru-Im probe is much more tightly bound to Fe$^{2+}$ P450. A strong preference for imidazole in the ferrous oxidation state is quite unusual for heme enzymes, and points to a complex equilibrium in the ferric state. Such ligand exchange processes should be pH sensitive.

The yield of reduced P450 (Ru$^{2+*}$/Fe$^{3+}$→$^{Ru3+}$/Fe$^{2+}$) appears to depend heavily on the excited-state driving force as well as the availability of a through-bond covalent pathway to the heme. The addition of eight methyl groups on the bipyridyl ligands lowers the reduction potential by approximately 160 mV which increases both the rate of reduction and yield of ET products by an order of magnitude. With both Ru-Im compounds, the reduction potential of the heme is roughly −300 mV vs. NHE (~50 mV higher than that expected for an imidazole-ligated P450 heme, due to the electrophilicity of perfluorobiphenyl). The excited-state reduction potential of (c) is approximately −1.0 V, providing substantial driving force for reduction (−ΔG~0.7 V) in a nearly activationless reaction.

The advantage of a directly covalent pathway for excited-state electron transfer is evident from the lack of ET products with (a). This Ru moiety is calculated to bind an additional 2 Å from the heme (FIG. 33), which would require a substantial through-space jump from the biphenyl to the iron. One exciting finding with (a) was that it forms a stable ternary complex with either imidazole or carbon monoxide, as shown by energy-transfer measurements. Photoexcitation of the P450:Ru-biphen:imidazole complex yielded reduced (Fe$^{2+}$-Im) protein, due presumably to either a shorter through-space jump or a lower reorganization energy for Fe$^{3+/2+}$-IM than for reduction of the ferric aquo heme. Successful photoinduced ET in this ternary complex bodes well for future studies of dioxygen activation and light-activated substrate turnover.

Accordingly, conjugated sensitizer-linked probes of the invention bound with high affinity and promote rapid electron transfer to the buried P450 heme. Submicrosecond rates of electron injection from Ru$^{2+*}$ to the iron agreed with experiment and theoretical predictions for well-coupled ET reactions that are nearly driving force optimized (R. A. Marcus, and N. Sutin, *Biochim. Biophys. Acta* 811, 265–322 (1985); H. B. Gray, and J. R. Winkler, *Annu. Rev. Biochem.* 65, 537–561 (1996); A. Helms, et al., *J. Am. Chem. Soc.* 114, 6227–6238 (1992); W. B. Davis, et al., *Nature* 396, 60–63 (1998)). Large enhancements of the rate and yield of ET were achieved with the use of tetramethylated bipyridyl ligands attached to the Ru photosensitizer. Quantification of the rate of electron injection was complicated by the difficulty of determining the yield of Fe$^{2+}$-Im formed in this reaction.

EXAMPLE VI

This Example Describes [Ru(phen)$_2$dppz]$^{2+}$ Based Luminescent Probes for Cytochrome P450$_{cam}$.

The luminescence of [Ru(phen)$_2$dppz]$^{2+}$ complexes when bound to DNA is the result of the protection of the dppz ligand from water by intercalation between the DNA base pairs.(Erkkila, K. E. et al., *Chem. Rev.* (1999) 99, 2777–2795; Kielkopf, C. L. et al., *Nature Str. Biol.* (2000) 7, 117–121) In principle, any similar shielding from aqueous environment should lead to luminescence. Accordingly, a series of compounds in analogy to [Ru(phen)$_2$dppz]$^{2+}$ that would luminesce upon binding to cytochrome P450 were synthesized.

Materials and Methods

General: P450cam was overexpressed in *E. coli* and purified as previously described (B. H. Campbell, *Anal. Chem.* 44, 1659–1663 (1972). Both transient absorption and emission data were collected on instruments already described in the literature. (Low, D. W. et al., *J. Am. Chem.* (1996) 118, 117–120; 14) NMR spectra were taken on a General Electron QE300 or Varian Mercury 300. Static absorption spectra were taken on a HP-8452A spectrophotometer. Steady state luminescence spectra were taken on an ISS K2 Fluorometer. Quantum yields were calculated relative to a [Ru(bpy)$_3$]$^{2+}$ standard, whose quantum yield was taken to be 0.42. Electrospray mass spec. data was collected on a Finnigan LCQ quadrupole ion trap mass spectrometer.

P450 was stored in small aliquots and thawed immediately before use. Samples were prepared in 50 mM Kphos buffer containing 100 mM KCl. P450 concentration was quantified using the heme soret absorption at 416.5 nm (115,000 M$^{-1}$ cm$^{-1}$). Samples were prepared in a custom quartz cuvette fitted with a Kontes Teflon stopcock. Oxygen was removed from the sample by completing at least 30 cycles of partial vacuum followed by an influx of argon.

Syntheses:

Ru(phen)$_2$Cl$_2$ and Ru(tmbpy)$_2$Cl$_2$ were synthesized as reported. (G. A. Mines, et al., *J. Am. Chem. Soc.* (1996) 118, 1961–1965). All other reagents were purchased from the Aldrich Chemical Co. and used as received. THF was dried by refluxing over calcium hydride for at least 3 days, and was then distilled onto activated 3 Å molecular sieves.

Synthesis of Ru(phen)$_2$dppa-C6-Ad 1. 0.30 g. Ru(phen)$_2$dppa (0.278 mmol) and 0.0972 g 6-amino-hexanoic-adamanyl amide (deprotected 5) (0.417 mmol) were mixed in 5 mL dry DMF with 217 mg BOP (0.417 mmol) and 144 mg DIPEA (1.11 mmol). The reaction was sealed and left to stir for 14 hrs. The crude reaction product was concentrated under vacuum, and the residue was purified by flash chromatography using 80/10/10 acetonitrilen/butanol/water mixture saturated with KNO$_3$. The fractions which contained product were pooled and concentrated until only butanol remained. The butanol solution was then diluted 5x with CHCl$_3$ and filtered to removed KNO$_3$ and silica. The filtered solution was then concentrated to yield 142 mg 5 (54.4%).

Synthesis of Ru(phen)$_2$dppa-gly-adm: 2 0.190 g Ru(phen)$_2$dppa (0.176 mmol), 0.107 g 6 (0.353 mmol) 183 mg BOP (0.353 mmol) and 0.123 mL DIPEA were dissolved in 3.4 mL anhydrous DMF. The reaction was left to stir overnight. DMF was removed under vacuum, and the residue purified via flash chromatography using a 70/15/15 acetonitrile/water/95% ethanol mixture saturated with KNO$_3$.eluent. The fractions containing product were pooled and concentrated under reduced pressure. The mixture of salts and product was washed with 5x100 mL CHCl$_3$ and the combined organic layers were concentrated under vacuum. The crude product was dissolved in water and precipitated with an excess of NH$_4$$^+$PF$_6$$^-$. The precipitate was washed with water, dissolved in acetonitrile and re-concentrated under vacuum. Yield was 156.5 mg (70%).

Synthesis of Ru(phen)$_2$dppa-adm. 3 132.5 g Ru(phen)$_2$dppa (0.123 mmol) 37.2 mg 2-adamanylamine (0.246 mmol) 128 mg BOP (0.246 mmol) and 0.1 mL DIPEA (0.615 mmol) were dissolved in 2.4 mL anhydrous DMF and sealed in a 10 mL round bottom flask. The reaction was left to stir overnight. The reaction mixture was concentrated in vacuo and purified using flash chromatography with a mixture of 80/10/10 acetonitrile/water/95% ethanol saturated with KNO$_3$ as eluent. The product containing fractions were concentrated under reduced pressure until only water remained. The product was then precipitated with excess NH$_4$$^+$PF$_6$$^-$, filtered over a fine frit, and washed with deionized water. The product was then dissolved in acetone and re-precipitated with (nBu)$_4$N$^+$Cl$^-$ collected on a frit, and washed with acetone. Total yield was 65.3 mg (53.6%).

Synthesis of Fmoc-protected 6-amino-hexanoic acid 4. 2.572 g Fmoc-succinimdyl ester (7.623 mmol) was dissolved in 50 mL dioxane. 1.00 g 6-amino-hexanoic acid (7.623 mmol) was dissolved in 100 mL pH 9 water, and cooled to 0° C. The Fmoc solution was added dropwise with constant stirring. A white precipitate formed immediately. The reaction vessel was sealed, and left to stir overnight. The reaction was then brought to neutral pH and extracted with 3x50 mL CH$_2$Cl$_2$. Product was isolated in >95% yield.

Synthesis of Fmoc-6-amino-hexanoic-adamanyl amide. 5 1.068 g 4 (3.025 mmol) 0.416 g 2-adamantyl amine (3.33 mmol) 0.460 g HOBT (3.025 mmol) and 0.71 mL DIPCI (4.54 mmol) were dissolved in CH$_2$Cl$_2$ and left to stir overnight in a sealed 50 mL round bottom flask. The contents of the flask were concentrated under reduced pressure and purified using flash chromatography with 50/50 ethyl acetate/hexanes increasing to 70/30 ethyl acetate/hexanes. Product eluted slightly after the residual starting material. The fractions containing product were pooled and concentrated under reduced pressure, yielding a white solid. 1.082 g (78.1%).

Synthesis of 1,10-phenanthroline-5,6-dione 6. The published synthesis gave inconsistent results. (Yamada, M. et al., *Bull. Chem. Soc. Jpn.* (1992) 65, 1006) A modified procedure described herein gives more reliable results. Conc. sulfuric acid (40 mL) and conc. (70%) nitric acid (20 mL) were cautiously, and thoroughly mixed. The mixture was cooled to −20° C. using a dry ice/acetone bath. Phenanthroline (4.00 g) and KBr (4.00 g) were placed in a 250 mL round bottom flask, and cooled in a dry ice/acetone bath. The acid solution was added all at once to the chilled flask, and the reaction vessel placed in an ice/salt bath held at about 0° C. A reflex condenser was attached, and the reaction was stirred as vigorously as possible. The bath was then heated to about 80° C., and refluxed for 3 hours, after which time the reaction mixture was cautiously poured over 250 mL ice. The yellow aqueous solution was then gradually neutralized with a total of 40 g NaOH, and then brought to pH 6 with NaHCO$_3$, at which time the product partially precipitates from solution. The aqueous mixture was then extracted with 3x250 mL CH$_2$Cl$_2$ and the collected organic phase concentrated to dryness at room temperature (the product is heat sensitive as a solid). Yield 3.347 g (71.9%) 90% pure by NMR. The characterization matched literature values. (Yamada, M. et al., *Bull Chem. Soc. Jpn.* (1992) 65, 1006)

Synthesis of N(2-adamanyl)glycine amide 7 0.75 g of fmoc-glycine (2.54 mmol), 0.349 g 2-adamantyl amine (2.79 mmol), 0.595 mL DIPSI (3.81 mmol), and 0.386 g HOBT (2.54 mmol) were dissolved in 25 mL CH$_2$Cl$_2$ at room temp. and stirred for 16 hours. The reaction mixture was then washed 2x with 100 mL of pH 7 water, and concentrated under vacuum. The solid residue was redissolved in a minimum of CH$_2$Cl$_2$ and then loaded on a flash chromatography column. The product was eluted with 70/30 ethyl acetate/hexanes, and the solvent containing fractions were pooled and concentrated in vacuo. Yield of the white, powdery product was >98%. Dppa 8. 1.00 g (4.76 mmol) of 6 was dissolved in 200 mL refluxing MeOH with fast stirring. 0.724 g (4.76 mmol) 3,4 diaminobenzoic acid was added as a solid to the reaction mixture, and the product immediately precipitated from solution as a white, nearly insoluble that was pure by NMR. Yield 1.380 g (88.9%)

Synthesis of [Ru(phen)$_2$dppa]$^{2+}$(PF$_6$)$_2$-9 326.5 mg Ru(phen)$_2$Cl$_2$ (0.613 mmol) and 200 mg 2 were suspended in 20 mL ethylene glycol and heated to 160° C. for 4 hrs under argon. The reaction mixture was then cooled to room temperature, diluted with 20 mL water, and the crude product was precipitated by the addition of 1.00 g H$_4$N$^+$PF$_6$$^-$. The crude product was isolated by filtration over a fine frit, and then purified by chromatography over a neutral alumina column using acetronitrile as solvent, followed by a 1–5% water in acetonitrile gradient. This elution was followed by a 5–10% water, 1% acetic acid in acetonitrile gradient, which appeared to be necessary to remove all of the desired product from the column. The fractions containing product were pooled, and the acetonitrile was removed under reduced pressure. The pH of the resulting aqueous solution was adjusted to 1 with dilute HCl, and the product precipitated with a large excess of H$_4$N$^{+PF}$$_6$$^-$. The product was isolated by filtration and dried under vacuum. The isolated yield was 0.385 g dark red powder (58.3%). Characterization matched previously reported values. (Hartshorn, R. M. and Barton, J. K. *J. Am. Chem. Soc.* (1992) 114, 5919–5925)

Results and Discussion

The molecules shown in FIG. 47 (as depicted, compound 1 is Ru-dppa-$C_6$-Ad, compound 2 is Ru-dppa-gly-Ad, and compound 3 is Ru-dppa-Ad) were synthesized. In this study, the parent ligand, dipyrido([3,2-a:2',3'c]phenazine (dppz) was modified to include a carboxylic acid moeity. The resulting ligand, 4,5,9,14-tetraazo-benzo[b]triphenylene-11-carboxylic acid, is refered to as dppa in keeping with previous nomenclature. (Hartshorn, R. M. and Barton, J. K. *J. Am. Chem. Soc.* (1992) 114, 5919–5925) The synthesis was performed using standard peptide coupling techniques, as described above (FIG. 48). Previous studies had shown that [Ru(bpy)$_3$]$^{2+}$ connected to an adamantyl unit by a long alkyl chain bound with sub-micromolar affinity to P450 (Wilker, J. J. et al., *Angew. Chem. Int. Ed.* (1999) 38, 90–92). Thus, it was decided to test the binding of a [Ru(phen)$_2$dppz]$^{2+}$ moiety attached to an adamantyl group by an alkyl chain of varying lengths. All of the compounds synthesized bound with micromolar affinity. Interestingly, 1 ($K_d$=0.25 μM) and 3 ($K_d$=0.18 μM) both bound more tightly than 2 ($K_d$=2.4 μM). All of the compounds synthesized have binding constants that compare favorably to camphor ($K_d$=1.6 μM).

The dissociation constants of the analogous Ru(bpy)$_3$-alkyl-adamantyl compounds, for example compound Ru—$C_9$-Ad, fall around 0.2 μM. The observed binding constant of 1 is reasonable in light of these previous results. The reduced binding constant of 2 cannot be explained by steric clashes between the ruthenium complex and the protein, because 3 binds even more tightly than 1. Compound 1 was manually docked into P450 (global change, capitalize P450) frozen in the conformation observed in the crystal structure of P450 bound to a similar tris-bipyridyl ruthenium complex (FIG. 48). (Dmochowski, I. J. et al., *Proc. Natl. Acad. Sci. USA* (1999) 96, 12987–12990) As modeled, there were no significant steric clashes. Further, a large portion of the hydrophobic complex was desolvated, which should lead to a favorable free energy of binding. While not wishing to be bound by any theory, possible explanations for the relatively low binding affinity of compound 2 include: (1) the additional peptide bond may produce an undesirable steric clash; (2) glycine is relatively hydrophilic, and the increased hydrophilicity of 2 in comparison to 1 and 3 should result in a higher $K_d$.

These results indicate that P450$_{cam}$ tolerates large, hydrophobic molecules in the channel leading to the active site.

The luminescence of compounds 1–3 was examined in acetonitrile, potassium phosphate buffer, and buffer in the presence of P450 (as described above). Compound 1 did not show a significant increase in luminescence over background levels. The complexes 2 and 3 show modest recoveries of luminescence, with integrated intensities that are 2.6 and 5.2% of their values in acetonitrile (FIG. 49). The luminescence from 3 is approximately 20 fold greater in the presence of P450 than in buffer alone.

The 20-fold increase in integrated luminescence observed when 3 binds to P450 is favorable. However, the luminescence itself is weak in absolute terms. The reported quantum yield for [Ru(phen)$_2$dppz]$^{2+}$ in aerated acetonitrile is 0.0073 (0.033 in deaerated acetonitrile). (Nair, R. B. et al., *Inorg. Chem.* (1997) 36, 962–965). Based on this measurement, the observed quantum yield of 3 bound to P450 would then be 0.00038. There is some overlap between the Q bands of the P450 UV-visible absorption spectrum and the emission of the ruthenium complexes. However, a rough comparison with the known extent of Förster quenching of Ru(bpy)$_3$$^{2+}$ complexes similarly bound to P450 suggests that energy transfer should be at most responsible for a 2-fold decrease in luminescence intensity. A more likely source of the low quantum yield is quenching by water. The model of 3 bound to P450 shows that the dppz phenazine nitrogens are still solvent-exposed (FIG. 48). Although this model does not include the conformational changes the protein may make to accommodate the [Ru(phen)$_2$dppz]$^{2+}$ complex, it illustrates the wide, solvent exposed channel that can be reasonably anticipated.

The concept of a molecular probe that emits light upon binding to its target enzyme has been successfully demonstrated to be conceptually sound. Detection may be improved in several ways. Luminescent probes can be designed to provide partial protection of the dppa ligand from solvent in order to achieve higher luminescence quantum yields in the presence of P450. For instance, the alkyl chain of the hypothetical molecule shown in FIG. 50 should help exclude water from around the dppa ligand. Optical detection strategies can also be applied in the luminescent NOS probes.

EXAMPLE VII

This Example Describes Luminescent Sensitizer-Linked Substrate Molecules as Probes Useful for Detection of NOS for Both In Vivo Imaging and Drug Design, a Luminescence-Based Screen for NOS Inhibitor Affinity and Isozyme Specificity NOS are involved in a plethora of both normal and pathological processes. Because of their biological and medicinal importance, it is crucial to develop modulators of activity, such as inhibitors for the NOS isozymes. The methods of the invention include a fluorescence-based screening technique lends itself to screening combinatorial libraries of NOS inhibitors. This assay is rapid, extremely sensitive, and provides accurate binding constants for the inhibitors being tested. The method can be applied for other heme enzymes, or any enzyme which absorbs light and for which an inhibitor or substrate is known.

The luminescent probes used for assessing the binding of isozyme specific inhibitors to NOS and for imaging the spatial distribution of NOS in living tissues are synthesized. Specifically, luminescent probes to be used for screening potential NOS inhibitors for binding are described.

Because the three NOS are involved in many different processes, it is desirable to inhibit only one isozyme at a time. This principle applies both to the molecular biology experiments necessary to elucidate the role of NOS isozymes in complex systems, and to the development of drugs to combat specific diseases. In order to achieve this goal a rapid, inexpensive, and sensitive screen must be developed to assay compounds for efficient and specific NOS inhibition. The luminescence assay of the invention meets all of these criteria.

Sensitizer-linked substrate molecules that bind competitively to the active site of NOS are synthesized. If the emission spectrum of the probe overlaps with the absorption of the heme, Förster energy transfer will quench virtually all of the probe's luminescence. However, if the probe is freed from NOS by competition with another inhibitor, luminescence will be restored. In order to demonstrate the promise of this technique, a brief discussion of the Förster theory is necessary.

The phenomenon of energy transfer between chromophores is well established, and has already found several uses in biotechnology and biophysics. (Wu, P.; Brand, L. *Analytical Biochemistry* (1994) 218, 1–13; Forster, T. in *Modern Quantum Chemistry* O. Sinanoglu, Ed. (Academic Press, New York, 1965), vol. 3, pp. 93–137) Briefly, the interaction between the energy donor and acceptor is modeled as the interaction of two dipoles, and thus falls off as $r^6$. The rate of energy transfer between donor and acceptor is characterized by a parameter $R_0$, which in turn depends on the overlap of the donor's fluorescence spectrum and the acceptor's absorption spectrum J:

$$R_0^6 = 8.8 \cdot 10^{-5}(\kappa^2 n^{-4}\phi_0 J)$$

$$J = \frac{\int_0^\infty F_0(\lambda)E_A(\lambda)\lambda^4 d\lambda}{\int_0^\infty F_0(\lambda)d\lambda}$$

$R_0$ also depends on $\phi_0$, the quantum yield in the absence of energy transfer, n, the index of refraction, and κ, an orientation factor dependent on the alignment of the donor and acceptor dipoles. If the orientation between the donor and acceptor is random, $\kappa^2 = 2/3$. The rate of energy transfer $k_{en}$ is:

$$k_{en} = k_0\left(\frac{R_0}{r}\right)^6$$

Here $k_0$ is the intrinsic rate of decay of the donor, and includes the rate of luminescent decay ($k_{lum}$) and the rate of non-radiative decay. Thus, a large $R_0$ or a short distance between donor and acceptor leads to fast energy transfer. In the absence of other decay paths, the decay rate of the donor in the presence of the acceptor will be:

$$k_{obs} = k_0 + k_{en}$$

The ratio of quantum yields of luminescence in the presence and absence of the acceptor is:

$$\frac{\phi_{obs}}{\phi_0} = \frac{k_{lum}}{k_0 + k_{en}} \cdot \frac{k_0}{k_{lum}} = \frac{k_0}{k_0 + k_{en}} = \frac{1}{1+\left(\frac{R_0}{r}\right)^6}$$

Physically, the luminescent decay of the donor, which constitutes part of the decay rate $k_0$, competes with the rate of energy transfer. In order to maximize the observed luminescence quenching, Ro should be large (good overlap between donor and acceptor) and r should be small.

The sensitizer-linked substrate molecules developed herein have several practical advantages. The Soret bands of thiolate-ligated hemes have extinction coefficients of ca. 100,000 $cm^{-1}M^{-1}$. Provided that the emission spectrum of the sensitizer (i.e. fluorophore) falls in the vicinity of 400–450 nm, the overlap J will be large, and the quenching by energy transfer very efficient. Second, it is not necessary to develop a probe that is itself an excellent NOS inhibitor. In fact, the probe should bind with only moderate affinity so that a superior inhibitor will efficiently displace it. Third, the onset of luminescence can be detected even at very low signal intensities. Fourth, screening for luminescence lends itself to high throughput screening techniques because of the possibility of examining many sample wells simultaneously. Fifth, the binding constant of the competing inhibitor will be easily determined based on the observed quantum yield in the presence of the competitor. (Dmochowski, I. J. et al., *Proc. Natl. Acad. Sci. USA* (1999) 96, 12987–12990) Sixth, the general method described above should be applicable to any enzyme that absorbs light, provided that a suitable luminescent partner can be found.

In one embodiment of the invention, coumarins are used as the chromophores (FIG. 51) (R is a known, NOS inhibitor). This choice was made for several reasons. First, various derivatives are available that fluoresce over a wide range of wavelengths. In particular, fluorophores A and B emit at about 446 and 410 nm, which provides good overlap with the heme Soret bands in both the high (~390 nm) and low (420 nm) spin $Fe^{III}$ states. (Leung, W.-Y. et al., *Bioorg. Med. Chem. Lett.* (1999) 9, 2229–2232; Takadate, A. et al., *Chem. Pharm. Bull.* (1989) 37, 373–376) Second, they both have high quantum yields: around 95% and 55% respectively. (Takadate, A. et al., *Chem. Pharm. Bull.* (1989) 37, 373–376; Arbeloa, T. L. et al., *J. Phys. Chem.* (1993) 97, 4704–4707) Third, they are small, and can therefore be placed close to the heme. Fourth, precursors are synthetically tractable and are commercially available (Sigma-Aldrich, St. Louis, Mo., Molecular Probes, Eugene, Oreg.). The $R_0$ of A with low spin $Fe^{III}$ heme should be between 45 and 50 Å based on the overlap between the P450 water-bound $Fe^{III}$ spectrum and the emission spectrum of A. Assuming a distance of 15 Å between A and the heme, the fluorescence quantum yield would decrease from about 95% to 0.1% upon binding to NOS.

Several classes of NOS inhibitors have been described in the literature. However, the dipeptide inhibitors based on $N^\omega$-nitro-arginine (NMA) are well suited for this example (Huang, H. et al., *J. Med. Chem.* (1999) 42, 3147–3153). The molecule NMA by itself is a good, but non-specific inhibitor of NOS. Fluorophores A and B are attached to the inhibitor directly, or through a tether if A and B prove to be too large to fit inside NOS (FIG. 52). The length of the linker between the fluorophore and the NOS inhibitor can be varied from n=1 to n=10. A preferred embodiment for the linker is an alkyl chain, $(CH_2)_n$, wherein n=1–13. Further, the linker may be replaced with an amino acid to vary binding affinity and specificity. The syntheses are based on standard peptide coupling reactions.

The detection method of the invention (for NOS luminescent probes) is not dependent on either a specific fluorophore or NOS inhibitor. Other fluorophores are also applicable to this technique, including, but are not limited to, 2-amino-benzoic acids, Texas red, 1-and 2-aminonaphthalenes, p,p'-diaminostilbenes, pyrenes, anthracenes, fluoresceins, rhodamines, and other generally known luminescent dyes.

Substrates of NOS that can be used in the compositions and methods of the invention, include, but are not limited to, NOS inhibitors, such as $N^G$-monomethyl, dimethyl, nitro, and amino arginines, $N^G$-nitro-L-arginine methyl ester, $N^\delta$-(iminoethyl-L-ornithine, 1-thiocitrulline, S-alkyl-L-thiocitrulines, bisthioureas, 7-nitroindazoles, aminogaunidine, 2-amino-5,6-dihydro-6-methyl-4H-1,3-thiazine, 2-iminoazahetercylces, N-phenylisothioureas, and N-Phenylamidines. (Collins, J. L. et al., *J. Med. Chem.* (1998) 41, 2858–2871; Hibbs, J. B. et al. *J. Immunol.* (1987) 138, 550–565; Lamber, L. E. et al., *Life Sci.* (1991) 48, 69–75; Rees, D. D. et al. *Br. J. Pharmacol.* (1990) 101, 746–752;

Gross, S. S. et al., *Biochem. Biophys. Res. Commun.* (1990) 270, 96–203; Furfine, E. S. et al., *Biochemistry* (1993) 32, 8512–8517; Narayanan, K. et al., *J. Med. Chem.* (1994) 37, 885–887; Narayanan, K. et al., *J. Biol. Chem.* (1995) 270, 11103–11110; Furfine, E. S. et al., *J. Biol. Chem.* (1994) 269, 26677–26683; Garvey, E. P. et al., *J. Biol. Chem.*, (1994) 269, 26669–26676; Wolff, D. J. et al., *Arch. Biochem. Biophys.* (1994) 311, 300–306; Hasan, K. J et al., *Pharmacol.* (1993) 249, 101–106; Moore, W. M. et al., *J. Med. Chem.* (1996) 39, 669–672; Moore, W. M. et al., *Bioorg. Med. Chem.* (1996) 4, 1559–1564; Shearer, B. G. et al., *J. Med. Chem.*, (1997) 40, 1901–1905; Garvey, E. P. et al., *J. Biol. Chem.* (1997) 272, 4959–4963. Cowart, M. et al., *J. Med. Chem.* (1998) 41, 2636–2642)

EXAMPLE VIII

This Example Describes Luminescent Probes for Imaging the Spatial Distribution of NOS in This example describes a class of sensitizer-linked substrate molecules (i.e. probe molecules) that begin to luminesce upon binding to NOS. The probes are designed to be specific to NOS isozymes. These sensitizer-linked substrate molecules offer researchers a new tool for studying the localization of NOS isozymes in vivo. Unlike many current techniques, this method is non-destructive. Because the probe molecules are reversible inhibitors, the probes should leave NOS function intact. Further, it offers the sensitivity inherent in luminescence assays. The Ruthenium tris-bipyridine $(Ru(bpy)_3)$ excitation (450 nm) and luminescence (620 nm) are far to the red of the excitation and emission spectra of biological molecules, and thus avoid the difficulties of background fluorescence from the sample. The general design of a $Ru(bpy)_3$ moiety tethered to a substrate that functions as a luminescence quencher is applicable in a wide variety of systems.

The Ruthenium tris-bipyridine based luminescent probes are designed such that upon excitation with light of around 450 nm, an electron transfers from the $Ru^{II}$ center to one of the bipyridine ligands (FIG. 53)(Horvath, O.; Stevenson, K. L. *Charge Transfer Photochemistry of Coordination Compounds* (VCH Publishers, inc., New York, N.Y., 1993)). Quenching does not necessarily lead to charge-separated products. Depending on the quencher, geminate recombination may be much faster than solvent cage excape. This excited state undergoes luminescent decay back to the ground state with a quantum yield of about 4.2%. The luminescence spectrum is centered around 620 nm, far to the red of the background fluorescence of biological samples. The excited state is both an excellent reductant and oxidant, and in the presence of a suitable redox partner can form either $[Ru(bpy)_3]3^+$ or $[Ru(bpy)_2(bpy^{*-})]^+$. The former process is called oxidative quenching, while the latter process is termed reductive quenching. When the excited state is intercepted by a quencher it does not luminesce. Quenching does not necessarily lead to charge-separated products. Depending on the quencher, geminate recombination may be much faster than solvent cage escape.

The synthetic strategy of luminescent probes of the invention is shown in FIG. 54. Nitrobenzene quenches the $Ru^{2+*}$ excited state through electron transfer. These probes should emit very little light when free in solution, but luminesce brightly upon binding to NOS. Two variations of probe molecules are shown. Class C is comprised of arginine mimics connected to nitrophenylalanine, which is in turn connected to $[Ru(bpy)_3]^{2+}$ though a long tether. A similar inhibitor, D-Phe-D-ArgNO$_2$—OMe binds n and eNOS with micromolar dissociation constants, but binds iNOS with a 3.6 mM $K_d$. (Huang, H. et al., *J. Med. Chem.* (1999) 42, 3147–3153) The probes in class D are based on the inhibitor 1400W, which is an irreversible inhibitor of iNOS, but a weak, reversible inhibitor of nNOS and eNOS. (Garvey, E. P. et al., *J. Biol. Chem.* (1997) 272,4959–4963).

The $[Ru(bpy)_3]^{2+}$ excited state is efficiently quenched by nitrobenzene through electron transfer. (Meyerstein, D. et al., *J. Phys. Chem.* (1978) 82, 1879–1885) However, the reverse electron transfer is extremely rapid, so no net charge separation occurs. In solution, the flexible linkers allow the quencher to fold back upon the ruthenium. Close proximity should lead to efficient quenching of the $[Ru(bpy)_3]^{2+}$ luminescence. In contrast, when the probe is bound to NOS the quencher is sequestered within the enzyme. Because the rate of electron transfer through saturated bonds decreases exponentially with distance, the ruthenium luminescence is no longer be quenched.

The through-bond model for electron transfer validates the detection system described. For a given path between electron donor and acceptor, the rate of electron transfer is predicted to depend on the number of intervening covalent bonds $N_C$, the number of hydrogen bonds $N_H$, the number of through space contacts $N_S$, and the total length of through space jumps $R_{space}$: (Beratan, D. N.; Skourtis, S. S. *Curr. Opin. Chem. Biol.* (1998) 2, 235–243).

Although more rigorous models exist, this one illustrates several important points. First, the rate of electron transfer through covalent, saturated bonds decreases exponentially with the number of bonds. Second, the rate of electron transfer through a van der Waals contact is roughly the same as through a covalent bond. Third, electron transfer through space is possible over short distances (1–3 Å), but very unfavorable over long distances. In solution, the nitrobenzene and ruthenium are able to make direct contact, so electron transfer should be fast. However, when the nitrobenzene moiety is bound inside the enzyme the electron will be forced to tunnel along the tether. If the tether connecting the ruthenium to the nitrobenzene moiety is 10 carbons long (11 bonds) the rate of electron transfer should be approximately $4 \times 10^5$ sec$^{-1}$ slower than electron transfer through one covalent contact. This corresponds to a predicted electron transfer rate of $1.4 \cdot 10^5$ sec$^{-1}$, or about one-tenth the normal rate of decay of photoexcited $[Ru(bpy)_3]^{2+}$.

Researchers interested in the rate of electron transfer through flexible hydrocarbon chains have observed that the rate of electron transfer became independent of chain length when the chain became more than 6 carbons long, with $k \approx 4 \cdot 10^7$ sec$^{-1}$ (FIG. 55). (Yonemoto, E. H. et al., *J. Am. Chem. Soc.* (1994) 116, 4786–4795). Methyl viologen is an efficient oxidative quencher. This rate of quenching is 20 times faster than the natural rate of decay of $[Ru(bpy)_3]^{2+}$ (about $2 \cdot 10^6$ sec$^{-1}$), and would decrease the luminescence quantum yield to about 5% of the normal $Ru(bpy)_3$ quantum yield. Because the methyl viologen quencher used by these researchers and nitrobenzene have similar bimolecular quenching rate constants, a nitrobenzene moiety connected to $[Ru(bpy)_3]^{2+}$ by an alkyl chain at least 6 carbons long should exhibit a similar rate of quenching when free in solution. (Meyerstein, D. et al., *J. Phys. Chem.* (1978) 82, 1879–1885; Hoffman, M. Z. et al., *J. Phys. Chem. Ref Data* (1989) 18,219–543).

Yonemoto et al. measured the rate of electron transfer between $Ru(bpy)_3$ and methyl viologen connected by an eight-carbon tether in the presence and absence of a β-cyclodextrin. When the alkyl chain was threaded through the β-cyclodextrin, the rate of electron transfer dropped from $2.4 \times 10^7$ to $1.8 \times 10^5$ sec$^{-1}$, which is again one tenth of the natural decay rate of Ru$^{II}$(bpy)$_3$. (Yonemoto, E. H. et al., *J. Am. Chem. Soc.* (1994) 116, 4786–4795) Thus, both previous research and order of magnitude calculations illustrate that the ruthenium luminescence should be efficiently quenched while the probe is free in solution, but restored when the nitrophenyl group is sequestered inside NOS, suggesting that such a probe would be optimal in the methods of the invention.

The syntheses of these inhibitors are based on standard peptide coupling reactions. Carboxylate terminated [Ru (bpy)$_3$]$^{2+}$ tethers have been synthesized previously(Wilker, J. J. et al., *Angew. Chem. Int. Ed. Eng.* (1999) 38, 90–92). The stereochemistry, length of the tether to Ru(bpy)$_3$, and arginine mimic can all be varied to optimize binding and selectivity. Both the inhibitors to be used and the nitrophenylalanine are commercially available. The syntheses of the class D probes are outlined in FIG. 56. 1400W is identical to 15 with the exception of the addition of the nitro group. The synthesis of the amidine functional group (conversion of 14 to D) follows the preparation reported by the discoverers of 1400W and related inhibitors. (Collins, J. L. et al., *J. Med. Chem.* (1998) 41, 2858–2871). 1400W and related inhibitors exhibit outstanding binding and selectivity and may make particularly advantageous probes.

The modular design of these probes makes them easy to test during their development. The bimolecular quenching rate constant of [Ru(bpy)$_3$]$^{2+}$ can be measured by nitrophenylalanine or by 12 and 15. Similarly, 15 and 13 are tested for binding affinity to NOS before being incorporated into the final probe molecules. In addition to the described probes, other probes may be made based on the wide variety of luminescent metal complexes and NOS inhibitors that are available. (Hoffman, M. Z. et al., *J. Phys. Chem. Ref Data* (1989) 18, 219–543; Furfine, E. S. et al., *J. Biol. Chem.* (1994) 269, 2667–26683; Garvey, E. P. et al., *J. Biol. Chem.* (1994) 269, 26669–26676; Shearer, B. G. et al., *J. Med. Chem.* (1997) 40, 1901–1905), and references therein.

Other inhibitors of NOS include, but are not limited to, N$^G$-monomethyl, dimethyl, nitro, and amino arginines, N$^G$-nitro-L-arginine methyl ester, N$^δ$-(iminoethyl-L-ornithine, L-thiocitrulline, S-alkyl-L-thiocitrulines, bisthioureas, 7-nitroindazoles, aminogaunidine, 2-amino-5,6-dihydro-6-methyl-4H-1,3-thiazine, 2-iminoazahetercylces, N-phenylisothioureas, N-phenylamidines and modifications of these compounds. (Collins, J. L. et al., *J. Med. Chem.* (1998) 41, 2858–2871; Hibbs, J. B. et al. *J. Immunol.* (1987) 138, 550–565; Lamber, L. E. et al., *Life Sci.* (1991) 48, 69–75; Rees, D. D. et al. *Br. J. Pharmacol.* (1990) 101, 746–752; Gross, S. S. et al., *Biochem. Biophys. Res. Commun.* (1990) 270, 96–203; Furfine, E. S. et al., *Biochemistry* (1993) 32, 8512–8517; Narayanan, K. et al., *J. Med. Chem.* (1994) 37, 885–887; Narayanan, K. et al., *J. Biol. Chem.* (1995) 270, 11103–11110; Furfine, E. S. et al., *J. Biol. Chem.* (1994) 269, 26677–26683; Garvey, E. P. et al., *J. Biol. Chem.*, (1994) 269, 26669–26676; Wolff, D. J. et al., *Arch. Biochem. Biophys.* (1994) 311, 300–306; Hasan, K. J. et al., *Pharmacol.* (1993) 249, 101–106; Moore, W. M. et al., *J. Med. Chem.* (1996) 39, 669–672; Moore, W. M. et al., *Bioorg. Med. Chem.* (1996) 4, 1559–1564; Shearer, B. G. et al., *J. Med. Chem.*, (1997) 40, 1901–1905; Garvey, E. P. et al., *J. Biol. Chem.* (1997) 272, 4959–4963. Cowart, M. et al., *J. Med. Chem.* (1998) 41, 2636–2642).

Other luminescent metal complexes include, but are not limited to, homo- and heteroleptic ruthenium terpyridine, bipyridine, pyridine, imidazole, cyano and carbonyl complexes, as well as complexes of other transition metals, including but are not limited to osmium, platinum, iridium, rhenium, rhodium, molybdenum, tungsten and copper. [Roundhill, D. M. *Photochemistry and Photophysics of Metal Complexes* (Plenum Press, New York, 1994); Horvath, O. and Stevenson, K. L. *Charge Transfer Photochemistry of Coordination Compounds* (VCH Publishers, Inc., New York, 1992)] Other luminescence quenchers include, but are not limited to, methyl viologens, quinones, N,N-dialkylanilines, N,N-dialkyl-p-methoxyanilines and triarylamines. [Hoffman, M. Z. *J. Phys. Chem. Ref Data* (1989) 18, 219–543).

What is claimed is:

1. A method of detecting and characterizing a target biomolecule in a sample comprising:
   (a) forming a complex comprising a target biomolecule and a substrate molecule, the substrate molecule including a substrate linked to a sensitizer, the substrate molecule being capable of recognizing the target biomolecule by contacting the target biomolecule with the substrate molecule;
   (b) irradiating the complex to cause an emission signal from the sensitizer;
   (c) determining the presence of the target biomolecule in the complex by detecting the signal emitted by the sensitizer; and
   (d) characterizing the target biomolecule by optically analyzing the same to determine the structural properties thereof, wherein said sensitizer is a photosensitizer, and wherein said sensitizer-linked substrate molecule is selected from the group consisting of compounds shown by structures (III) and (IV) the sensitizer being linked to the substrate molecule by an alkyl chain, (CH$_2$)$_n$, wherein n=1–13

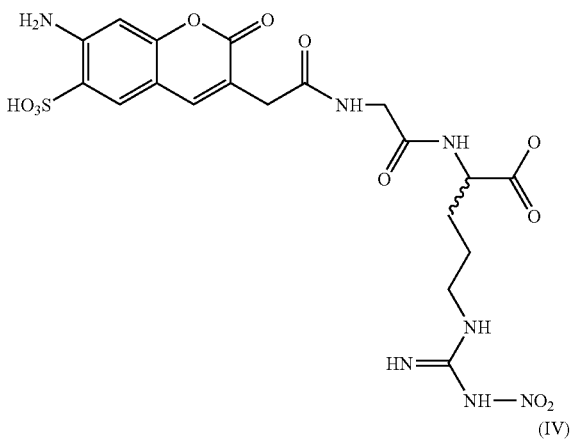

(III)

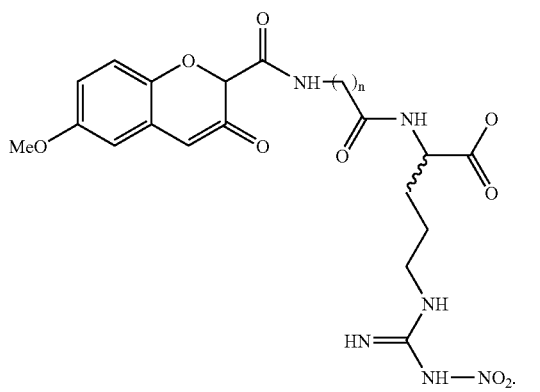

(IV)

2. A method of detecting a target biomolecule in a sample comprising:
   (a) forming a complex comprising a target biomolecule and a substrate molecule, the substrate molecule including a substrate linked to a sensitizer, the substrate molecule being capable of recognizing the target biomolecule by contacting the target biomolecule with the substrate molecule;
   (b) irradiating the complex to cause an emission signal from the sensitizer; and
   (c) determining the presence of the target biomolecule in the complex by detecting the signal emitted by the sensitizer, wherein said sensitizer is a photosensitizer and said sensitizer-linked substrate molecule is selected from the group consisting of compounds shown by structures (III) and (IV) the sensitizer being linked to the substrate molecule by an alkyl chain, $(CH_2)_n$, wherein n=1–13

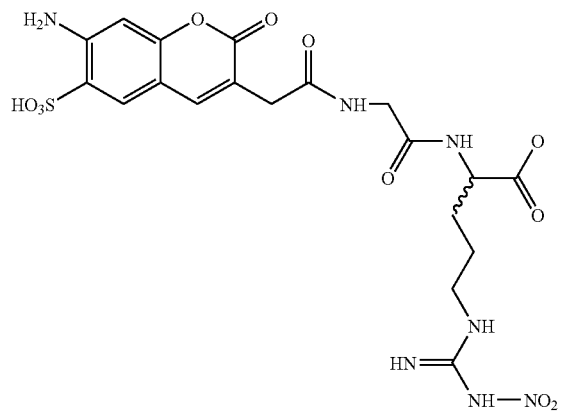

(III)

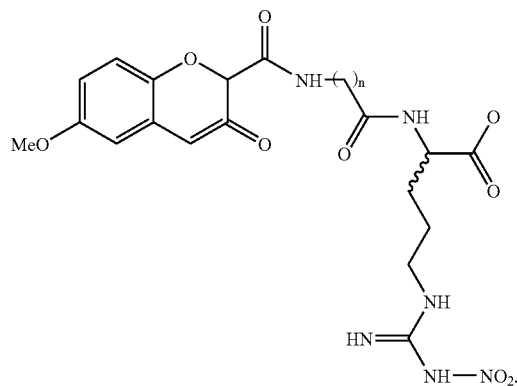

(IV)

3. The method of claim 2, wherein said substrate is a binding element of the substrate molecule.

4. The method of claim 2, wherein said sensitizer is located at or near the surface of the target biomolecule when the substrate of the substrate molecule is bound to the target biomolecule.

5. The method of claim 2, wherein said biomolecule is a metalloprotein.

6. The method of claim 5, wherein said metalloprotein is a heme protein.

* * * * *